United States Patent
Tada et al.

(10) Patent No.: US 10,361,378 B2
(45) Date of Patent: Jul. 23, 2019

(54) ORGANIC ELECTROLUMINESCENT DEVICE

(71) Applicants: NIPPON STEEL & SUMIKIN CHEMICAL CO., LTD., Tokyo (JP); PIONEER CORPORATION, Kawasaki-shi, Kanagawa (JP); TOHOKU PIONEER CORPORATION, Tendo-shi, Yamagata (JP)

(72) Inventors: Masashi Tada, Kitakyushu (JP); Takahiro Kai, Kitakyushu (JP); Katsuhide Noguchi, Kitakyushu (JP); Yasuhiro Takahashi, Kawasaki (JP); Yuhki Terao, Kawasaki (JP); Taishi Tsuji, Kawasaki (JP); Yusuke Nakajima, Yonezawa (JP); Toshinao Yuki, Yonezawa (JP)

(73) Assignees: NIPPON STEEL CHEMICAL & MATERIAL CO., LTD., Tokyo (JP); PIONEER CORPORATION, Kanagawa (JP); TOHOKU PIONEER CORPORATION, Yamagata (JP)

( * ) Notice: Subject to any disclaimer, the term of this patent is extended or adjusted under 35 U.S.C. 154(b) by 502 days.

(21) Appl. No.: 14/652,067

(22) PCT Filed: Nov. 21, 2013

(86) PCT No.: PCT/JP2013/081370
§ 371 (c)(1),
(2) Date: Jun. 12, 2015

(87) PCT Pub. No.: WO2014/097813
PCT Pub. Date: Jun. 26, 2014

(65) Prior Publication Data
US 2015/0325796 A1 Nov. 12, 2015

(30) Foreign Application Priority Data

Dec. 17, 2012 (JP) .................................. 2012-274437

(51) Int. Cl.
*H01L 51/00* (2006.01)
*H01L 51/50* (2006.01)
(Continued)

(52) U.S. Cl.
CPC ........ *H01L 51/0072* (2013.01); *C07D 405/14* (2013.01); *C07D 409/14* (2013.01);
(Continued)

(58) Field of Classification Search
CPC ............. H01L 51/0067; H01L 51/0068; H01L 51/0072–0074; H01L 51/0085;
(Continued)

(56) References Cited

U.S. PATENT DOCUMENTS

| 5,942,340 A | 8/1999 | Hu et al. |
| 2009/0167162 A1* | 7/2009 | Lin ...................... C07D 409/14 313/504 |

(Continued)

FOREIGN PATENT DOCUMENTS

| EP | 2 521 196 A1 | 11/2012 |
| JP | 2012-49518 A | 3/2012 |

(Continued)

OTHER PUBLICATIONS

Supplementary European Search Report for the Application No. EP 13 86 5073 dated Jun. 28, 2016.
(Continued)

*Primary Examiner* — Ruiyan Zhang
(74) *Attorney, Agent, or Firm* — Cheng Law Group, PLLC

(57) ABSTRACT

Provided is a practically useful organic EL element having high efficiency and high driving stability while being
(Continued)

capable of being driven at a low voltage. The organic EL element has a light-emitting layer and any other organic layer between an anode and a cathode opposite to each other. The light-emitting layer contains at least two host materials and at least one light-emitting dopant. At least one of the host materials is a host material selected from compounds each having one or two indolocarbazole skeletons, and at least one of the other host materials is a host material selected from carbazole compounds each substituted with a dibenzofuran or a dibenzothiophene.

13 Claims, 1 Drawing Sheet

(51) Int. Cl.
```
H01L 51/52      (2006.01)
C07D 405/14     (2006.01)
C07D 409/14     (2006.01)
C07D 487/04     (2006.01)
C09K 11/06      (2006.01)
```

(52) U.S. Cl.
CPC ............ *C07D 487/04* (2013.01); *C09K 11/06* (2013.01); *H01L 51/0067* (2013.01); *H01L 51/0068* (2013.01); *H01L 51/0073* (2013.01); *H01L 51/0074* (2013.01); *H01L 51/0085* (2013.01); *H01L 51/504* (2013.01); *H01L 51/5278* (2013.01); *C09K 2211/1029* (2013.01); *C09K 2211/185* (2013.01); *H01L 51/5016* (2013.01); *H01L 2251/5384* (2013.01)

(58) Field of Classification Search
CPC ............... H01L 51/504; H01L 51/5016; H01L 2251/5384; C09K 11/06; C09K 2211/1029; C09K 2211/185; C07D 405/14; C07D 409/14; C07D 487/04

USPC .......... 428/690, 691, 917; 257/40, 102, 103, 257/E51.022, E51.026; 252/500; 544/212, 331; 548/418; 546/281.1, 546/276.7

See application file for complete search history.

(56) References Cited

U.S. PATENT DOCUMENTS

| | | |
|---|---|---|
| 2010/0187977 A1 | 7/2010 | Kai et al. |
| 2011/0062862 A1 | 3/2011 | Yamamoto et al. |
| 2011/0278555 A1 | 11/2011 | Inoue et al. |
| 2011/0279020 A1 | 11/2011 | Inoue et al. |
| 2011/0315975 A1* | 12/2011 | Kai ...................... C07D 487/04 257/40 |
| 2012/0001158 A1 | 1/2012 | Asari et al. |
| 2012/0138915 A1 | 6/2012 | Nishimura et al. |
| 2013/0341602 A1* | 12/2013 | Hikime ................. C09K 11/06 257/40 |
| 2014/0151647 A1 | 6/2014 | Mizuki et al. |
| 2014/0209885 A1 | 7/2014 | Tada et al. |

FOREIGN PATENT DOCUMENTS

| | | |
|---|---|---|
| WO | WO-2009/086028 A2 | 7/2009 |
| WO | WO 2011/136755 A1 | 11/2011 |
| WO | WO-2012/087955 A1 | 5/2012 |
| WO | WO-2013/145923 A1 | 10/2013 |
| WO | WO-2013/168688 A1 | 11/2013 |

OTHER PUBLICATIONS

International Search Report for the Application No. PCT/JP2013/081370 dated Feb. 10, 2014.

Written Opinion of the International Searching Authority PCT/ISA/237) for Application No. PCT/JP2013/081370 dated Feb. 10, 2014 (English Translation dated Jul. 2, 2015).

* cited by examiner

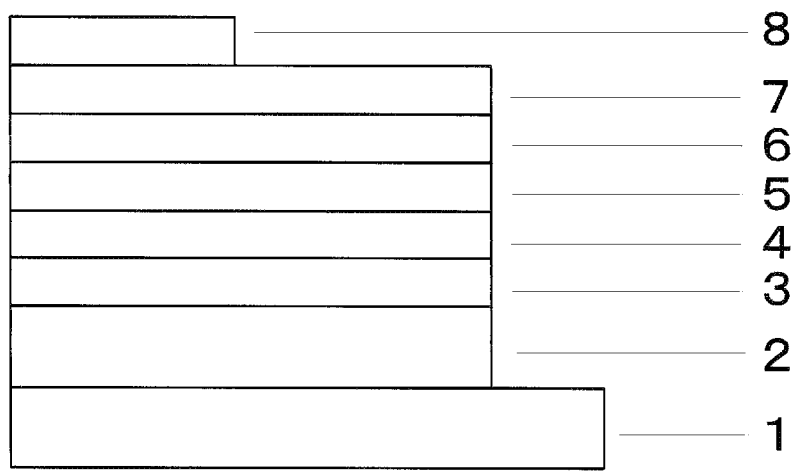

ORGANIC ELECTROLUMINESCENT DEVICE

TECHNICAL FIELD

The present invention relates to an organic electroluminescent element (hereinafter referred to as "organic EL element").

BACKGROUND ART

In general, an organic EL element includes a light-emitting layer and a pair of counter electrodes interposing the light-emitting layer therebetween in its simplest structure. That is, the organic EL element uses the phenomenon that, when an electric field is applied between both the electrodes, electrons are injected from a cathode and holes are injected from an anode, and each electron and each hole recombine in the light-emitting layer to emit light as energy.

In recent years, progress has been made in developing an organic EL element using an organic thin film. In particular, development has been made to enhance luminous efficiency. In the course of the development, the efficiency of injection of carriers from the electrodes has been improved through the optimization of the kind of electrodes. In addition, there has been developed an element in which a hole-transporting layer formed of an aromatic diamine and a light-emitting layer-cum-electron-transporting layer formed of an 8-hydroxyquinoline aluminum complex (hereinafter referred to as Alq3) are used, resulting in a significant improvement in luminous efficiency, as compared to related-art elements. Thus, the development of the organic EL element has been promoted with a view to accomplishing its practical application to a high-performance flat panel having features such as self-luminescence and rapid response.

Investigations have also been made on using a phosphorescent light-emitting material rather than a fluorescent light-emitting material as an attempt to raise the luminous efficiency of an element. Many kinds of elements including the element in which a hole-transporting layer formed of an aromatic diamine and a light-emitting layer formed of Alq3 are formed use fluorescent light emission. However, by using phosphorescent light emission, that is, by using light emission from a triplet excited state, luminous efficiency is expected to be improved by about three times to four times, as compared to the case of using related-art elements in which fluorescent light (light emission from a singlet excited state) is used. In order to accomplish this purpose, investigations have been made on adopting a coumarin derivative or a benzophenone derivative as a light-emitting layer, but extremely low luminance has only been provided. After that, investigations have been made on using a europium complex as an attempt to use a triplet excited state, but highly efficient light emission has not been accomplished. Among the investigations involving using phosphorescent light emission, many investigations on a phosphorescent light-emitting dopant centered on an organometallic complex such as an iridium complex have been made, and ones capable of highly efficient light emission have been found.

CITATION LIST

Patent Literature

[PTL 1] JP 11-176578 A
[PTL 2] WO 2008/056746 A1
[PTL 3] WO 2009/136596 A1
[PTL 4] WO 2010/098246 A1
[PTL 5] WO 2011/132683 A1
[PTL 6] WO 2011/132684 A1
[PTL 7] JP 2012-028634 A
[PTL 8] WO 2009/086028 A2
[PTL 9] JP 2012-49518 A

Examples of a host material to be used in the light-emitting layer of the organic EL element include a carbazole-based compound, an oxazole-based compound, and a triazole-based compound. However, none of the compounds can be put into practical use in terms of both efficiency and lifetime.

In addition, Patent Literature 1 discloses an indolocarbazole compound. However, the literature recommends the use of the indolocarbazole compound as a hole-transporting material, and does not disclose the use of the indolocarbazole compound as a mixed host material.

In addition, Patent Literature 2 discloses the use of an indolocarbazole compound as a host material, but does not teach the usefulness of the indolocarbazole compound as a mixed host material.

In addition, each of Patent Literatures 3 and 4 discloses the use of an indolocarbazole compound as a mixed host, but does not teach that the combination of the compound with a specific carbazole compound expresses a useful effect.

In addition, each of Patent Literatures 5, 6, and 7 discloses the use of an indolocarbazole compound and a carbazole compound as a mixed host, but does not teach any useful effect of the combination of a specific indolocarbazole compound and a specific carbazole compound.

In addition, each of Patent Literatures 8 and 9 discloses a specific carbazole compound, but does not teach any useful effect of its combination with a specific indolocarbazole compound.

SUMMARY OF INVENTION

In order to apply an organic EL element to a display element in a flat panel display or the like, or to a light source, it is necessary to improve the luminous efficiency of the element and also to ensure sufficiently the stability in driving the element. The present invention has an object to provide, in view of the above-mentioned circumstances, a practically useful organic EL element that has high efficiency and high driving stability while being capable of being driven at a low voltage.

The present invention relates to an organic electroluminescent element, including one or more light-emitting layers between an anode and a cathode opposite to each other, in which:

at least one of the one or more light-emitting layers contains at least two host materials and at least one light-emitting dopant; and the at least two host materials include at least one host material selected from compounds each represented by any one of the following general formulae (1) and (2), and at least one host material selected from compounds each represented by the following general formula (3).

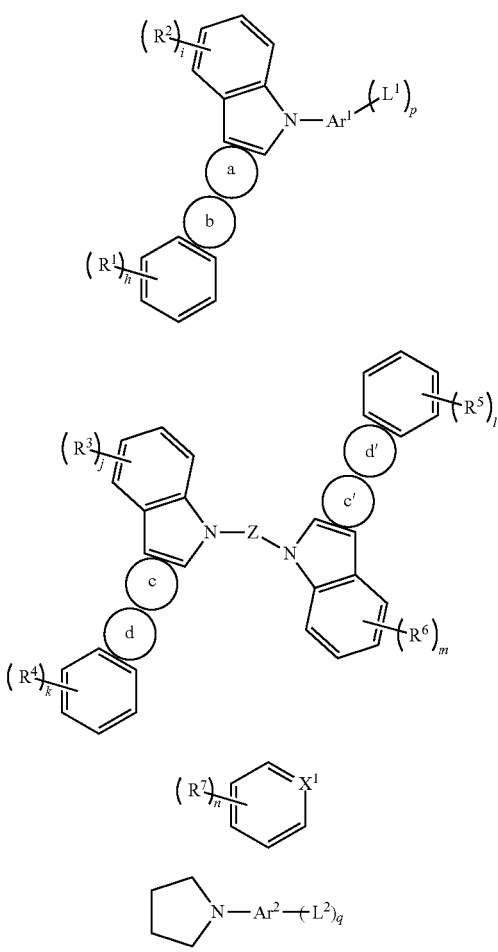

In the formulae: a ring a, a ring c, and a ring c' each independently represent an aromatic ring or heterocycle represented by the formula (a1) fused at arbitrary positions of two adjacent rings;

a ring b, a ring d, and a ring d' each independently represent a heterocycle represented by the formula (b1) fused at arbitrary positions of two adjacent rings;

$X^1$ represents $CR^7$ or N;

$Ar^1$ and $Ar^2$ each independently represent an aromatic hydrocarbon group having 6 to 22 carbon atoms, or a monocyclic aromatic heterocyclic group having 3 to 6 carbon atoms;

Z represents a divalent linking group selected from an aromatic hydrocarbon group having 6 to 22 carbon atoms, an aromatic heterocyclic group having 3 to 16 carbon atoms, and a linked aromatic group obtained by linking 2 to 10 aromatic rings of the aromatic hydrocarbon group and the aromatic heterocyclic group, and a group bonded to N includes an aromatic hydrocarbon group having 6 to 22 carbon atoms, or a monocyclic aromatic heterocyclic group having 3 to 6 carbon atoms;

$R^1$ to $R^7$ each independently represent hydrogen, a cyano group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a dialkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 22 carbon atoms, or an aromatic heterocyclic group having 3 to 16 carbon atoms;

$L^1$ and $L^2$ each independently represent an aromatic hydrocarbon group having 6 to 22 carbon atoms, an aromatic heterocyclic group having 3 to 16 carbon atoms, or a linked aromatic group obtained by linking 2 to 10 aromatic rings of the aromatic hydrocarbon group and the aromatic heterocyclic group; and p and q each represent an integer of from 0 to 7, h, i, j, k, l, and m each represent an integer of 4, n represents an integer of 2, when a plurality of $L^1$'s, $L^2$'s, $R^1$'s, $R^2$'s, $R^3$'s, $R^4$'s, $R^5$'s, $R^6$'s, or $R^7$'s exist, the plurality of groups may be identical to or different from each other, and the aromatic hydrocarbon group or aromatic heterocyclic group in any one of $Ar^1$, $Ar^2$, $L^1$, $L^2$, Z, and $R^1$ to $R^7$ may have a substituent, and when the group has a substituent, the substituent includes a cyano group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a dialkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, or an alkylsulfonyl group having 1 to 20 carbon atoms.

(In the formula, $L^3$'s each independently represent hydrogen or a monovalent group, and E represents oxygen or sulfur.

In addition, part or all of the hydrogen atoms in the general formulae (1) and (2) and the general formula (3) may each be substituted with deuterium.

It is desirable that, in the general formulae (1) and (2), at least one of $Ar^1$ and $Ar^2$ represent a monocyclic aromatic heterocyclic group having 3 to 6 carbon atoms, and $X^1$ represent $CR^7$.

It is desirable that at least one of $L^3$'s in the general formula (3) represent a monovalent group represented by the formula (e1).

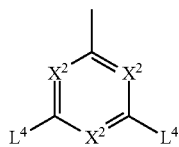

(e1)

In the formula: $L^4$'s each independently represent hydrogen, a cyano group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a dialkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 22 carbon atoms, an aromatic heterocyclic group having 3 to 16 carbon atoms, or a linked aromatic group obtained by linking 2 to 10 aromatic rings of the aromatic hydrocarbon group and the aromatic heterocyclic group;

$X^2$'s each independently represent $CL^4$ or nitrogen and a plurality of $L^4$'s may be identical to or different from each other; and the aromatic hydrocarbon group or aromatic heterocyclic group in $L_4$ may have a substituent, and when the group has a substituent, the substituent includes a cyano group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a dialkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, or an alkylsulfonyl group having 1 to 20 carbon atoms.

It is preferred that the compounds each represented by the general formula (3) include compounds each represented by the general formula (4) and it is preferred that the compounds each represented by the general formula (4) include compounds each represented by the general formula (5).

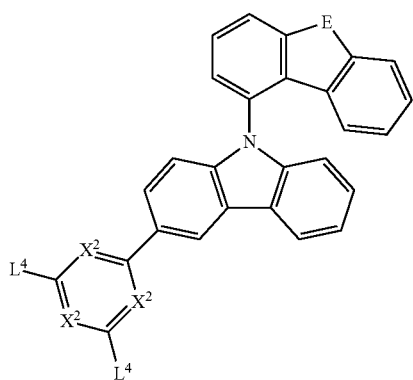

(4)

(In the formula, $X^2$, $L^4$, and E are identical in meaning to $X^2$, $L^4$, and E in the general formula (3) and the formula (e1), respectively.)

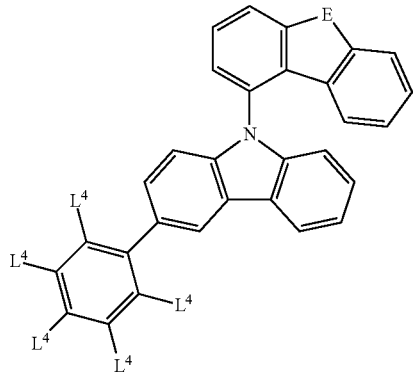

(5)

(In the formula, $L^4$ and E are identical in meaning to $L_4$ and E in the general formula (4), respectively.)

Further, it is desirable that a difference (ΔEA) in electron affinity between the material selected from the compounds each represented by any one of the general formulae (1) and (2), and the material selected from the compounds each represented by the general formula (3) be more than 0.1 eV.

It is desirable that the light-emitting dopant include an organometallic complex containing at least one metal selected from ruthenium, rhodium, palladium, silver, rhenium, osmium, iridium, platinum, and gold.

The organic EL element of the present invention uses specific compounds as a mixed host, and hence has lowest excited triplet energy high enough to confine the lowest excited triplet energy of a phosphorescent light-emitting molecule while being capable of being driven at a low voltage. Accordingly, the outflow of energy from the inside of its light-emitting layer does not occur, and the element can achieve high efficiency and a long lifetime.

BRIEF DESCRIPTION OF DRAWINGS

FIG. 1 is a schematic sectional view for illustrating an example of an organic EL element.

DESCRIPTION OF EMBODIMENTS

An organic electroluminescent element of the present invention is an organic electroluminescent element including one or more light-emitting layers between an anode and a cathode opposite to each other, in which: at least one of the light-emitting layers contains at least two host materials and at least one light-emitting dopant; and one of the two host materials is a host material selected from compounds each represented by any one of the following general formulae (1) and (2), and another thereof is a host material selected from compounds each represented by the following general formula (3).

In the general formula (1) or (2), a ring a, a ring c, and a ring c' each independently represent an aromatic ring or heterocycle represented by the formula (a1) fused at arbitrary positions of two adjacent rings, and a ring b, a ring d, and a ring d' each independently represent a heterocycle represented by the formula (b1) fused at arbitrary positions of two adjacent rings. In the formula (a1), $X^1$ represents $CR^7$ or N, preferably $CR^7$.

In a compound represented by the general formula (1) or (2), the aromatic hydrocarbon ring or heterocycle represented by the formula (a1) can be fused with two adjacent rings at arbitrary positions, but at some positions, the aromatic hydrocarbon ring or heterocycle cannot be structurally fused therewith. The aromatic hydrocarbon ring or heterocycle represented by the formula (a1) has six sides, but is not fused with the two adjacent rings on two adjacent sides. In addition, in the general formula (1) or (2), the heterocycle represented by the formula (b1) can be fused with two adjacent rings at arbitrary positions, but at some positions, the heterocycle cannot be structurally fused therewith. That is, the heterocycle represented by the formula (b1) has five sides, but is not fused with the two adjacent rings on two adjacent sides. In addition, the heterocycle is not fused with any adjacent ring on a side containing a nitrogen atom. Therefore, the kinds of the skeletons of the isomers of the compounds represented by the general formulae (1) and (2) are limited.

In the general formulae (1) and (2), $Ar^1$ and $Ar^2$ each represent an aromatic hydrocarbon group having 6 to 22 carbon atoms, or a monocyclic aromatic heterocyclic group having 3 to 6 carbon atoms, and such aromatic hydrocarbon group or aromatic heterocyclic group may have a substituent. It should be noted that the term "general formula (1)" or "general formula (2)" is interpreted as including the formula (a1) and the formula (b1).

$Ar^1$ and $Ar^2$ each preferably represent an aromatic hydrocarbon group having 6 to 18 carbon atoms, or a monocyclic aromatic heterocyclic group having 3 to 5 carbon atoms, and the monocyclic aromatic heterocyclic group is preferably a six-membered ring. $Ar^1$ represents a (p+1)-valent group and $Ar^2$ represents a (q+1)-valent group.

Specific examples of $Ar^1$ and $Ar^2$ include groups each produced by removing p+1 or q+1 hydrogen atoms from benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, helicene, hexaphene, rubicene, coronene, trinaphthylene, heptaphene, pyranthrene, furan, thiophene, pyrrole, pyrazole, tellurazole, selenazole, thiazole, isothiazole, oxazole, furazan, thiadiazole, pyridine, pyrazine, pyrimidine, pyridazine, or triazine.

In the general formula (2), Z represents a divalent linking group selected from an aromatic hydrocarbon group having 6 to 22 carbon atoms, an aromatic heterocyclic group having 3 to 16 carbon atoms, and a linked aromatic group obtained by linking 2 to 10 aromatic rings of the aromatic hydrocarbon group and the aromatic heterocyclic group, and a group bonded to N in the linked aromatic group is an aromatic hydrocarbon group having 6 to 22 carbon atoms, or a monocyclic aromatic heterocyclic group having 3 to 6 carbon atoms. It is preferred that Z represent an aromatic hydrocarbon group having 6 to 22 carbon atoms, an aromatic heterocyclic group having 3 to 16 carbon atoms, or a divalent linked aromatic group obtained by linking 2 to 7 aromatic rings of such groups, a group linked to N be an aromatic hydrocarbon group having 6 to 18 carbon atoms, or a monocyclic aromatic heterocyclic group having 3 to 5 carbon atoms, and the monocyclic aromatic heterocyclic group be a six-membered ring. The aromatic rings may each independently have a substituent.

Specific examples of Z include the same examples as those in the description of an aromatic hydrocarbon group, aromatic heterocyclic group, or linked aromatic group in $L^1$ or $L^2$, but an aromatic heterocyclic group bonded to N is a monocyclic aromatic heterocyclic group having 3 to 6 carbon atoms.

In the general formula (1) and the formula (b1), $L^1$ and $L^2$ each represent an aromatic hydrocarbon group having 6 to 22 carbon atoms, an aromatic heterocyclic group having 3 to 16 carbon atoms, or a linked aromatic group obtained by linking 2 to 10 aromatic rings of such groups, and these groups may each have a substituent. $L^1$ and $L^2$ each preferably represent an aromatic hydrocarbon group having 6 to 18 carbon atoms, an aromatic heterocyclic group having 3 to 16 carbon atoms, or a linked aromatic group obtained by linking 2 to 7 aromatic rings of such groups.

Specific examples of $L^1$ and $L^2$ include groups each produced by removing one hydrogen atom from benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, helicene, hexaphene, rubicene, coronene, trinaphthylene, heptaphene, pyranthrene, furan, benzofuran, isobenzofuran, xanthene, oxanthrene, dibenzofuran, peri-xanthenoxanthene, thiophene, thioxanthene, thianthrene, phenoxathiin, thionaphthene, isothianaphthene, thiophthene, thiophanthrene, dibenzothiophene, pyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolizine, isoquinoline, carbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisoxazole, or benzisothiazole, or a linked aromatic compound obtained by linking a plurality of these aromatic compounds.

Here, examples of the linked aromatic group in any one of $L^1$ and $L^2$ include such linking modes as represented by the formulae (7) to (9). Examples of the linked aromatic group in Z include such linking modes as represented by the formulae (10) to (12).

(7)

(8)

(9)

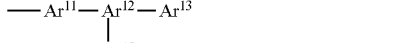

(10)

(11)

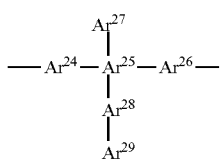

(12)

In the formulae (7) to (12), $Ar^4$ to $Ar^{29}$ each represent a substituted or unsubstituted aromatic ring. The aromatic ring means a ring of an aromatic hydrocarbon compound or of an aromatic heterocyclic compound, and means a group that is monovalent or more. When the aromatic ring is a substituted aromatic ring, the substituent is not an aromatic ring. $Ar^{17}$, $Ar^{20}$, $Ar^{22}$, $Ar^{24}$, and $Ar^{26}$ each represent a group bonded to N.

Specific examples of the formulae (7) to (12) include groups each produced by removing one or two hydrogen atoms from, for example, biphenyl, terphenyl, bipyridine, bipyrimidine, bitriazine, terpyridine, binaphthalene, phenylpyridine, diphenylpyridine, phenylpyrimidine, diphenylpyrimidine, phenyltriazine, phenylnaphthalene, diphenylnaphthalene, carbazolylbenzene, biscarbazolylbenzene, biscarbazolyltriazine, dibenzofuranylbenzene, bisdibenzofuranylbenzene, dibenzothiophenylbenzene, or bisdibenzothiophenylbenzene.

Symbols p and q each represent an integer of from 0 to 7, preferably from 0 to 5, more preferably from 0 to 3. h, i, j, k, l, and m each represent an integer of 4, and n represents an integer of 2. When a plurality of $L^1$'s, $L^2$'s, $R^1$'s, $R^2$'s, $R^3$'s, $R^4$'s, $R^5$'s, $R^6$'s, or $R^7$'s exist, the plurality of groups may be identical to or different from each other.

In addition, the aromatic hydrocarbon group or aromatic heterocyclic group in any one of $Ar^1$, $Ar^2$, $L^1$, $L^2$, Z, and $R^1$ to $R^7$ may have a substituent. When the group has a substituent, the substituent is a cyano group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a dialkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, or an alkylsulfonyl group having 1 to 20 carbon atoms, preferably an alkyl group having 1 to 10 carbon atoms, an aralkyl group having 7 to 24 carbon atoms, an alkoxy group having 1 to 10 carbon atoms, or a diarylamino group having 12 to 36 carbon atoms. It should be noted that the number of substituents is from 0 to 5, preferably from 0 to 2.

Specific examples of the substituent include cyano, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, phenylmethyl, phenylethyl, phenylicosyl, naphthylmethyl, anthranylmethyl, phenanthrenylmethyl, pyrenylmethyl, vinyl, propenyl, butenyl, pentenyl, decenyl, icosenyl, ethynyl, propargyl, butynyl, pentynyl, decynyl, icosynyl, dimethylamino, ethylmethylamino, diethylamino, dipropylamine, dibutylamino, dipentynylamino, didecylamino, diicosylamino, diphenylamino, naphthylphenylamino, dinaphthylamino, dianthranylamino, diphenanthrenylamino, dipyrenylamino, diphenylmethylamino, diphenylethylamino, phenylmethylphenylethylamino, dinaphthylmethylamino, dianthranylmethylamino, diphenanthrenylmethylamino, acetyl, propionyl, butyryl, valeryl, benzoyl, acetyloxy, propionyloxy, butyryloxy, valeryloxy, benzoyloxy, methoxy, ethoxy, propoxy, butoxy, pentoxy, hexoxy, heptoxy, octoxy, nonyloxy, decoxy, undecyloxy, dodecoxy, tridecoxy, tetradecoxy, pentadecoxy, hexadecoxy, heptadecoxy, octadecoxy, nonadecoxy, icosoxy, methoxycarbonyl, ethoxycarbonyl, propoxycarbonyl, butoxycarbonyl, pentoxycarbonyl, methoxycarbonyloxy, ethoxycarbonyloxy, propoxycarbonyloxy, butoxycarbonyloxy, pentoxycarbonyloxy, methylsulfonyl, ethylsulfonyl, propylsulfonyl, butylsulfonyl, and pentylsulfonyl. Of those, there is preferred a C1-12 alkyl group such as methyl, ethyl, propyl, butyl, pentyl, hexyl, heptyl, octyl, nonyl, or decyl, a C7-20 aralkyl group such as phenylmethyl, phenylethyl, naphthylmethyl, anthranylmethyl, phenanthrenylmethyl, or pyrenylmethyl, a C1-10 alkoxy group such as methoxy, ethoxy, propoxy, butoxy, pentoxy, hexoxy, heptoxy, octoxy, nonyloxy, or decoxy, or a diarylamino group having two C6-15 aromatic hydrocarbon groups such as diphenylamino, naphthylphenylamino, dinaphthylamino, dianthranylamino, or diphenanthrenylamino.

In the general formulae (1) and (2), $R^1$ to $R^7$ each independently represent hydrogen, a cyano group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a dialkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 22 carbon atoms, or an aromatic heterocyclic group having 3 to 16 carbon atoms. Of those, an alkyl group having 1 to 10 carbon atoms, an aralkyl group having 7 to 24 carbon atoms, an alkoxy group having 1 to 10 carbon atoms, a diarylamino group having 12 to 36 carbon atoms, an aromatic hydrocarbon group having 6 to 18 carbon atoms, or an aromatic heterocyclic group having 3 to 16 carbon atoms is preferred, and an aromatic hydrocarbon group having 6 to 18 carbon atoms, or an aromatic heterocyclic group having 3 to 16 carbon atoms is more preferred. It should be noted that each of the groups may have a substituent.

Specific examples of the alkyl group having 1 to 20 carbon atoms, the aralkyl group having 7 to 38 carbon atoms, the alkenyl group having 2 to 20 carbon atoms, the alkynyl group having 2 to 20 carbon atoms, the dialkylamino group having 2 to 40 carbon atoms, the diarylamino group having 12 to 44 carbon atoms, the diaralkylamino group having 14 to 76 carbon atoms, the acyl group having 2 to 20 carbon atoms, the acyloxy group having 2 to 20 carbon atoms, the alkoxy group having 1 to 20 carbon atoms, the alkoxycarbonyl group having 2 to 20 carbon atoms, the alkoxycarbonyloxy group having 2 to 20 carbon atoms, and the alkylsulfonyl group having 1 to 20 carbon atoms include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, phenylmethyl, phenylethyl, phenylicosyl, naphthylmethyl, anthranylmethyl, phenanthrenylmethyl, pyrenylmethyl, vinyl, propenyl, butenyl, pentenyl, decenyl, icosenyl, ethynyl, propargyl, butynyl, pentynyl, decynyl, icosynyl, dimethylamino, ethylmethylamino, diethylamino, dipropylamino, dibutylamino, dipentynylamino, didecylamino, diicosylamino, diphenylamino, naphthylphenylamino, dinaphthylamino, dianthranylamino, diphenanthrenylamino, dipyrenylamino, diphenylmethylamino, diphenylethylamino, phenylmethylphenylethylamino, dinaphthylmethylamino, dianthranylmethylamino, diphenanthrenylmethylamino, acetyl, propionyl, butyryl, valeryl, benzoyl, acetyloxy, propionyloxy, butyryloxy, valeryloxy, benzoyloxy, methoxy, ethoxy, propoxy, butoxy, pentoxy, hexoxy, heptoxy, octoxy, nonyloxy, decoxy, undecyloxy, dodecoxy, tridecoxy, tetradecoxy, pentadecoxy, hexadecoxy, heptadecoxy, octadecoxy, nonadecoxy, icosoxy, methoxycarbonyl, ethoxycarbonyl, propoxycarbonyl, butoxycarbonyl, pentoxycarbonyl, methoxycarbonyloxy, ethoxycarbonyloxy, propoxycarbonyloxy, butoxycarbonyloxy, pentoxycarbonyloxy, methylsulfonyl, ethylsulfonyl, propylsulfonyl, butylsulfonyl, and pentylsulfonyl. Of those, there is preferred an alkyl group having 1 to 10 carbon atoms such as methyl, ethyl, propyl, butyl, pentyl, hexyl, heptyl, octyl, nonyl, or decyl, an aralkyl group having 7 to 17 carbon atoms such as phenylmethyl, phenylethyl, naphthylmethyl, anthranylmethyl, phenanthrenylmethyl, or pyrenylmethyl, an alkoxy group having 1 to 10 carbon atoms such as methoxy, ethoxy, propoxy, butoxy, pentoxy, hexoxy, heptoxy, octoxy, nonyloxy, or decoxy, or a diarylamino group having 12 to 28 carbon atoms such as diphenylamino, naphthylphenylamino, dinaphthylamino, dianthranylamino, or diphenanthrenylamino.

In the case of the aromatic hydrocarbon group having 6 to 22 carbon atoms or the aromatic heterocyclic group having 3 to 16 carbon atoms, specific examples thereof include groups each produced by removing hydrogen from benzene, pentalene, indene, naphthalene, azulene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, furan, benzofuran, isobenzofuran, xanthene, oxanthrene, dibenzofuran, peri-xanthenoxanthene, thiophene, thioxanthene, thianthrene, phenoxathiin, thionaphthene, isothianaphthene, thiophthene, thiophanthrene, dibenzothiophene, pyrrole, pyrazole, tellurazole, selenazole, thiazole, isothiazole, oxazole, furazan, thiadiazole, pyridine, pyrazine, pyrimidine, pyridazine, triazine, indolizine, indole, isoindole, indazole, purine, quinolizine, isoquinoline, carbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisoxazole, or benzisothiazole. Of those, there is preferred a group produced by removing hydrogen from benzene, naphthalene, anthracene, pyridine, pyrazine, pyrimidine, pyridazine, triazine, isoindole, indazole, purine, isoquinoline, imidazole, naphthyridine, phthalazine, quinazoline, benzodiazepine, quinoxaline, cinnoline, quinoline, pteridine, phenanthridine, acridine, perimidine, phenanthroline, phenazine, carboline, indole, carbazole, dibenzofuran, or dibenzothiophene.

In the general formulae (1) and (2), when any one $R^1$ to $R^7$ further has a substituent, the substituent is desirably a cyano group an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, or an alkylsulfonyl group having 1 to 20 carbon atoms. Of those, an alkyl group having 1 to 10 carbon atoms, an aralkyl group having 7 to 24 carbon atoms, an alkoxy group having 1 to 10 carbon atoms, or a diarylamino group having 12 to 36 carbon atoms is preferred. It should be noted that the number of substituents is preferably from 0 to 3, more preferably from 0 to 2 per one of $R^1$ to $R^7$.

Specific examples of the alkyl group having 1 to 20 carbon atoms, the aralkyl group having 7 to 38 carbon atoms, the alkenyl group having 2 to 20 carbon atoms, the alkynyl group having 2 to 20 carbon atoms, the dialkylamino group having 2 to 40 carbon atoms, the diarylamino group having 12 to 44 carbon atoms, the diaralkylamino group having 14 to 76 carbon atoms, the acyl group having 2 to 20 carbon atoms, the acyloxy group having 2 to 20 carbon atoms, the alkoxy group having 1 to 20 carbon atoms, the alkoxycarbonyl group having 2 to 20 carbon atoms, the alkoxycarbonyloxy group having 2 to 20 carbon atoms, and the alkylsulfonyl group having 1 to 20 carbon atoms are the same as the specific examples of $R^1$ to $R^7$.

Hydrogen atoms in the compounds represented by the general formulae (1) and (2) can each be substituted with deuterium.

Preferred specific examples of the compounds represented by the general formulae (1) and (2) are shown below, but compounds are not limited thereto.

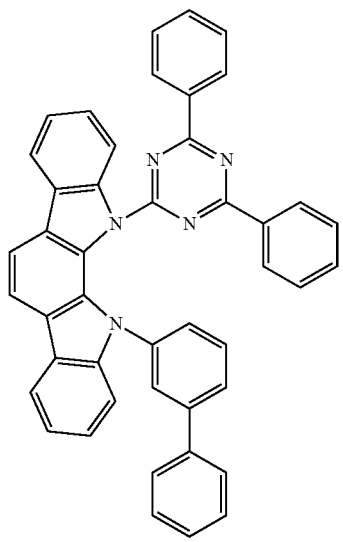

1-1

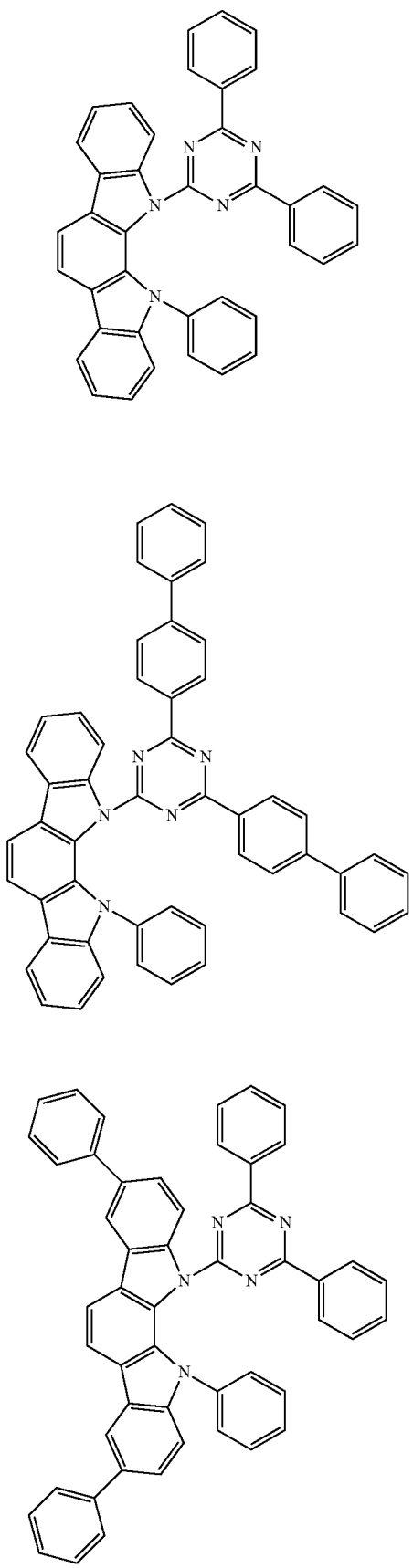
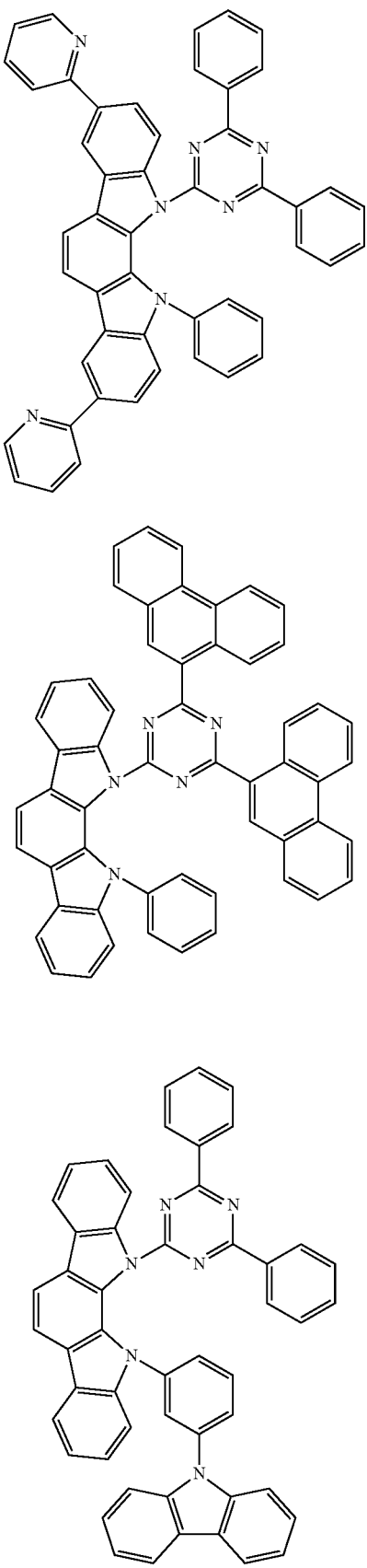

1-8
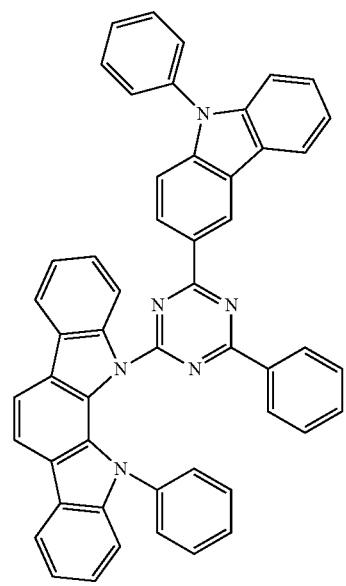
1-9
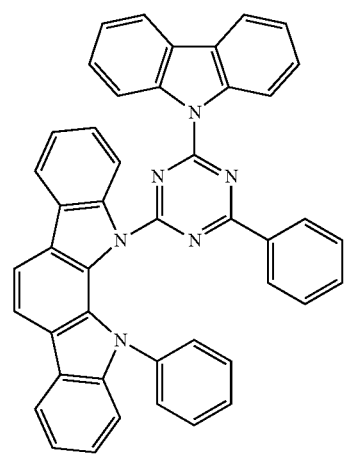
1-10
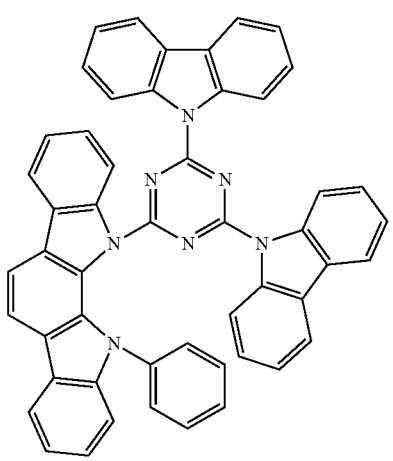
1-11
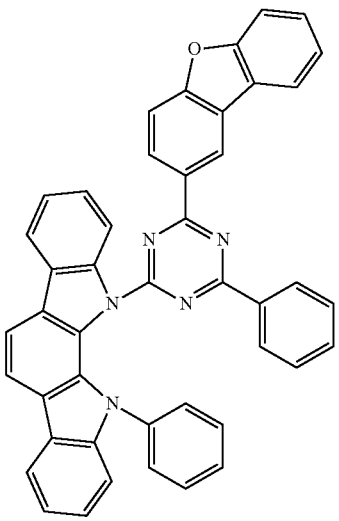
1-12
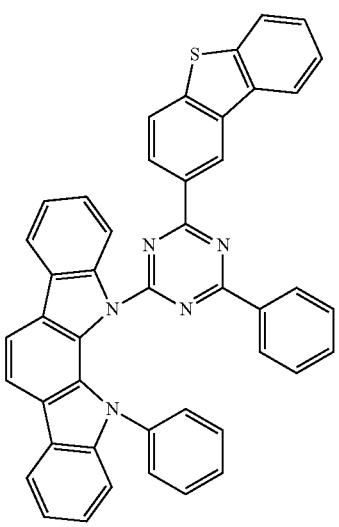
1-13
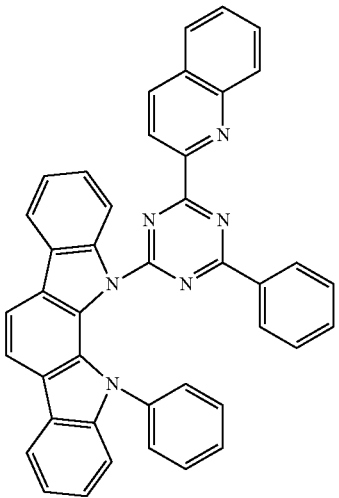

1-14
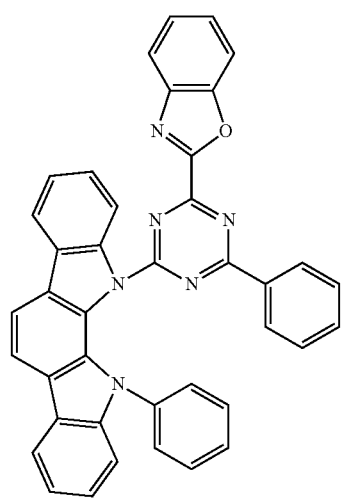
1-15
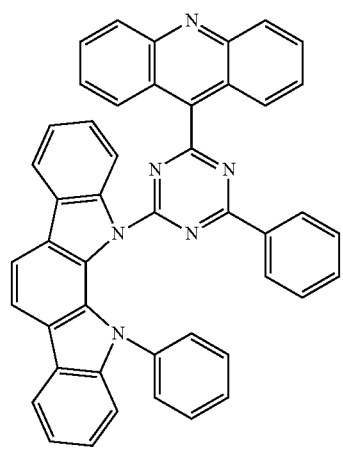
1-16
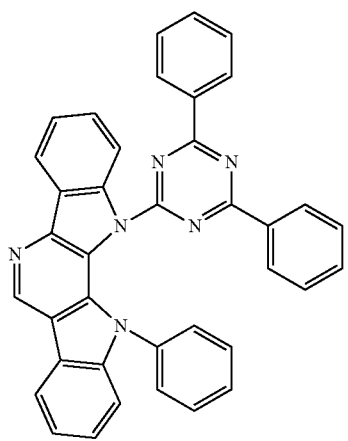
1-17
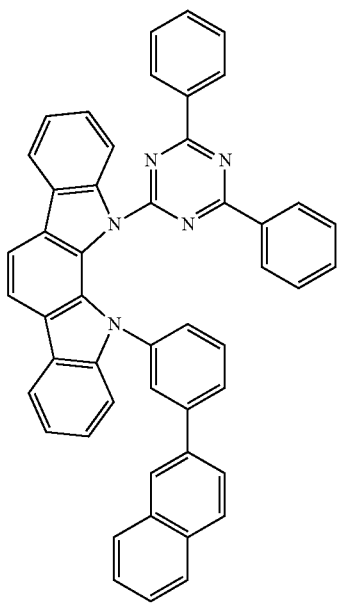
1-18
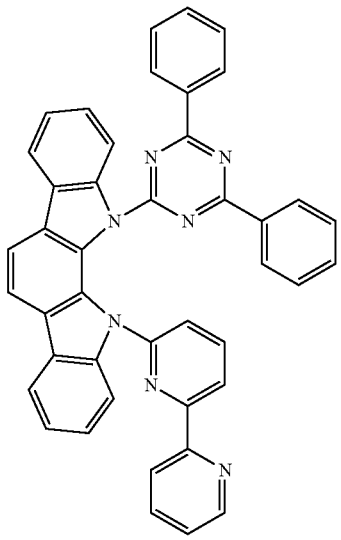
1-19
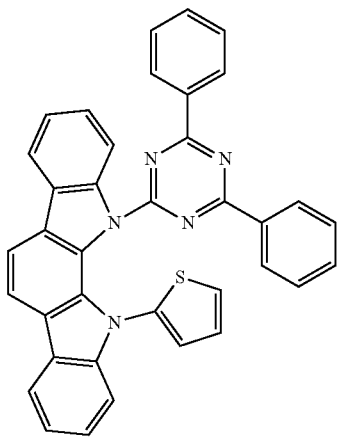

1-20
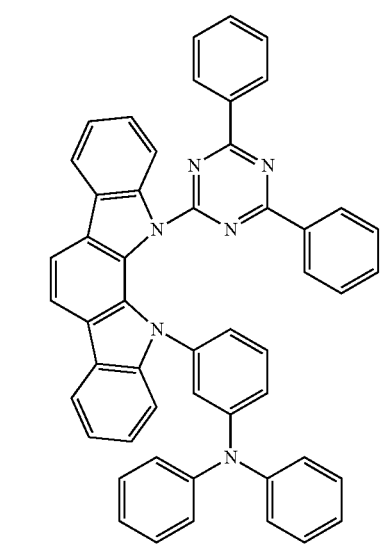
1-21
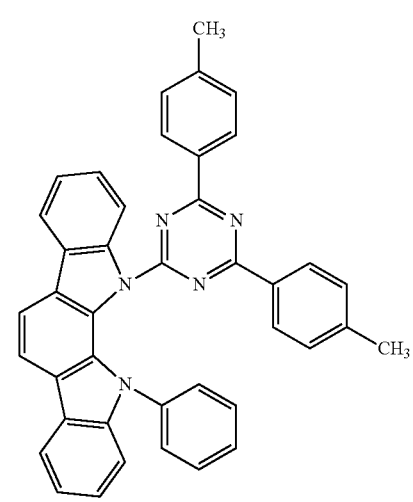
1-22
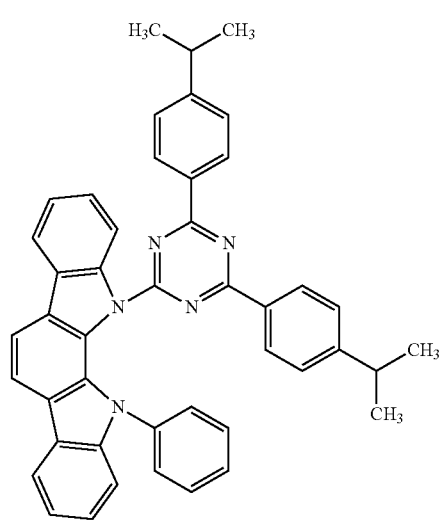
1-23
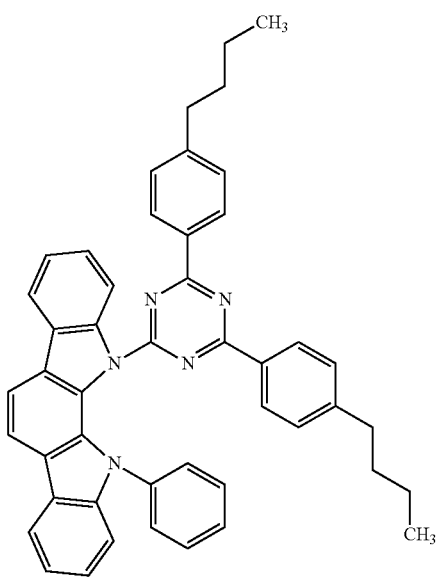
1-24
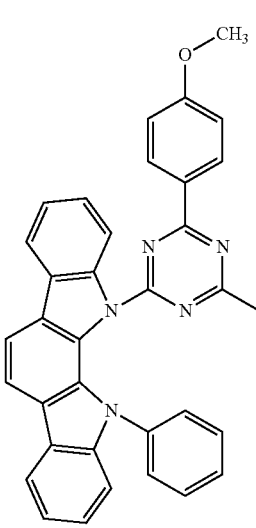
1-25
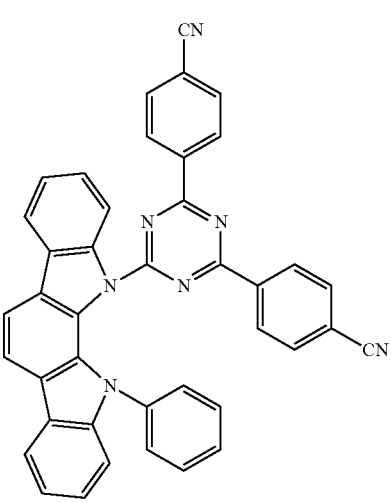

-continued
1-26
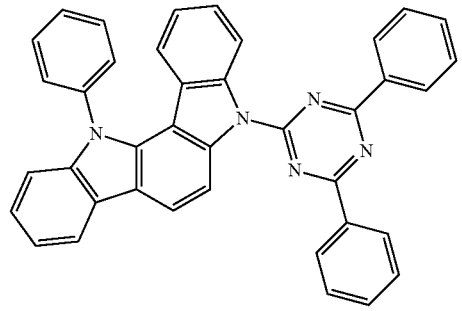
1-27
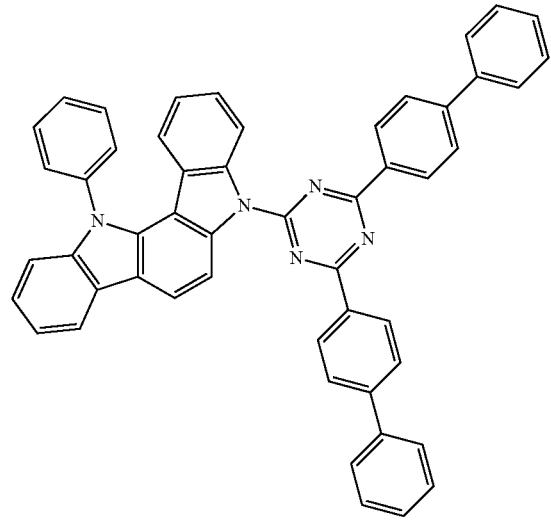
1-28
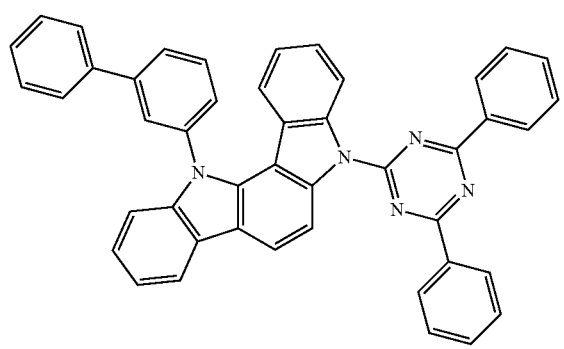
1-29
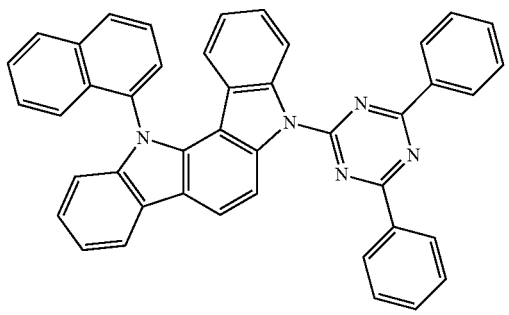
-continued
1-30
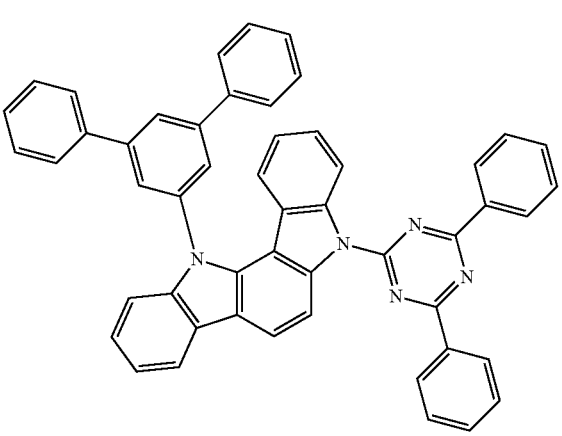
1-31
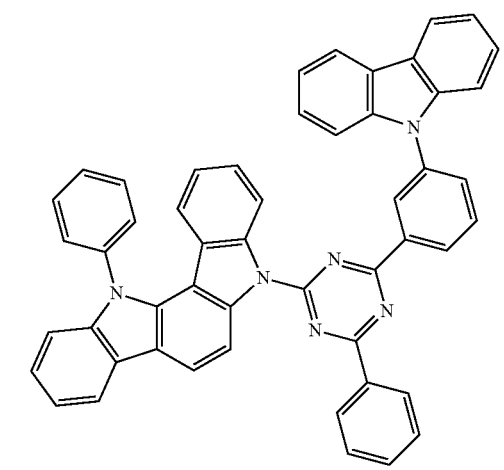
1-32
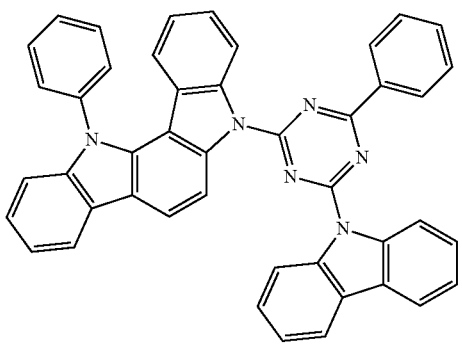

1-33
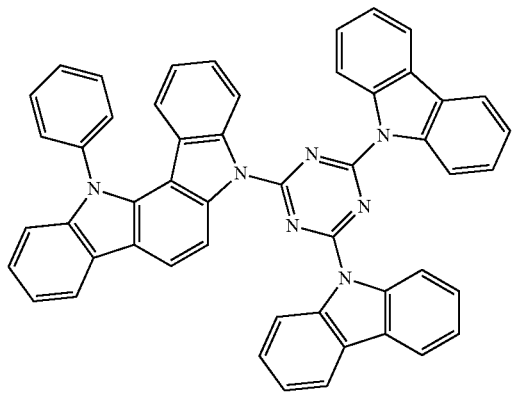
1-34
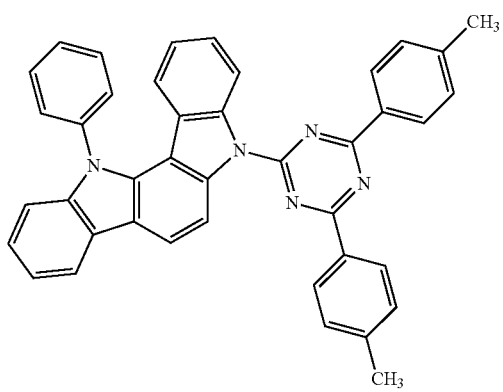
1-35
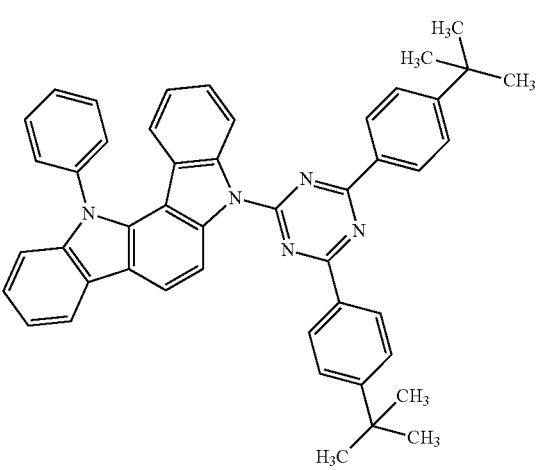
1-36
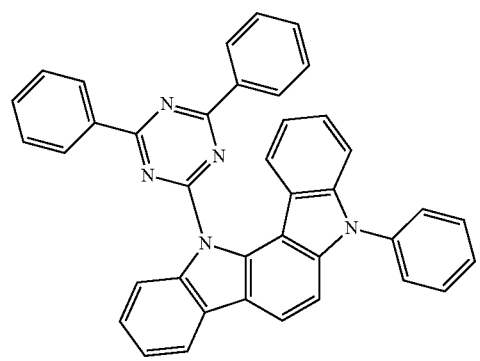
1-37
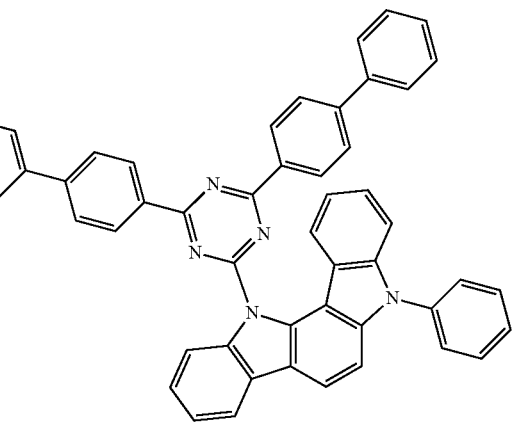
1-38
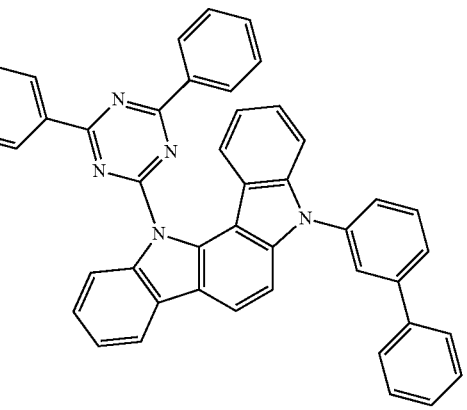
1-39
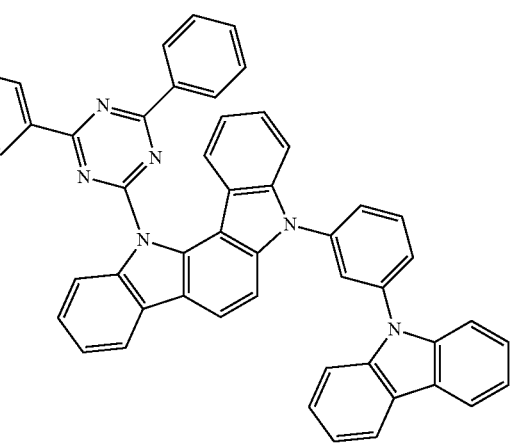

1-40
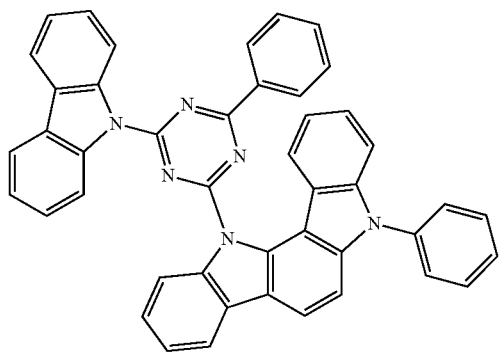
1-41
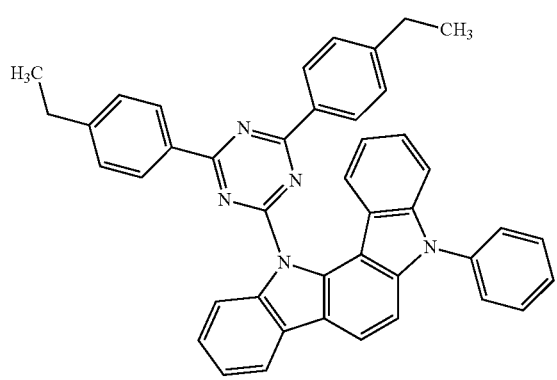
1-42
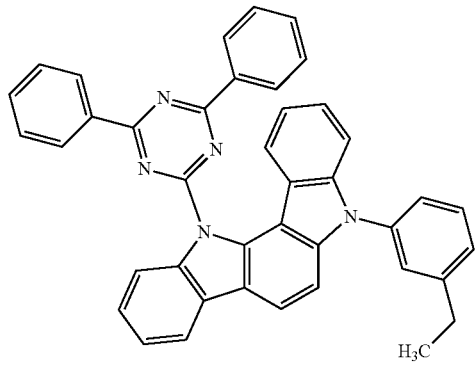
1-43
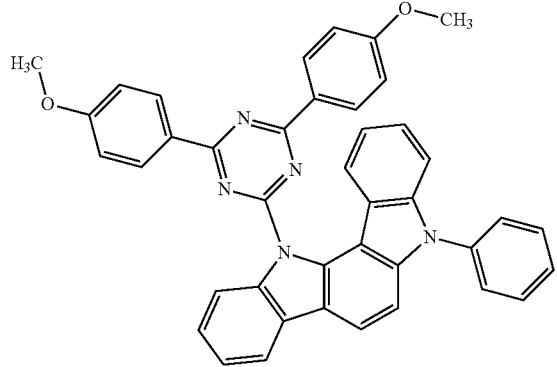
1-44
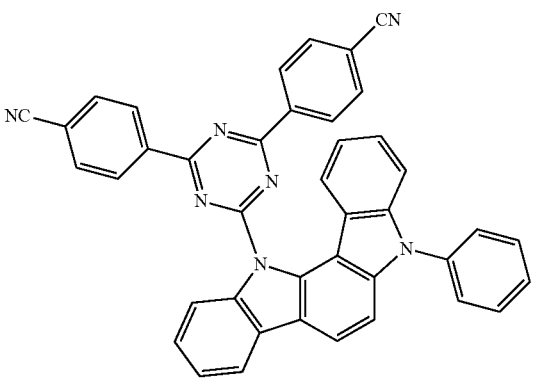
1-45
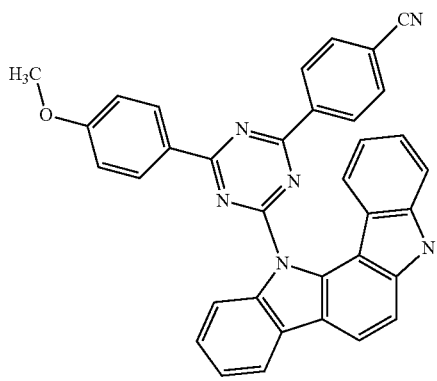
1-46
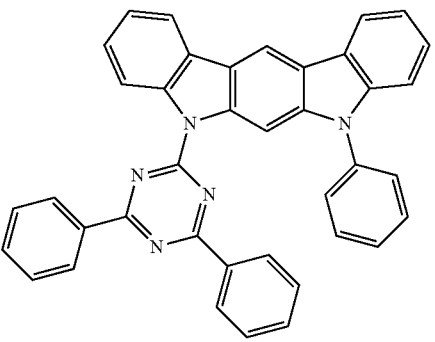
1-47
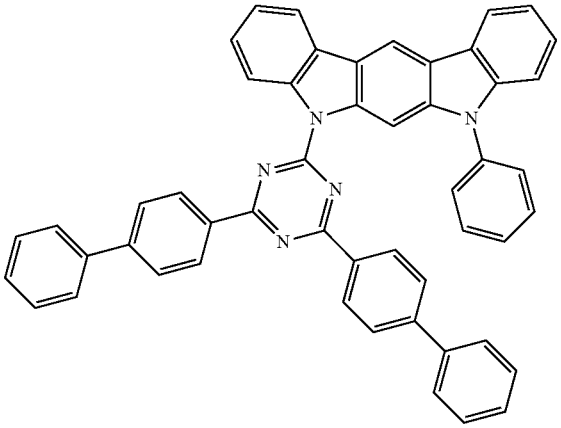

-continued
1-48
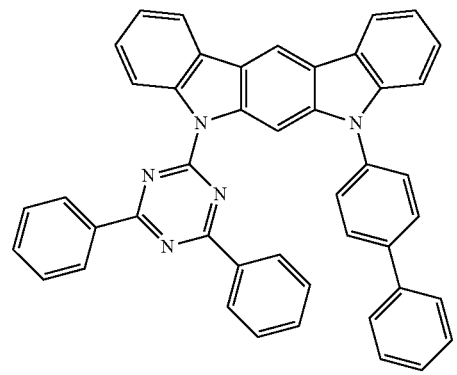
1-49
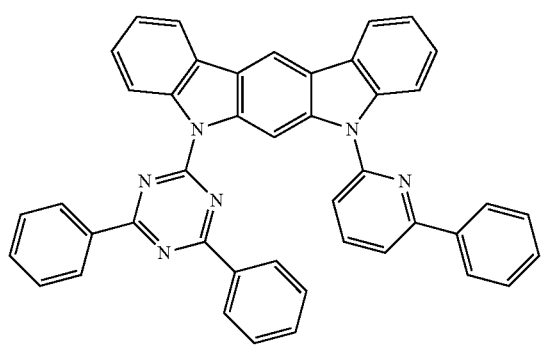
1-50
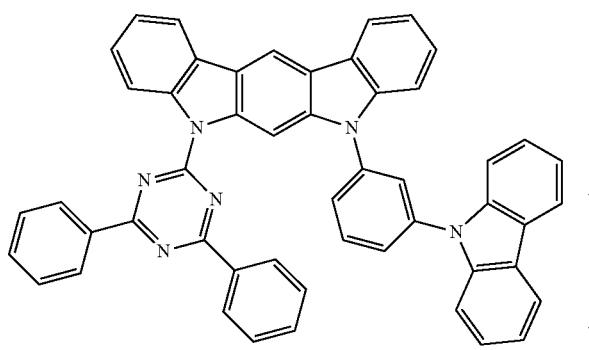
1-51
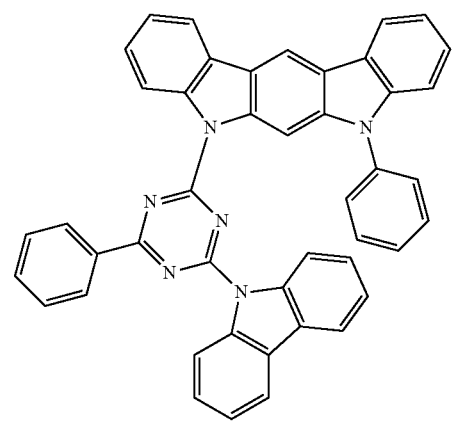
-continued
1-52
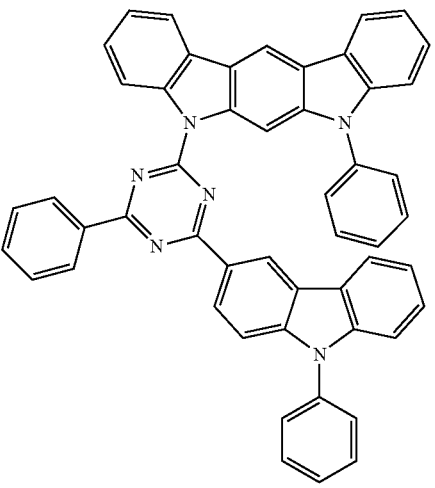
1-53
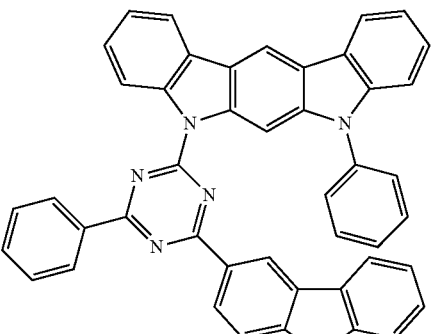
1-54
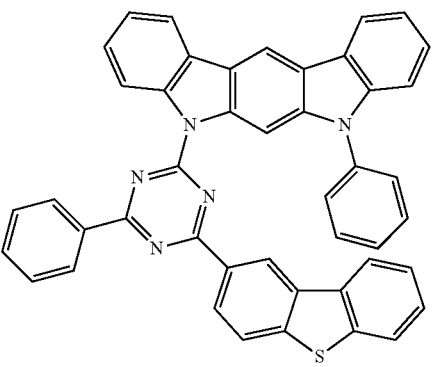
1-55
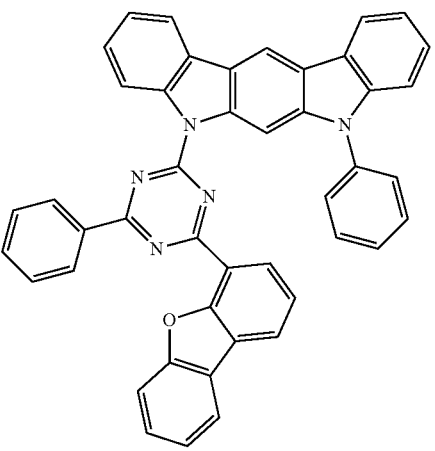

1-56
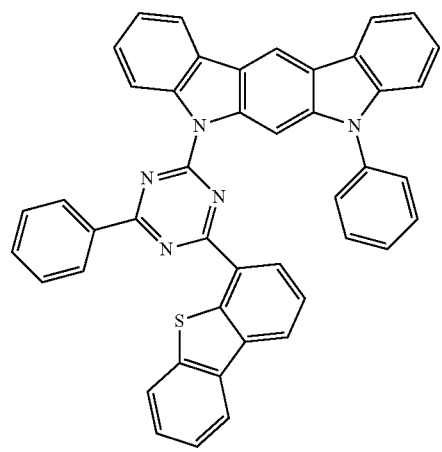
1-57
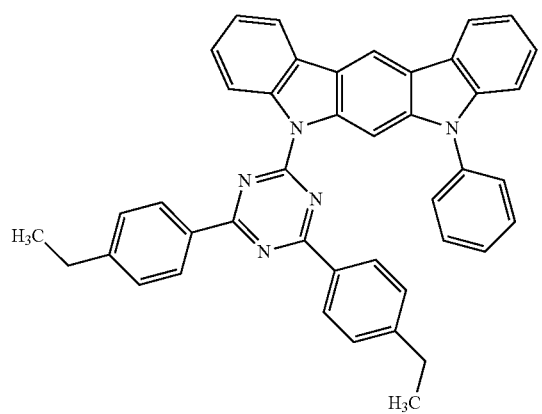
1-58
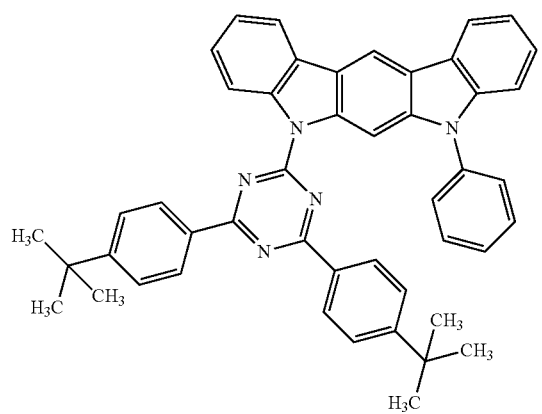
1-59
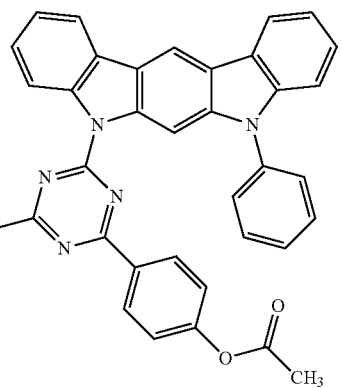
1-60
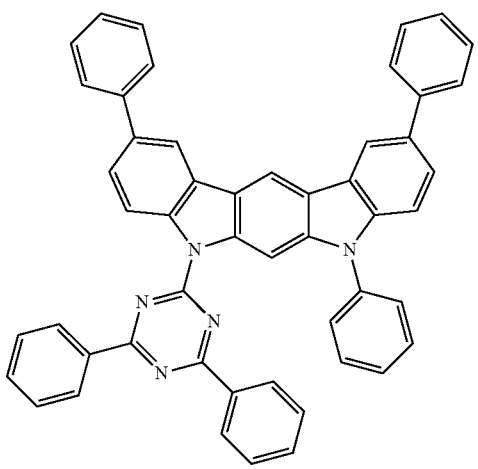
1-61
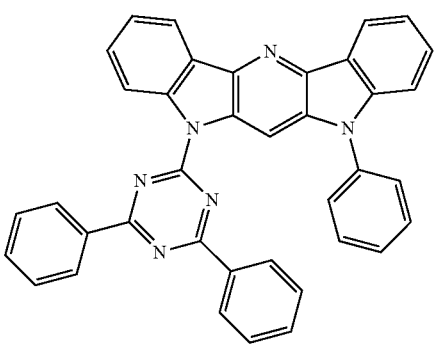
1-62
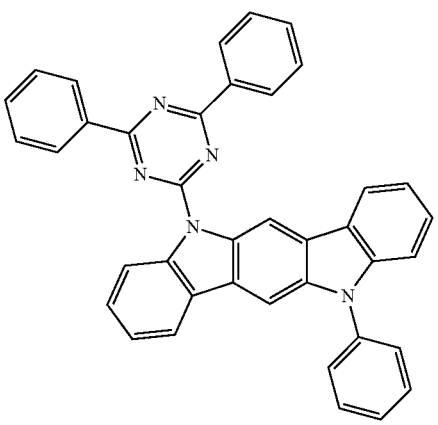

-continued
1-63
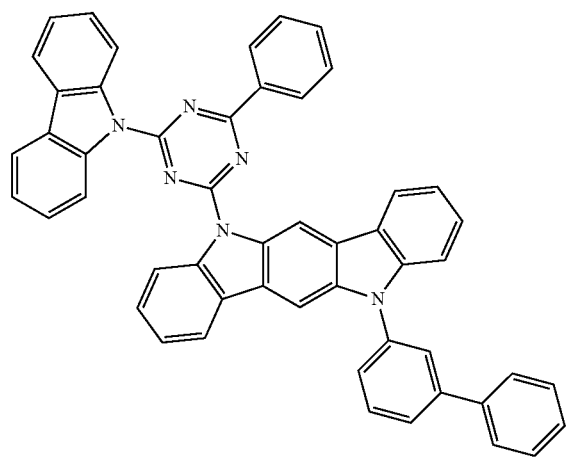
1-64
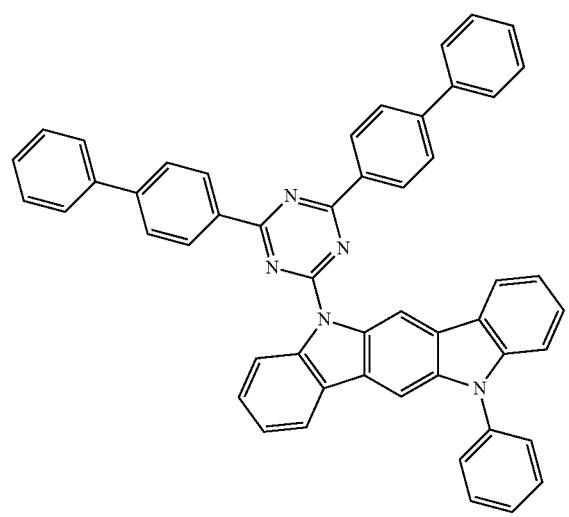
1-65
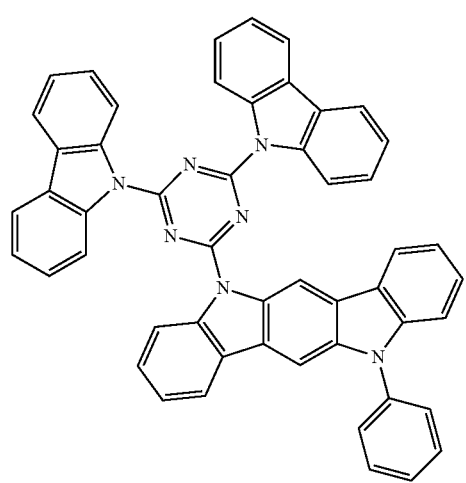
-continued
1-66
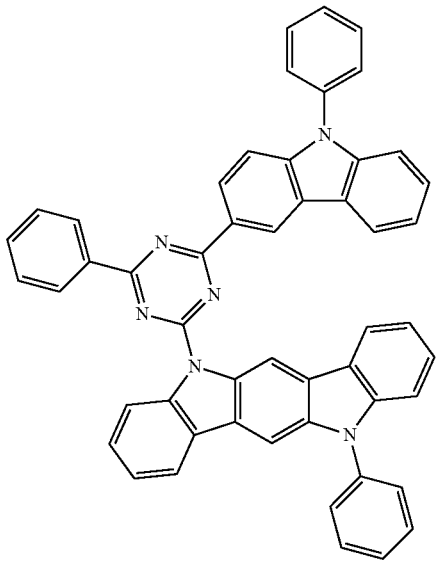
1-67
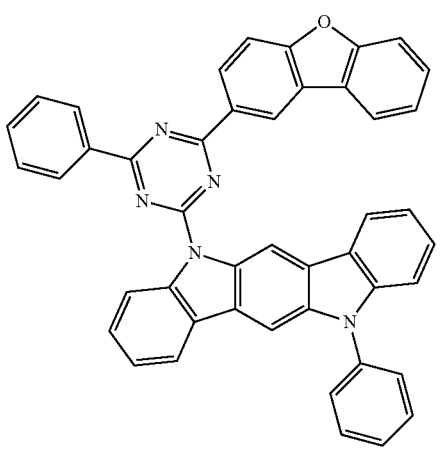
1-68
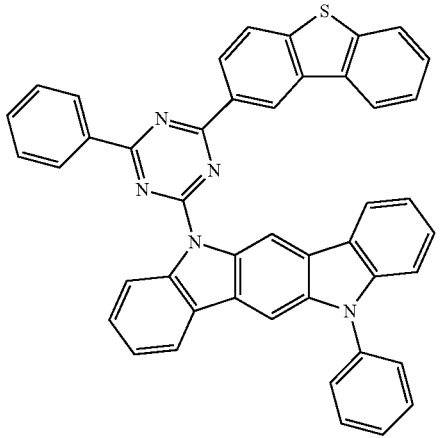

1-69
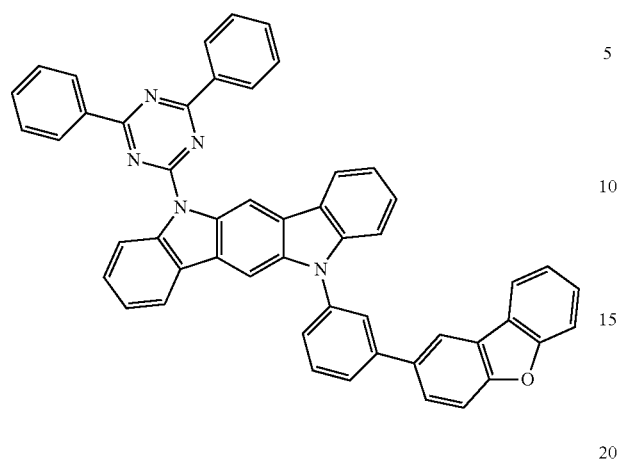
1-70
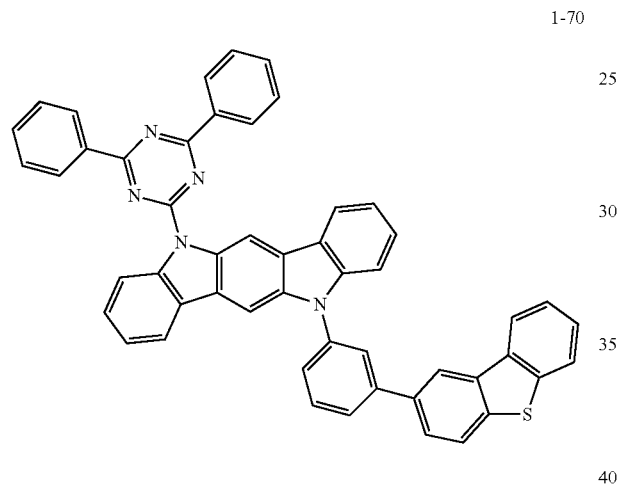
1-71
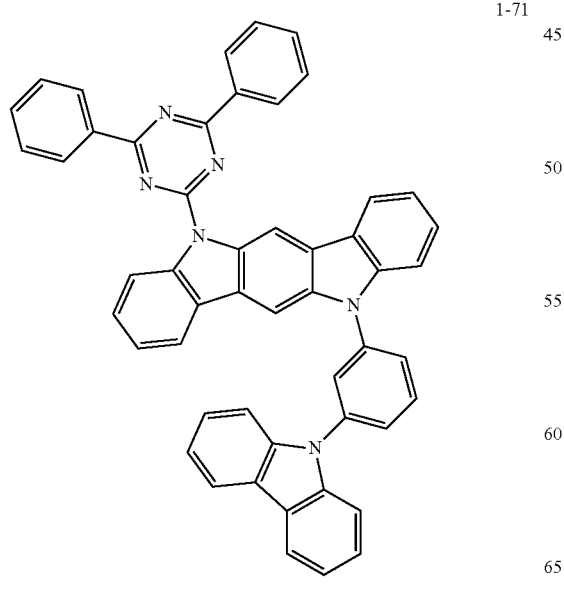
1-72
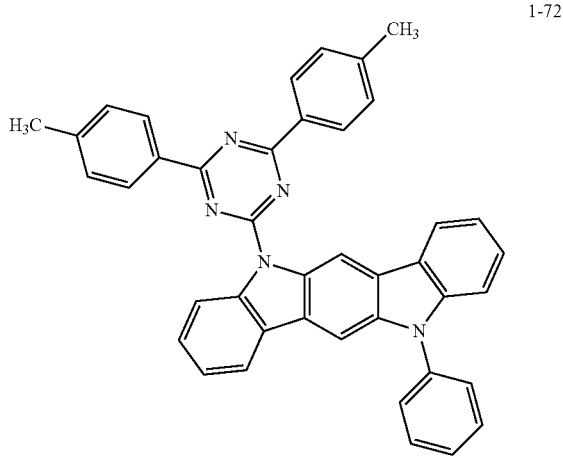
1-73
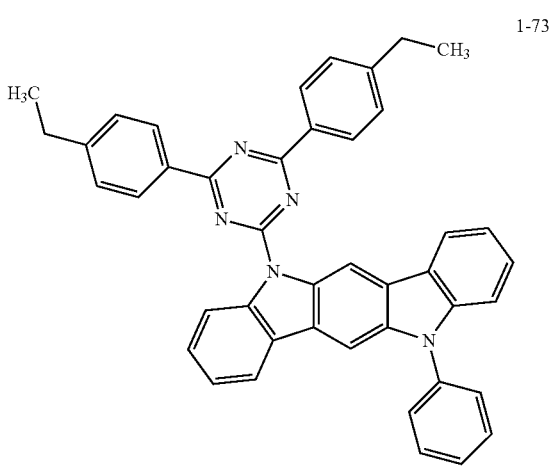
1-74
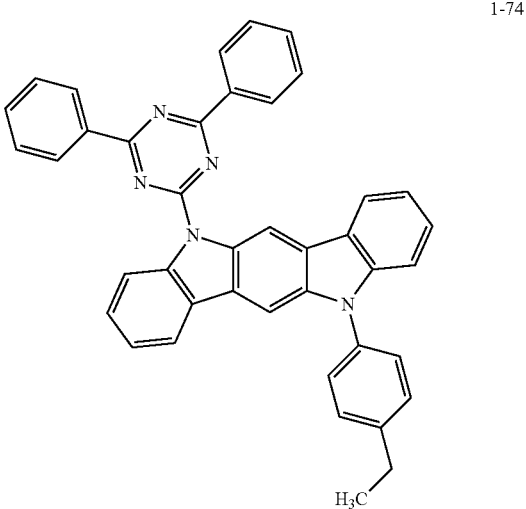

1-75
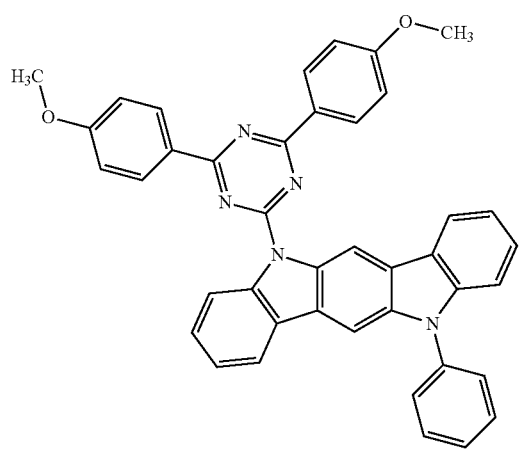
1-76
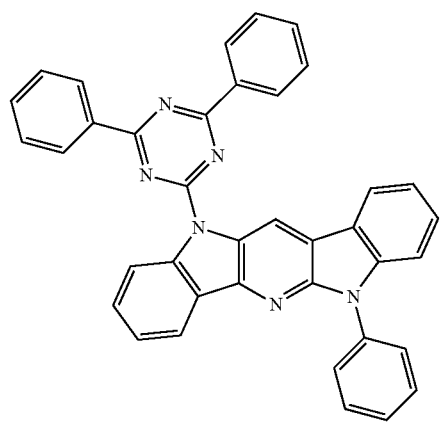
1-77
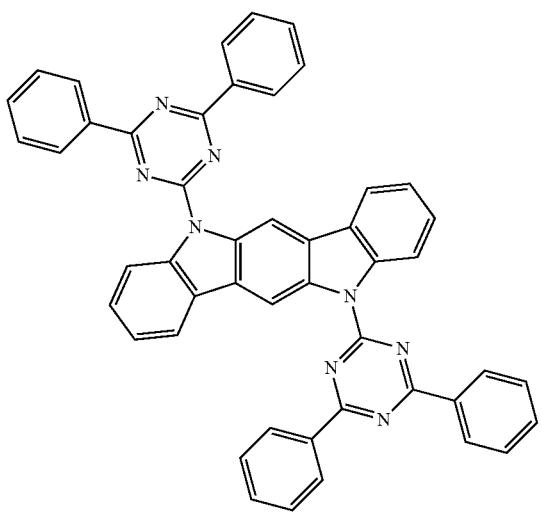
1-78
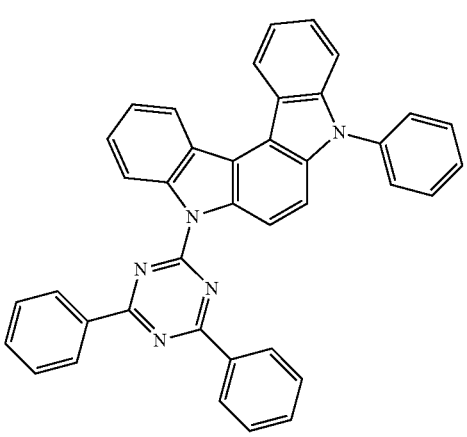
1-79
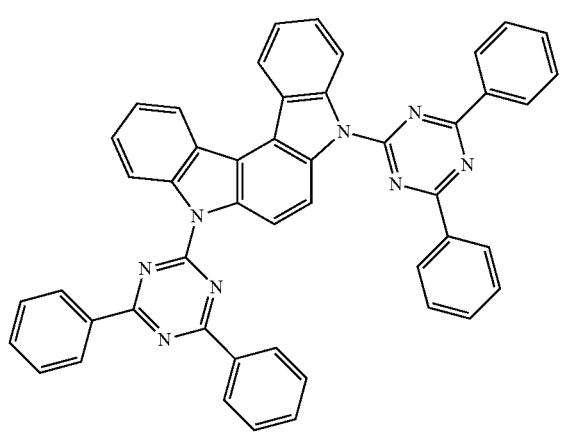
1-80
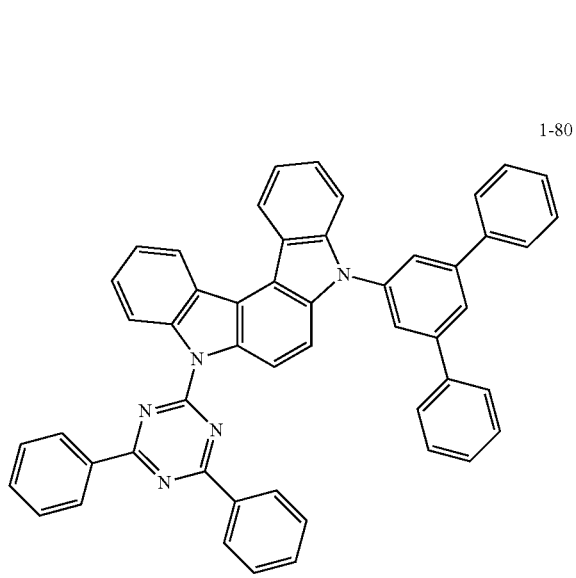

1-81
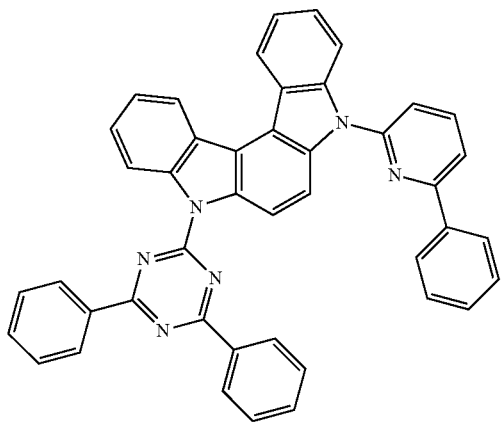
1-82
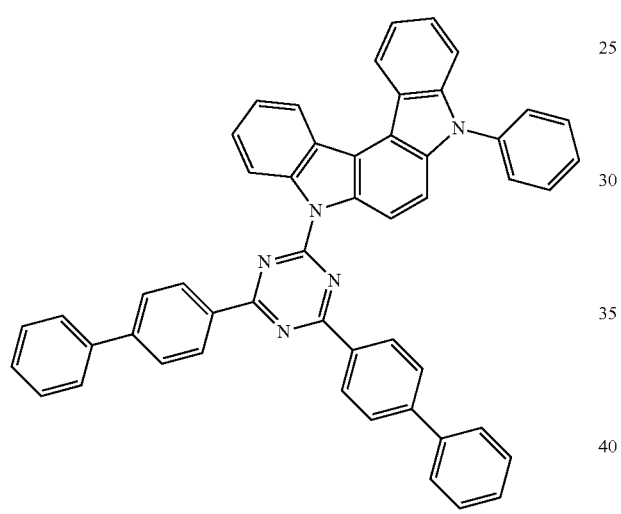
1-83
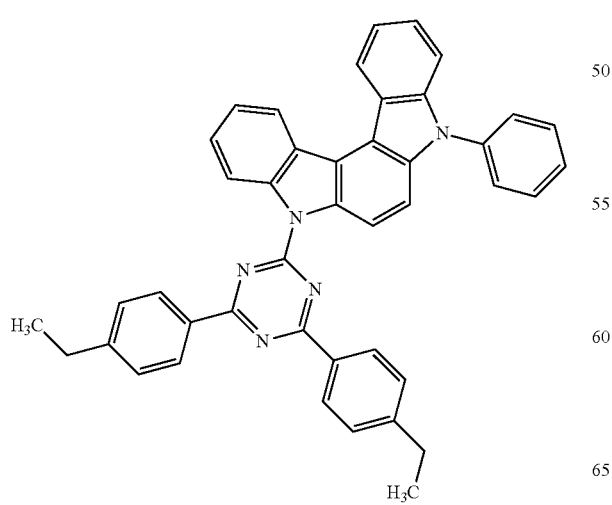
1-84
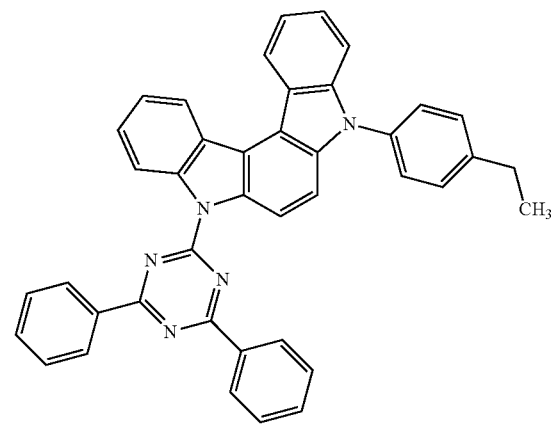
1-85
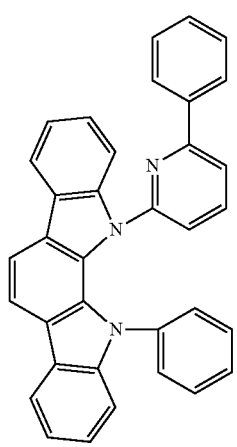
1-86
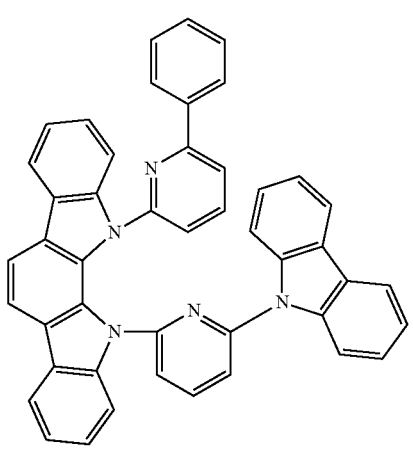

1-87 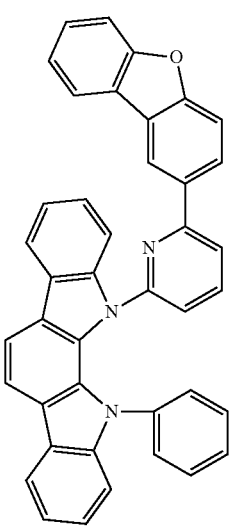
1-88 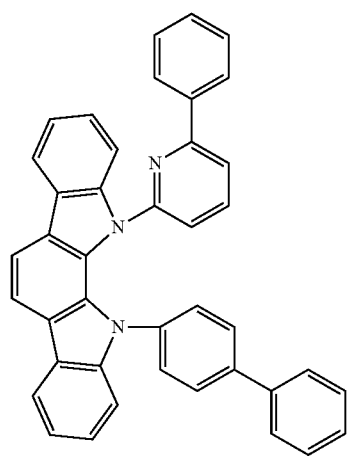
1-89 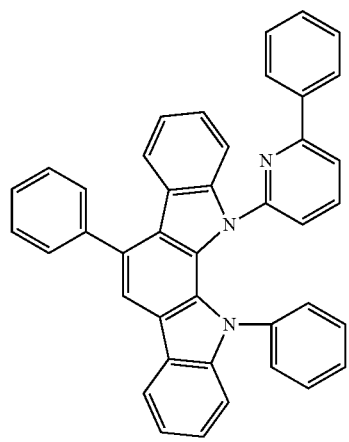
1-90 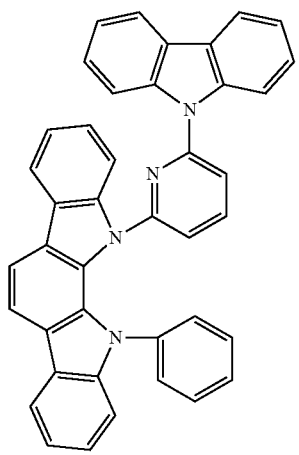
1-91 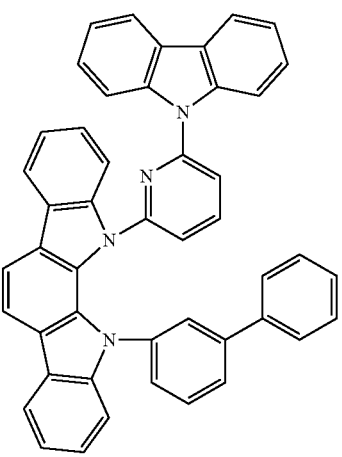
1-92 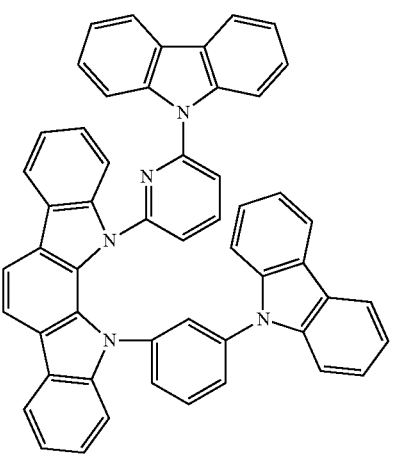

1-93
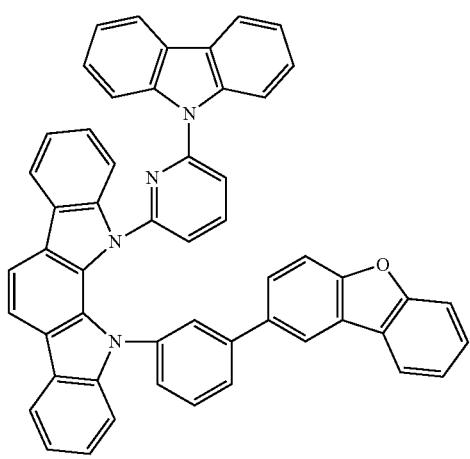
1-94
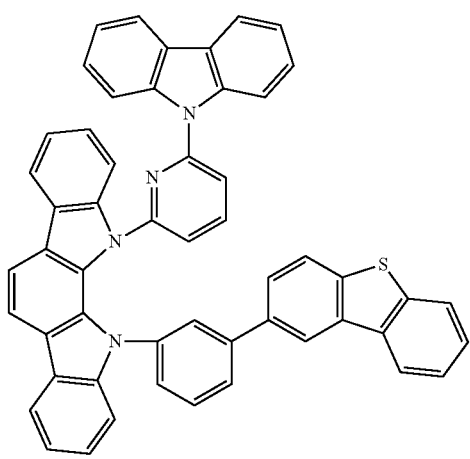
1-95
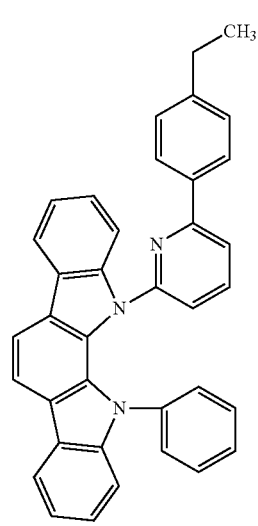
1-96
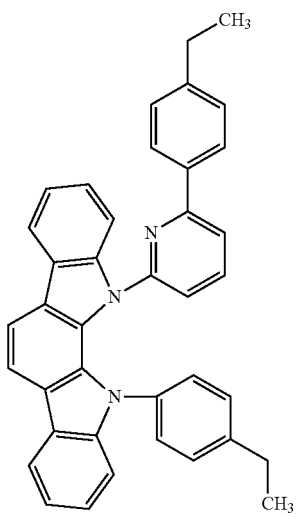
1-97
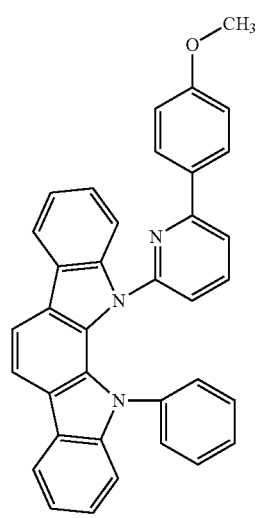
1-98
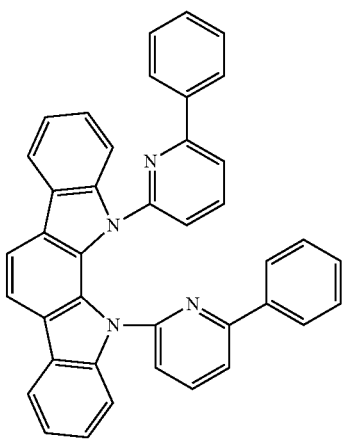

1-99
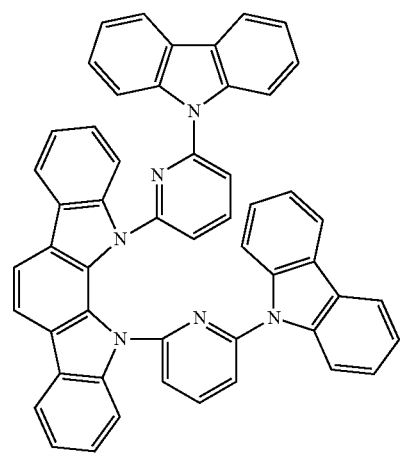
1-103
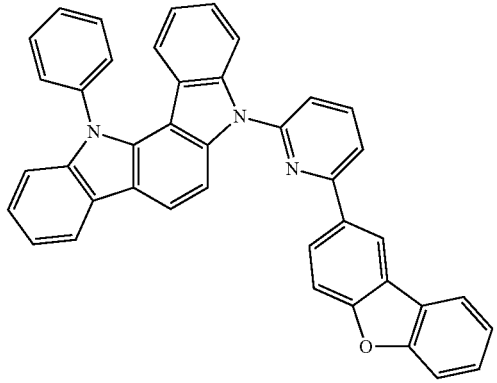
1-100
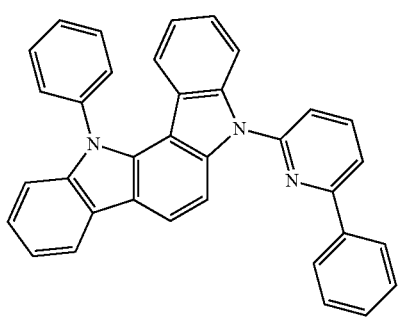
1-104
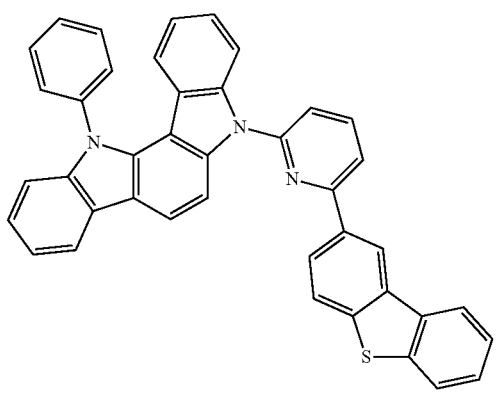
1-101
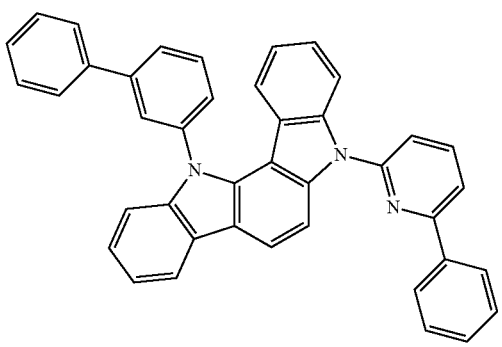
1-105
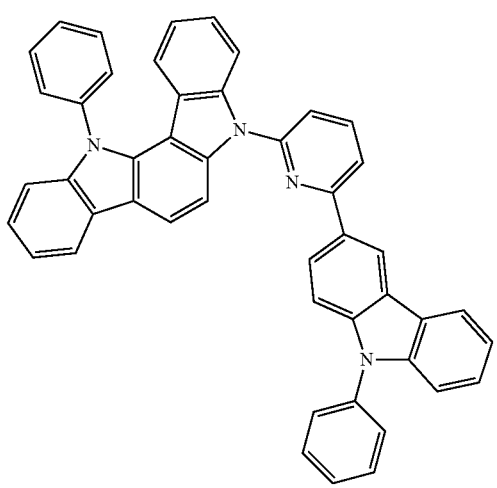
1-102
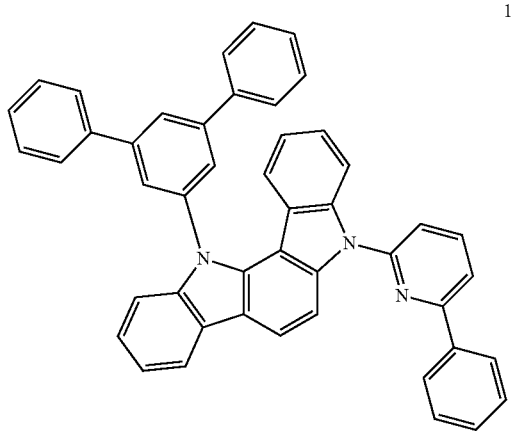
1-106
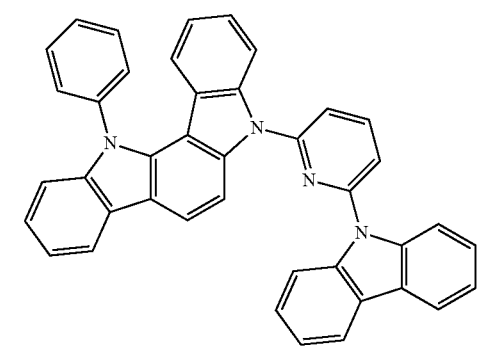

1-107
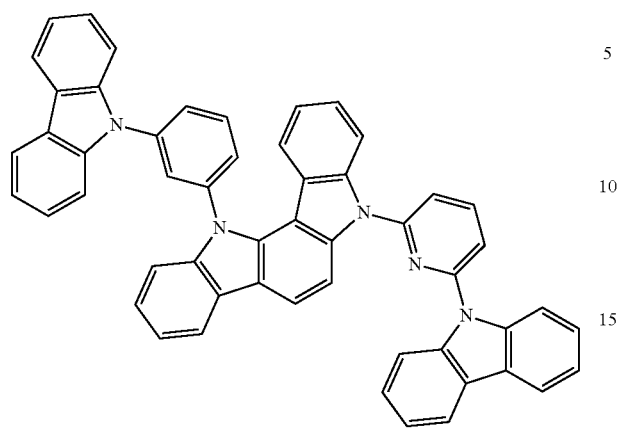
1-108
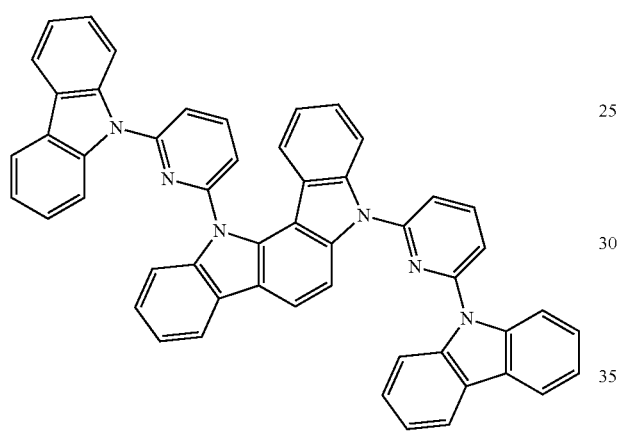
1-109
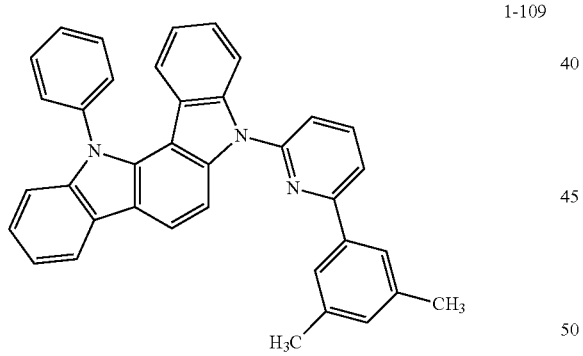
1-110
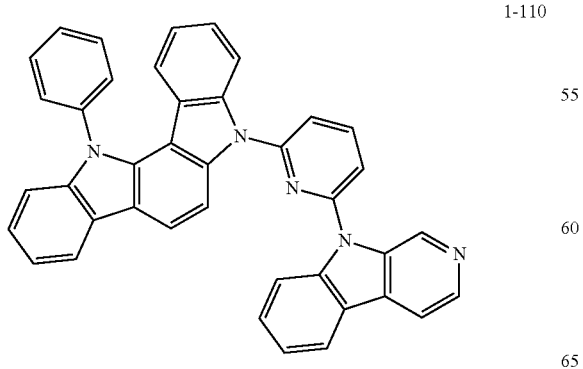
1-111
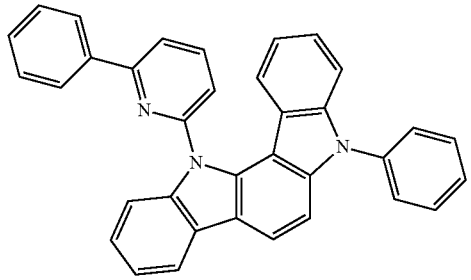
1-112
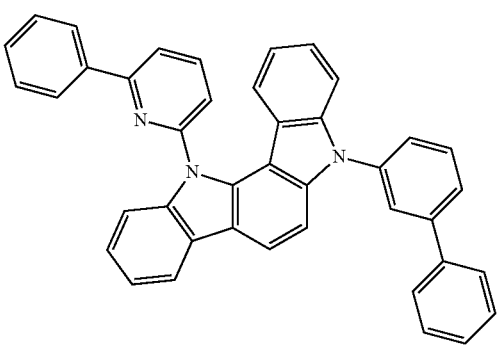
1-113
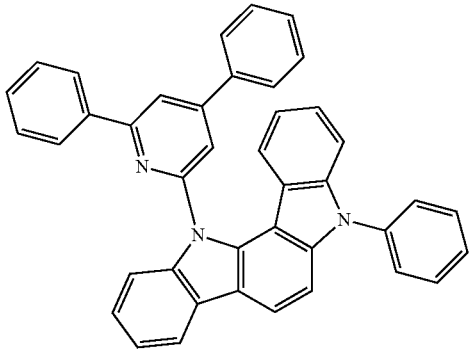
1-114
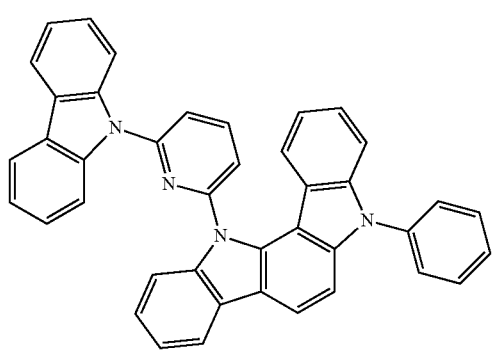

1-115
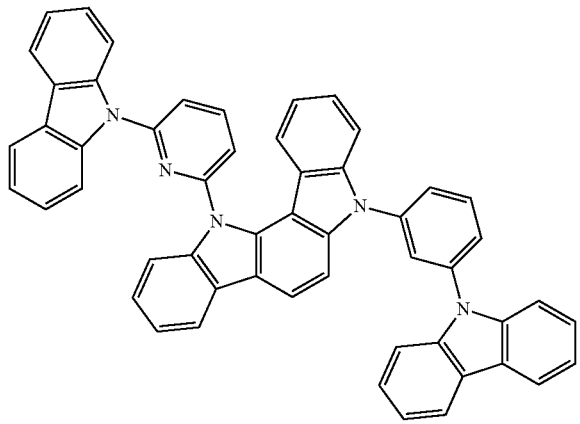
1-116
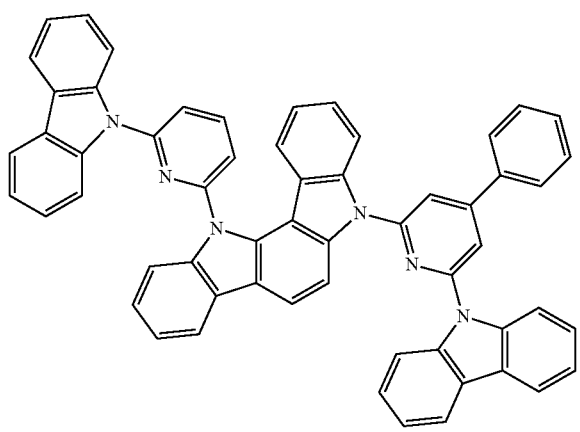
1-117
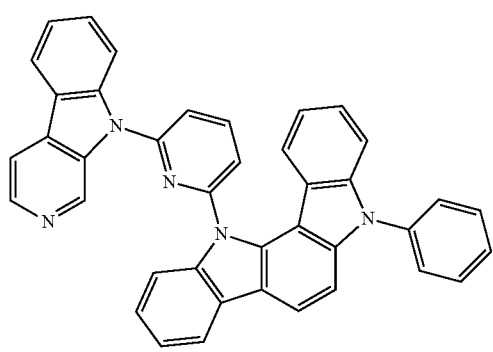
1-118
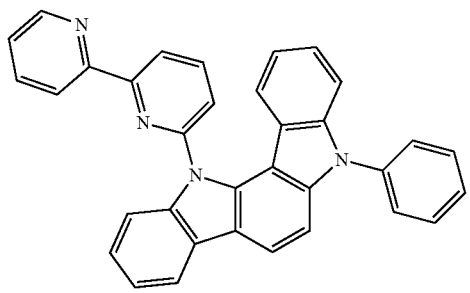
1-119
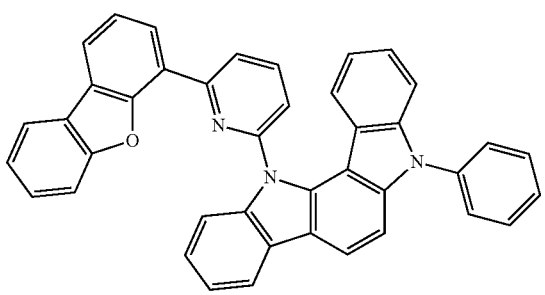
1-120
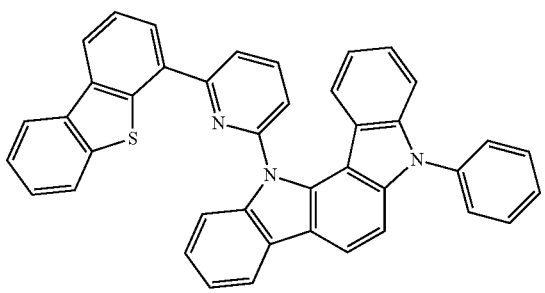
1-121
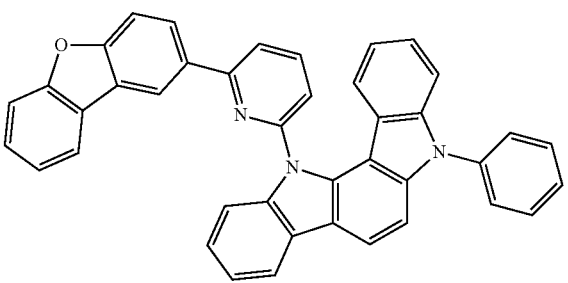
1-122
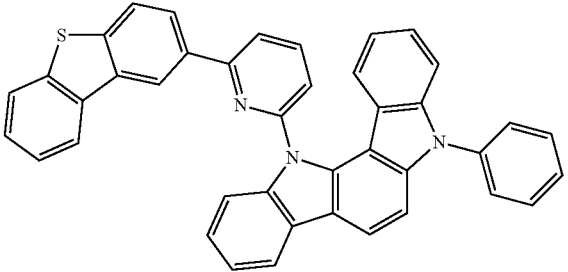
1-123
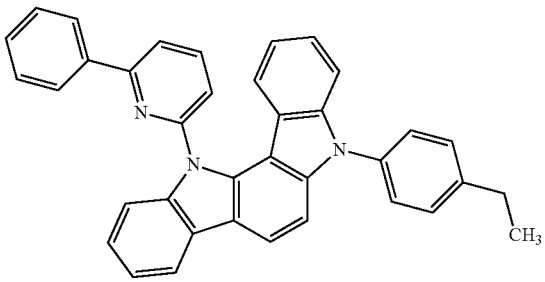

1-124
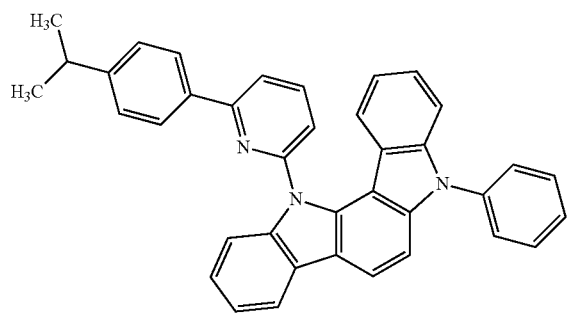
1-125
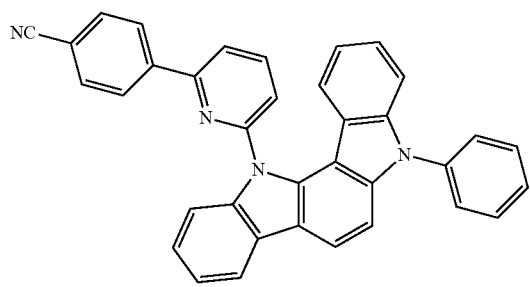
1-126
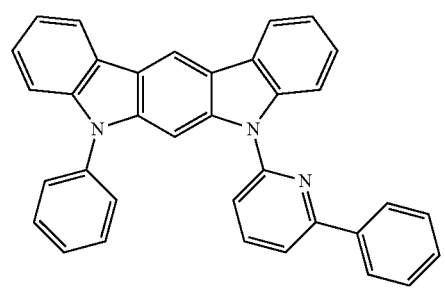
1-127
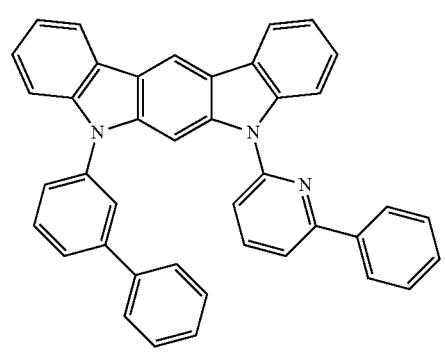
1-128
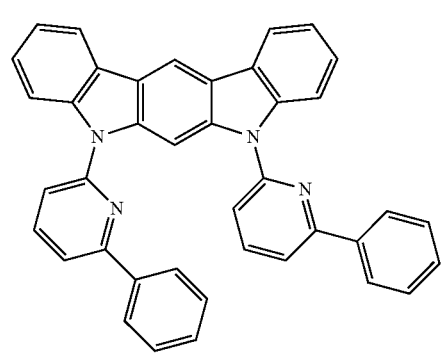
1-129
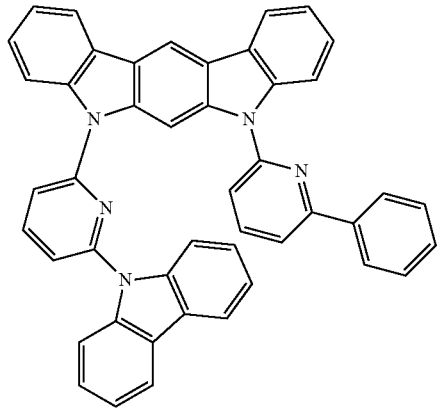
1-130
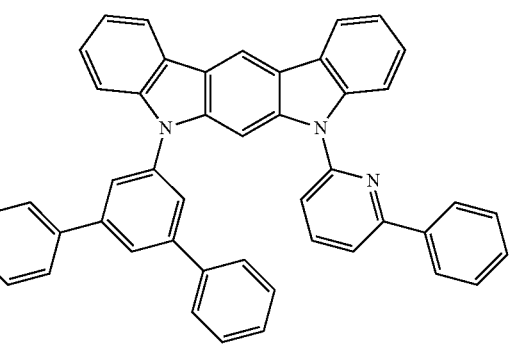
1-131
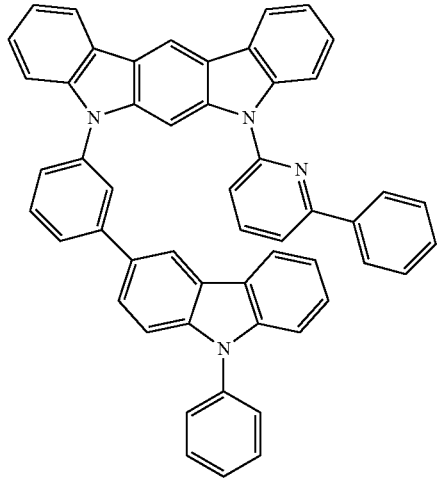
1-132
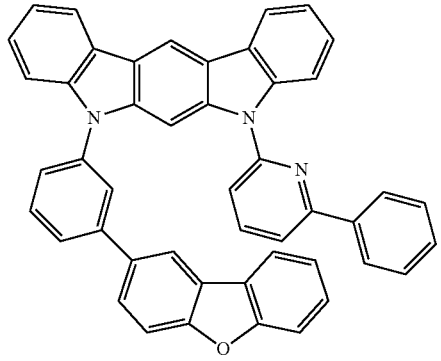

1-133
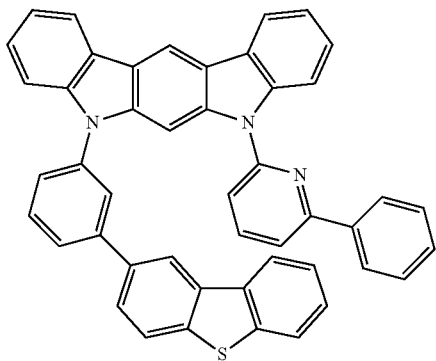
1-134
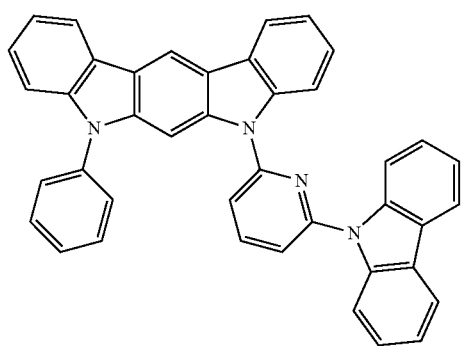
1-135
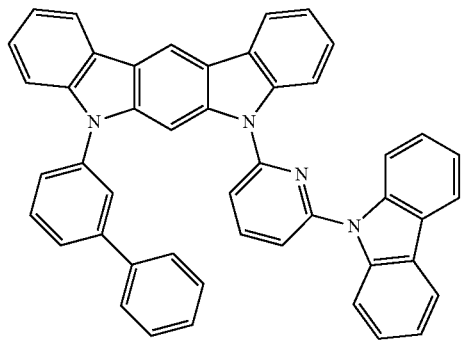
1-136
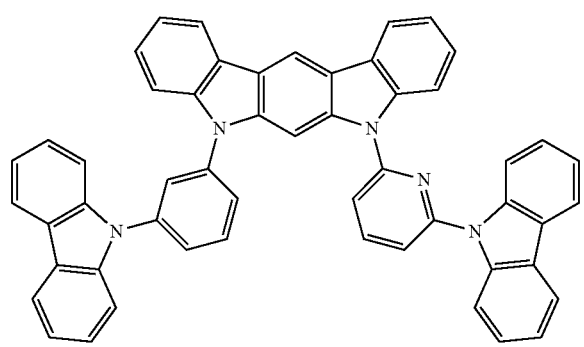
1-137
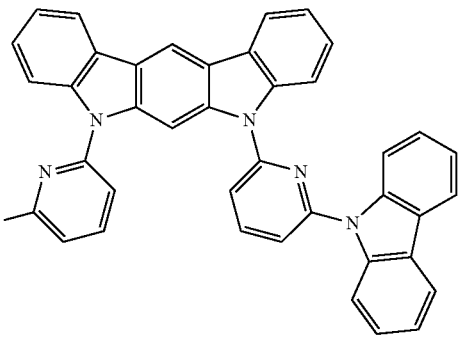
1-138
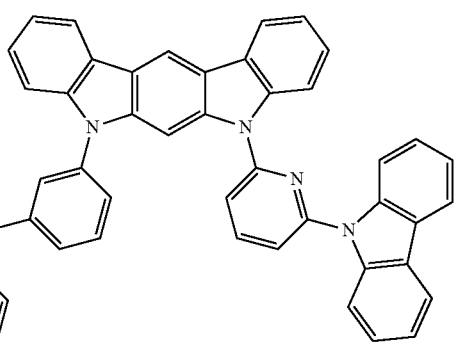
1-139
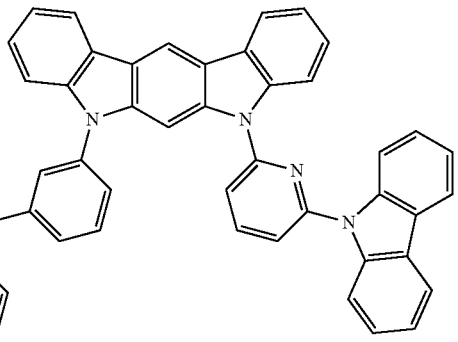
1-140
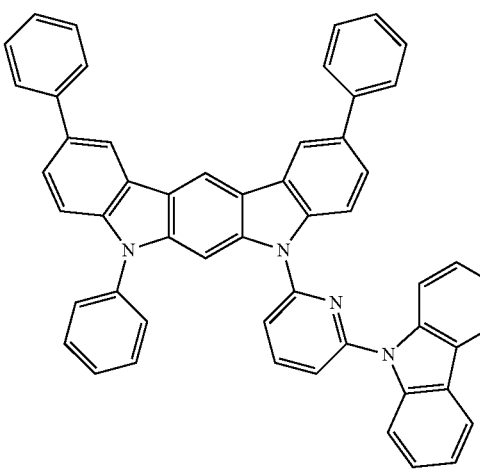

1-141
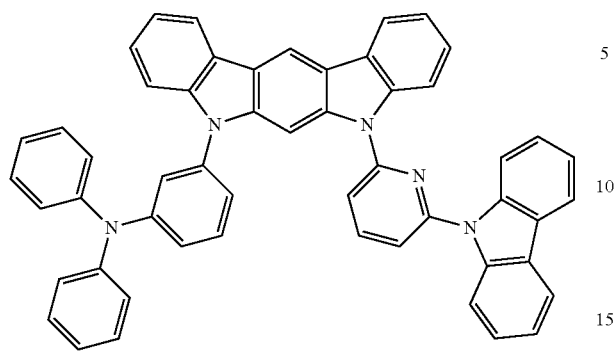
1-142
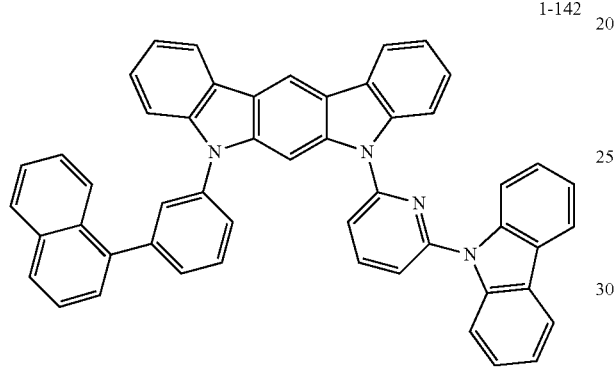
1-143
1-144
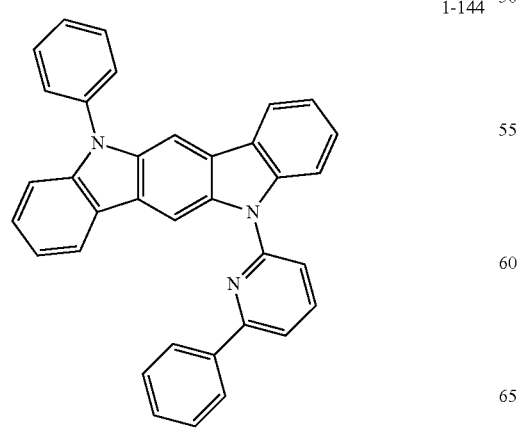
1-145
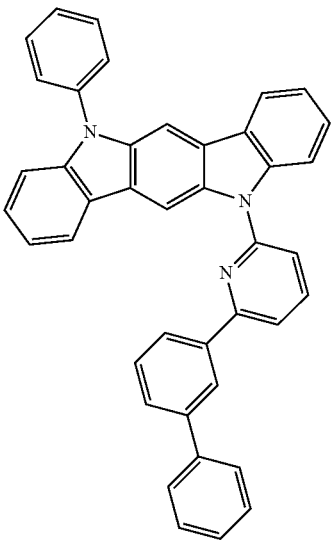
1-146
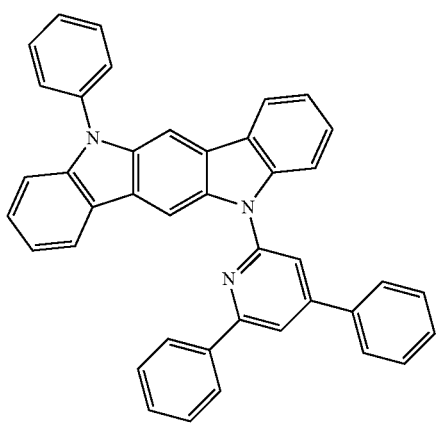
1-147
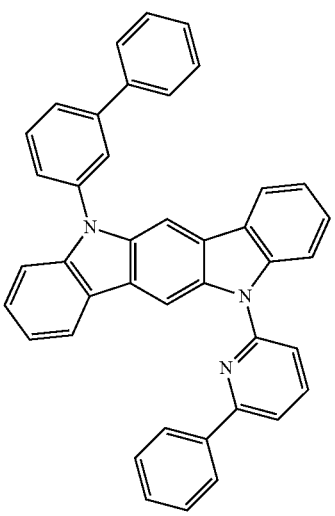

1-148
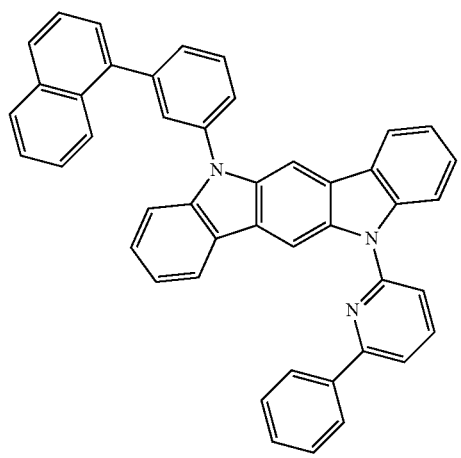
1-151
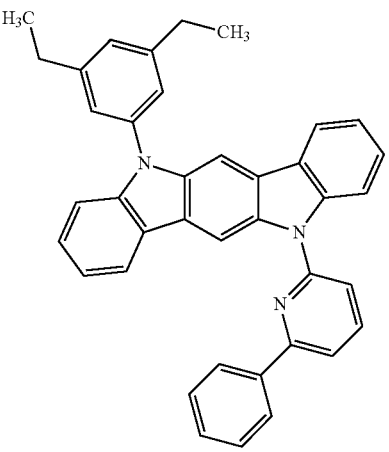
1-149
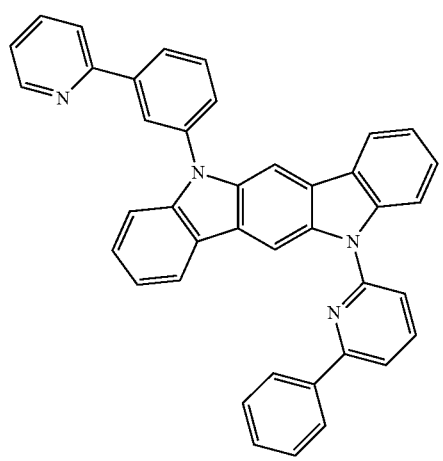
1-152
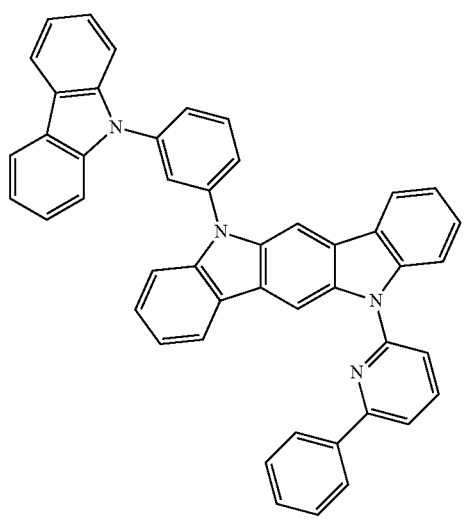
1-150
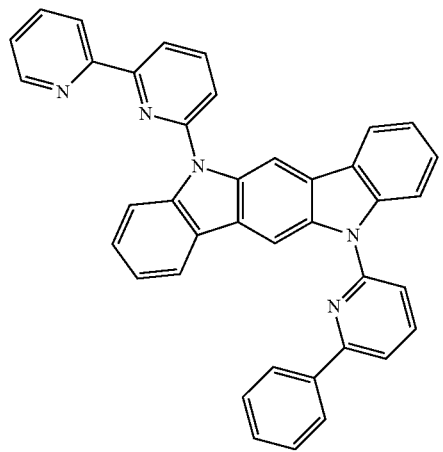
1-153
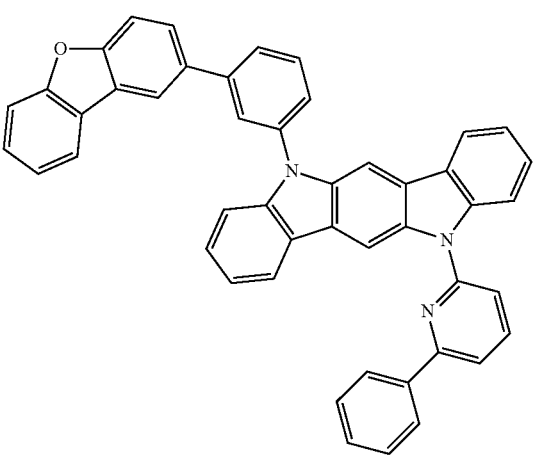

1-154
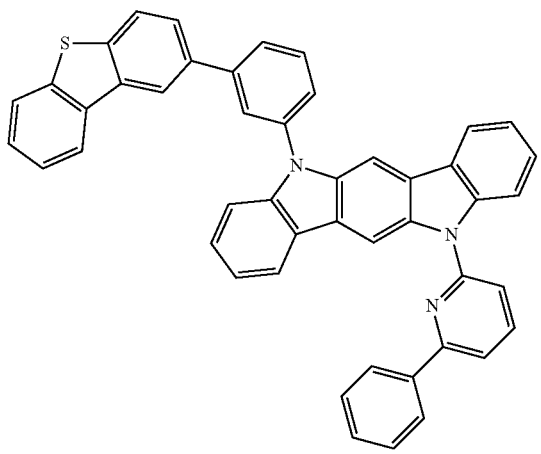
1-155
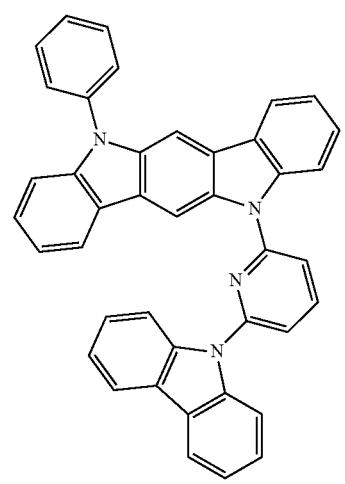
1-156
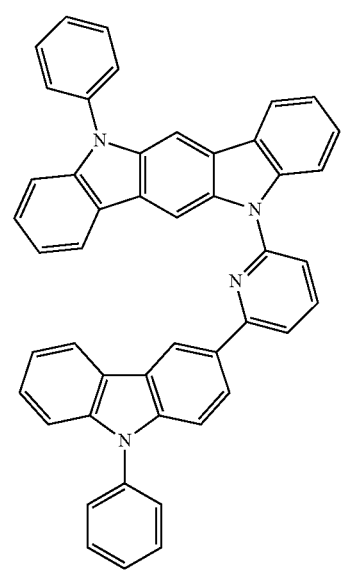
1-157
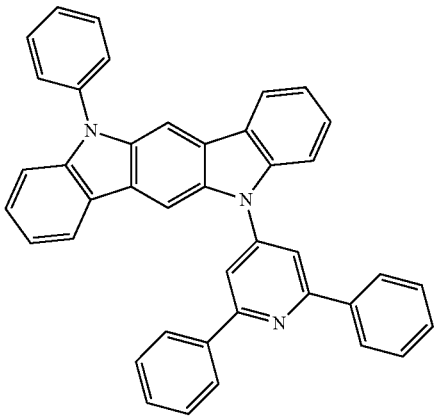
1-158
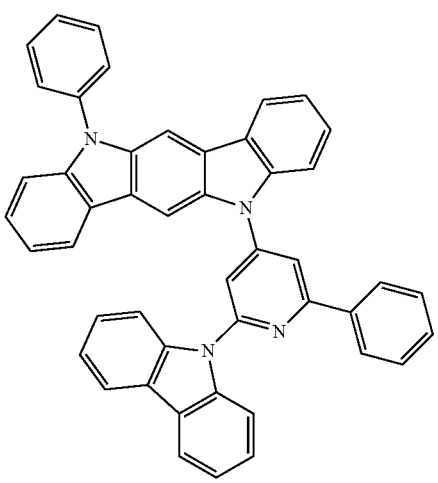
1-159
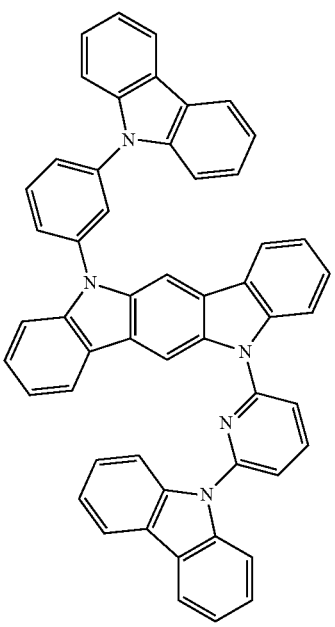

1-160
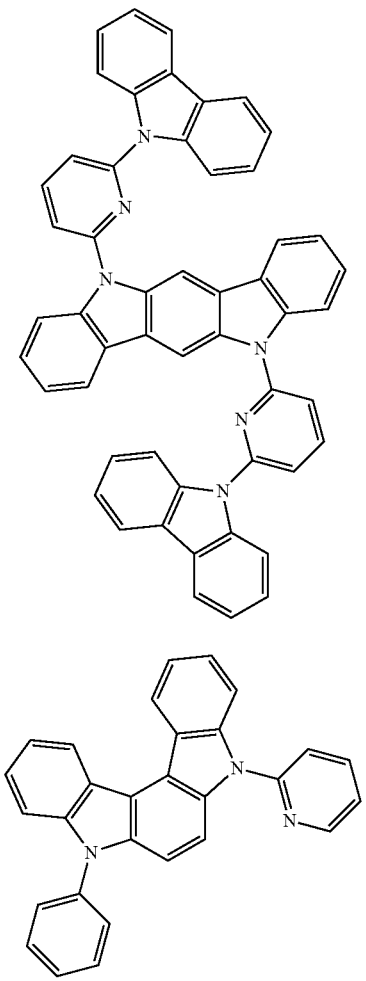
1-161
1-162
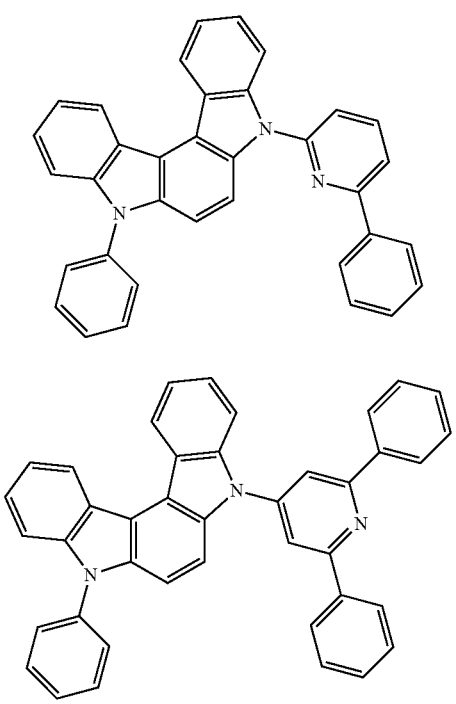
1-163
1-164
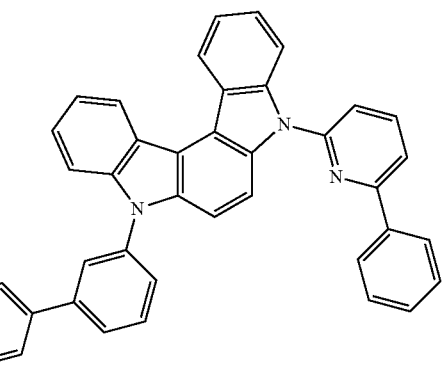
1-165
1-166
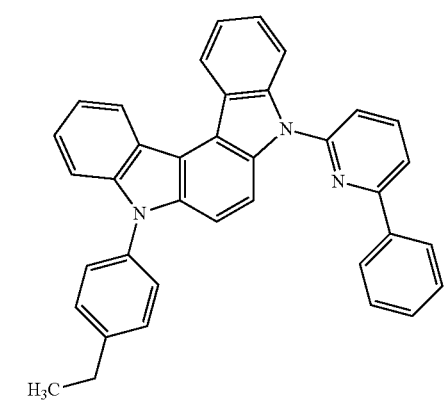
1-167
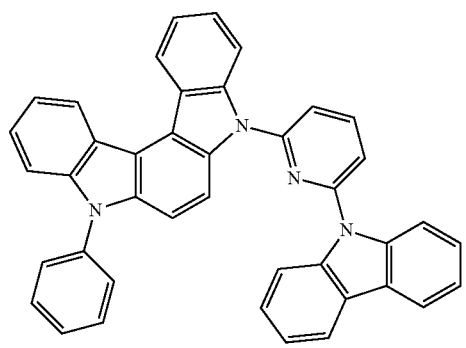

1-168
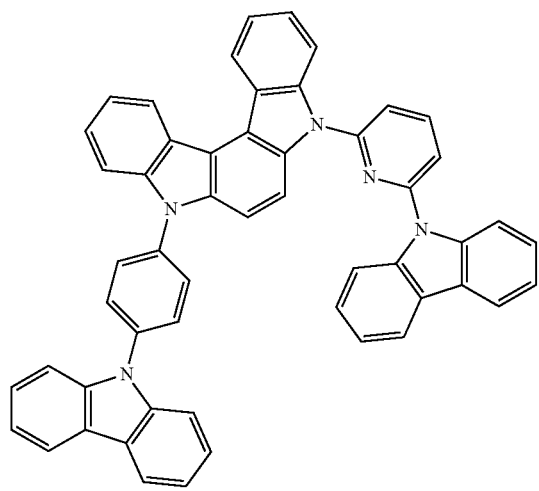
1-169
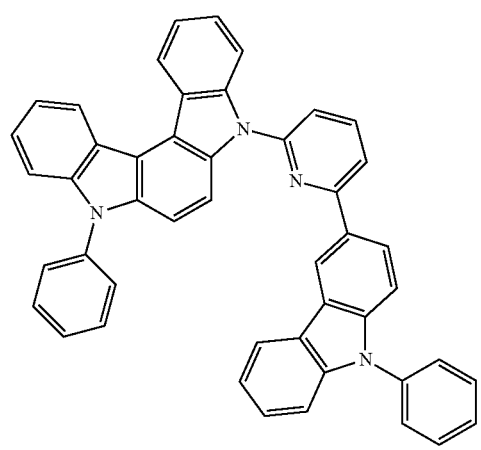
1-170
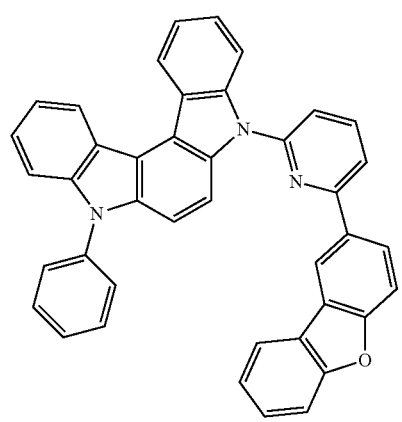
1-171
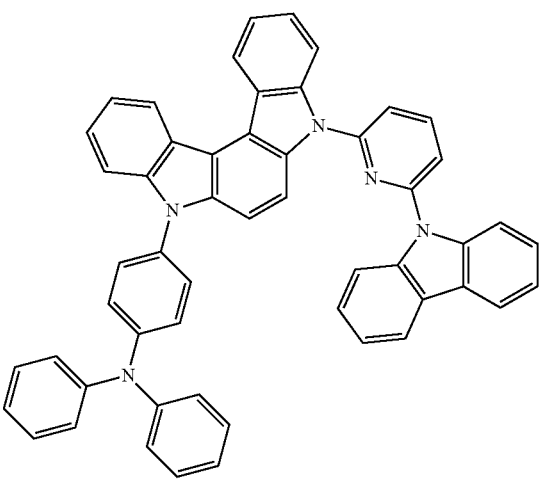
1-172
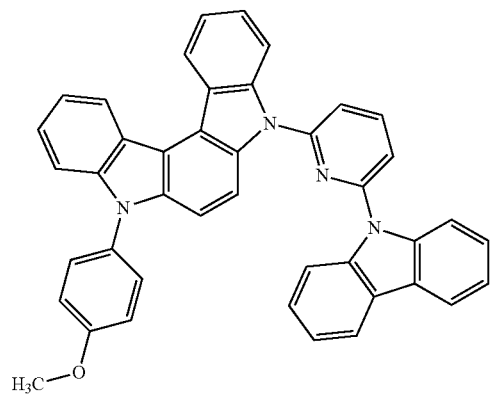
1-173
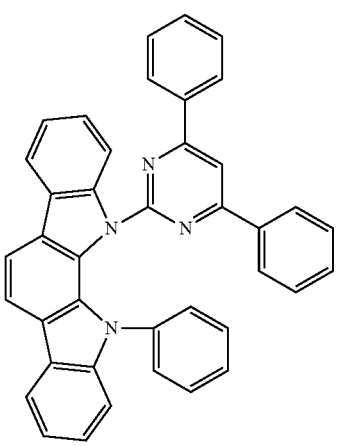

1-174
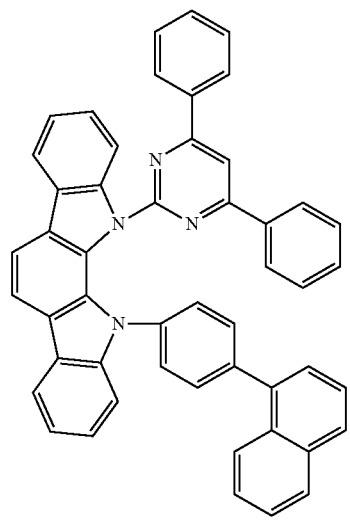
1-175
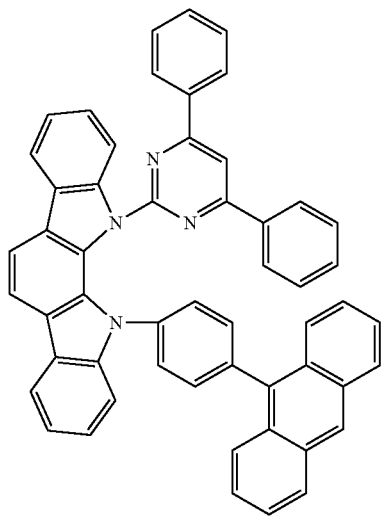
1-176
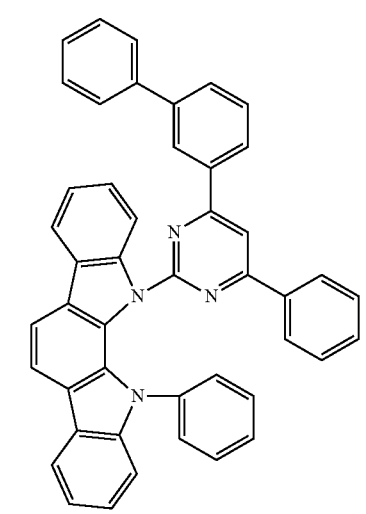
1-177
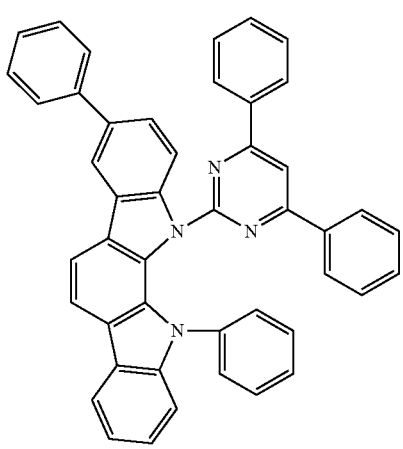
1-178
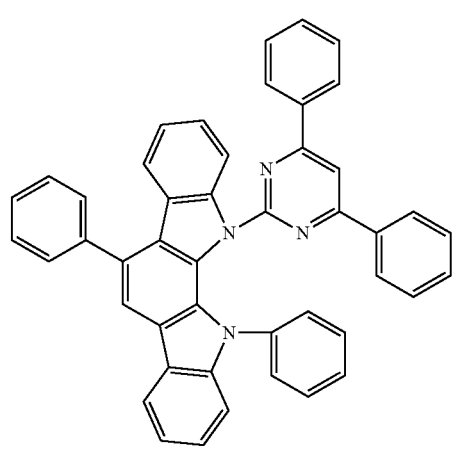
1-179
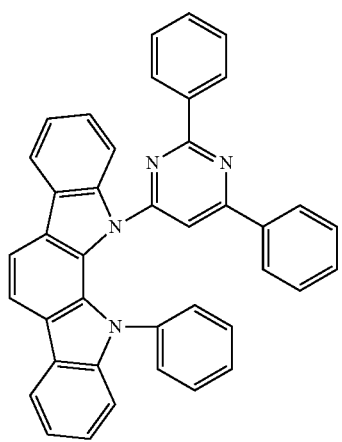

1-180
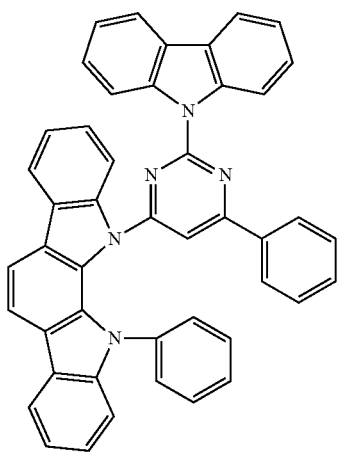
1-181
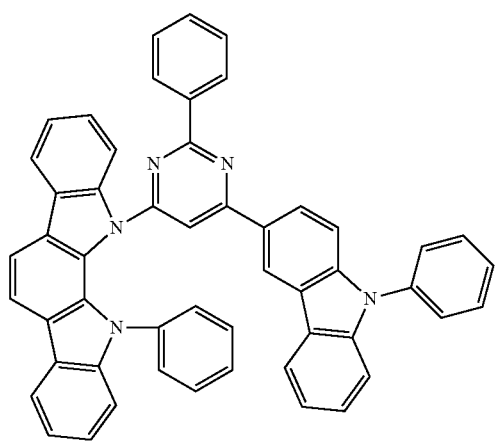
1-182
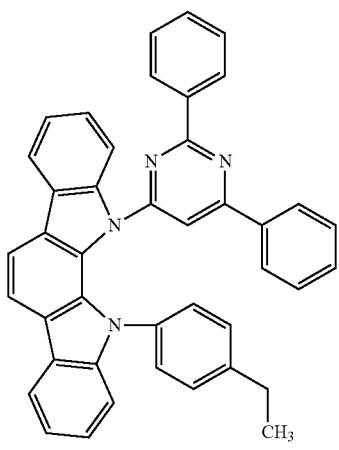
1-183
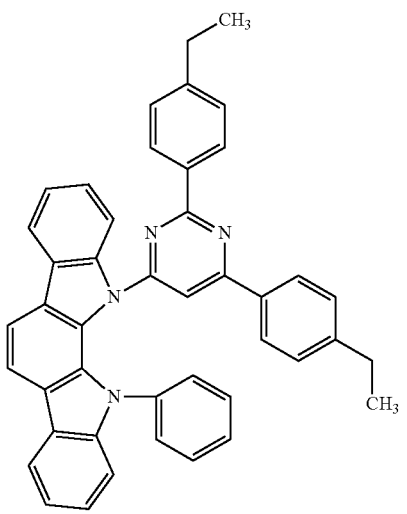
1-184
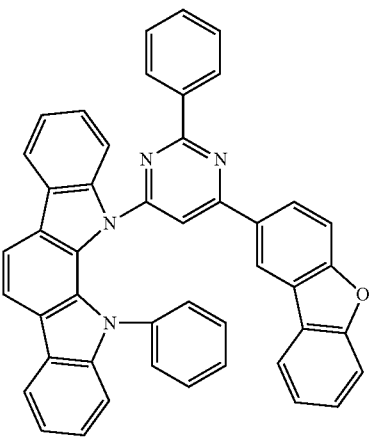
1-185
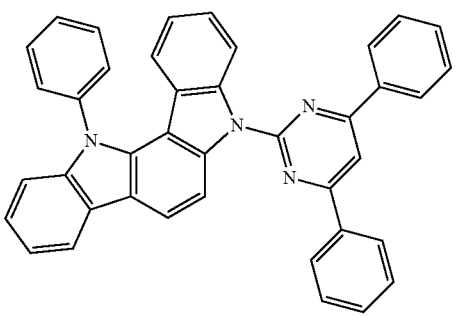
1-186
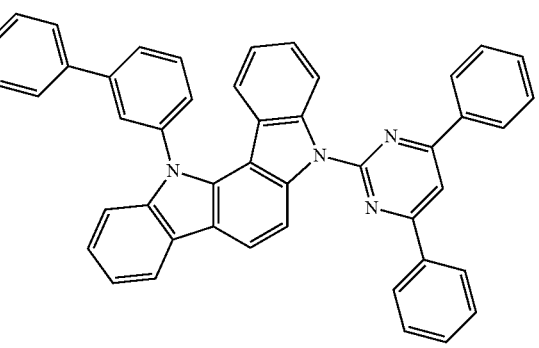

1-187
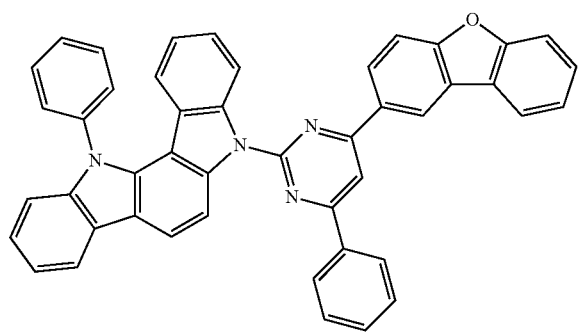
1-188
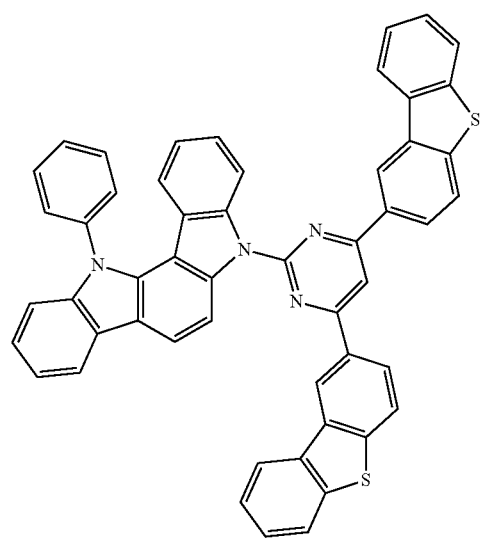
1-189
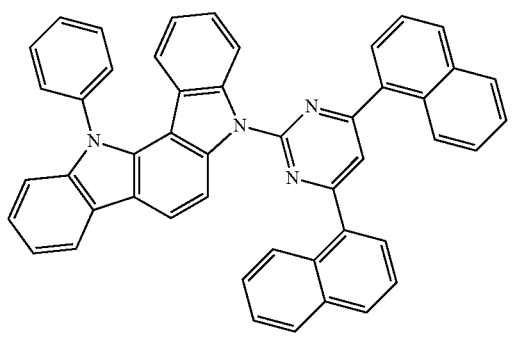
1-190
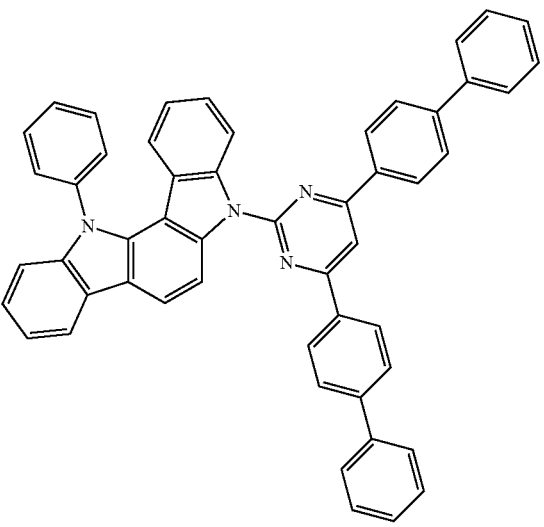
1-191
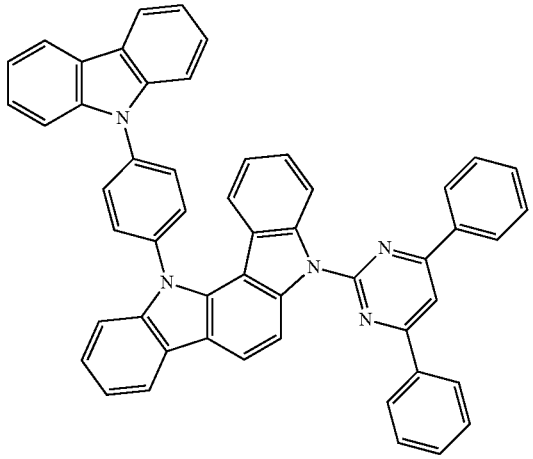
1-192
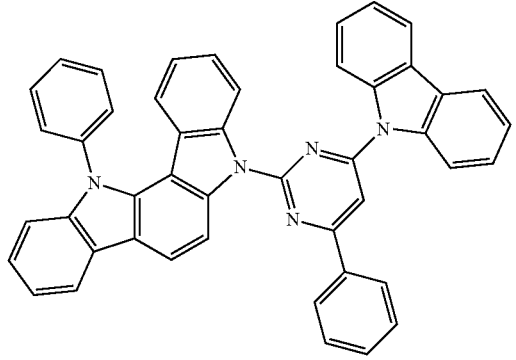

1-193
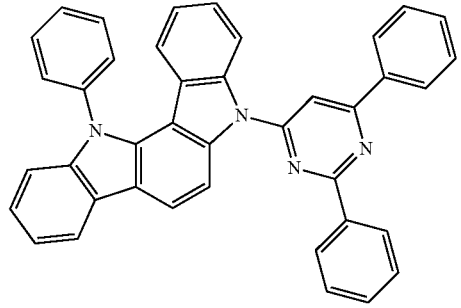
1-194
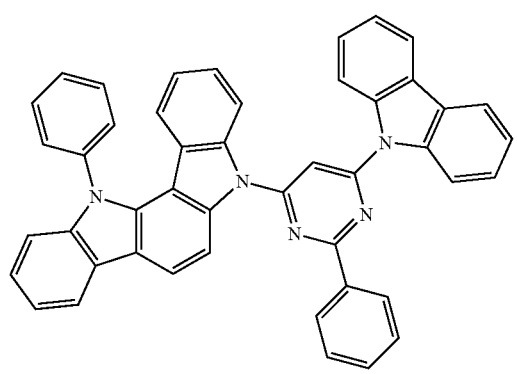
1-195
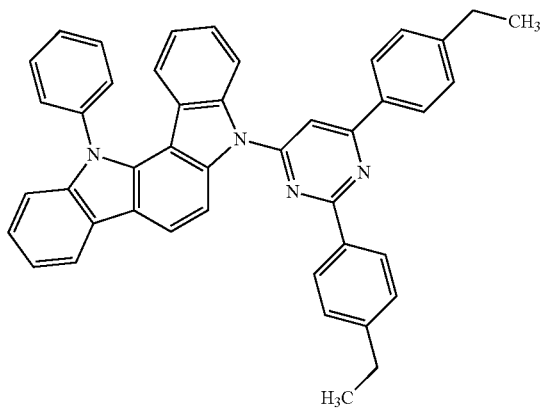
1-196
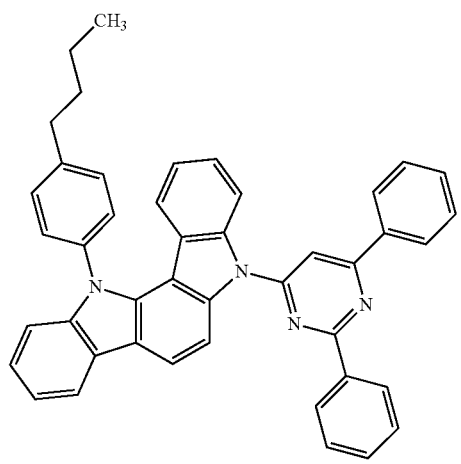
1-197
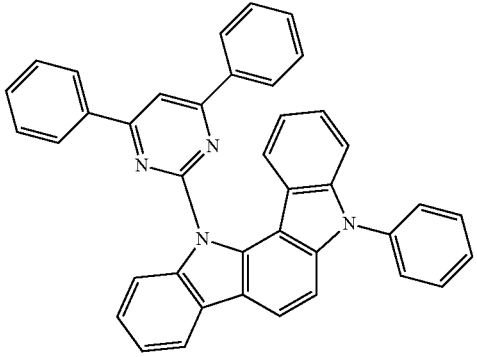
1-198
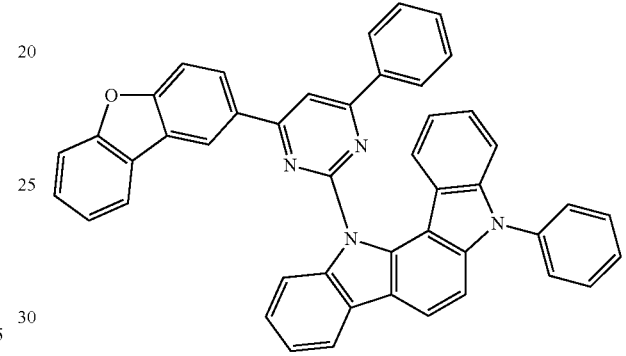
1-199
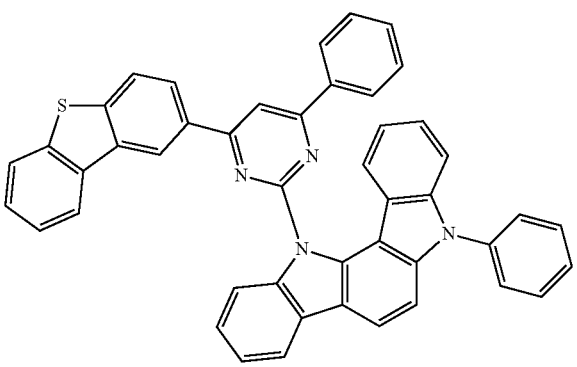
1-200
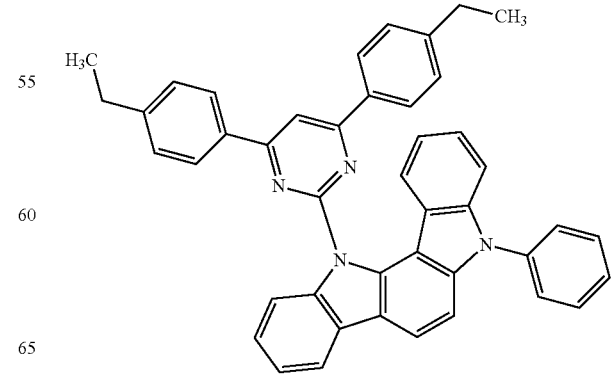

1-201 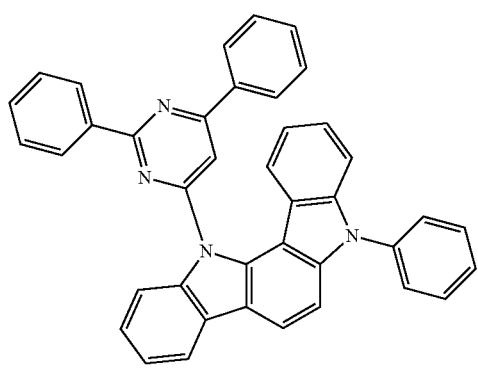
1-202 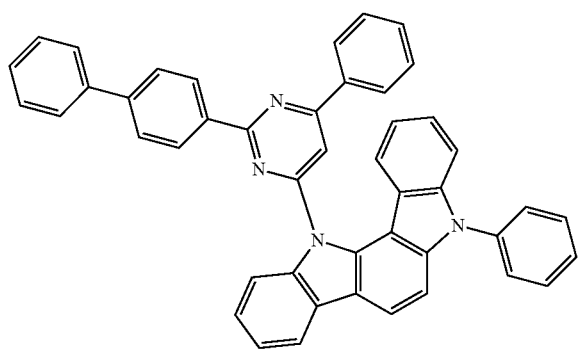
1-203 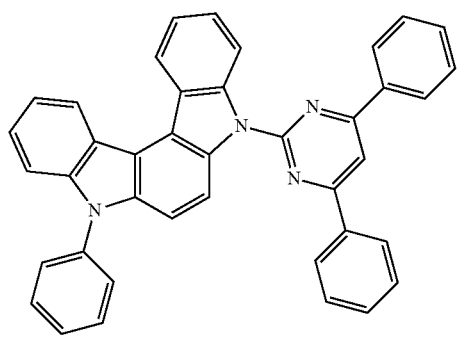
1-204 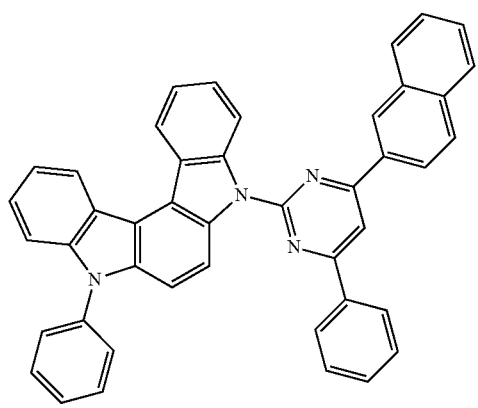
1-205 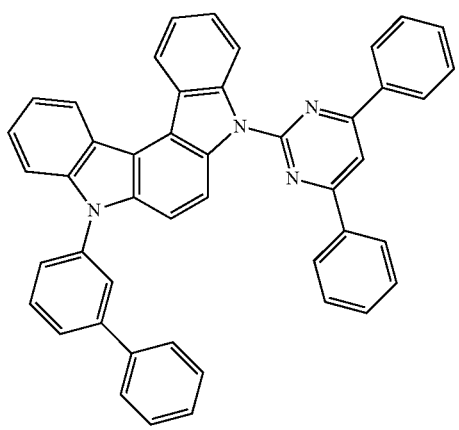
1-206 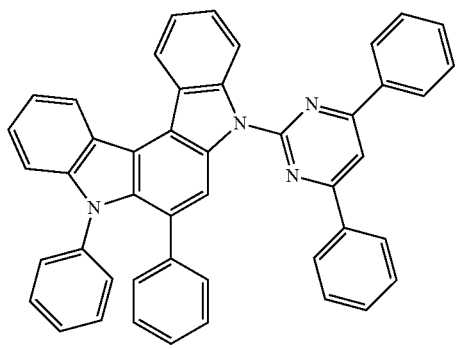
1-207 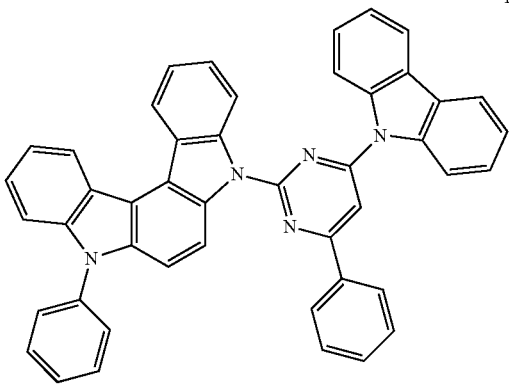
1-208 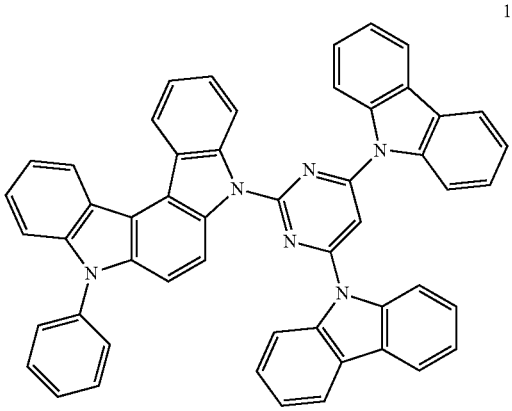

1-209
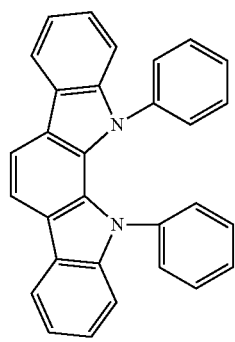
1-210
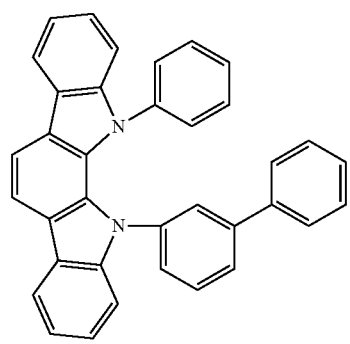
1-211
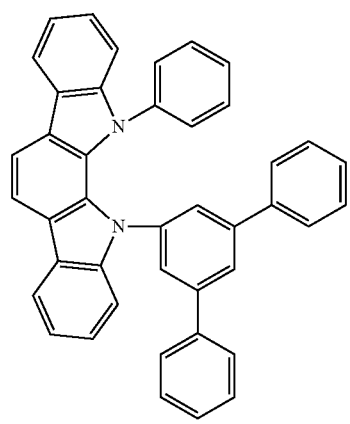
1-212
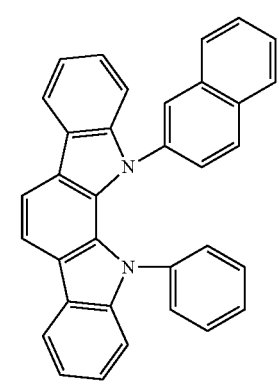
1-213
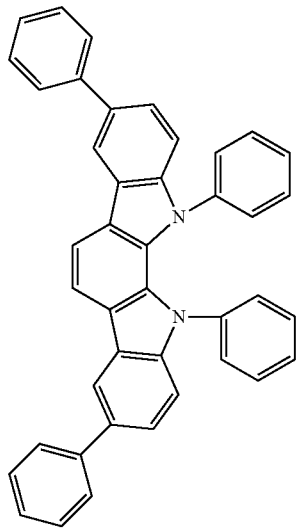
1-214
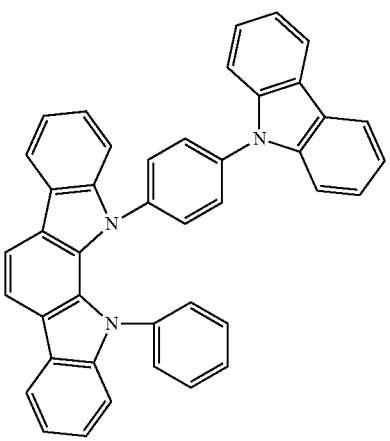
1-215
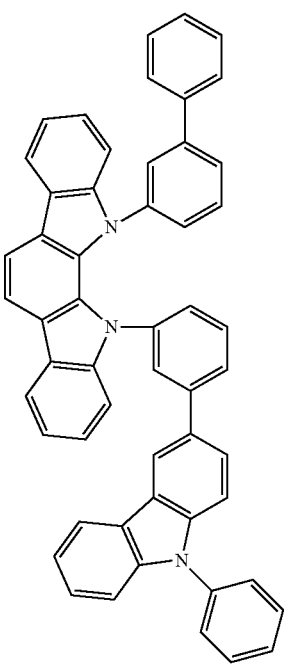

1-216
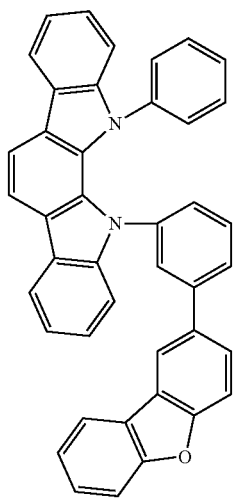
1-217
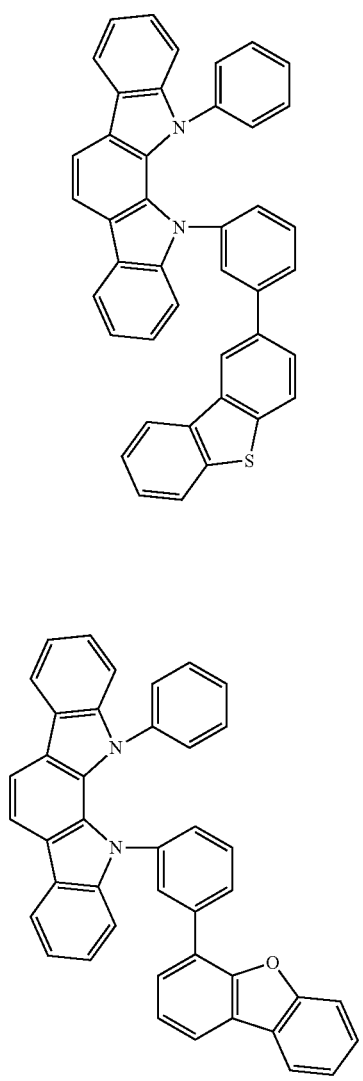
1-218
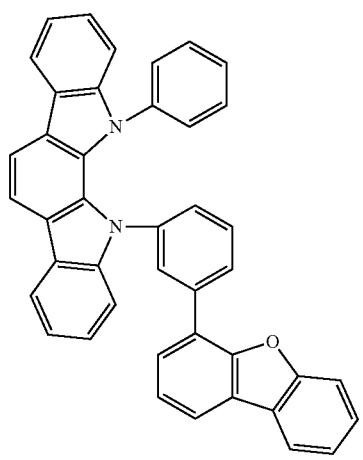
1-219
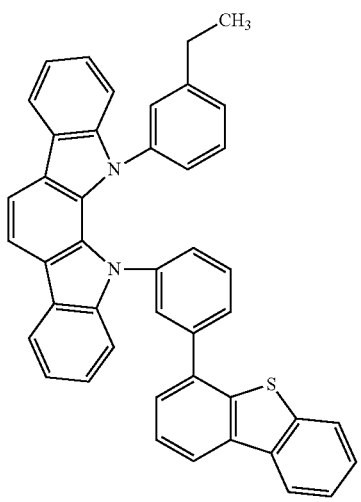
1-220
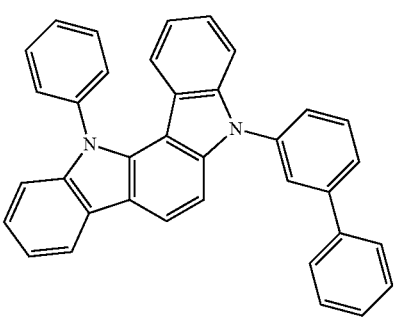
1-221
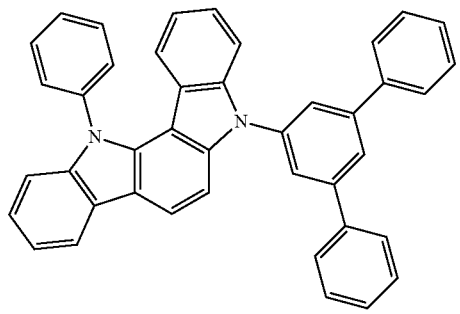
1-222
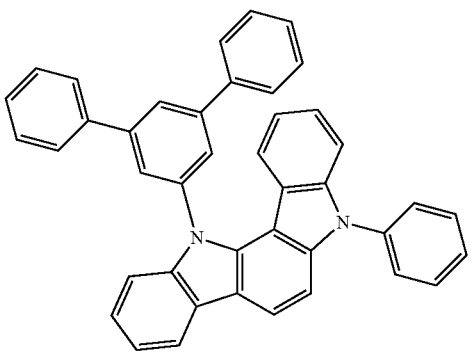

1-223
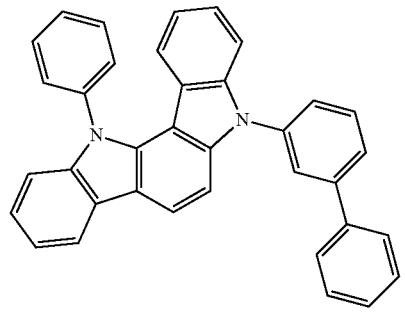
1-224
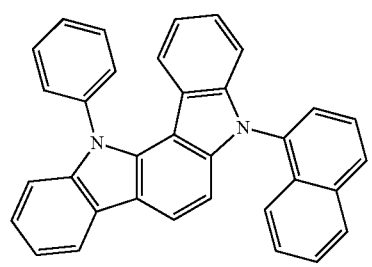
1-225
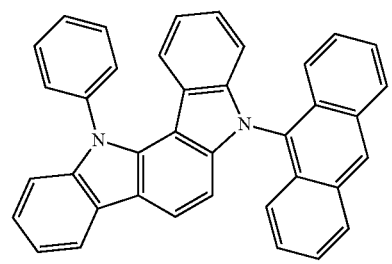
1-226
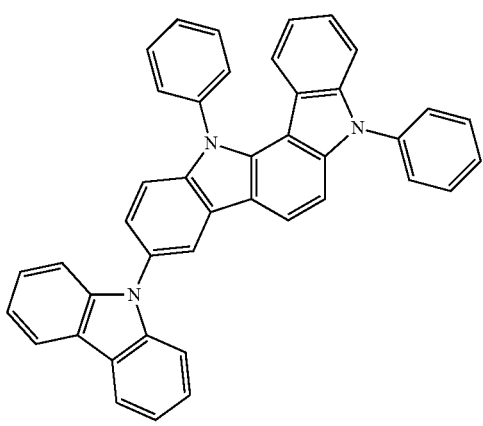
1-227
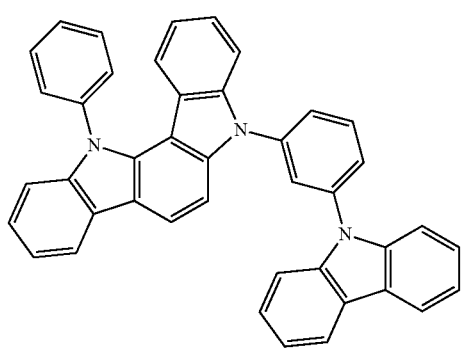
1-228
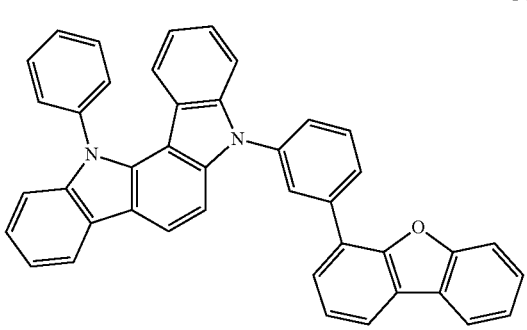
1-229
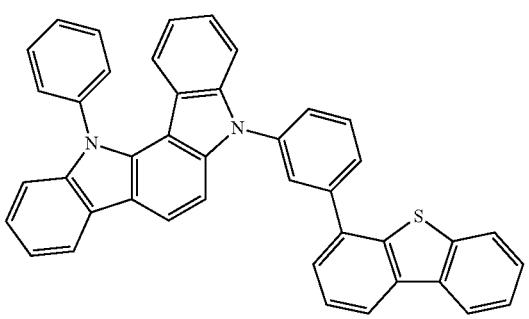
1-230
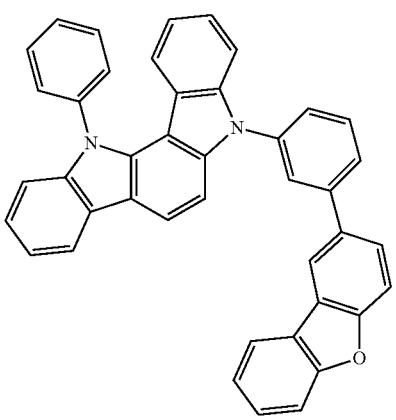
1-231
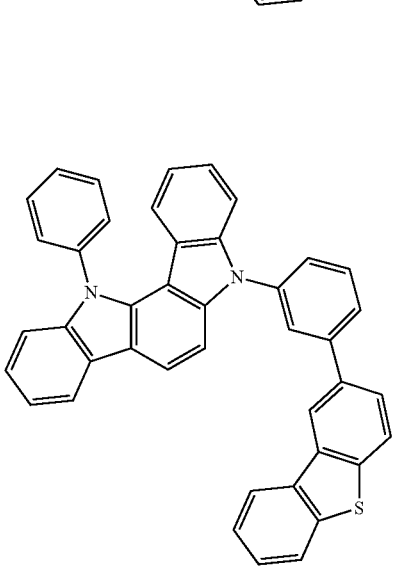

1-232
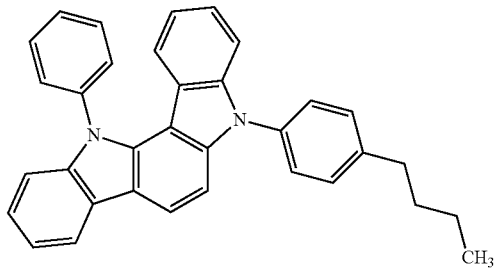
1-233
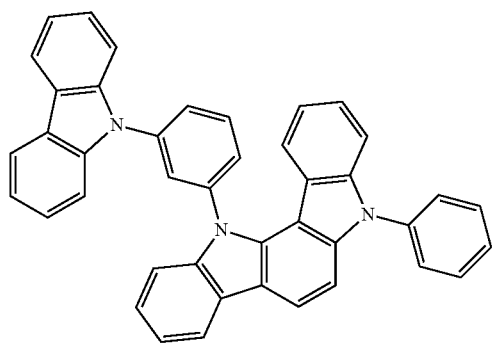
1-234
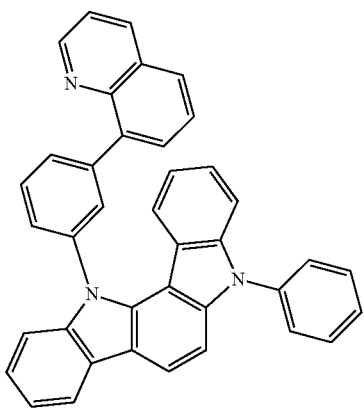
1-235
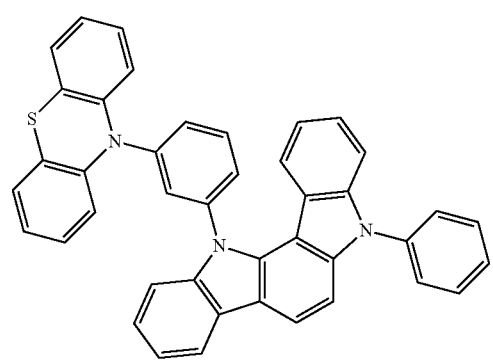
1-236
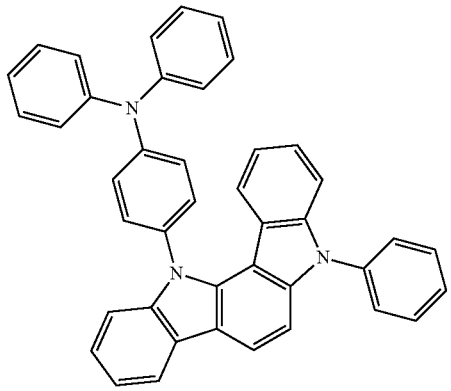
1-237
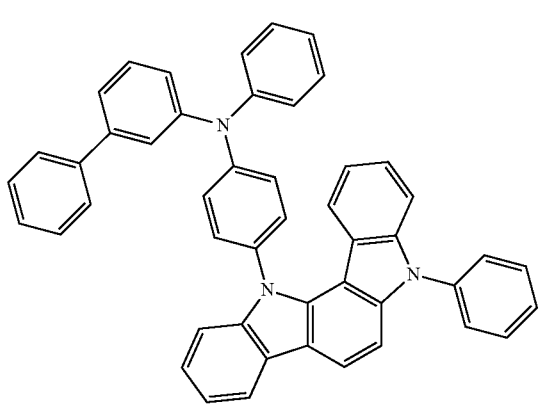
1-238
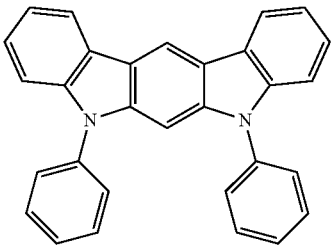
1-239
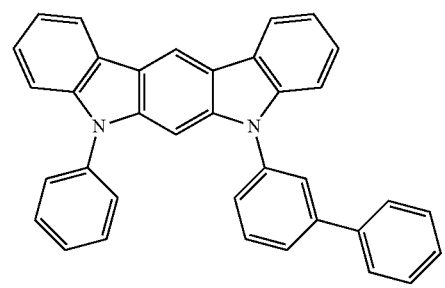

-continued
1-240
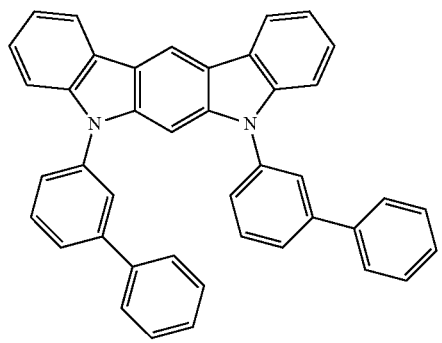
1-240
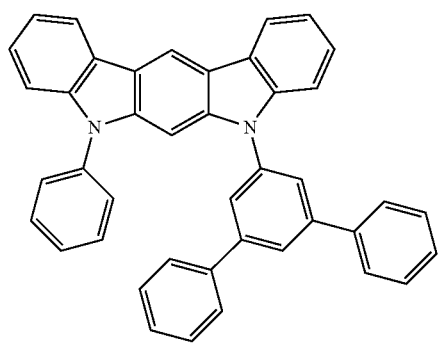
1-241
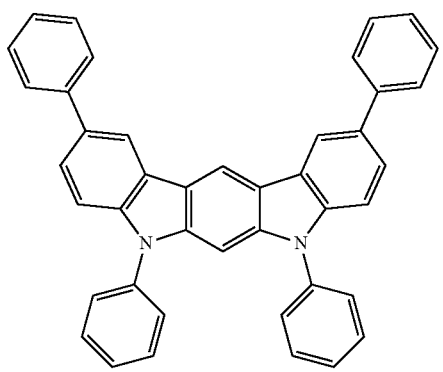
1-242
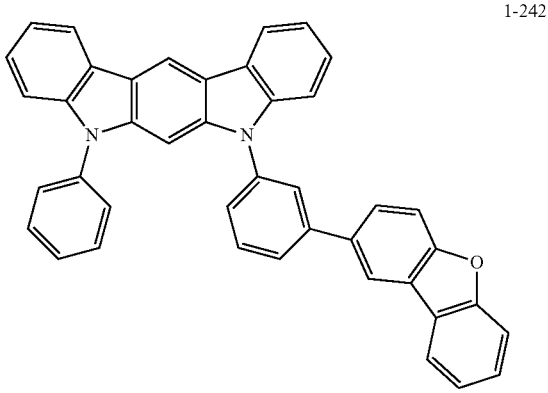
-continued
1-243
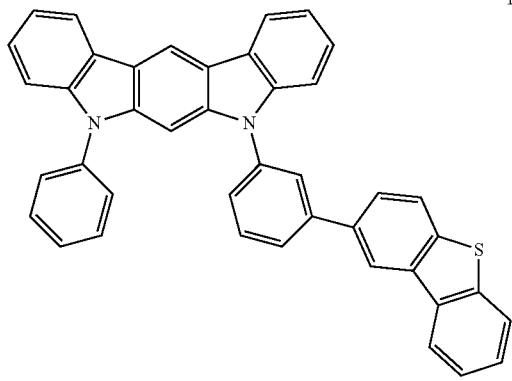
1-244
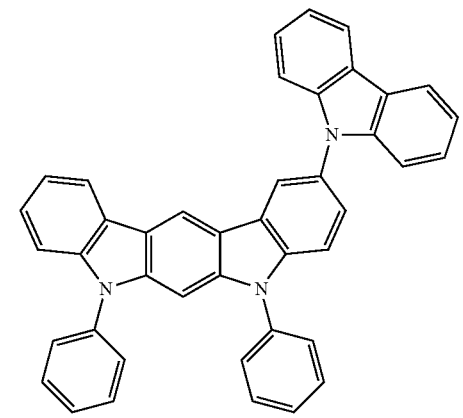
1-245
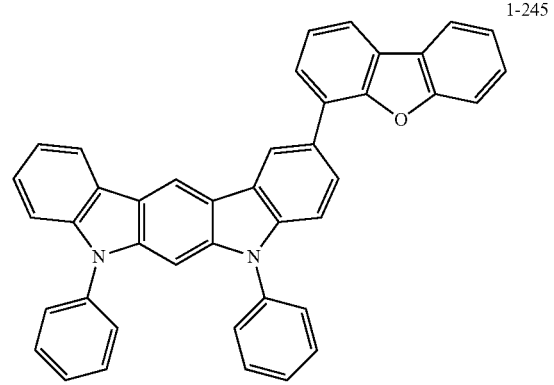
1-246
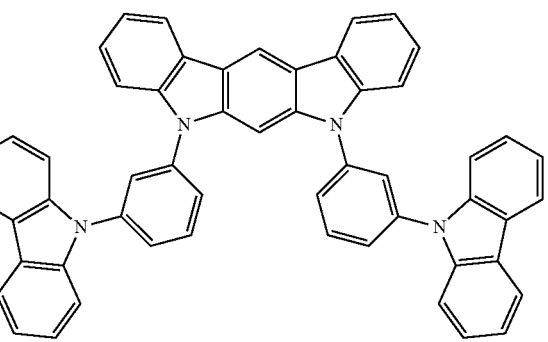

-continued
1-247
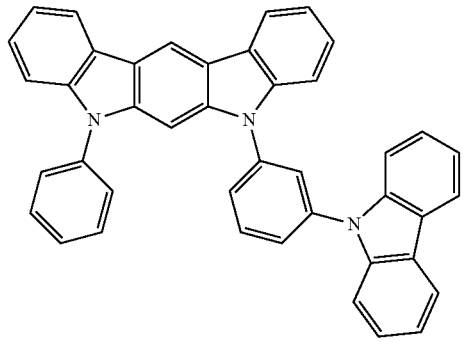
1-248
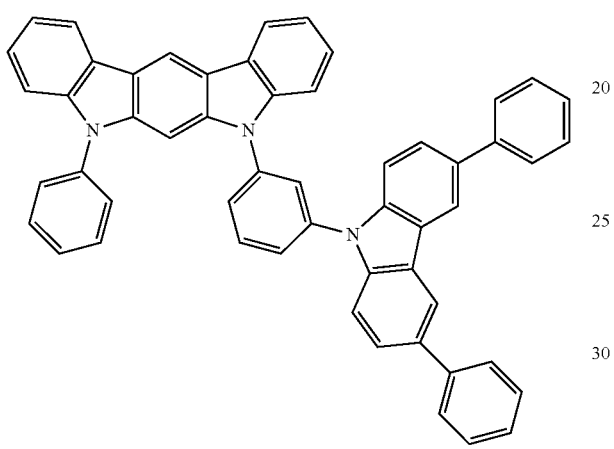
1-249
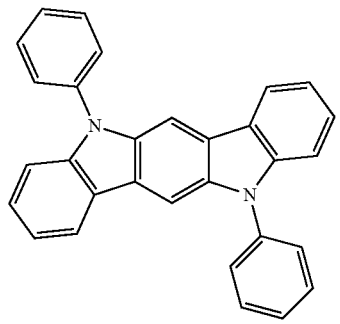
1-250
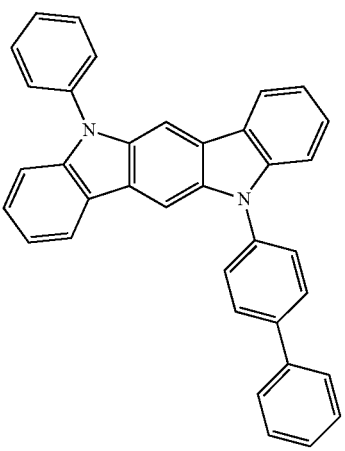
-continued
1-251
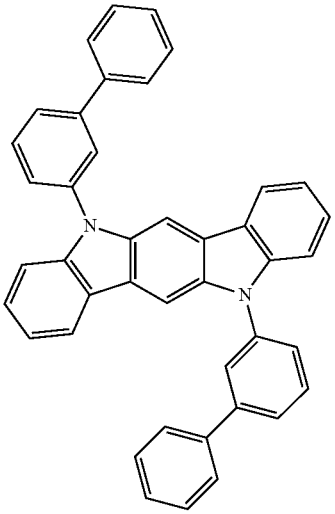
1-252
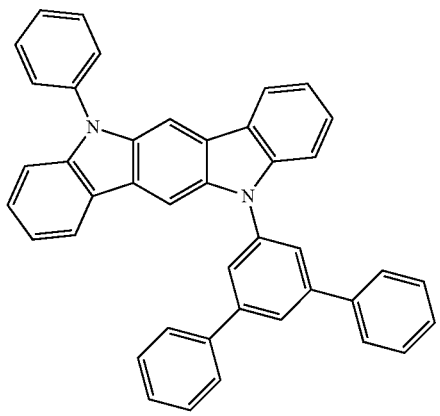
1-253
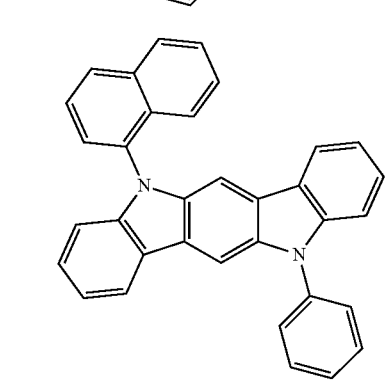
1-254
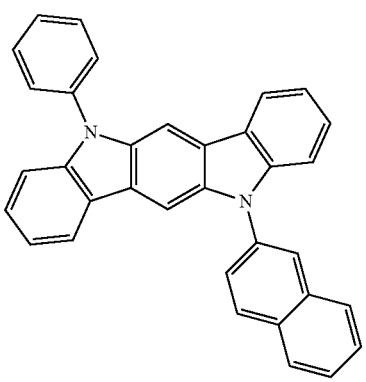

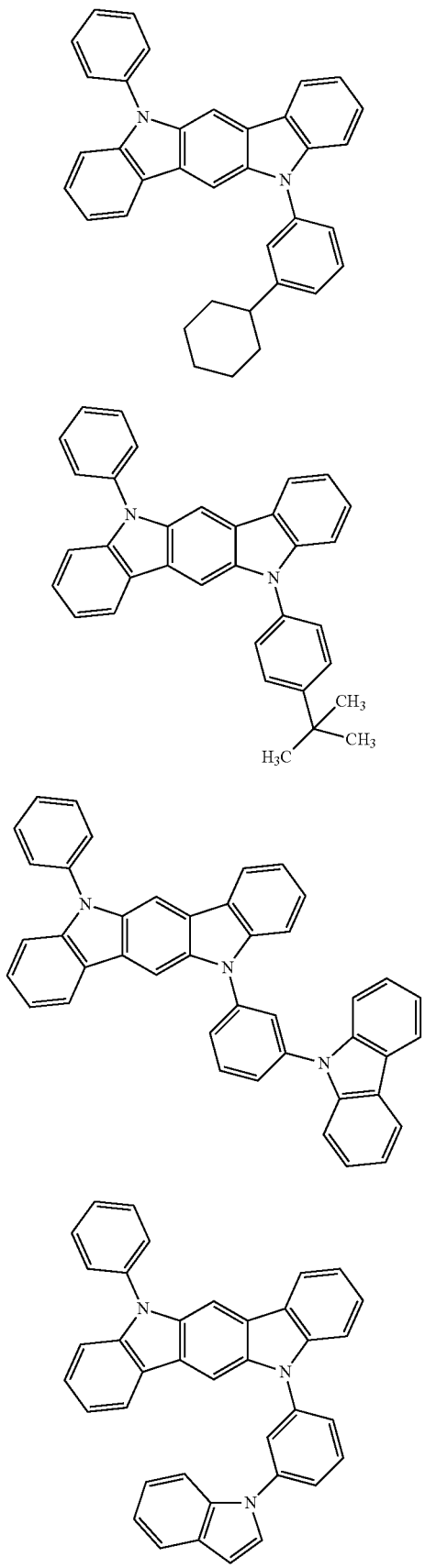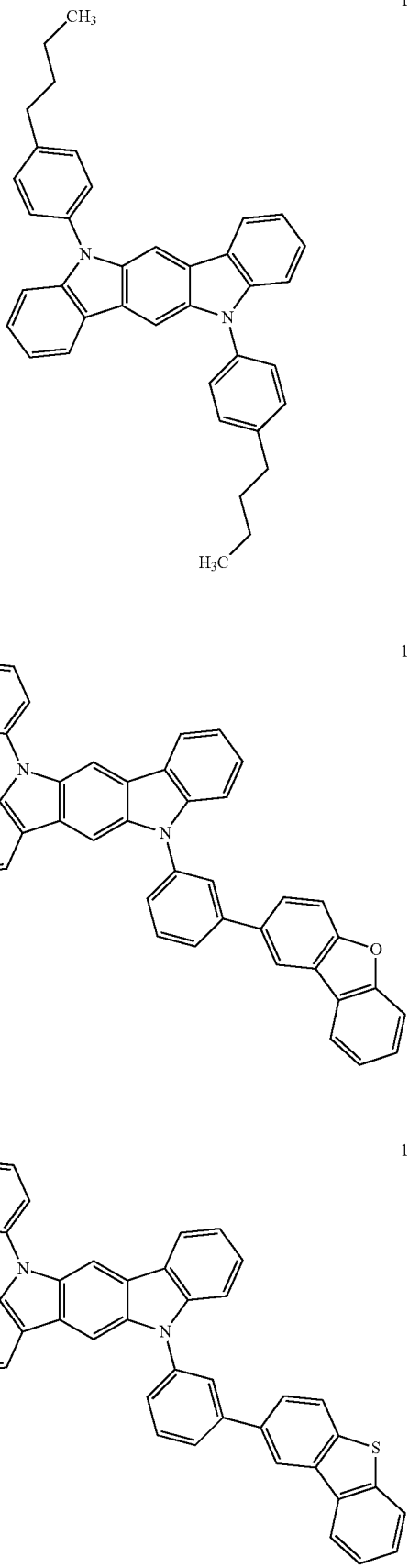

1-262
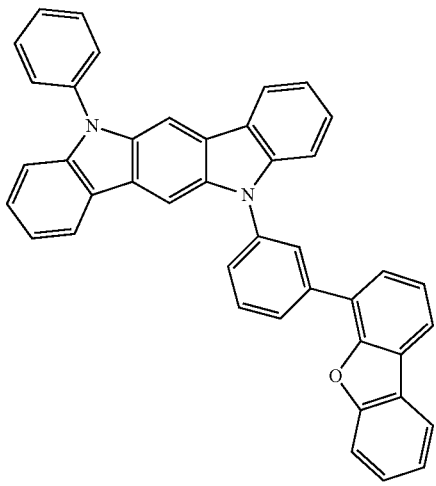
1-263
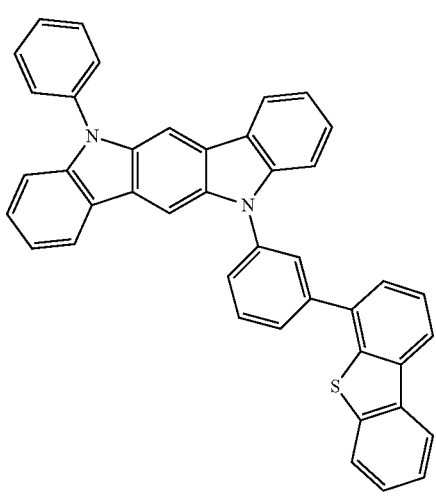
1-264
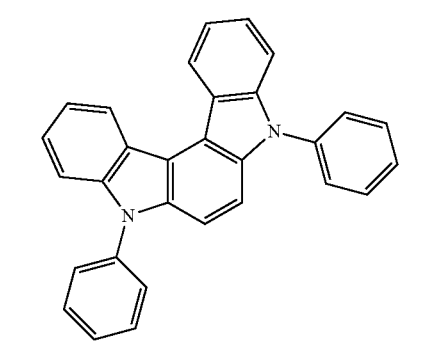
1-265
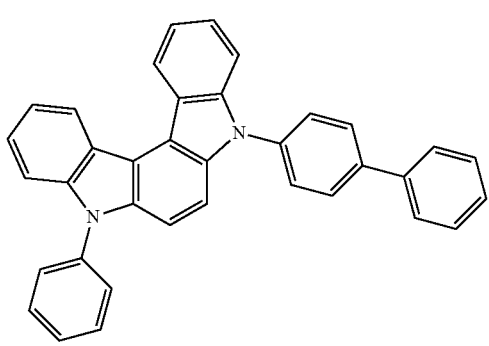
1-266
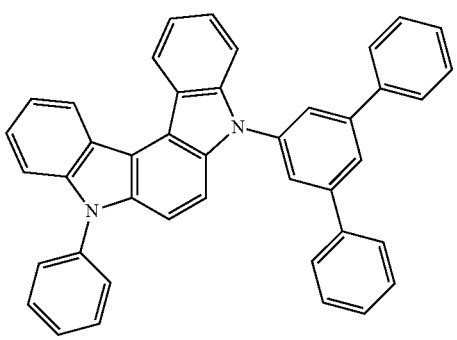
1-267
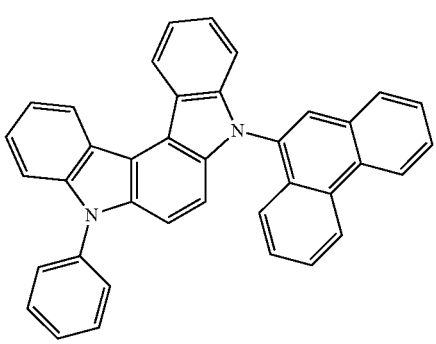
1-268
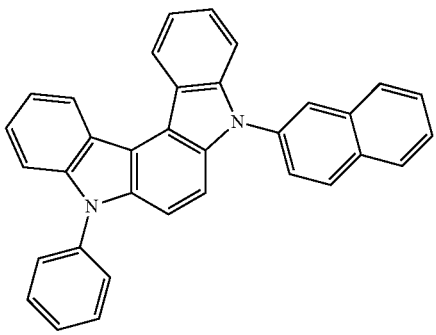
1-269
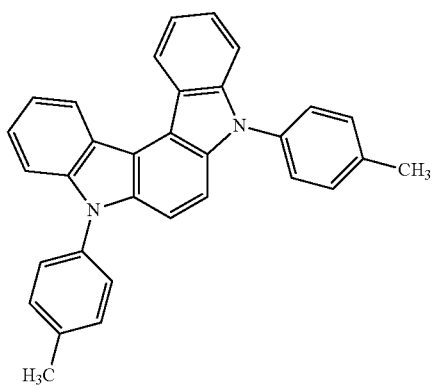

1-270
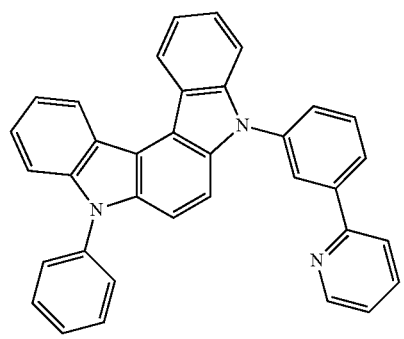
1-271
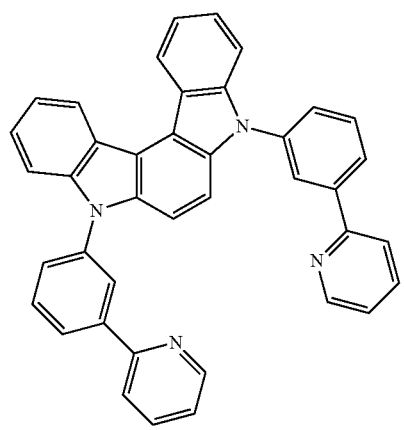
1-272
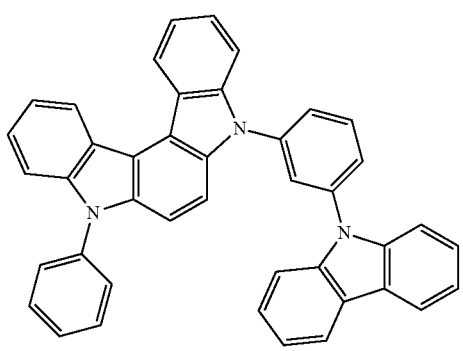
1-273
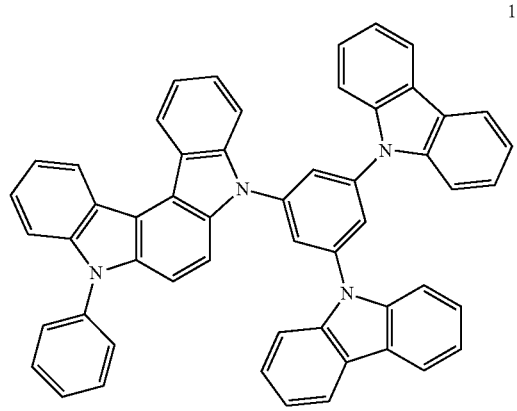
1-274
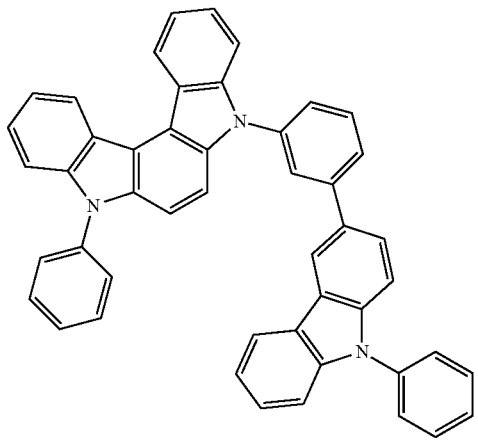
1-275
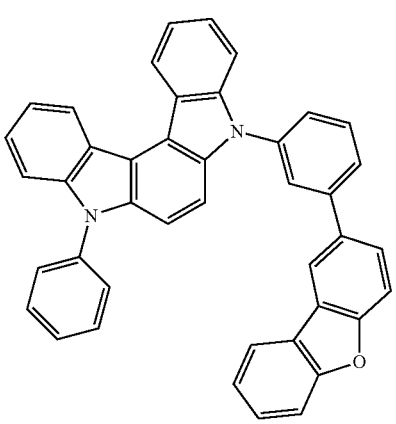
1-276
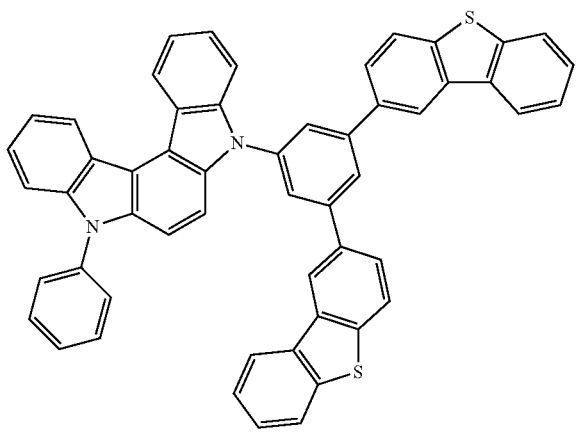
2-1
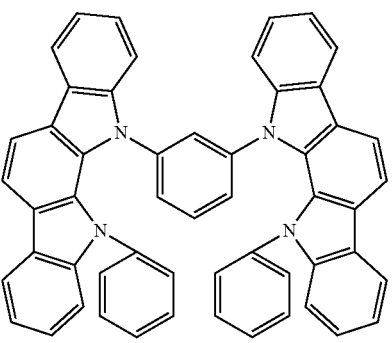

-continued
2-2
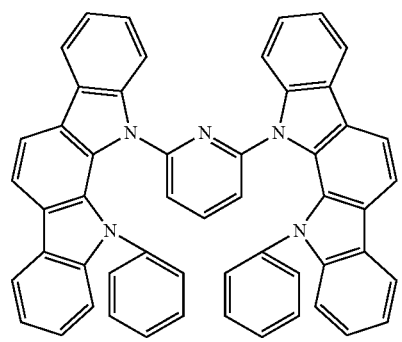
2-3
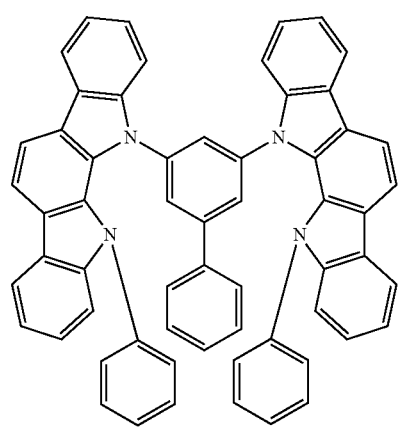
2-4
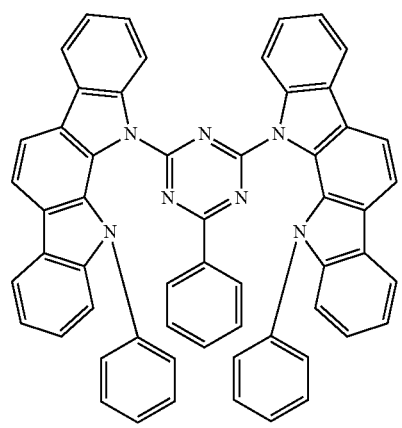
-continued
2-5
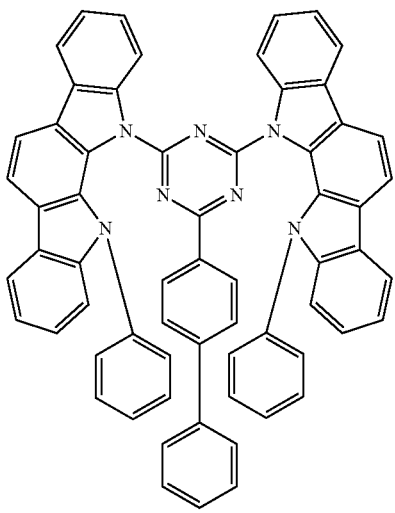
2-6
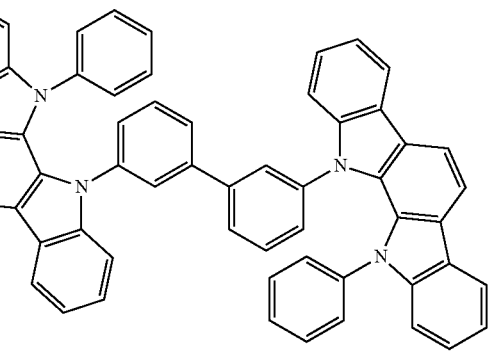
2-7
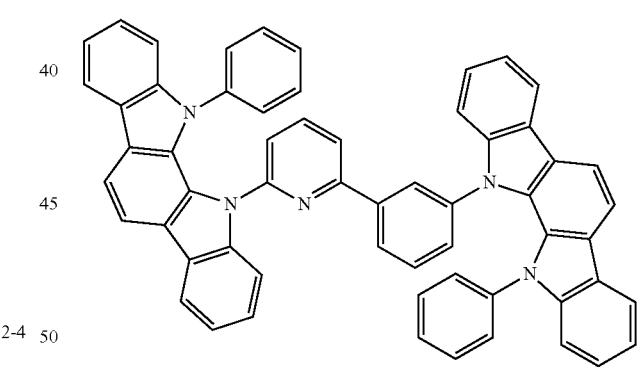
2-8
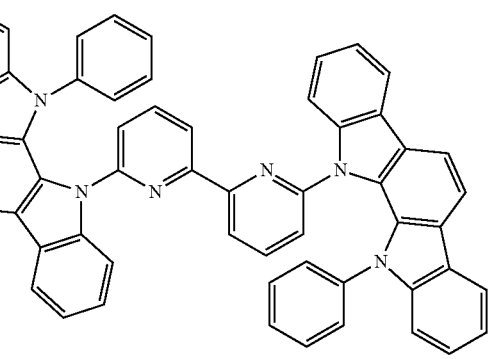

2-9
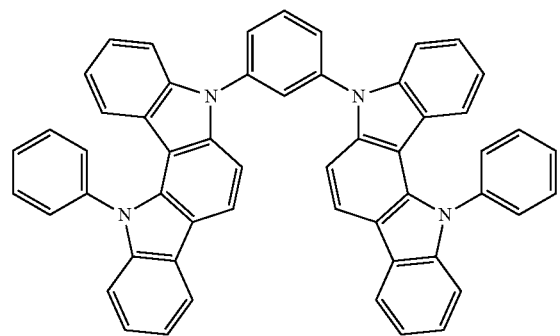
2-10
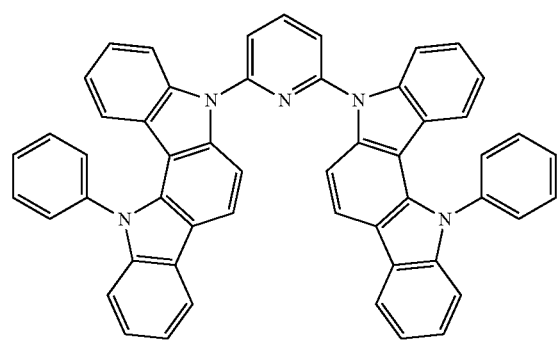
2-11
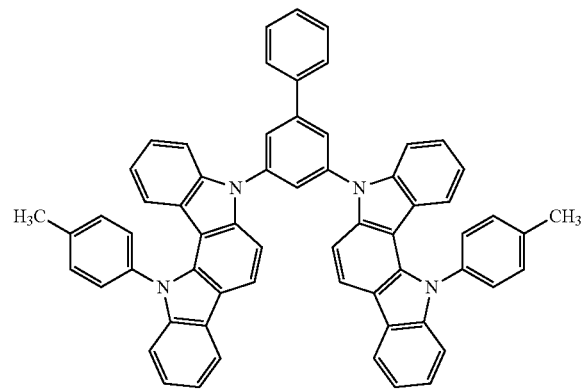
2-12
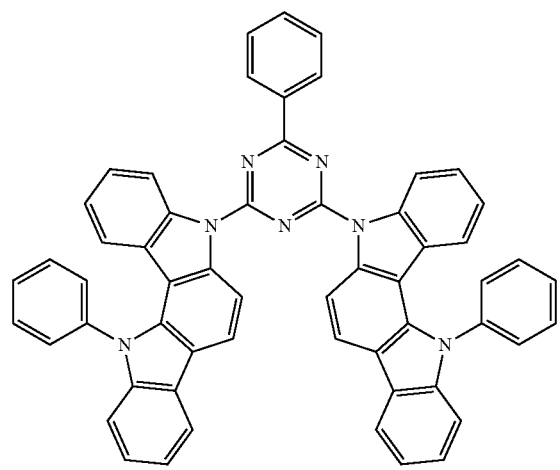
2-13
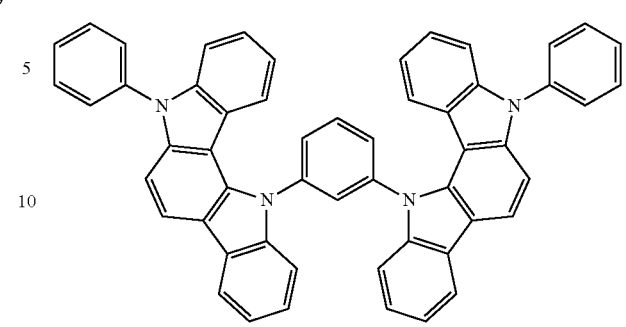
2-14
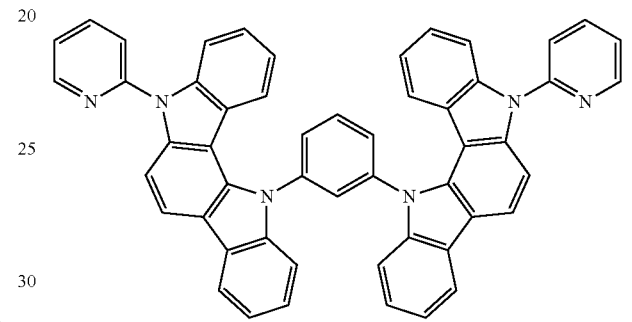
2-15
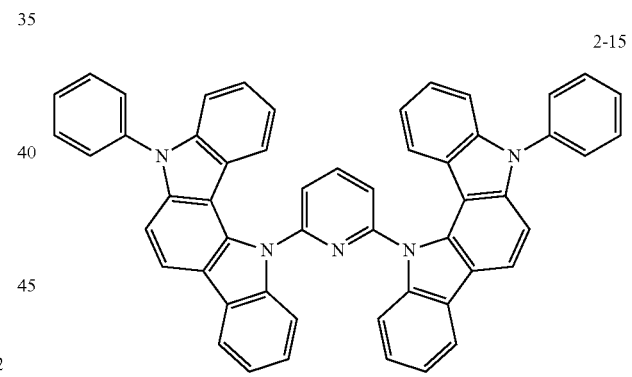
2-16
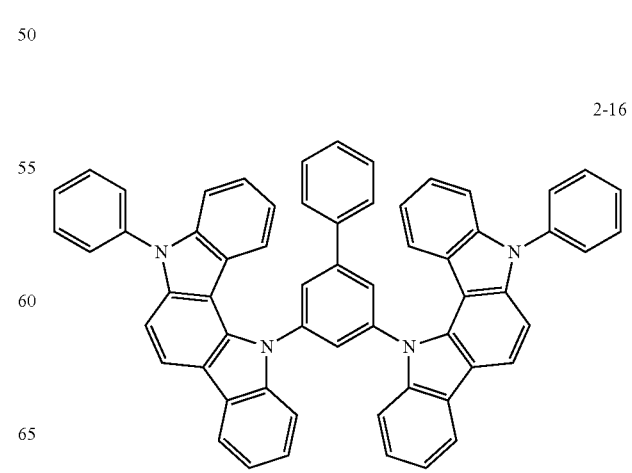

2-17
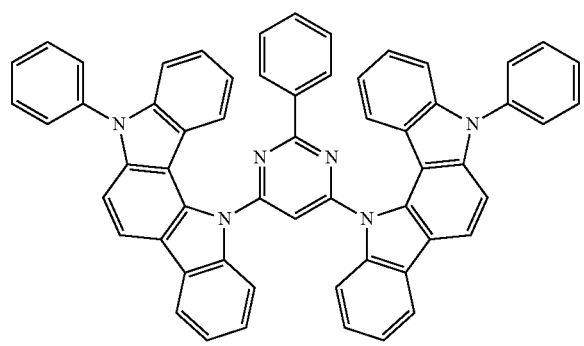
2-18
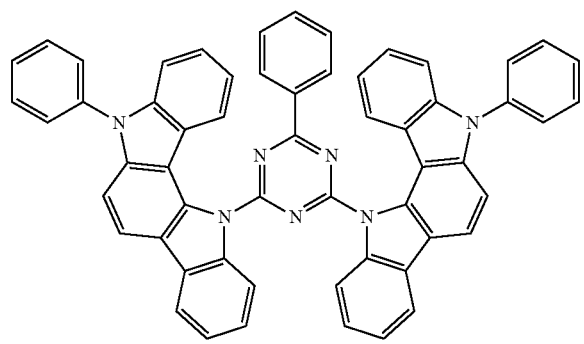
2-19
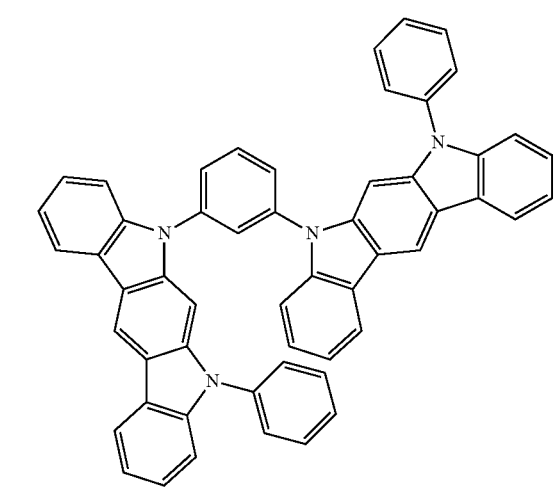
2-20
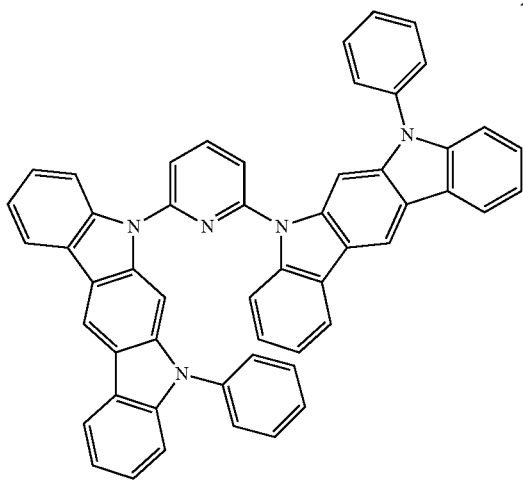
2-21
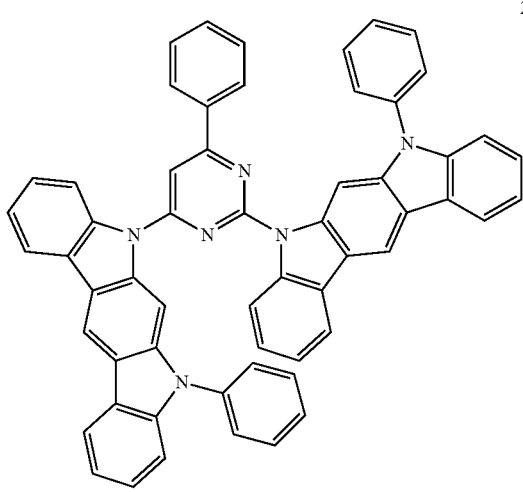
2-22
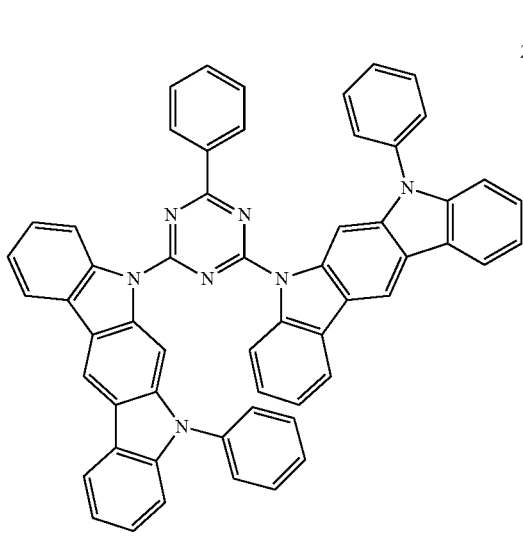

-continued
2-23
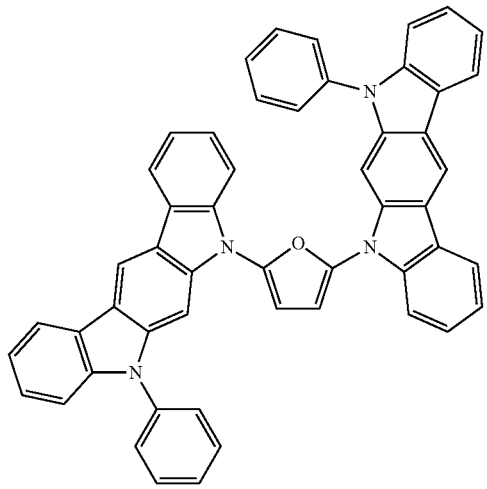
2-27
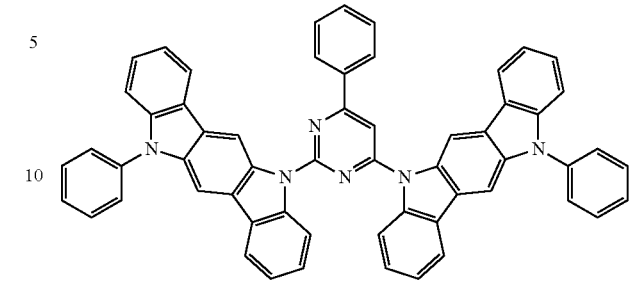
2-28
2-24
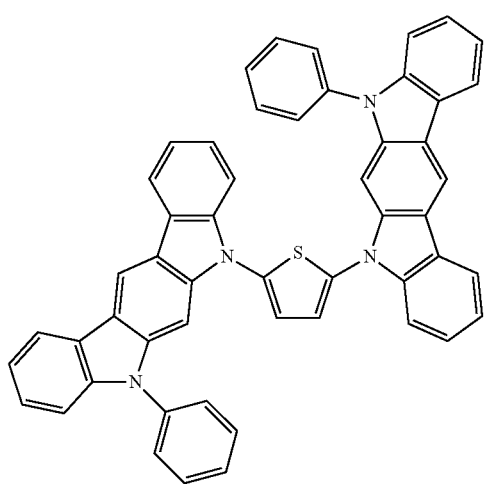
2-29
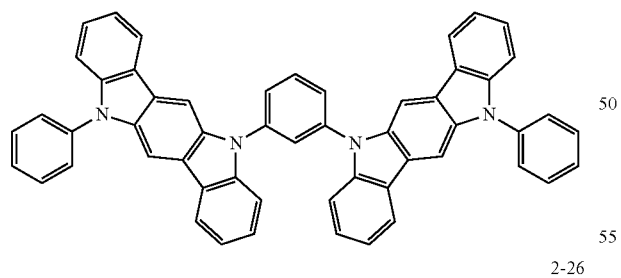
2-25
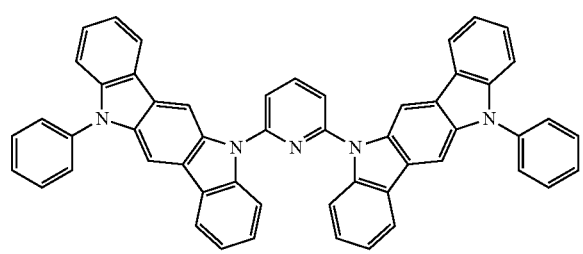
2-30
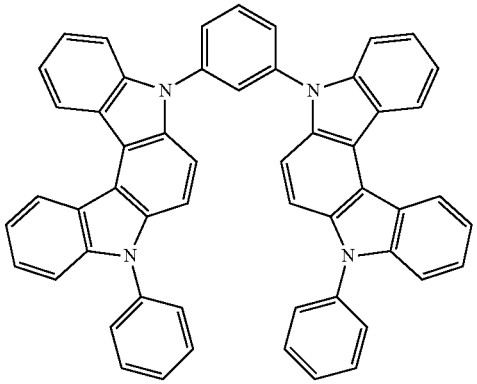
2-26

2-31
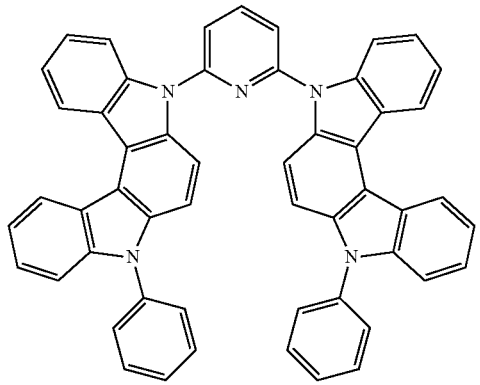
2-32
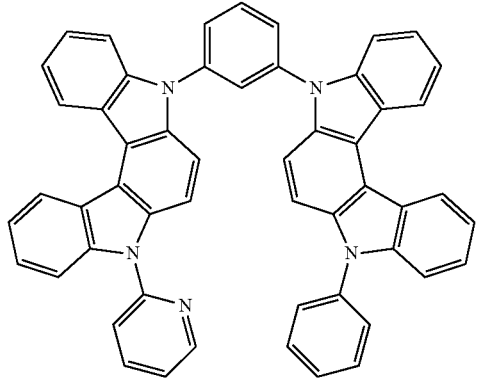
2-33
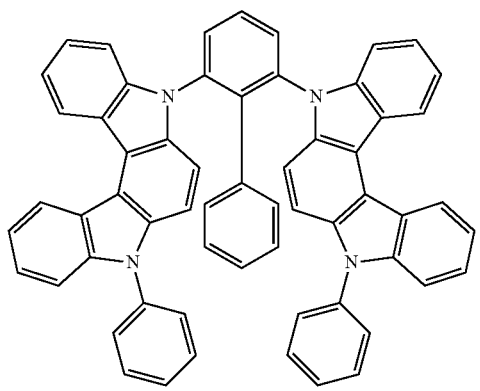
2-34
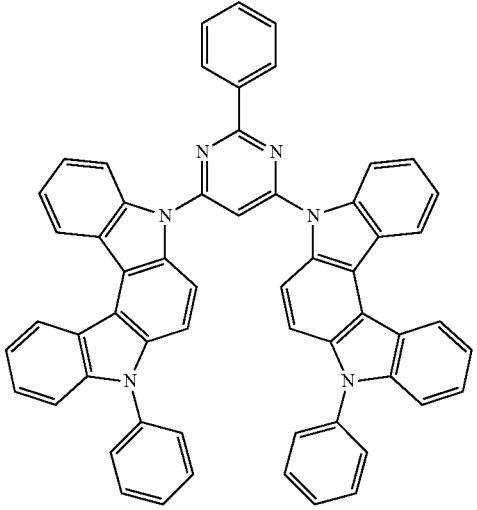
2-35
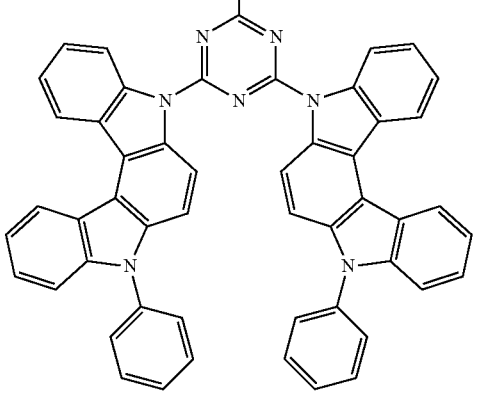
2-36
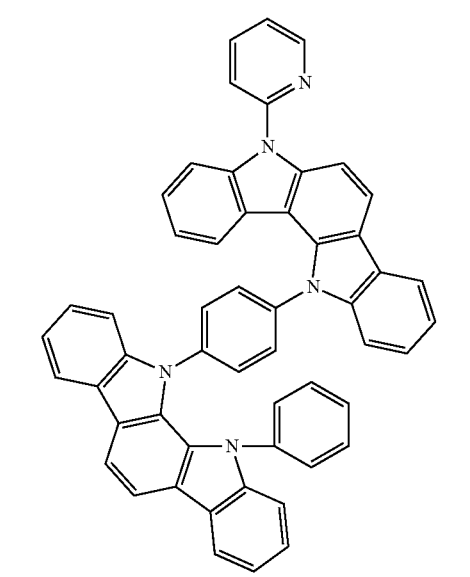

2-37
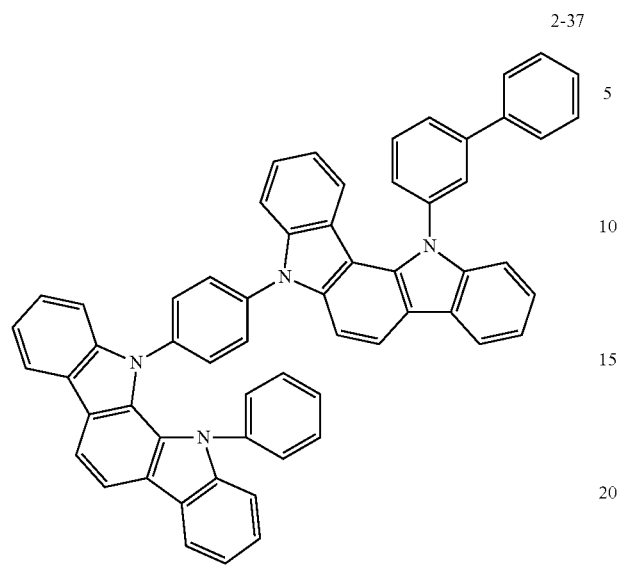
2-40
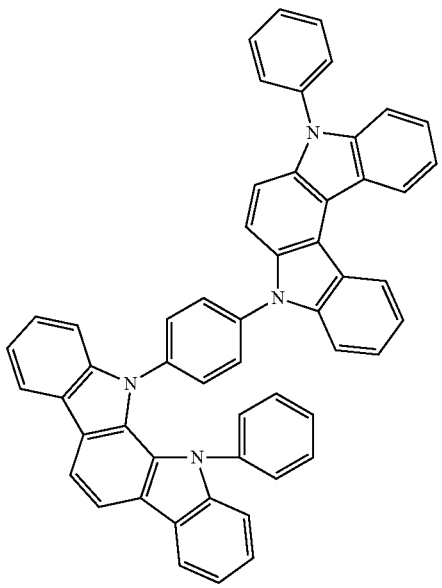
2-38
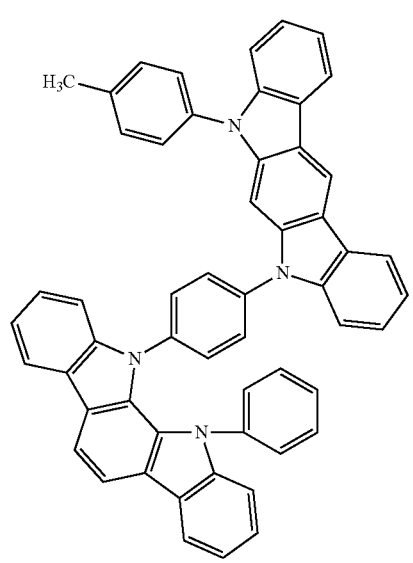
2-41
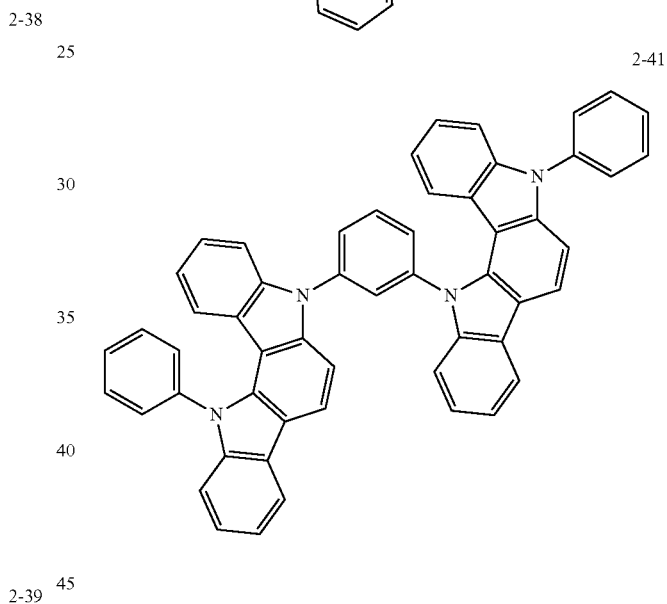
2-39
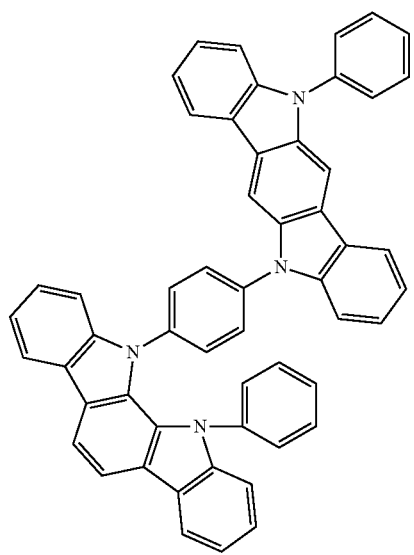
2-42
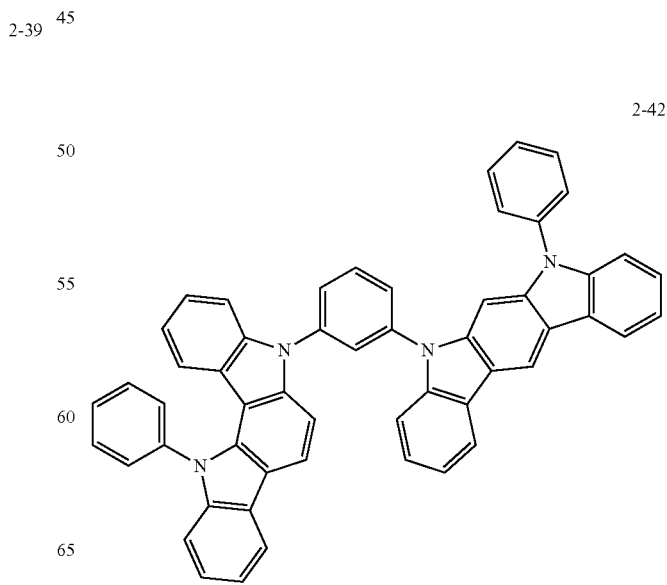

2-43
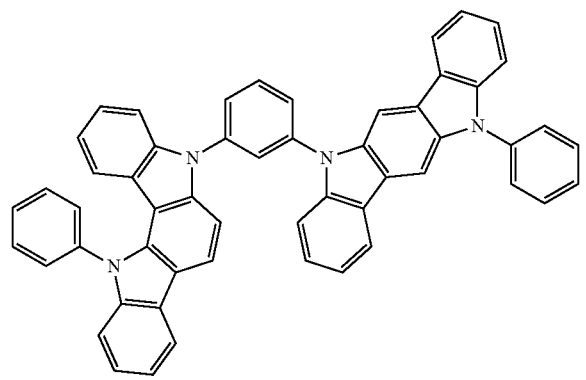
2-44
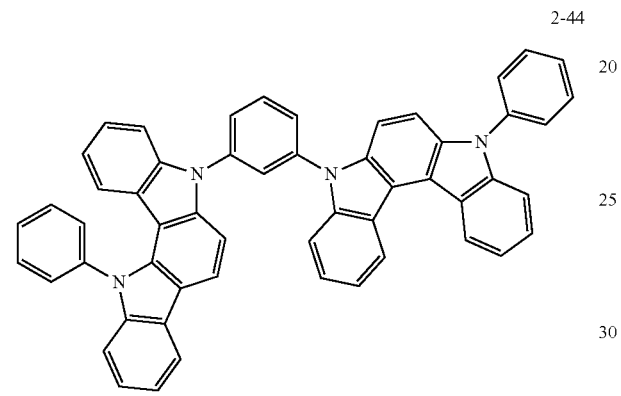
2-45
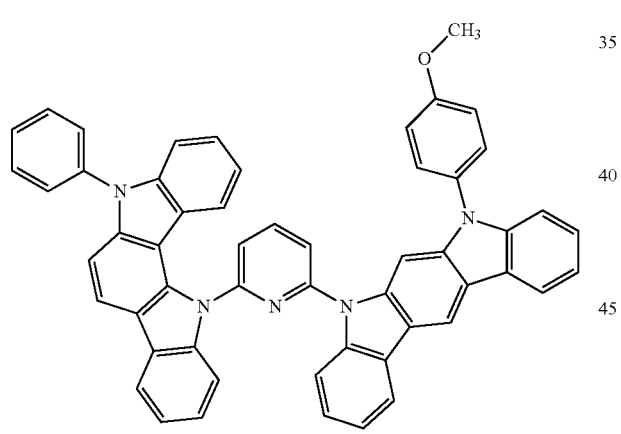
2-46
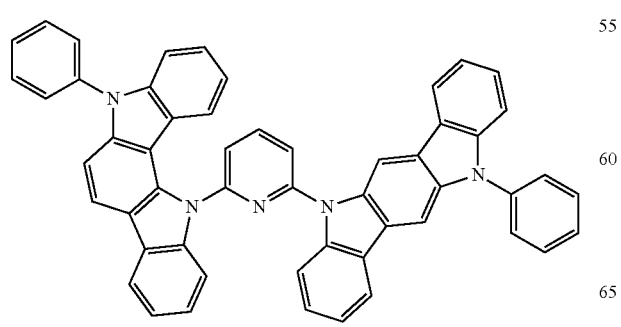
2-47
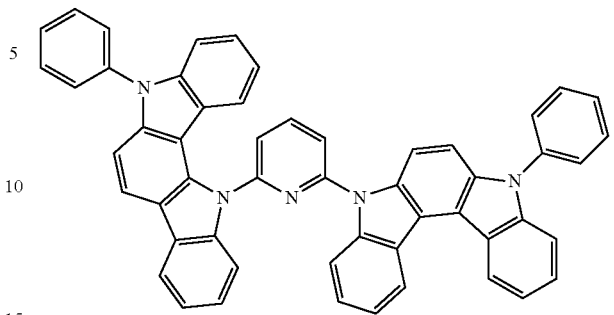
2-48
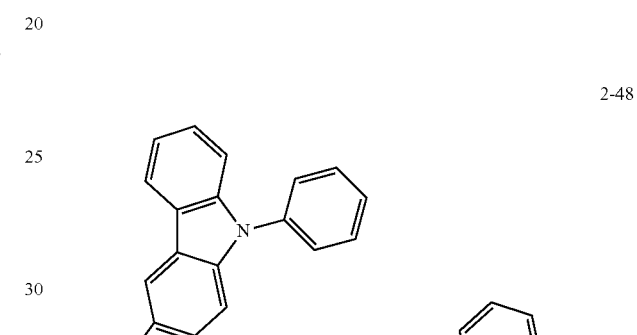
2-49
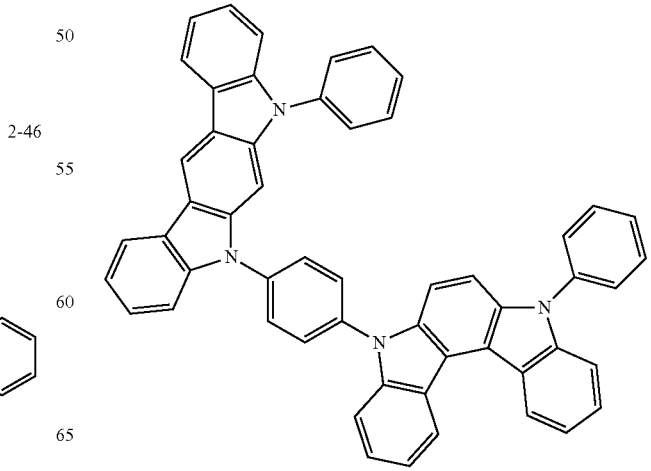

2-50

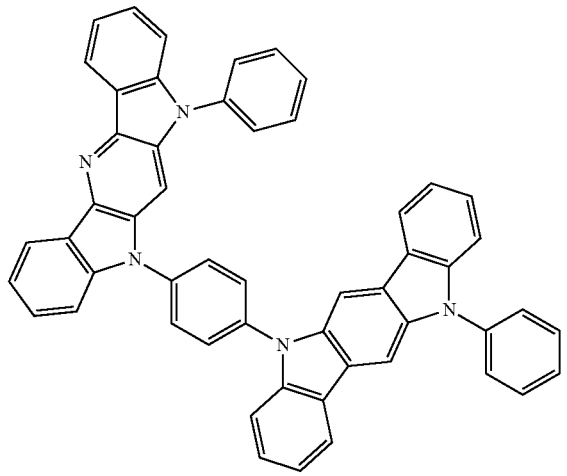

2-51

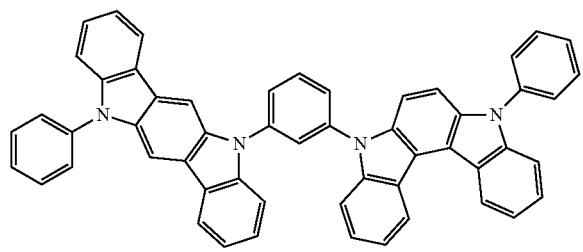

2-52

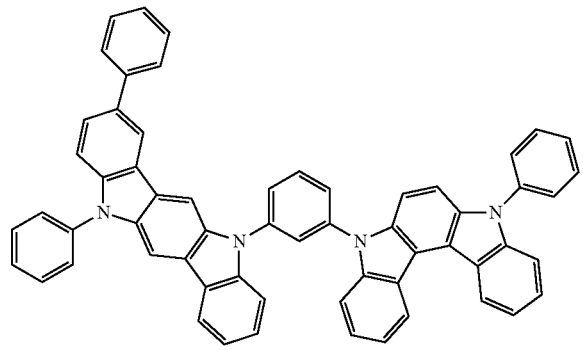

In the general formula (3), $L^3$'s each independently represent hydrogen or a monovalent group. The monovalent group is preferably a cyano group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a dialkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 22 carbon atoms, an aromatic heterocyclic group having 3 to 16 carbon atoms, or a linked aromatic group obtained by linking 2 to 10 aromatic rings of the aromatic hydrocarbon group and the aromatic heterocyclic group. Specific examples of the alkyl group, the aralkyl group, the alkenyl group, the alkynyl group, the dialkylamino group, the diarylamino group, the dialkylamino group, the acyl group, the acyloxy group, the alkoxy group, the alkoxycarbonyl group, the alkoxycarbonyloxy group, or the alkylsulfonyl group include the same specific examples as those of $R^1$ to $R^7$, and specific examples of the aromatic hydrocarbon group, the aromatic heterocyclic group, or the linked aromatic group obtained by linking 2 to 10 aromatic rings of the aromatic hydrocarbon group and the aromatic heterocyclic group include the same specific examples as those of $L^1$ and $L^2$. The aromatic hydrocarbon group or aromatic heterocyclic group in $L^3$ may have a substituent, and when the group has a substituent, the substituent is a cyano group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a dialkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, or an alkylsulfonyl group having 1 to 20 carbon atoms.

In the general formula (3), at least one of $L^3$'s preferably represents a group represented by the formula (e1). In addition, the compounds each represented by the general formula (3) are preferably compounds each represented by the general formula (4).

In the formula (e1) and the general formula (4), $L^4$'s each independently represent hydrogen, a cyano group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a dialkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 22 carbon atoms, an aromatic heterocyclic group having 3 to 16 carbon atoms, or a linked aromatic group obtained by linking 2 to 10 aromatic rings of the aromatic hydrocarbon group and the aromatic heterocyclic group; $X^2$'s each independently represent $CL^4$ or nitrogen, and a plurality of $L^4$'s may be identical to or different from each other; and the aromatic hydrocarbon group or aromatic heterocyclic group in $L^4$ may have a substituent, and when the group has a substituent, the substituent is the same as that in $L^3$. In addition, E is the same as that in the general formula (3).

The compounds each represented by the general formula (4) are preferably compounds each represented by the general formula (5). In the general formula (5), E and $L^4$ are identical in meaning to those in the general formula (4).

When $L^4$ represents an alkyl group, an aralkyl group, an alkenyl group, an alkynyl group, a dialkylamino group, a diarylamino group, a dialkylamino group, an acyl group, an acyloxy group, an alkoxy group, an alkoxycarbonyl group, an alkoxycarbonyloxy group, an alkylsulfonyl group, an aromatic hydrocarbon group, an aromatic heterocyclic group, or the like, specific examples thereof are the same as those described above for $L^3$.

In each of the general formulae (3) to (5), E represents oxygen or sulfur. In addition, part or all of hydrogen atoms in the compounds represented by the general formulae (3) to (5) can each be substituted with deuterium.
Specific examples of the compounds each represented by the general formula (3) are shown below, but the compounds are not limited to these exemplified compounds.
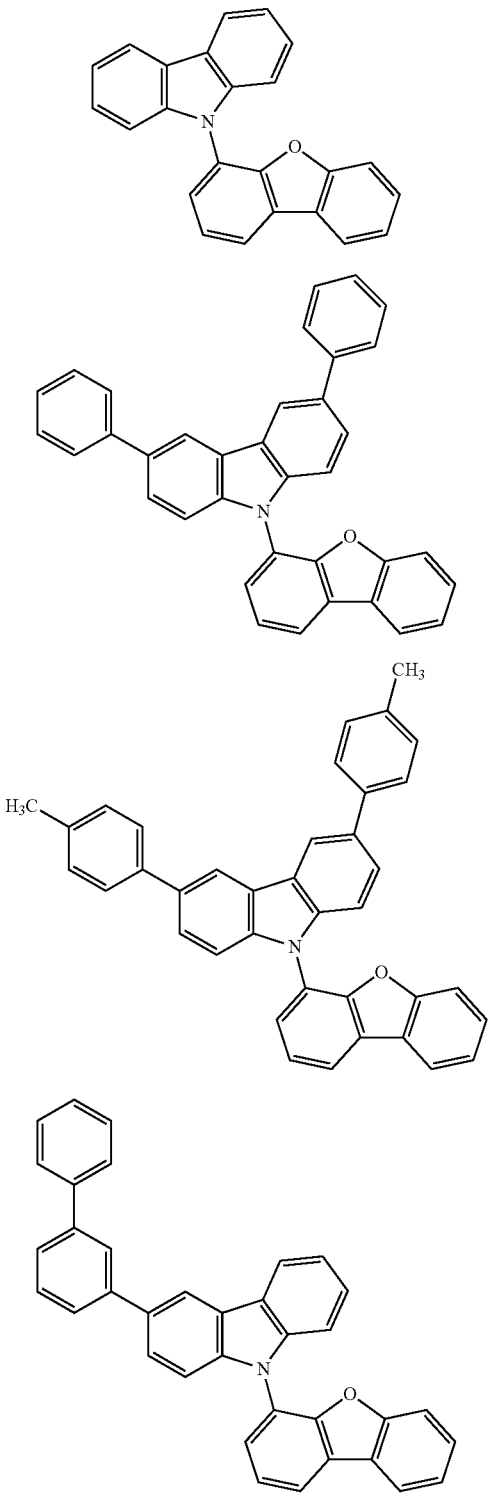
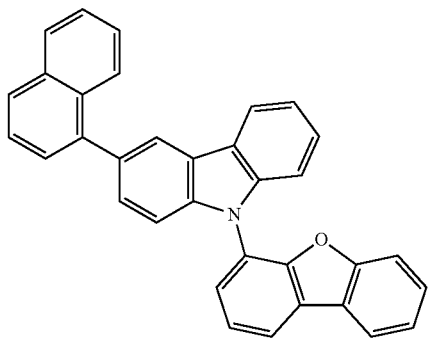
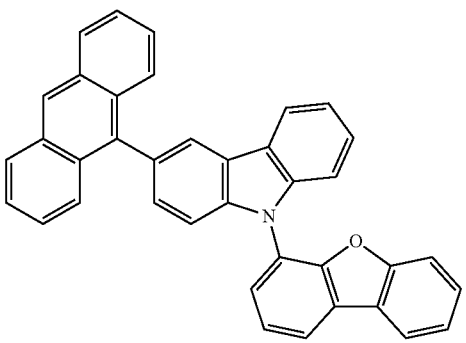
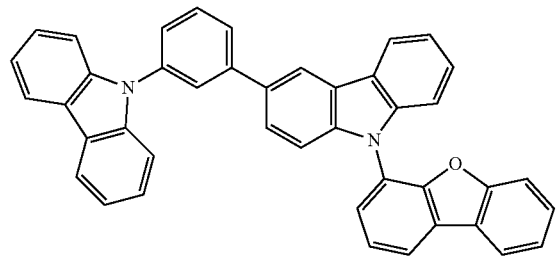
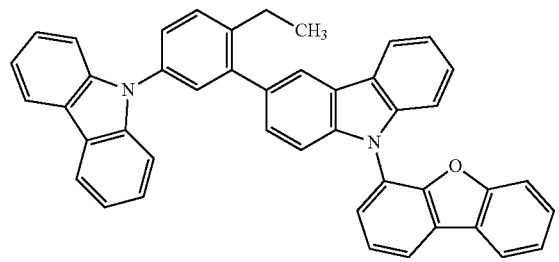

3-9
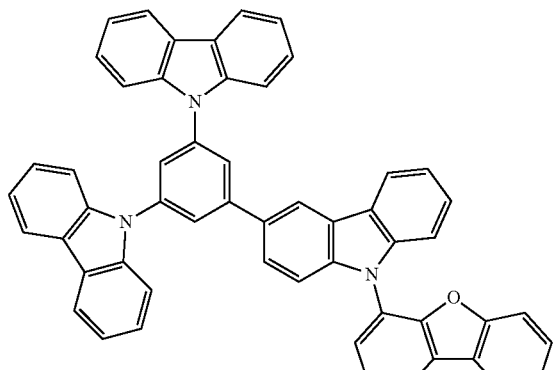
3-10
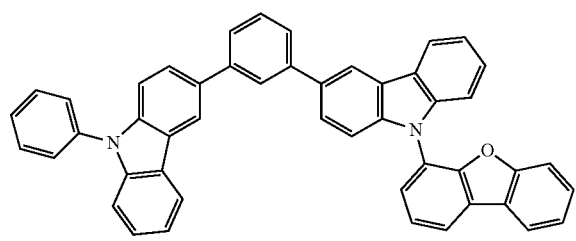
3-11
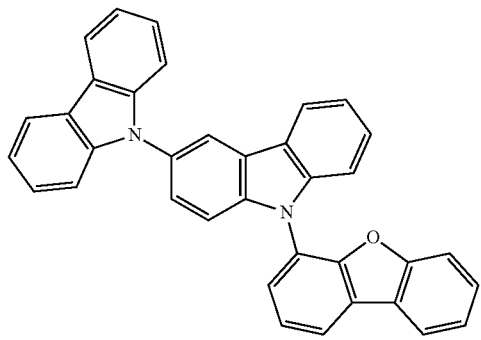
3-12
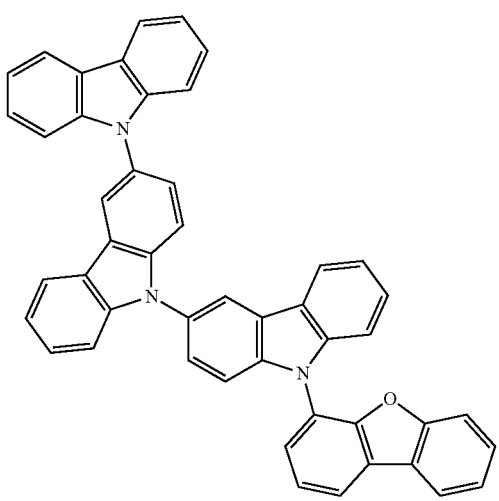
3-13
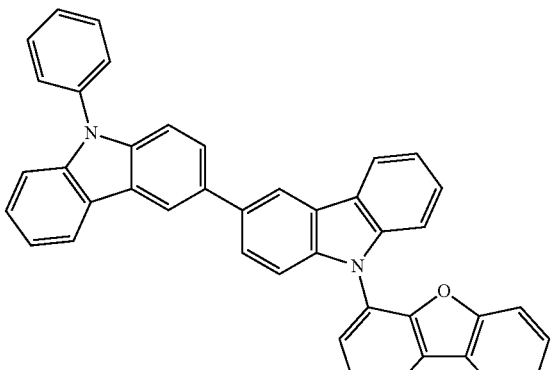
3-14
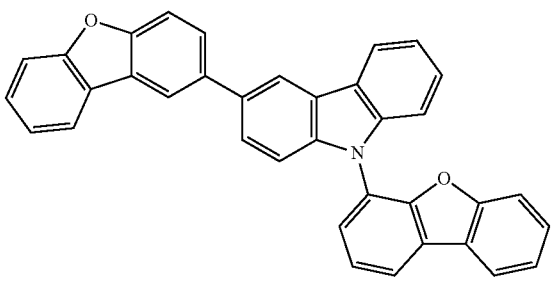
3-15
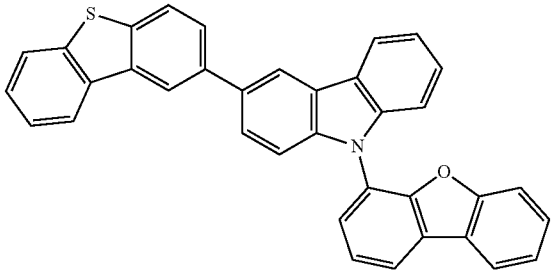
3-16
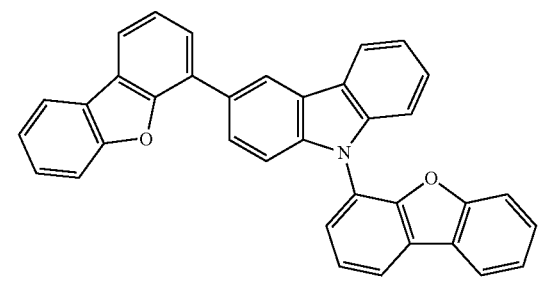
3-17
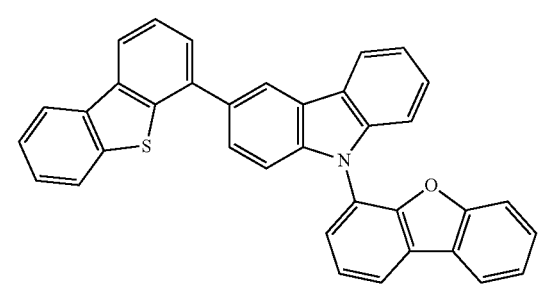

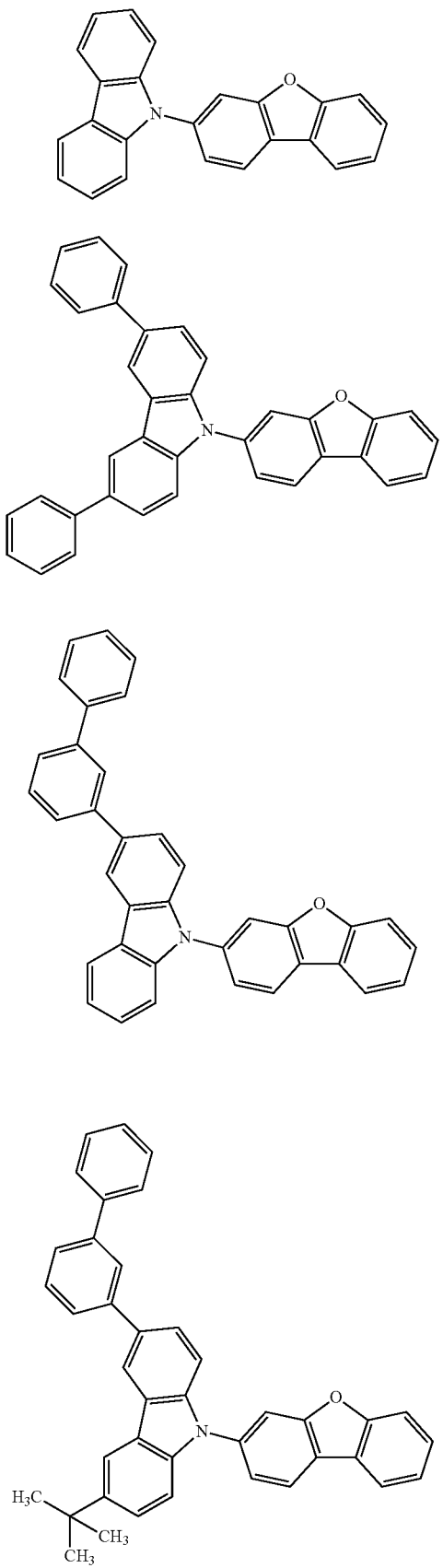
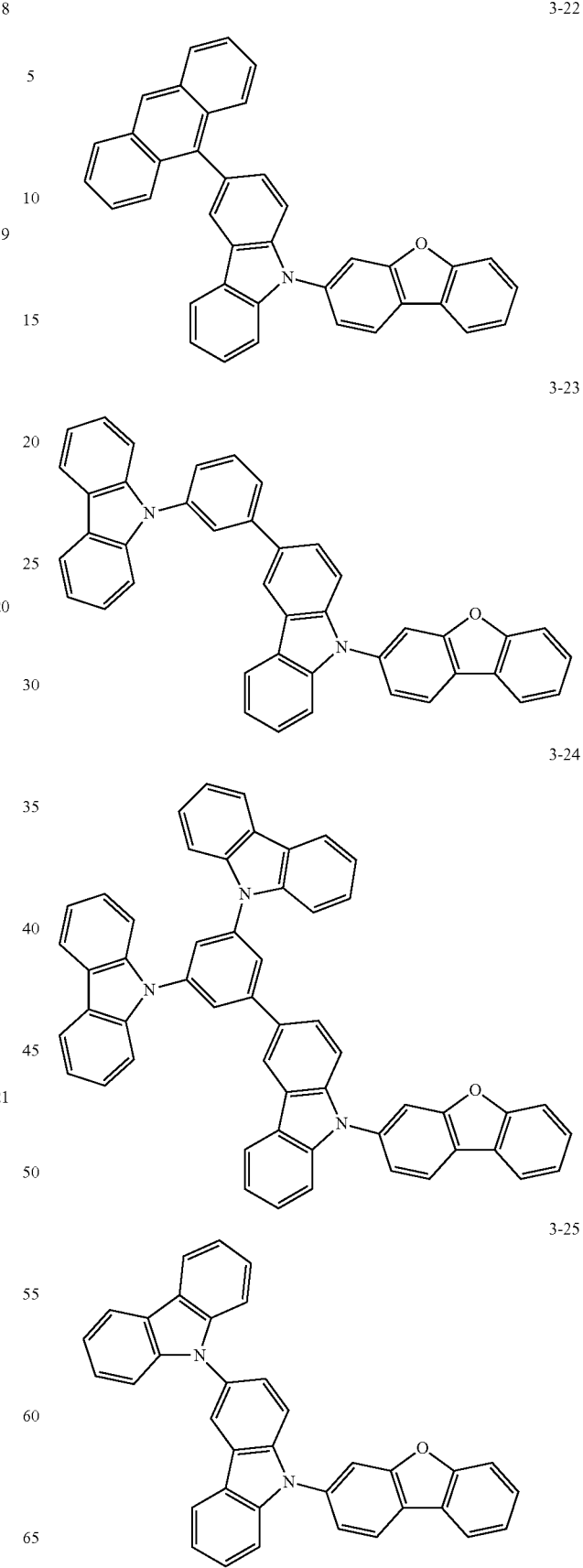

3-26
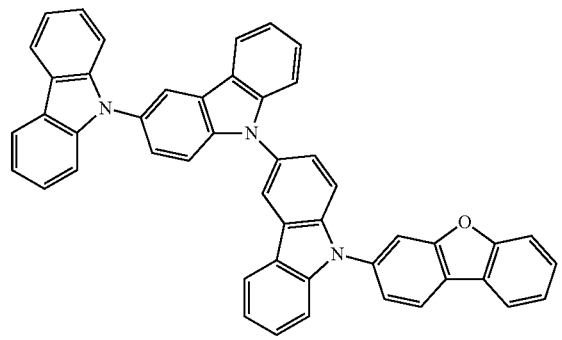
3-30
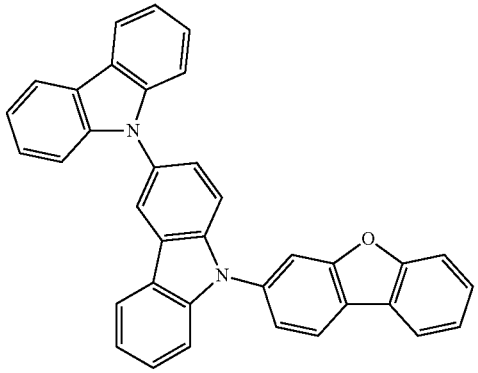
3-27
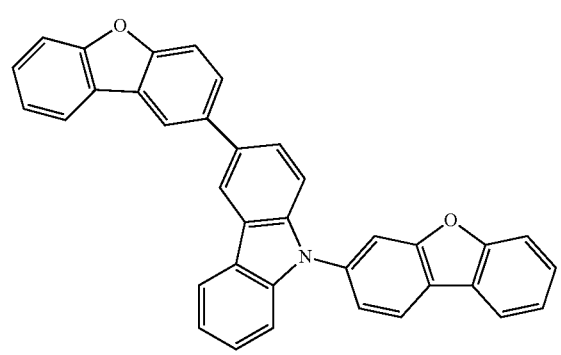
3-31
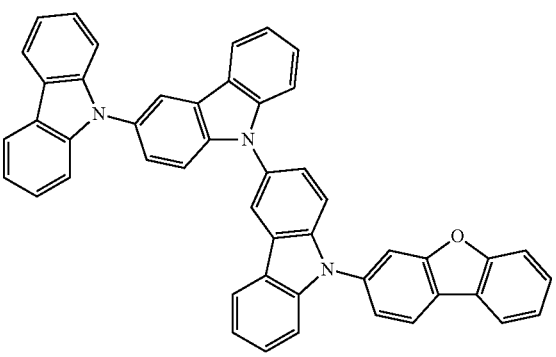
3-28
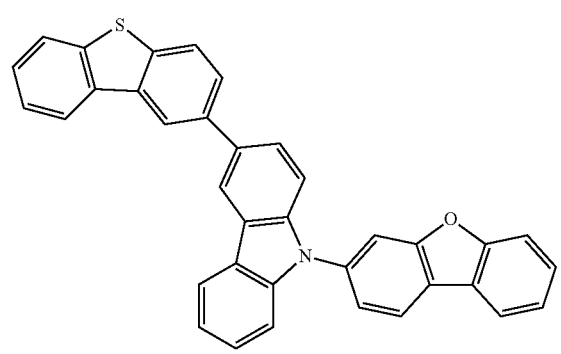
3-32
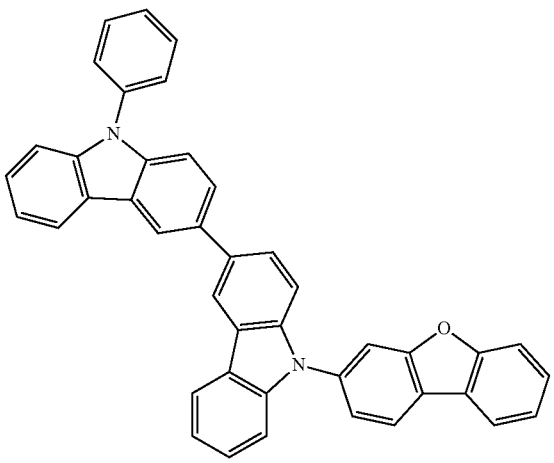
3-29
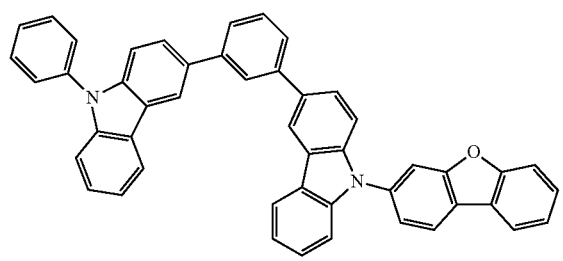
3-33
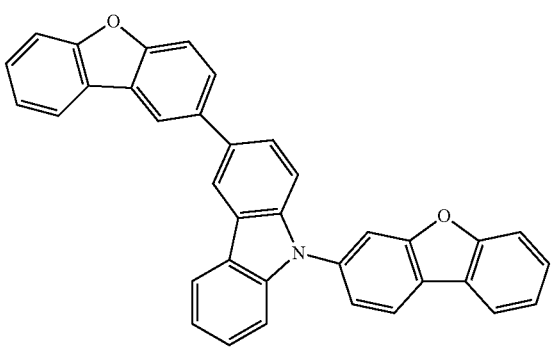

-continued
3-34
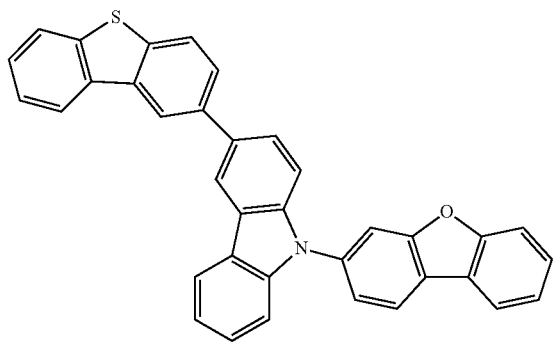
3-38
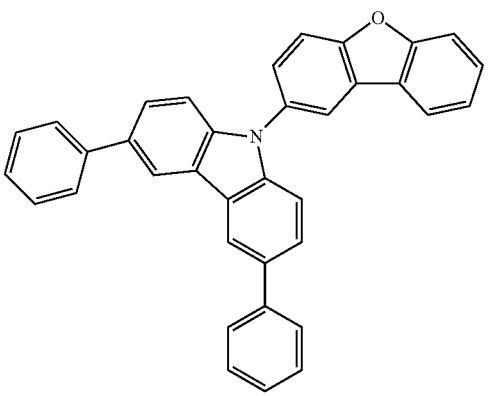
3-35
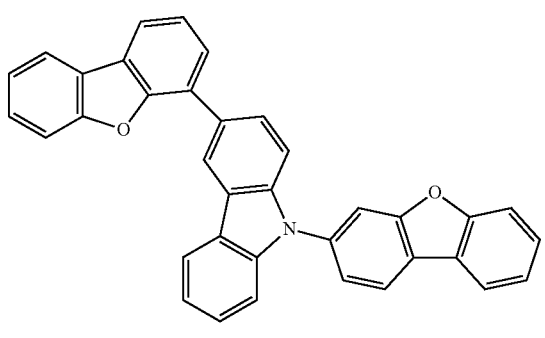
3-39
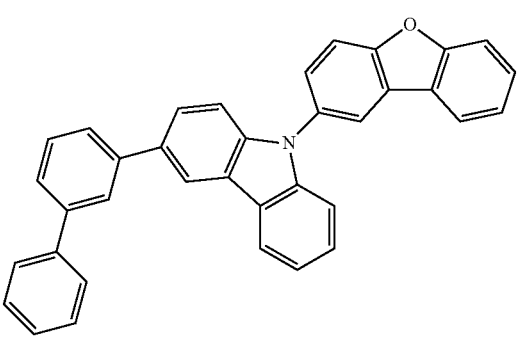
3-36
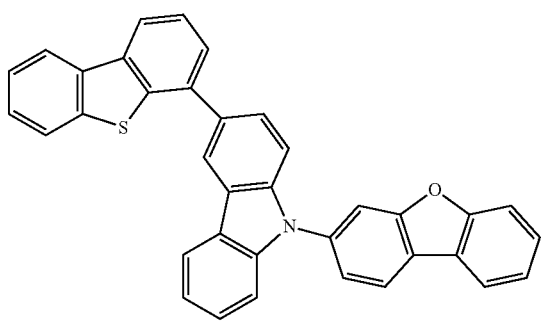
3-40
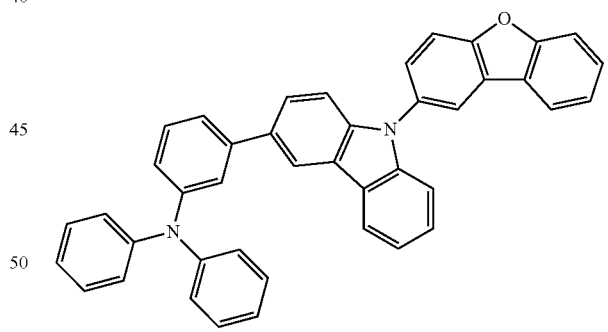
3-37
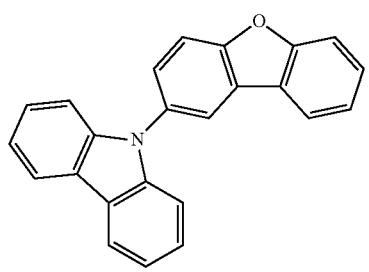
3-41
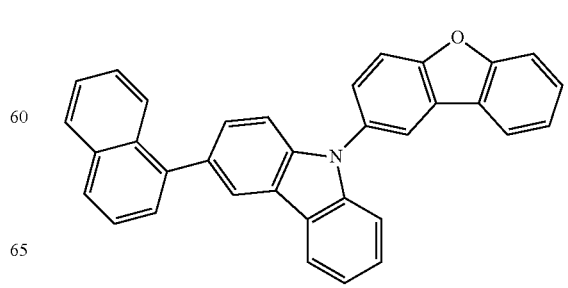

3-42
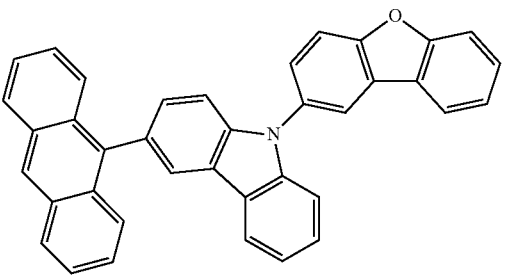
3-43
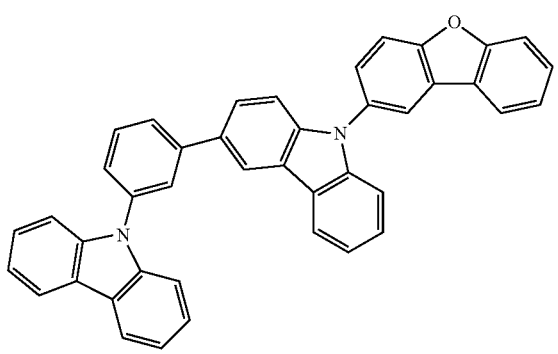
3-44
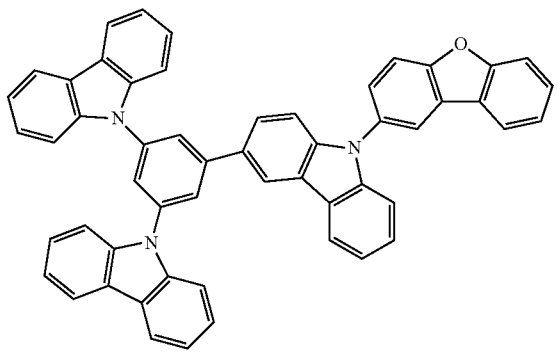
3-46
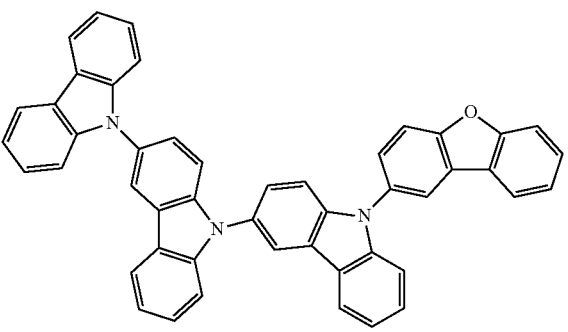
3-47
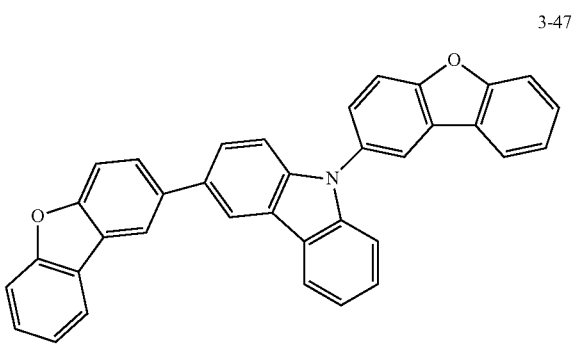
3-48
3-49
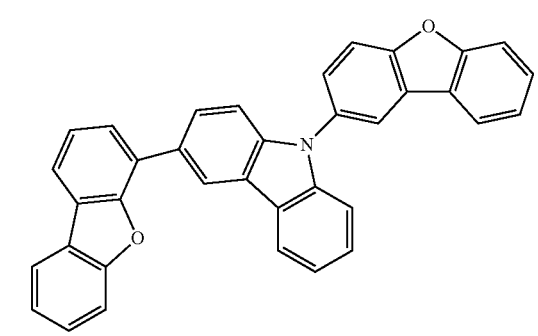
3-45

3-50
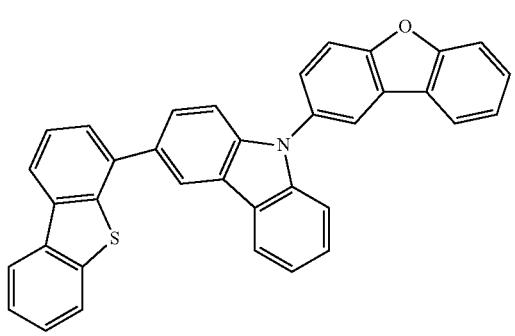
3-54
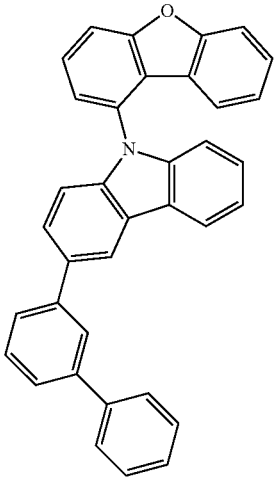
3-51
3-55
3-52
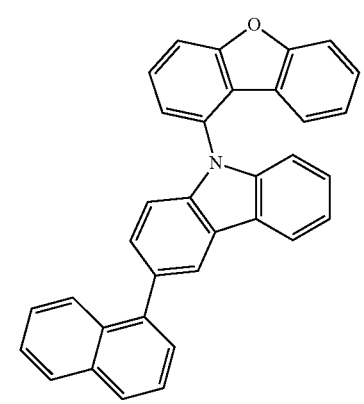
3-53
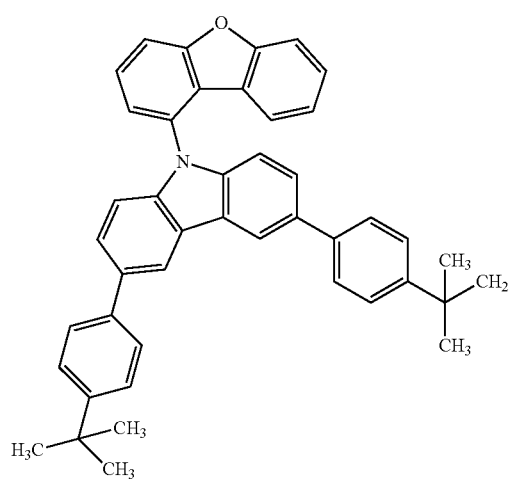
3-56
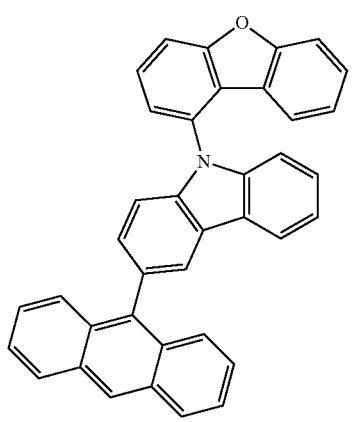

3-57
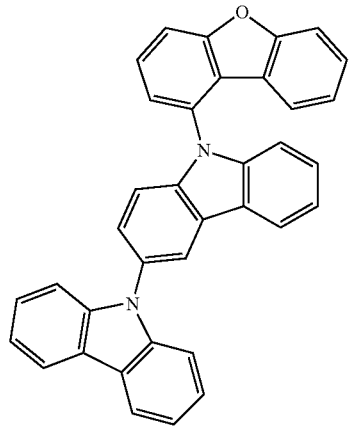
3-58
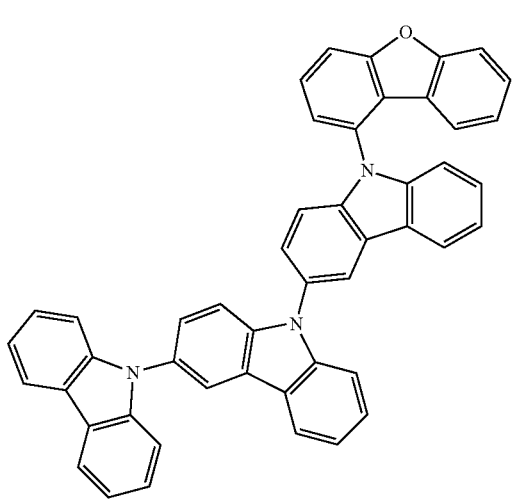
3-59
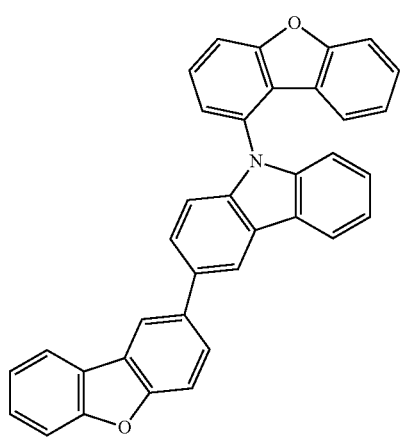
3-60
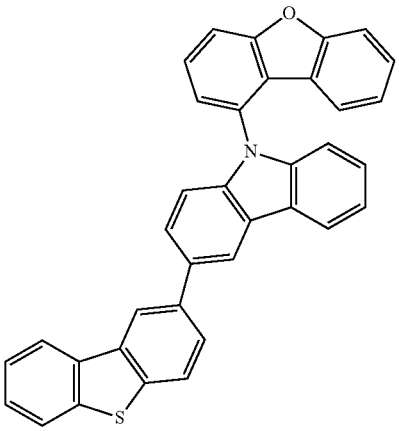
3-61
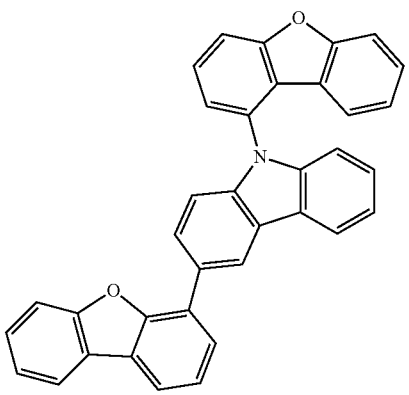
3-62
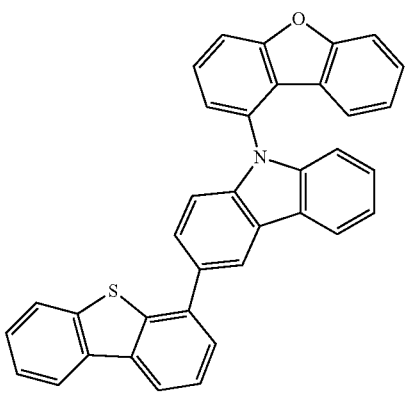
3-63
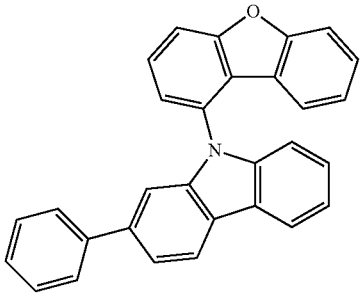

-continued
3-64
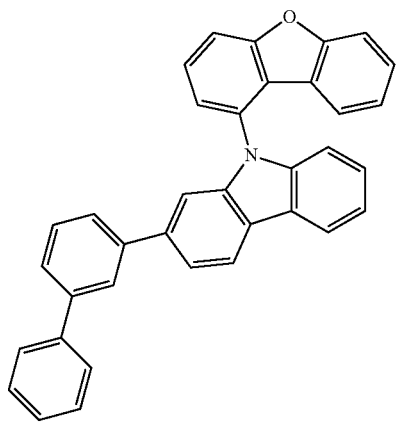
3-65
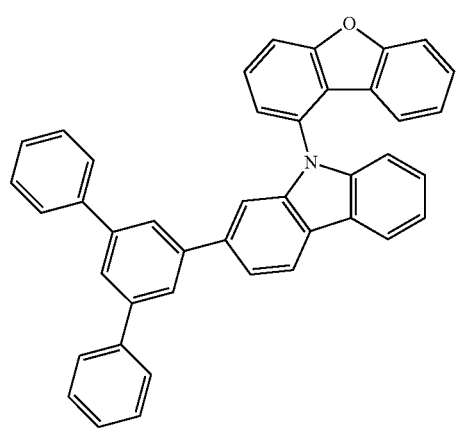
3-66
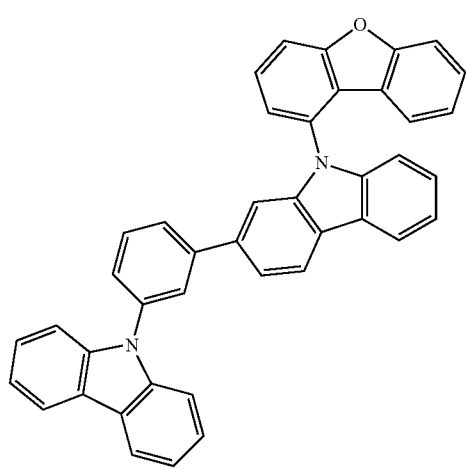
-continued
3-67
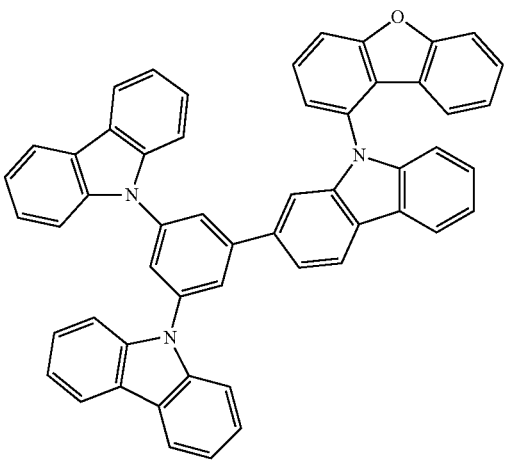
3-68
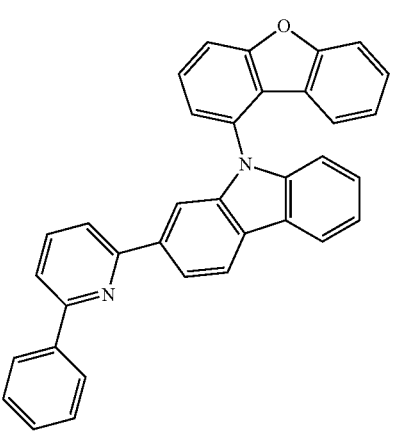
3-69
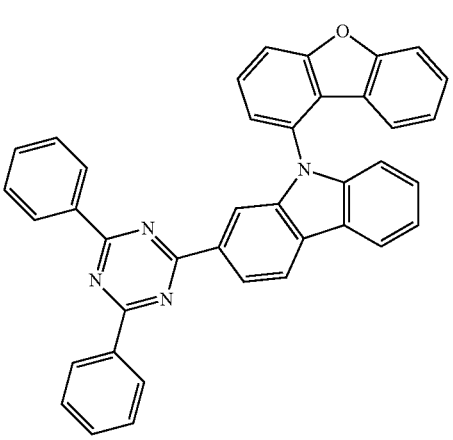

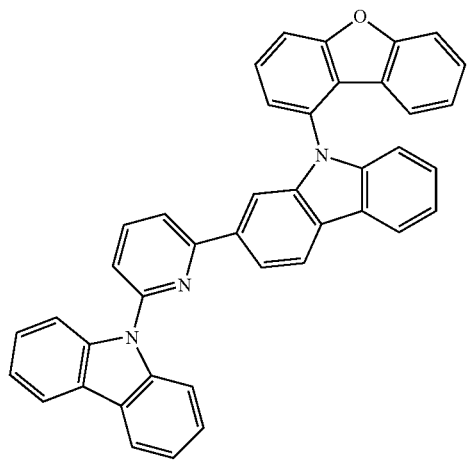
3-70
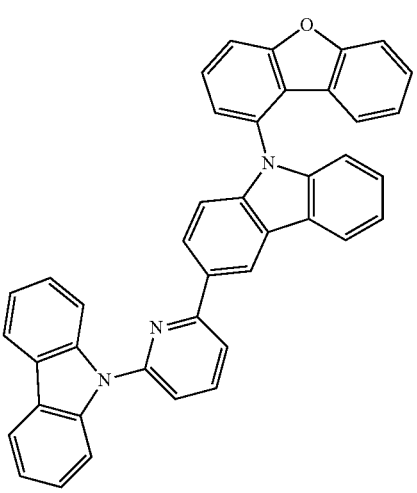
3-73
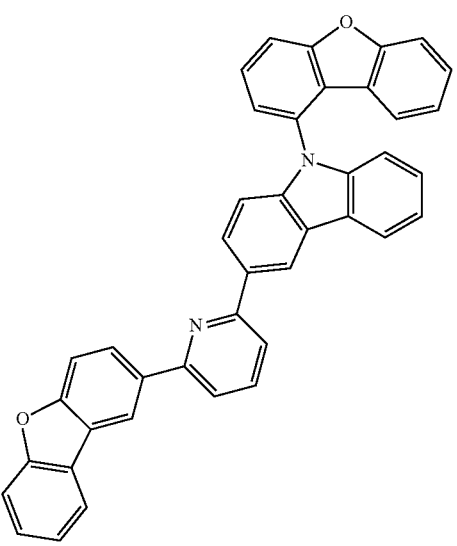
3-74
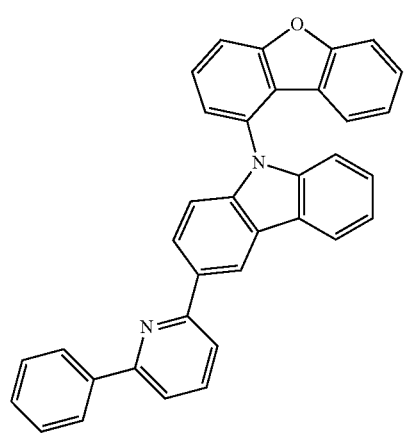
3-72

3-76
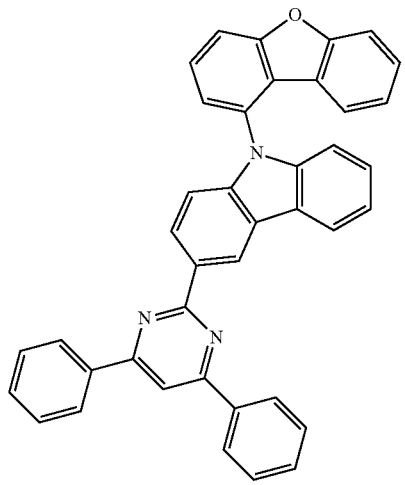
3-77
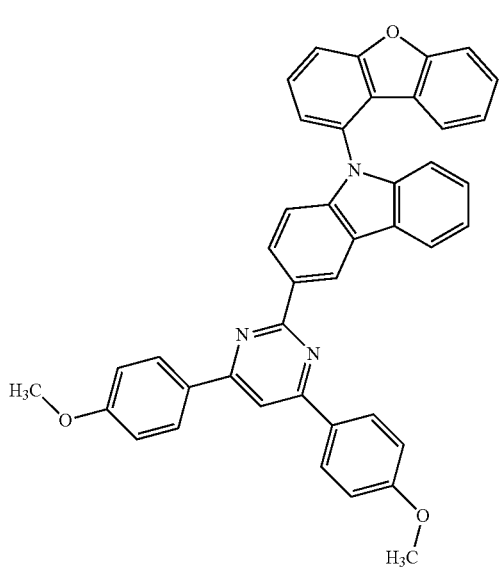
3-78
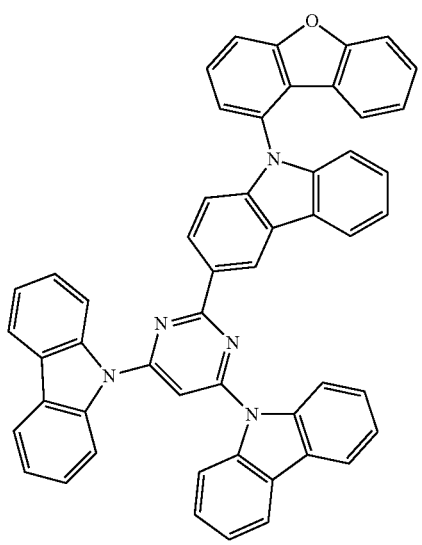
3-79
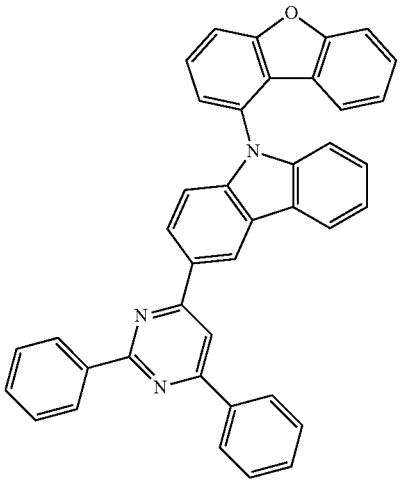
3-80
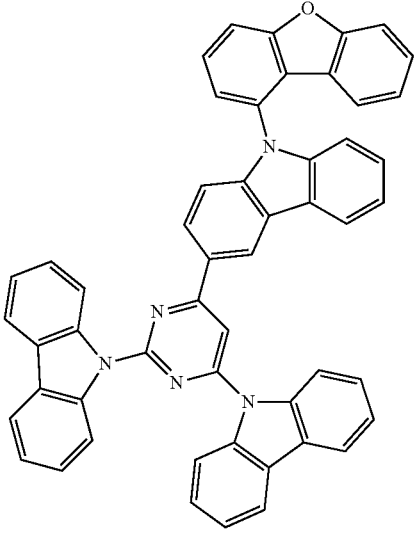
3-81
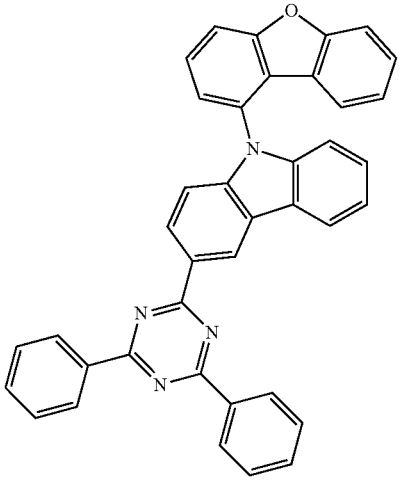

3-82
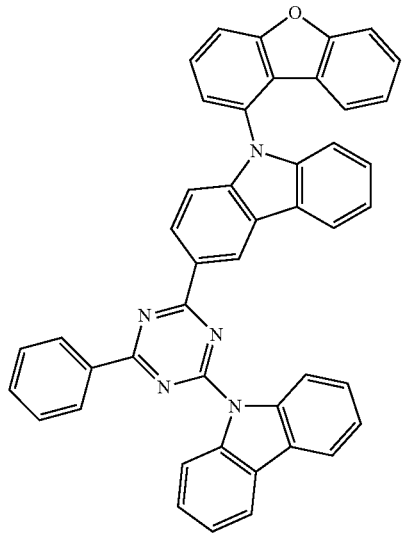
3-83
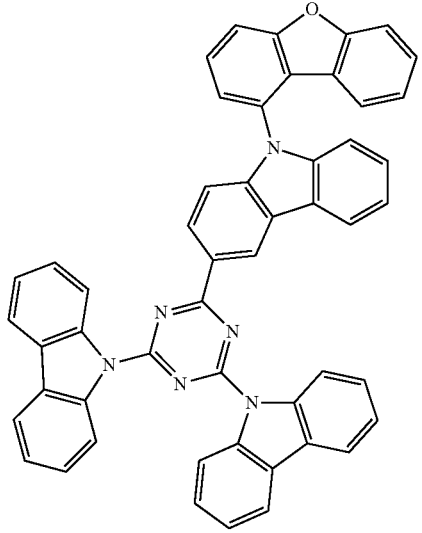
3-84
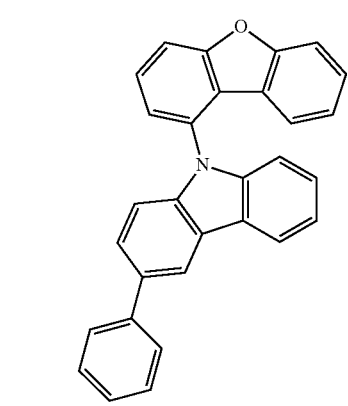
3-85
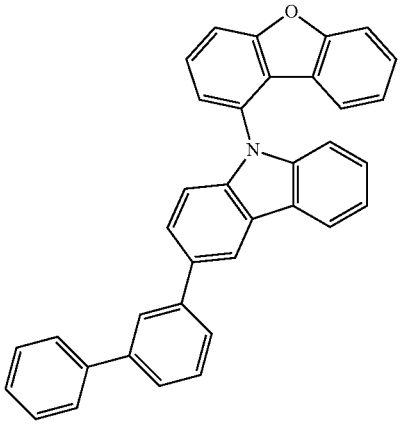
3-86
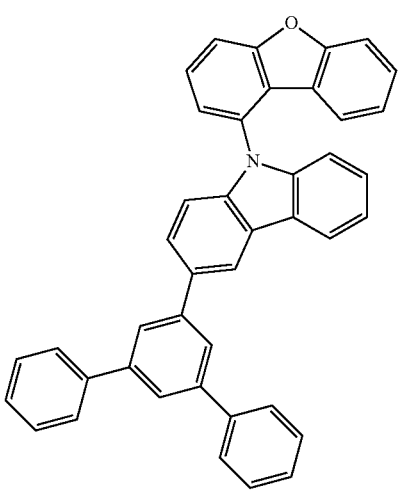
3-87
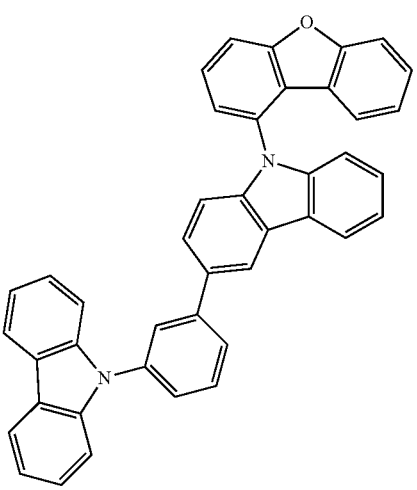

3-88
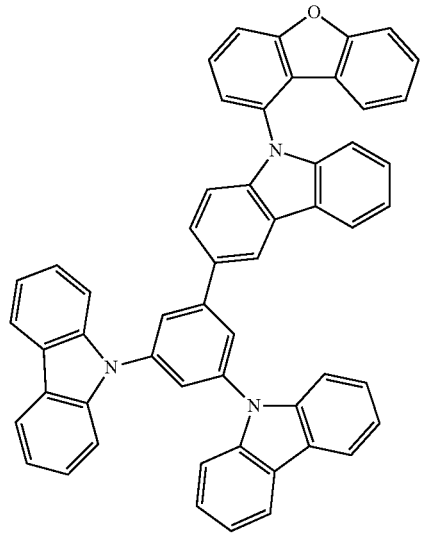
3-89
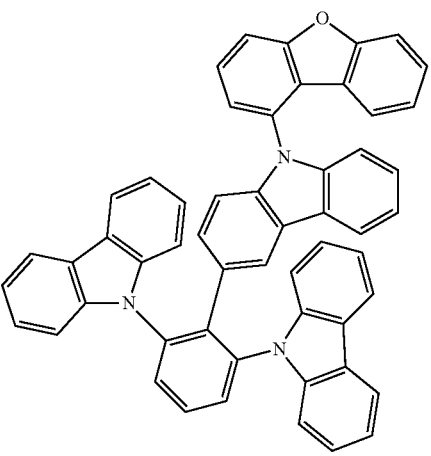
3-90
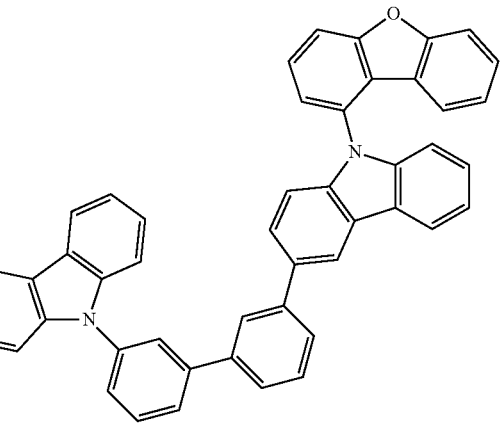
3-91
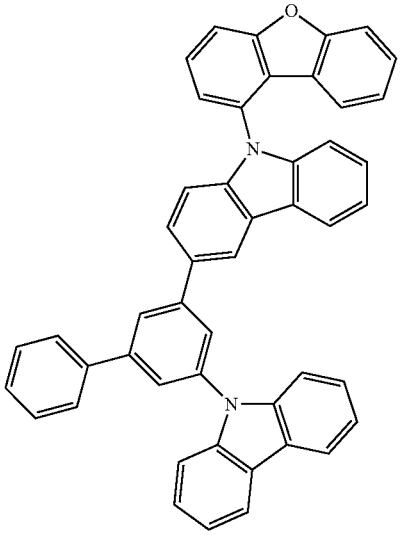
3-92
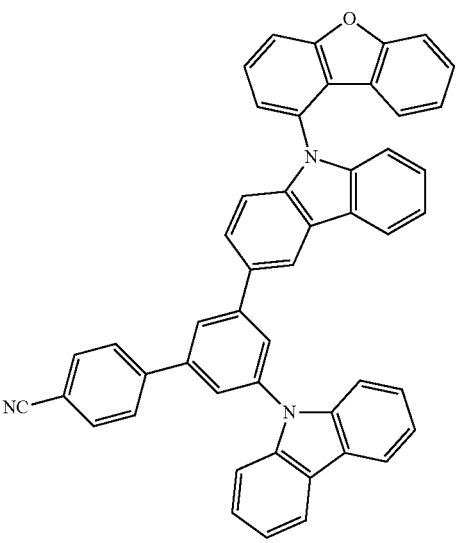
3-93
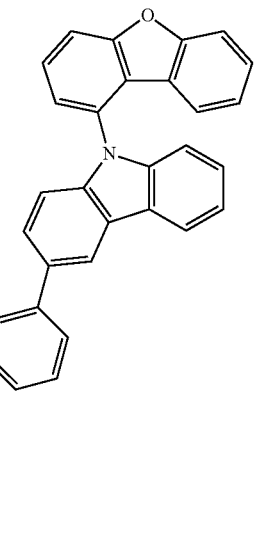

3-94
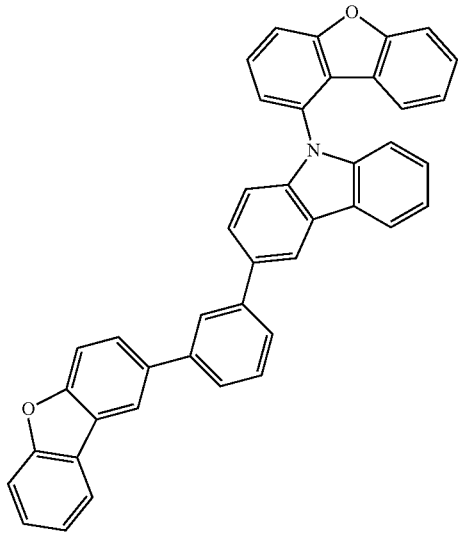
3-95
3-96
3-97
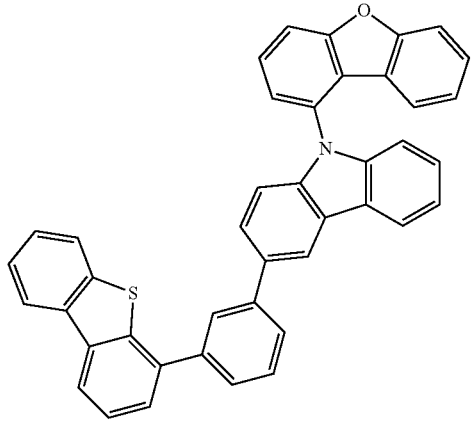
3-98
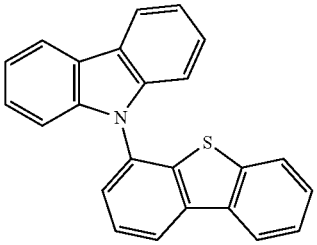
3-99
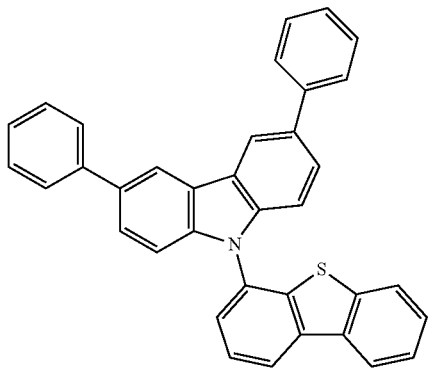
3-100
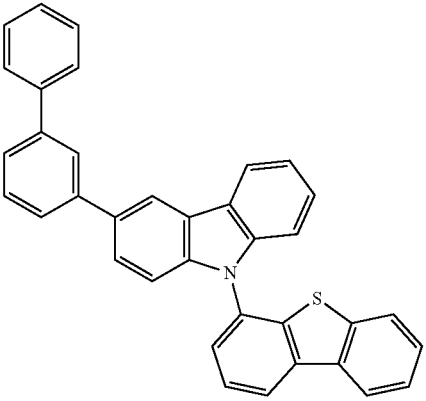

3-101
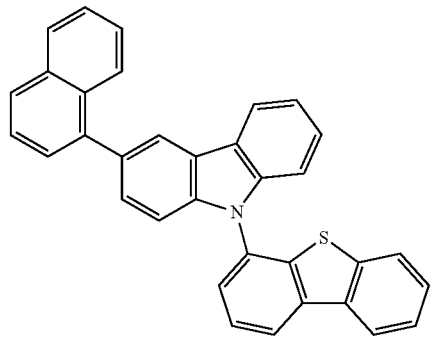
3-102
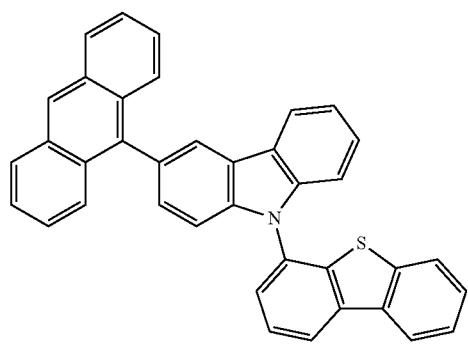
3-103
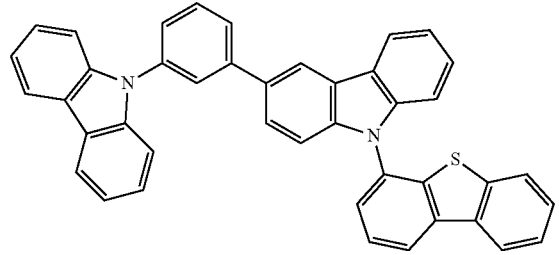
3-104
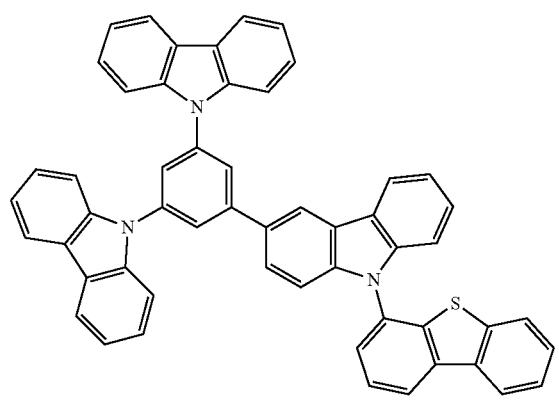
3-105
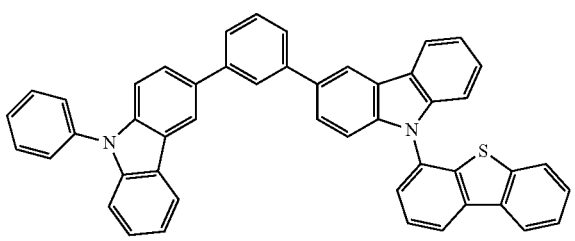
3-106
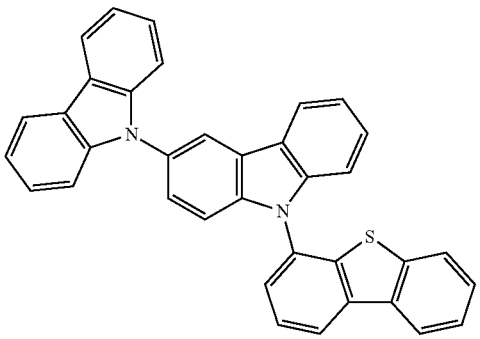
3-107
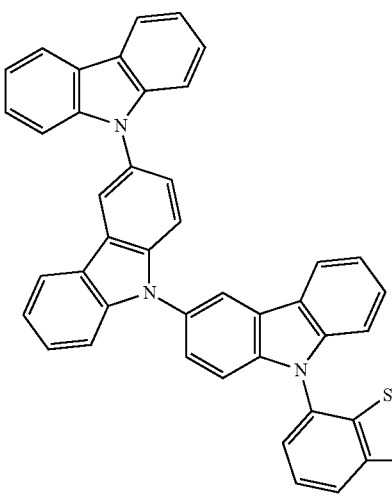
3-108
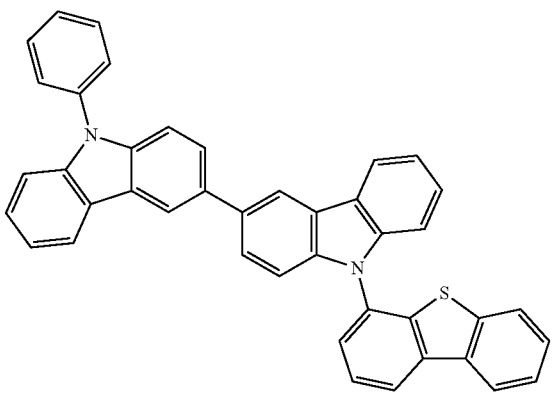
3-109
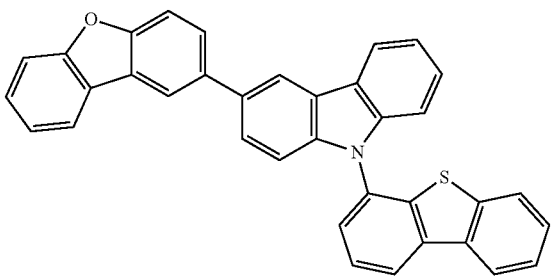

3-110
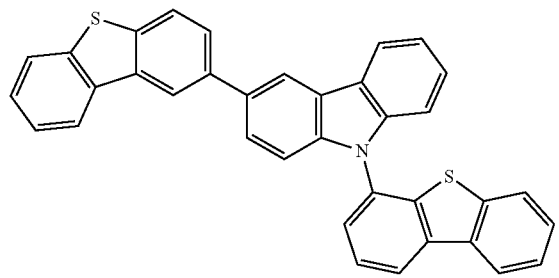
3-111
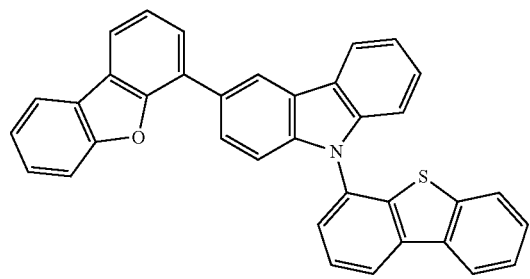
3-112
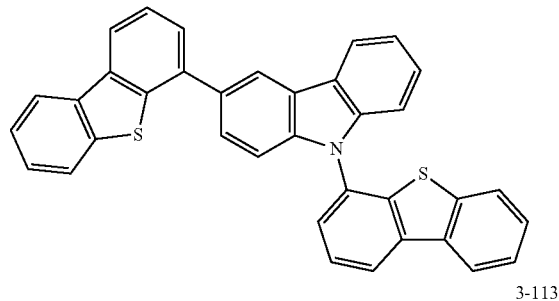
3-113
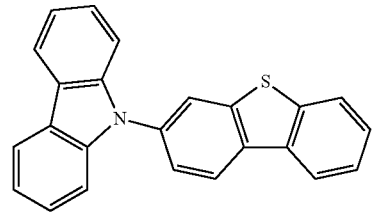
3-114
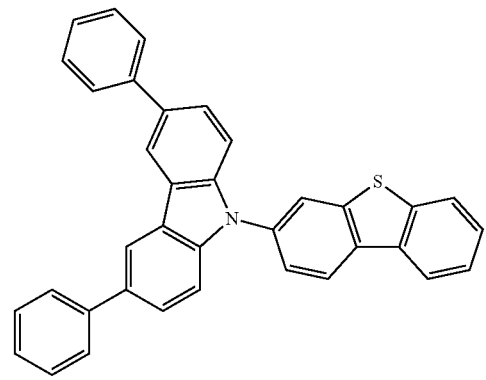
3-115
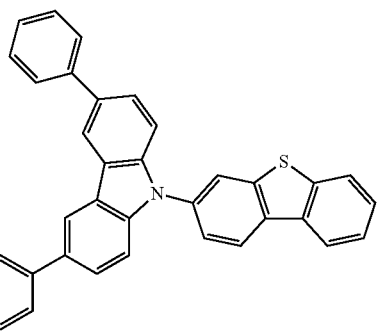
3-116
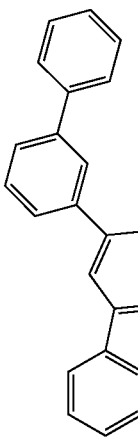
3-117
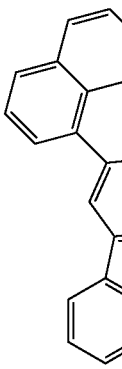
3-118
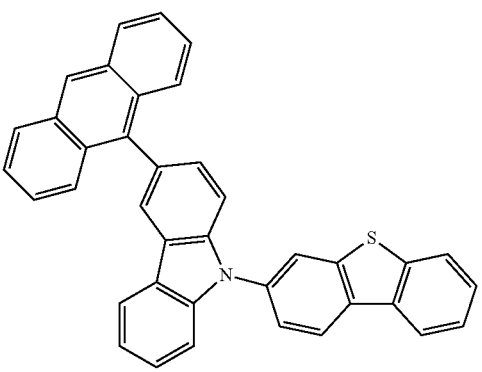

3-119
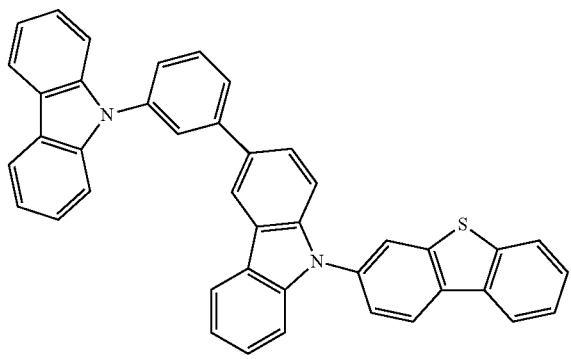
3-120
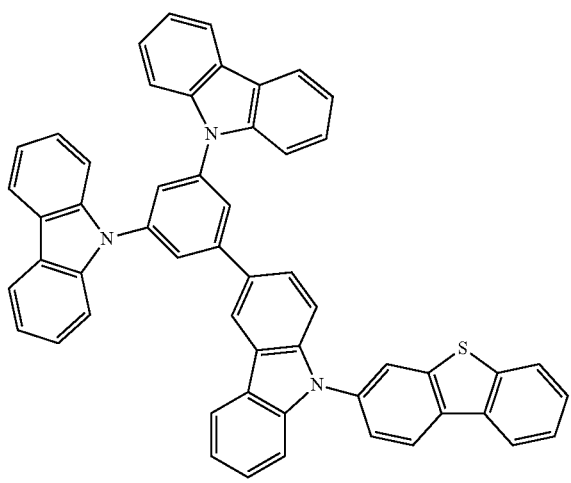
3-121
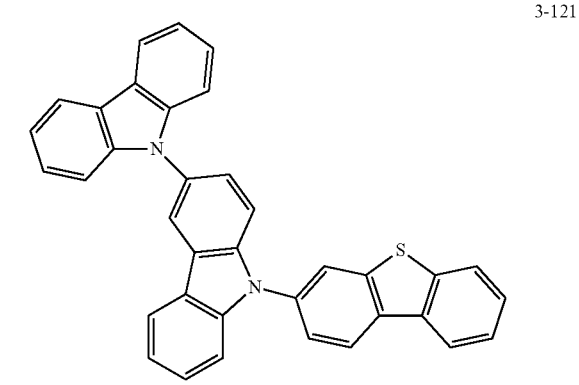
3-122
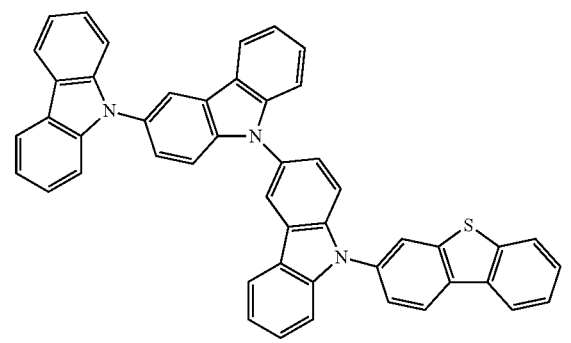
3-123
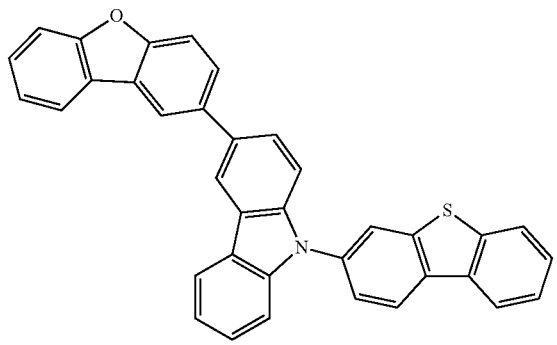
3-124
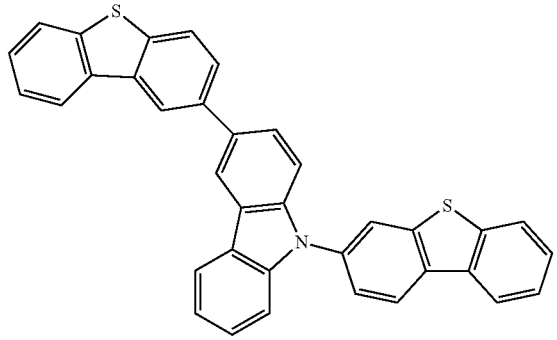
3-125
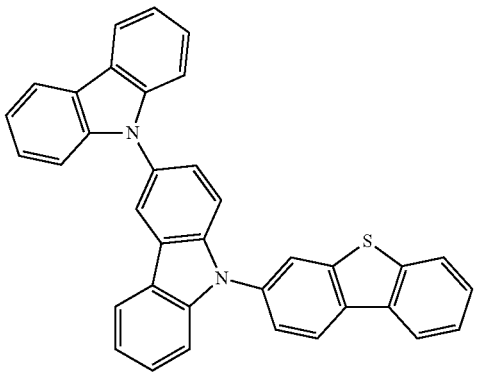
3-126
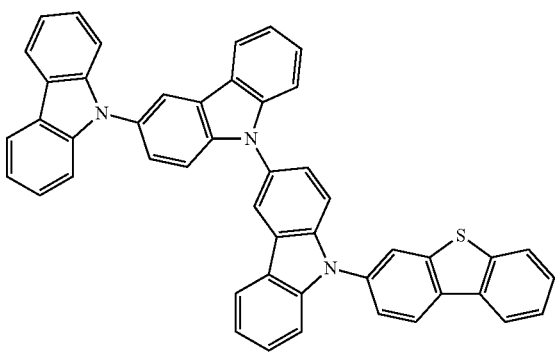

3-127
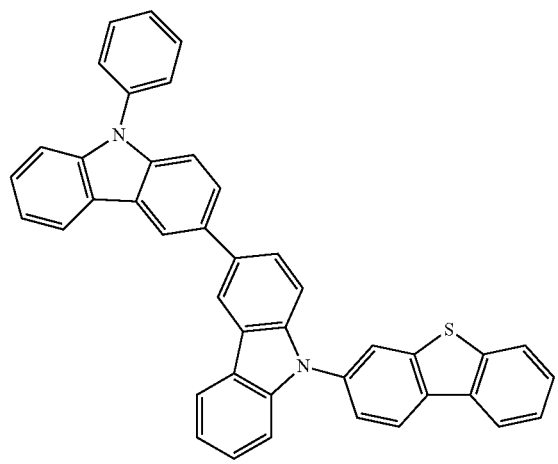
3-128
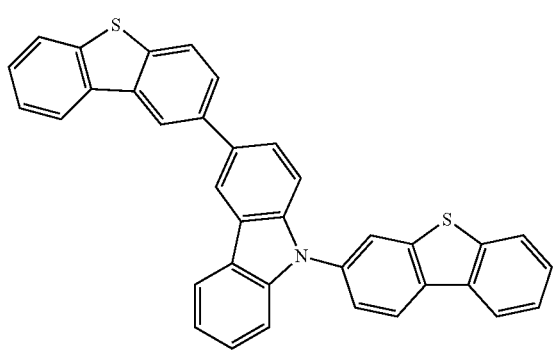
3-129
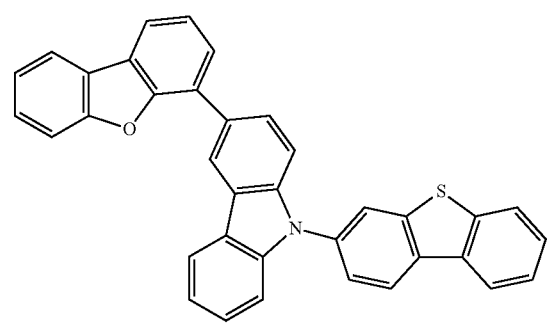
3-130
3-131
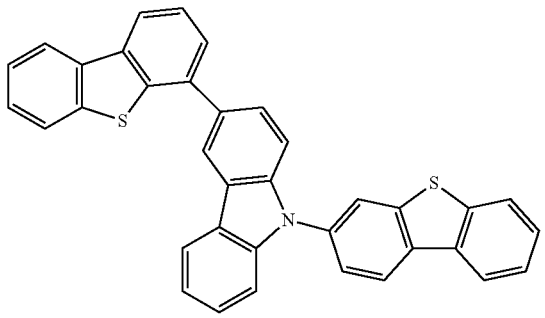
3-132
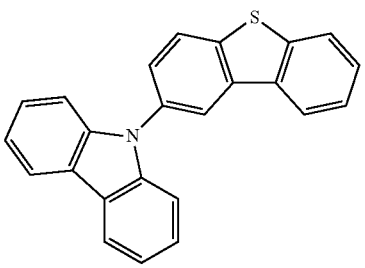
3-133
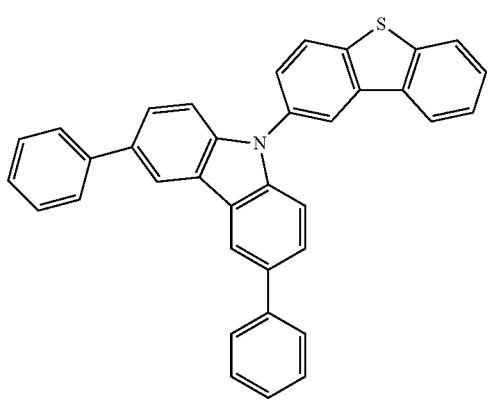
3-134
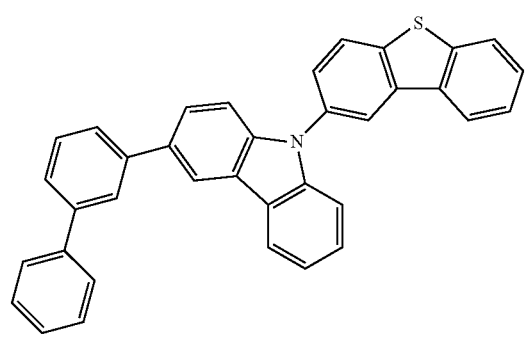
3-135
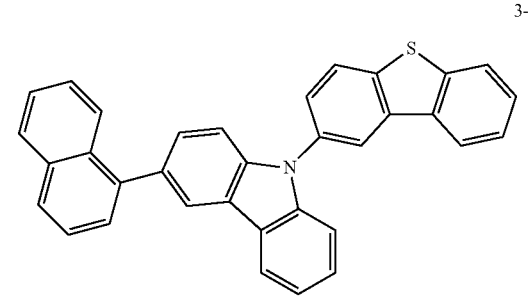

3-136
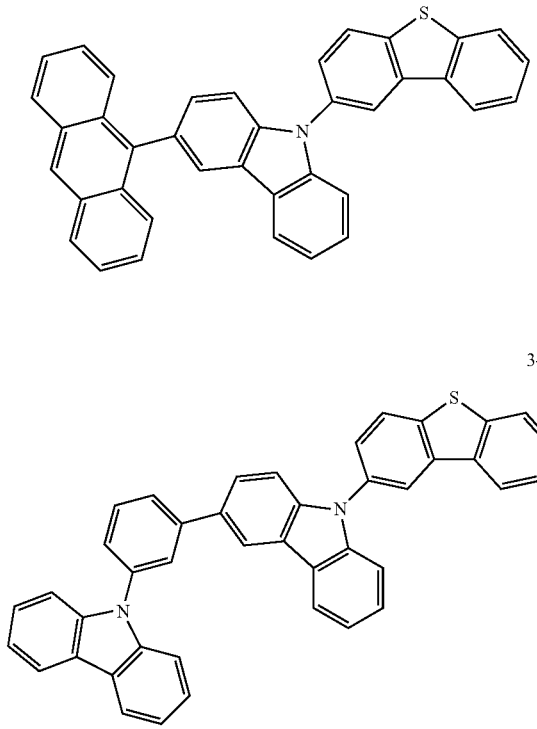
3-137
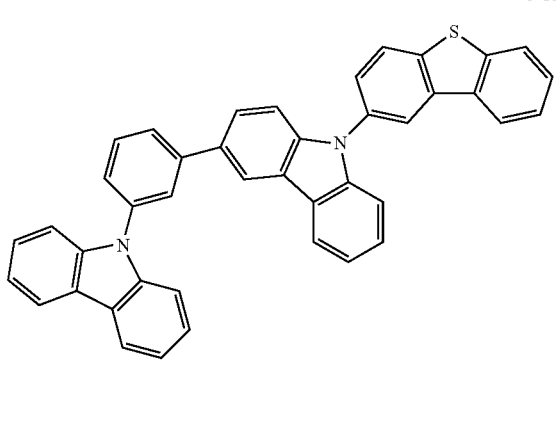
3-138
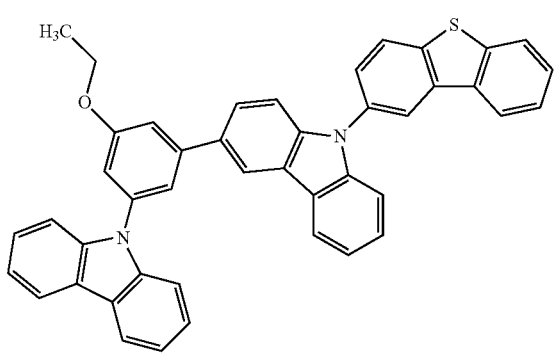
3-139
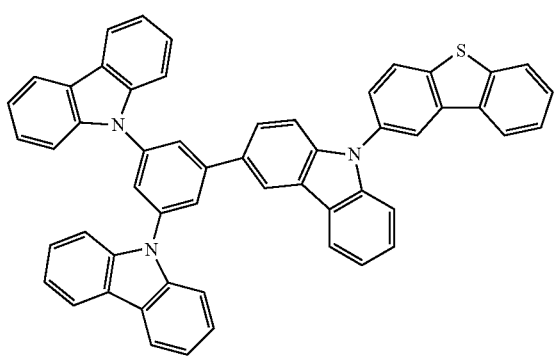
3-140
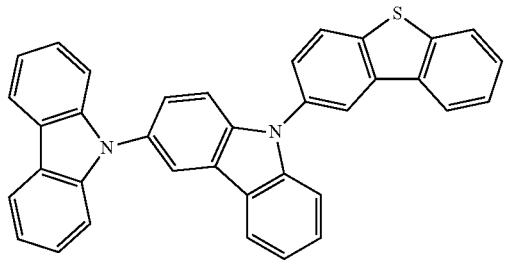
3-141
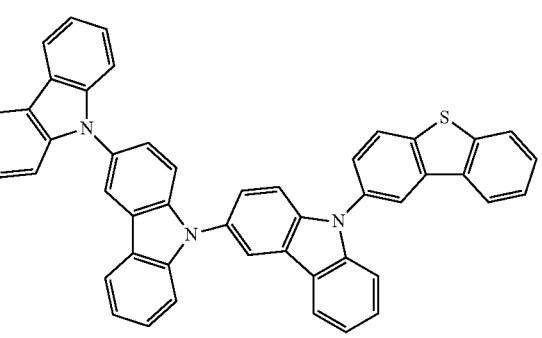
3-142
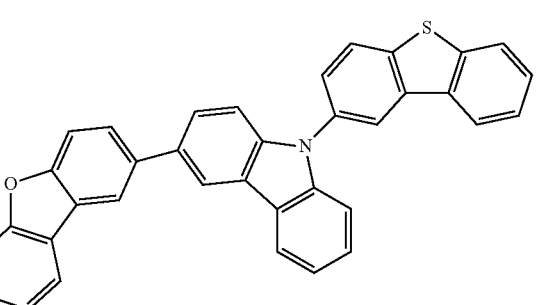
3-143
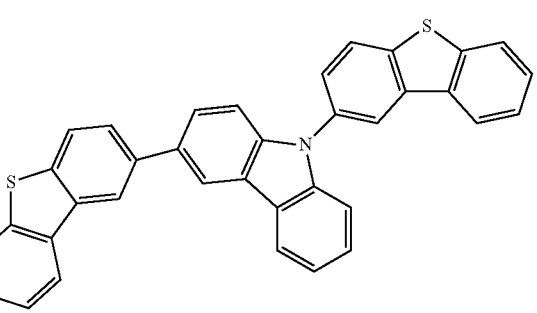
3-144
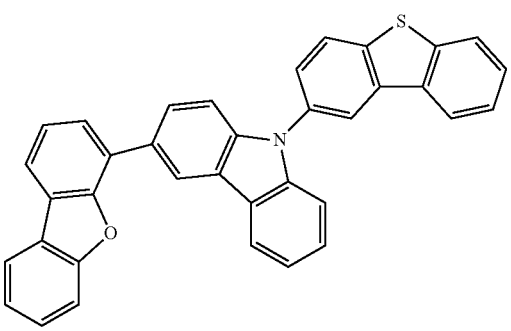

3-145
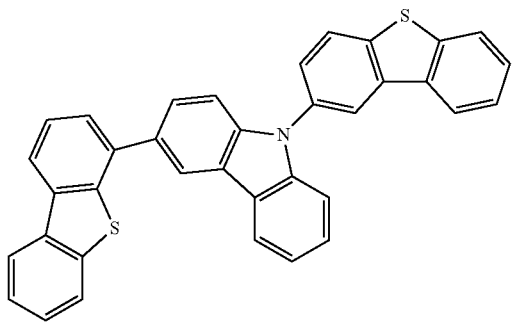
3-146
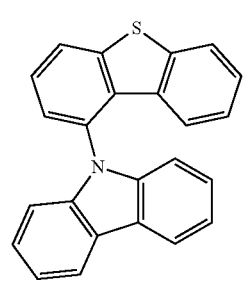
3-147
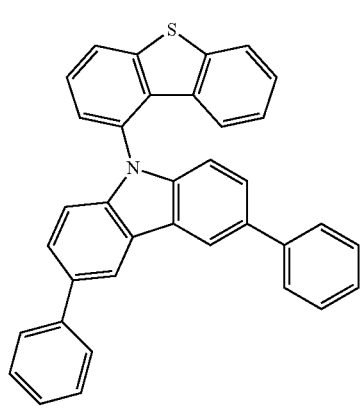
3-148
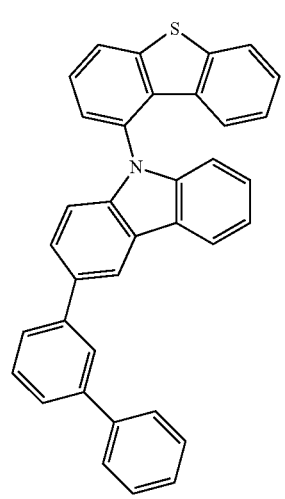
3-149
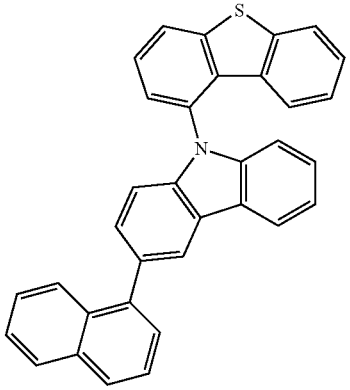
3-150
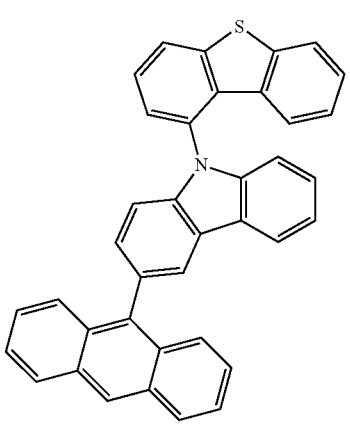
3-151

3-153
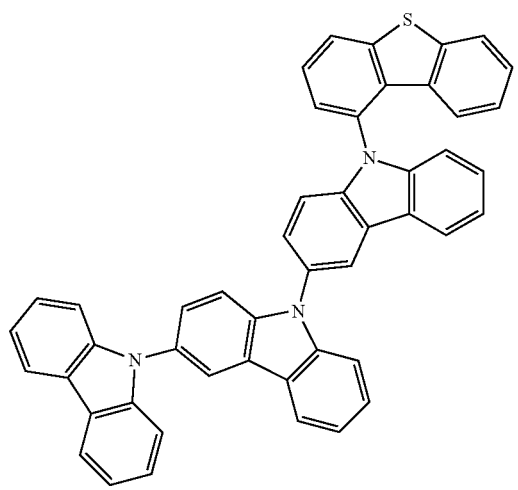
3-154
3-155
3-156
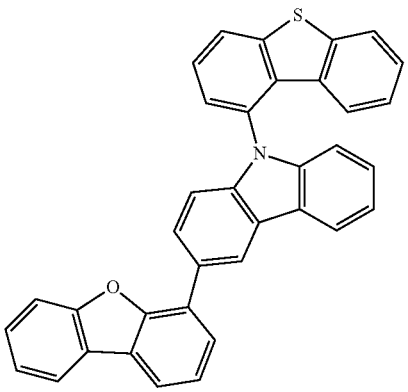
3-157
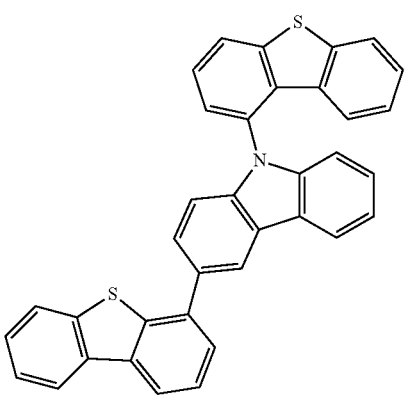
3-158
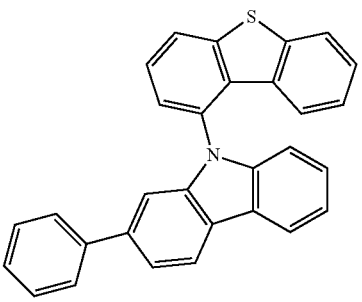
3-159
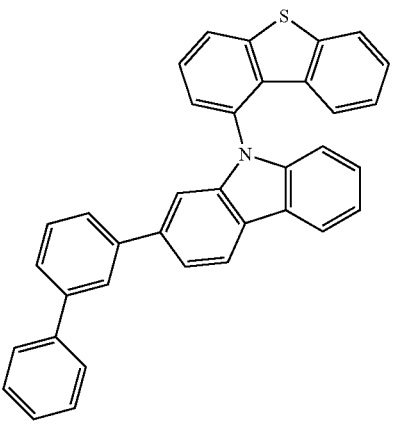

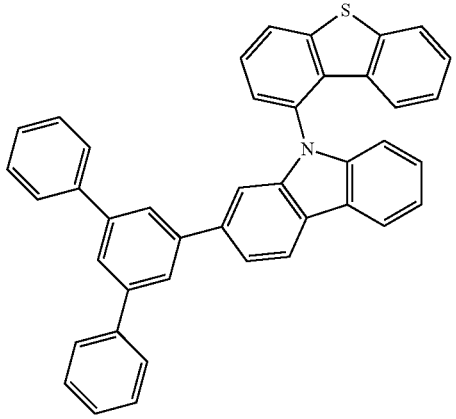
3-160
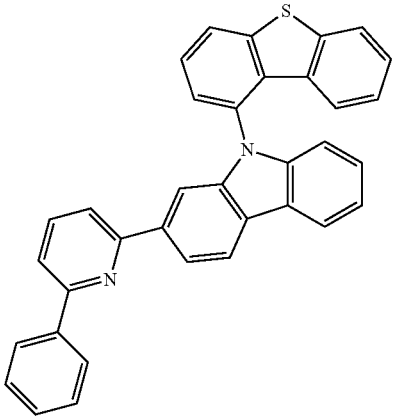
3-163
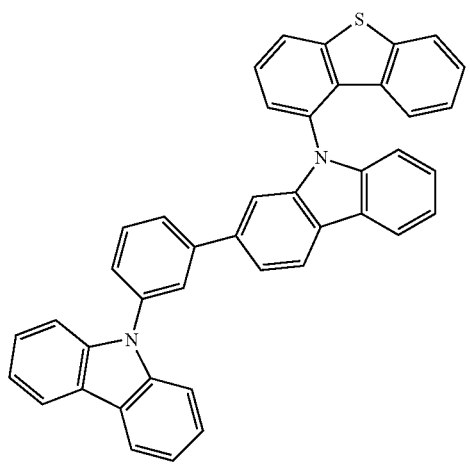
3-161
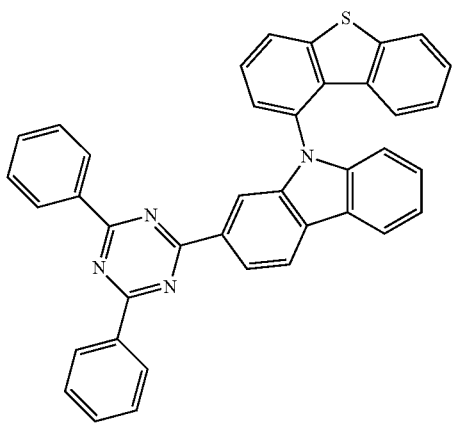
3-164
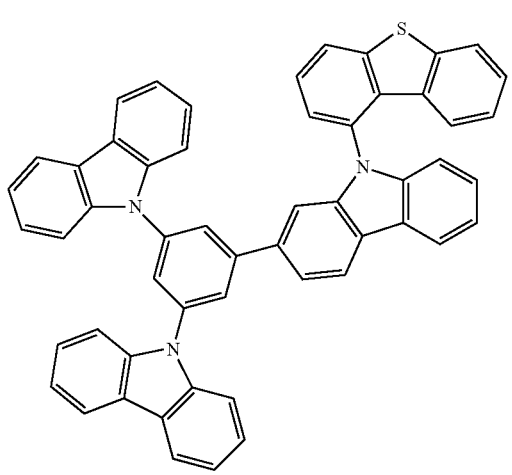
3-162
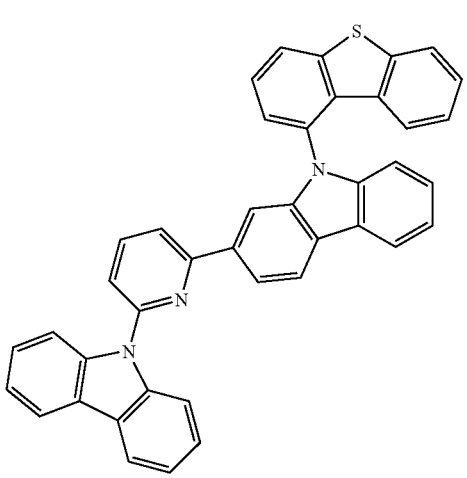
3-165

3-166
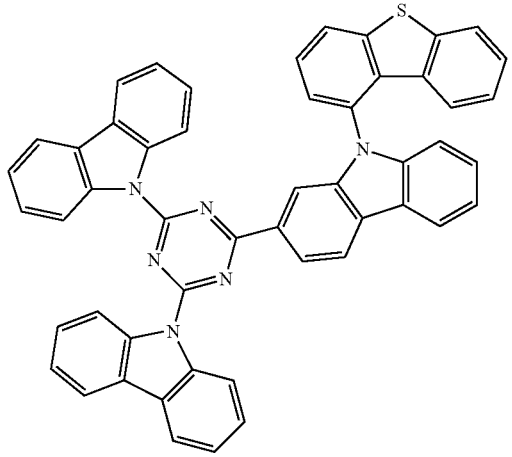
3-167
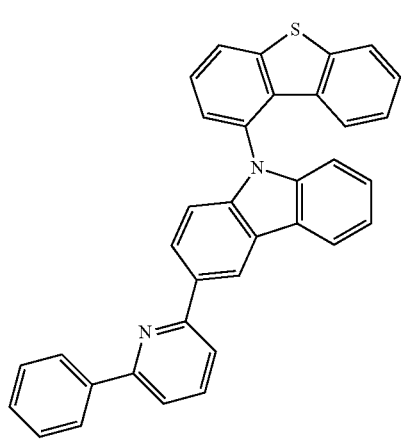
3-168
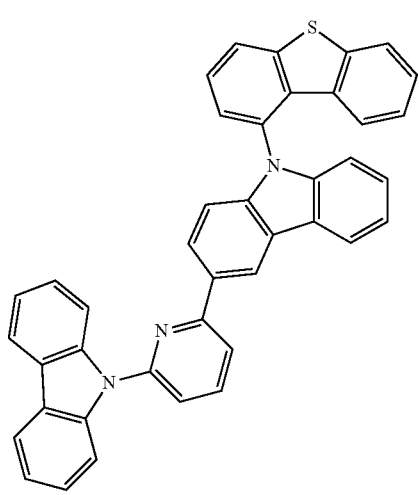
3-169
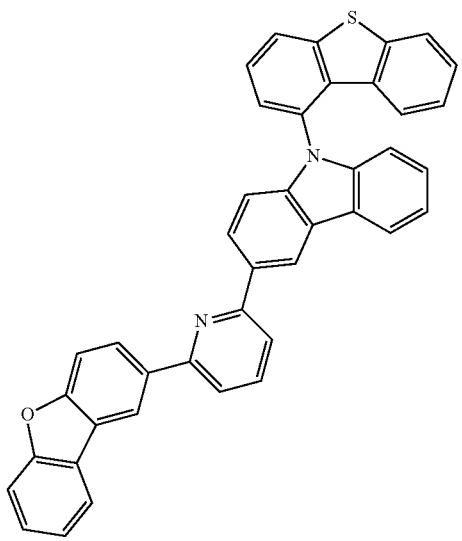
3-170
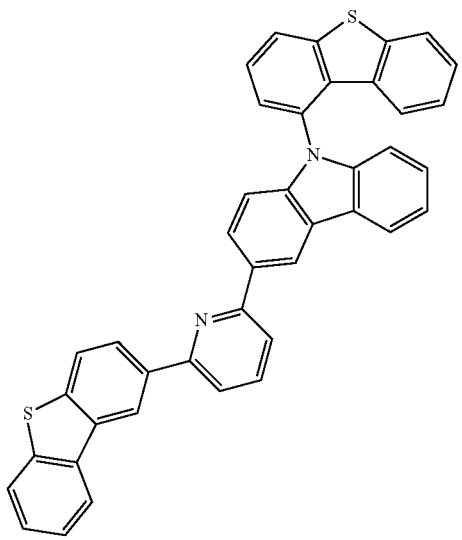
3-171
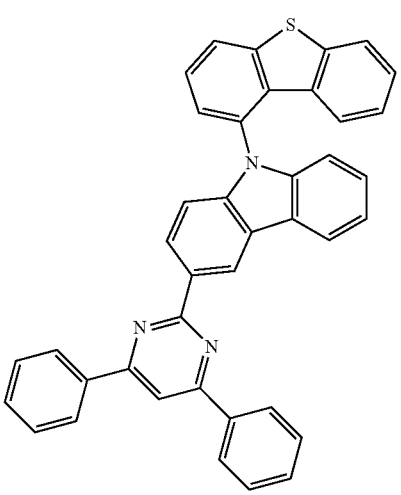

3-172
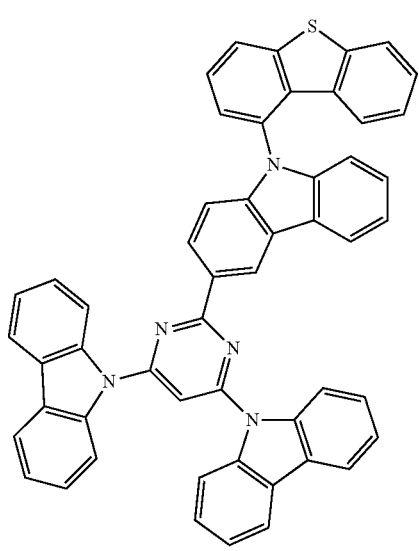
3-173
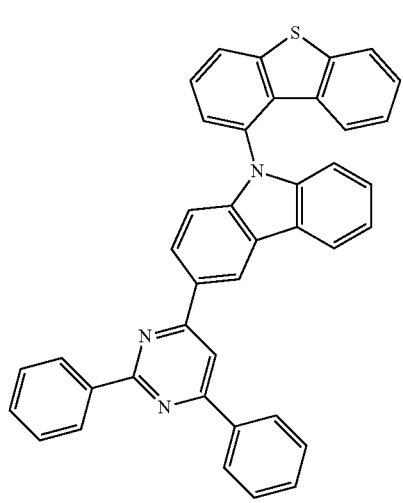
3-174
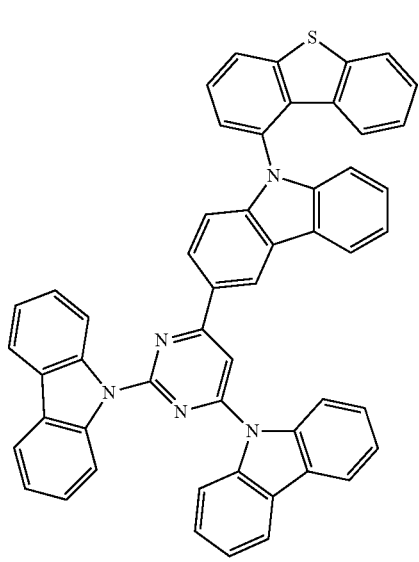
3-175
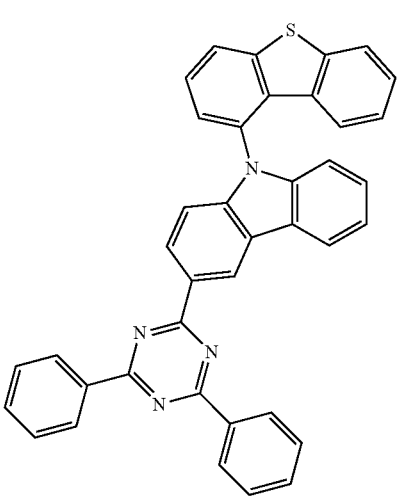
3-176
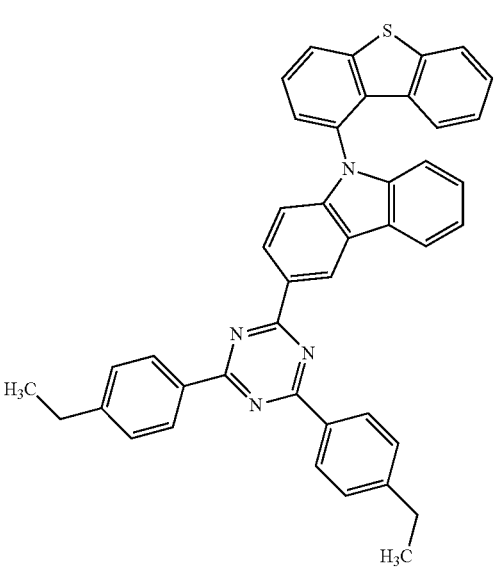
3-177
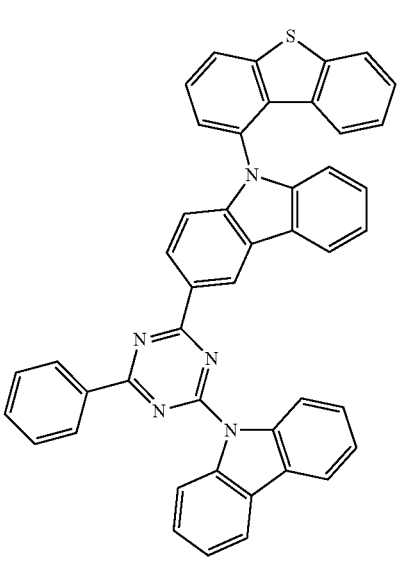

3-178
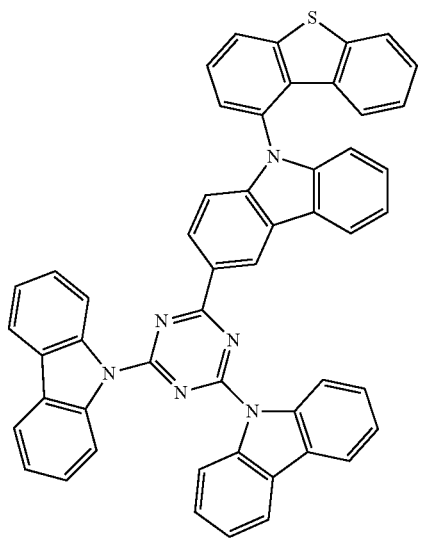
3-179
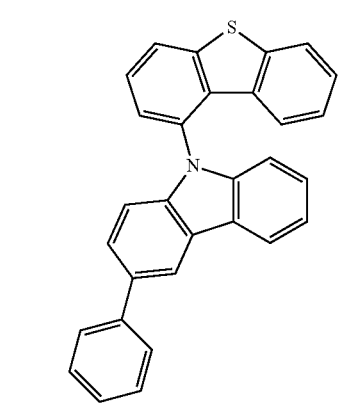
3-180
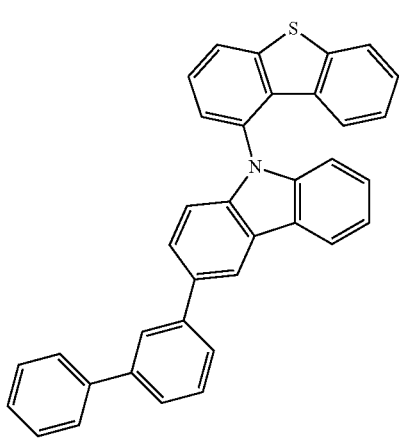
3-181
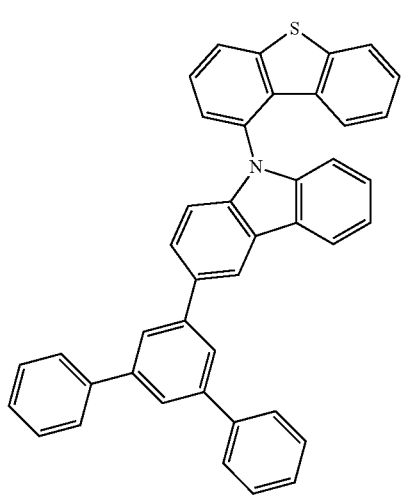
3-182
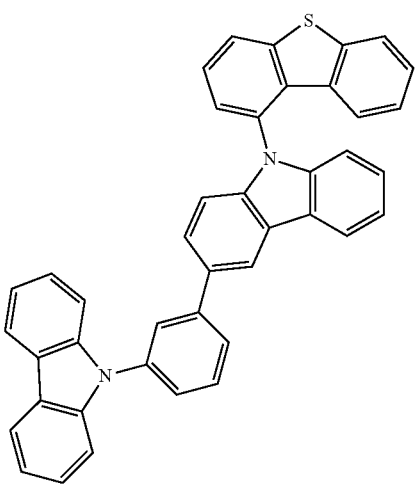
3-183
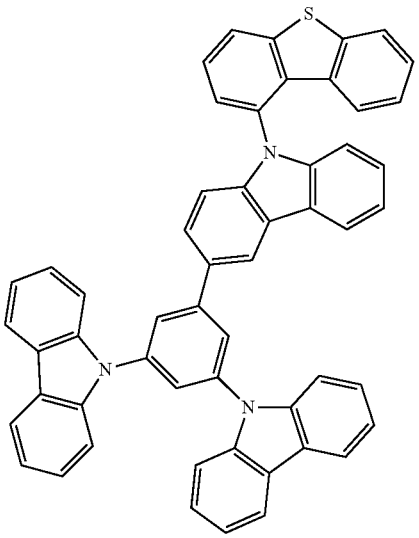

3-184
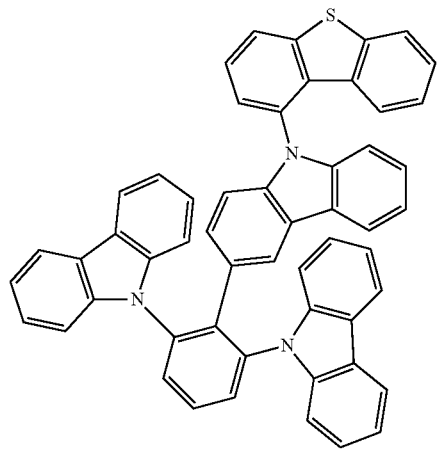
3-185
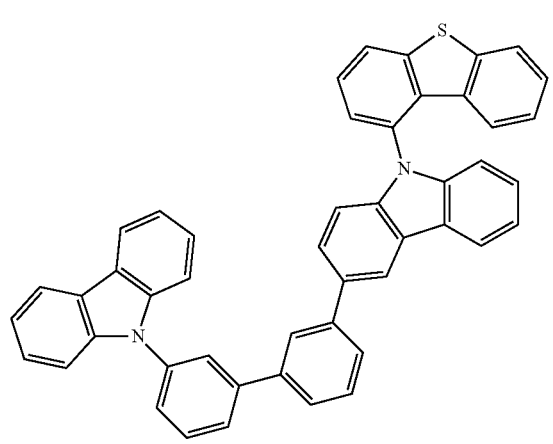
3-186
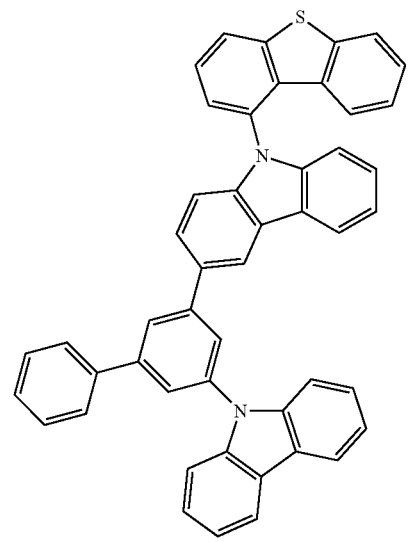
3-187
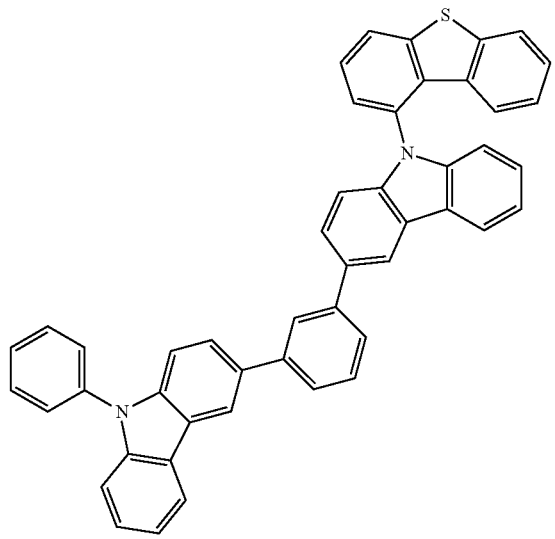
3-188
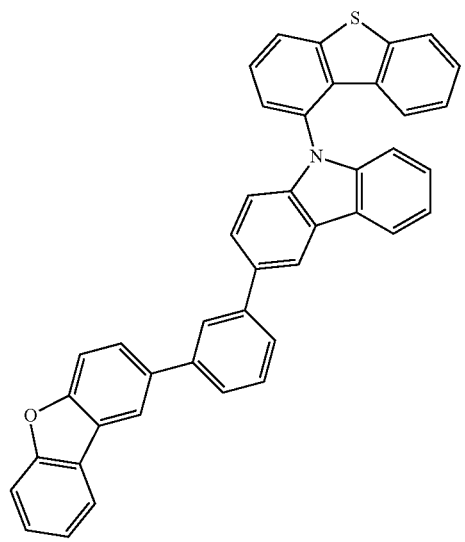
3-189
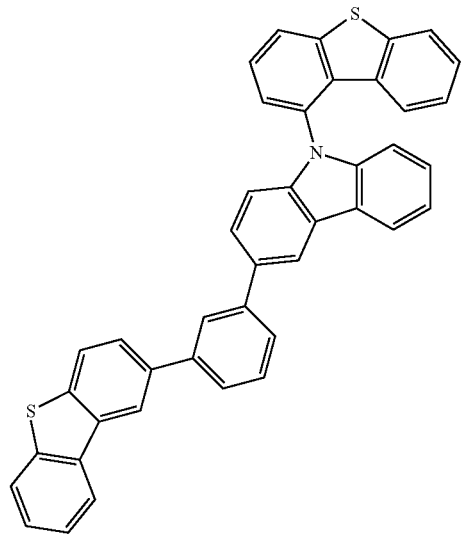

-continued 3-190

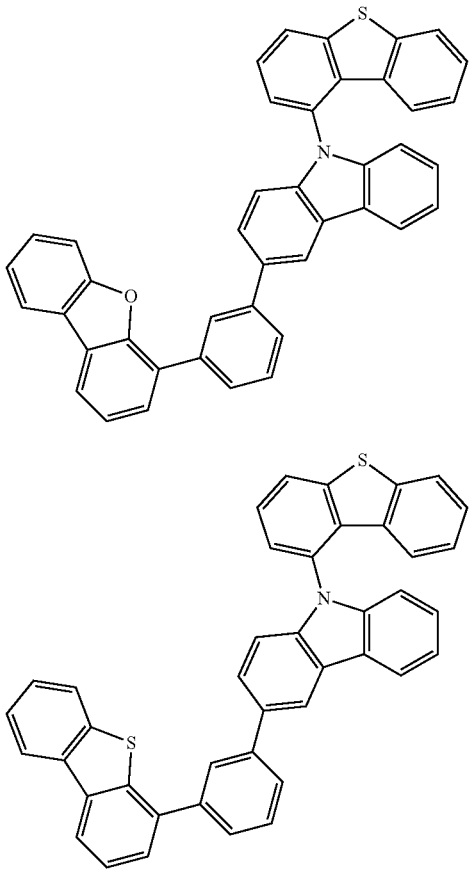

3-191

In addition, a good result is obtained when a difference in EA between the two host materials is more than 0.1 eV. When hosts different from each other in EA by 0.1 eV or less are mixed, a property of injecting an electron into a light-emitting layer remains nearly unchanged. However, when hosts different from each other in EA by more than 0.1 eV are mixed, the property of injecting an electron into alight-emitting layer and a property of transporting an electron in the light-emitting layer can be suppressed. As a result, an electron can be easily confined in the light-emitting layer, and hence an element having a long lifetime while maintaining high efficiency can be provided. The difference in EA preferably falls within the range of from 0.2 eV to 1.5 eV. It should be noted that a value for an EA can be calculated by using a value for an ionization potential in a host material thin film obtained by photoelectron spectroscopy and a value for an energy gap determined from an absorption edge of an ultraviolet-visible absorption spectrum measured for the film; provided that a measurement method is not limited thereto. It should be noted that three or more host materials can be used. In this case, however, a difference in EA between a material (H1) having the highest EA and a material (H2) having the lowest EA is desirably more than 0.1 eV.

The two host materials may be mixed before the production of the element and deposited from the vapor by using one vapor deposition source, or may be mixed at the time of the production of the element by an operation such as co-deposition involving using a plurality of vapor deposition sources. A mixing ratio (weight ratio) between the host materials, which is not particularly limited, preferably falls within the range of from 95:5 to 5:95, more preferably falls within the range of from 90:10 to 10:90.

Next, the structure of the organic EL element of the present invention is described with reference to the drawings. However, the structure of the organic EL element of the present invention is by no means limited to one illustrated in the drawings.

(1) Construction of Organic EL Element

FIG. 1 is a sectional view for schematically illustrating a structure example of a general organic EL element to be used in the present invention. Reference numeral 1 represents a substrate, reference numeral 2 represents an anode, reference numeral 3 represents a hole-injecting layer, reference numeral 4 represents a hole-transporting layer, reference numeral 5 represents a light-emitting layer, reference numeral 6 represents an electron-transporting layer, reference numeral 7 represents an electron-injecting layer, and reference numeral 8 represents a cathode. The organic EL element of the present invention includes the anode, the light-emitting layer, the electron-transporting layer, and the cathode as its essential layers, and may include any other layer as required. Examples of the other layer include, but not limited to, a hole-injecting/transporting layer, an electron-blocking layer, and a hole-blocking layer. It should be noted that the hole-injecting/transporting layer means any one or both of the hole-injecting layer and the hole-transporting layer.

(2) Substrate

The substrate 1 serves as a support for the organic electroluminescent element, and a quartz or glass plate, a metal plate or a metal foil, a plastic film or sheet, or the like is used. A glass plate, or a smooth and transparent plate made of a synthetic resin such as polyester, polymethacrylate, polycarbonate, or polysulfone is particularly preferred. When a synthetic resin substrate is used, attention needs to be paid to its gas barrier property. The case where the gas barrier property of the substrate is excessively small is not preferred because the organic electroluminescent element may deteriorate owing to outside air that has passed the substrate. Accordingly, a method involving providing at least one surface of the synthetic resin substrate with a dense silicon oxide film or the like to secure the gas barrier property is one preferred method.

(3) Anode

The anode 2 is formed on the substrate 1 and the anode serves to inject a hole into the hole-transporting layer. The anode is typically formed of, for example, a metal such as aluminum, gold, silver, nickel, palladium, or platinum, a metal oxide such as an oxide of indium and/or tin, or an oxide of indium and/or zinc, a metal halide such as copper iodide, carbon black, or a conductive polymer such as poly(3-methylthiophene), polypyrrole, or polyaniline. The formation of the anode is typically performed by, for example, a sputtering method or a vacuum deposition method in many cases. In addition, in the case of, for example, a metal fine particle made of silver or the like, a fine particle made of copper iodide or the like, carbon black, a conductive metal oxide fine particle, or conductive polymer fine powder, the anode can be formed by dispersing such particle or powder in a proper binder resin solution and applying the dispersion onto the substrate. Further, in the case of a conductive polymer, the anode can be formed by directly forming a thin film of the conductive polymer on the substrate through electrolytic polymerization or by applying the conductive polymer onto the substrate 1 (Appl. Phys. Lett., Vol. 60, p. 2711, 1992). The anode can also be formed by laminating different substances. The thickness of the anode varies depending on transparency to be required. When the transparency is required, the visible light transmittance of the anode is desirably set to 60% or more, preferably 80% or more in ordinary cases. In such cases, the thickness is typically from about 5 nm to 1,000 nm, preferably from about 10 nm to 500 nm. When the anode may be opaque, the anode may be same as the substrate. In addition, another conductive material can be further laminated on the anode.

(4) Hole-Transporting Layer

The hole-transporting layer 4 is formed on the anode 2. The hole-injecting layer 3 can be formed therebetween. A material for the hole-transporting layer is required to satisfy the following conditions: the material needs to have high efficiency with which a hole is injected from the anode and be capable of efficiently transporting the injected hole. To this end, the material is required to have a small ionization potential, have high transparency for visible light, have a large hole mobility, be excellent in stability, and to hardly produce an impurity serving as a trap at the time of the production or use. In addition, the layer is in contact with the light-emitting layer 5, and is hence required neither to quench light emitted from the light-emitting layer nor to form an exciplex between itself and the light-emitting layer to reduce the efficiency. In addition to the general requirements described above, the element is required to further have heat resistance when its application to an on-vehicle display is considered. Therefore, a material having a Tg of 85° C. or more is desirable.

A known compound that has heretofore been used in the layer can be used as a hole-transporting material that can be used in the present invention. Examples thereof include: an aromatic diamine that contains two or more tertiary amines and in which a nitrogen atom is substituted with two or more fused aromatic rings (JP 5-234681 A); an aromatic amine compound having a starburst structure such as 4,4',4"-tris (1-naphthylphenylamino)triphenylamine (J. Lumin., Vols. 72 to 74, p. 985, 1997); an aromatic amine compound formed of a tetramer of triphenylamine (Chem. Commun., p. 2175, 1996); and a spiro compound such as 2,2',7,7'-tetrakis-(diphenylamino)-9,9'-spirobifluorene (Synth. Metals, Vol. 91, p. 209, 1997). One kind of those compounds may be used alone, or two or more kinds thereof may be used as a mixture as required.

In addition, examples of the material for the hole-transporting layer other than the above-mentioned compounds include polymer materials such as polyvinylcarbazole, polyvinyltriphenylamine (JP 7-53953 A), and tetraphenylbenzidine-containing polyarylene ether sulfone (Polym. Adv. Tech., Vol. 7, p. 33, 1996).

When the hole-transporting layer is formed by an application method, the hole-transporting layer is formed by: adding and dissolving one or two or more kinds of hole-transporting materials, and as required, an additive that does not serve as a trap for a hole such as a binder resin or an applicability improver to prepare an application solution; applying the solution onto the anode by a method such as a spin coating method; and drying the applied solution Examples of the binder resin include polycarbonate, polyarylate, and polyester. When the binder resin is added in a large amount, a hole mobility reduces. Accordingly, the addition amount is desirably as small as possible and is preferably 50 wt % or less in ordinary cases.

When the hole-transporting layer is formed by the vacuum deposition method, the hole-transporting layer is formed by: loading a hole-transporting material into a crucible placed in a vacuum chamber; evacuating the inside of the vacuum chamber to about $10^{-4}$ Pa with a proper vacuum pump; and heating the crucible after the evacuation to evaporate the hole-transporting material. Thus, the hole-transporting layer is formed on the substrate having formed thereon the anode, the substrate being placed to face the crucible. The thickness of the hole-transporting layer is typically from 1 nm to 300 nm, preferably from 5 nm to 100 nm. In general, the vacuum deposition method is frequently employed for uniformly forming such thin film.

(5) Hole-Injecting Layer

The hole-injecting layer 3 has been inserted between the hole-transporting layer 4 and the anode 2 for the purposes of additionally improving the hole injection efficiency and improving the adhesive force of the entire organic layer to the anode. The insertion of the hole-injecting layer provides the following effects: the initial driving voltage of the element reduces, and at the same time, an increase in voltage when the element is continuously driven at a constant current is suppressed. A material to be used in the hole-injecting layer is required to satisfy the following conditions: the material can be formed into a uniform thin film, which can be satisfactorily brought into contact with the anode, and is thermally stable, i.e., has a high glass transition temperature. The material is required to have a glass transition temperature of 100° C. or more. Further, the material is required to satisfy, for example, the following conditions: the material has a low ionization potential and hence facilitates the injection of a hole from the anode; and the material has a large hole mobility.

For this purpose, the following materials have been reported hitherto: a phthalocyanine compound (JP 63-295695 A) such as copper phthalocyanine, an organic compound such as polyaniline (Appl. Phys. Lett., Vol. 64, p. 1245, 1994) or polythiophene (Optical Materials, Vol. 9, p. 125, 1998), a sputtered carbon film (Synth. Met., Vol. 91, p. 73, 1997), a metal oxide (J. Phys. D, Vol. 29, p. 2750, 1996) such as a vanadium oxide, a ruthenium oxide, or a molybdenum oxide, and a P-type organic substance (WO 2005-109542 A1) such as 1,4,5,8-naphthalenetetracarboxylic dianhydride (NTCDA) or hexanitrilehexaazatriphenylene (HAT). One kind of those compounds may be used alone, or two or more kinds thereof may be used as a mixture as required. A thin film serving as the hole-injecting layer can be formed as in the hole-transporting layer. In the case of inorganic matter, however, the sputtering method, an electron beam deposition method, or a plasma CVD method is further employed. The thickness of the hole-injecting layer to be formed as described above is typically from 1 nm to 300 nm, preferably from 5 nm to 100 nm.

(6) Light-Emitting Layer

The light-emitting layer 5 is formed on the hole-transporting layer 4. The light-emitting layer may be formed of a single light-emitting layer, or may be formed by laminating a plurality of light-emitting layers so that the layers may be in direct contact with each other. The light-emitting layer contains at least two host materials and a light-emitting dopant. The light-emitting dopant is desirably a fluorescent light-emitting material or a phosphorescent light-emitting material. The at least two host materials are a combination of at least one of the compounds each represented by the general formula (1) or (2), and at least one of the compounds each represented by the general formula (3).

A fused ring derivative such as perylene or rubrene, a quinacridone derivative, phenoxazone 660, DCM1, perinone, a coumarin derivative, a pyrromethene (diazaindacene) derivative, a cyanine dye, or the like can be used as the fluorescent light-emitting material as the light-emitting dopant.

It is recommended to use, as the phosphorescent light-emitting material as the light-emitting dopant, a material containing an organometallic complex including at least one metal selected from, for example, ruthenium, rhodium, palladium, silver, rhenium, osmium, iridium, platinum, and gold. Specific examples thereof include, but not limited to, the compounds disclosed in the following patent publications.

For example, WO 2009/073245 A1, WO 2009/046266 A1, WO 2007/095118 A2, WO 2008/156879 A1, WO 2008/140657 A1, US 2008/261076 A1, JP 2008-542203 A, WO 2008/054584 A1, JP 2008-505925 A, JP 2007-522126 A, JP 2004-506305 A, JP 2006-513278 A, JP 2006-50596 A, WO 2006/046980 A1, WO 2005/113704 A2, US 2005/260449 A1, US 2005/2260448 A1, US 2005/214576 A1, WO 2005/076380 A2, US 2005/119485 A1, WO 2004/045001 A2, WO 2004/045000 A2, WO 2006/100888 A1, WO 2007/004380 A1, WO 2007/023659 A1, and WO 2008/035664 A1.

Preferred examples of the phosphorescent light-emitting dopant include complexes such as Ir(ppy) 3, complexes such as Ir(bt)2.acac3, and complexes such as PtOEt3, the complexes each having a noble metal element such as Ir as a central metal. Specific examples of those complexes are shown below, but the complexes are not limited to the compounds described below.

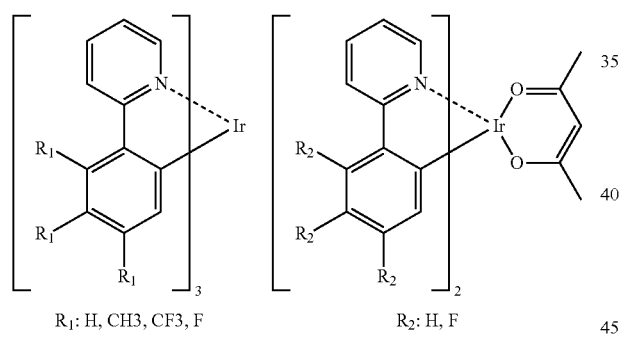

R$_1$: H, CH3, CF3, F        R$_2$: H, F

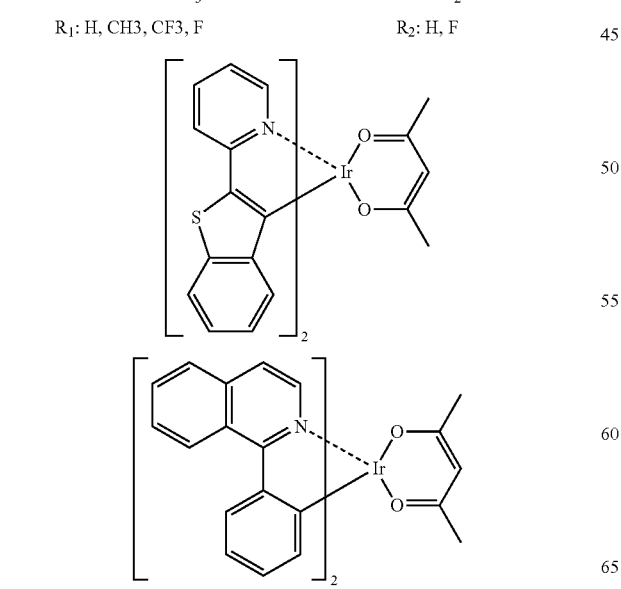

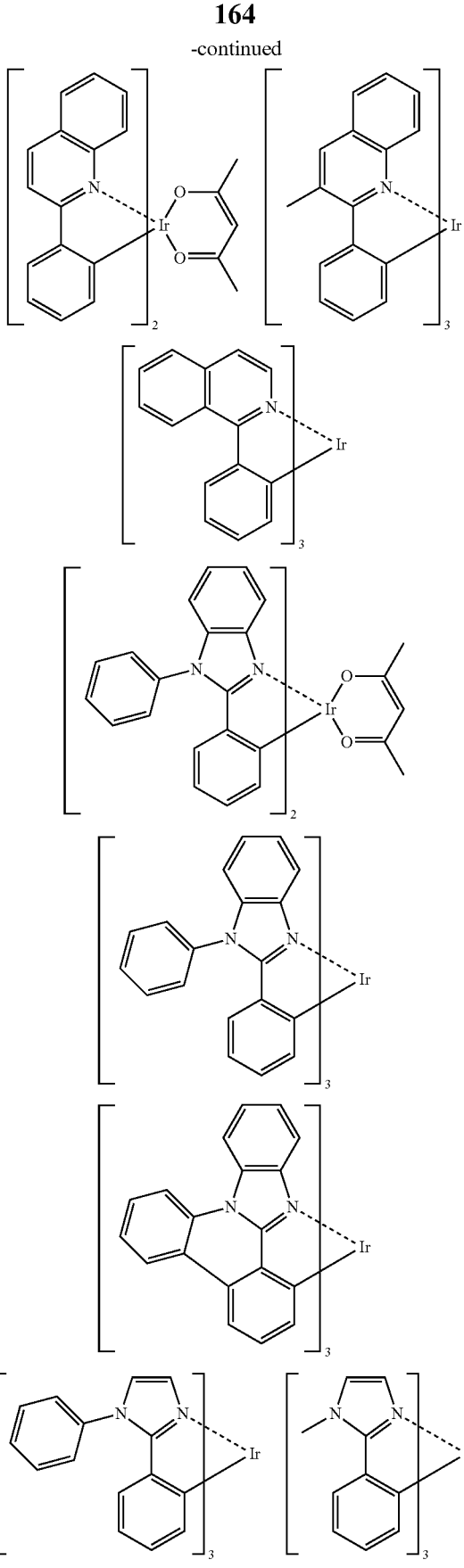

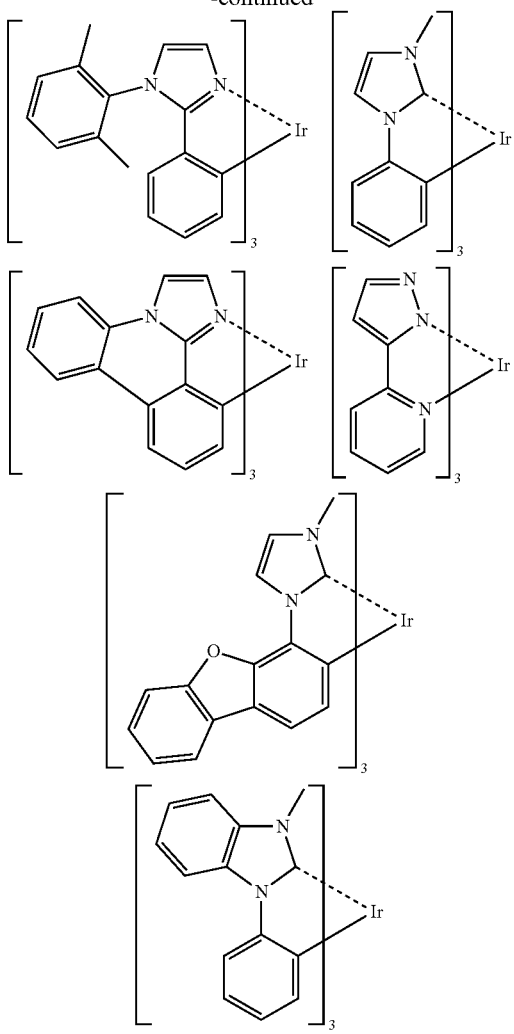
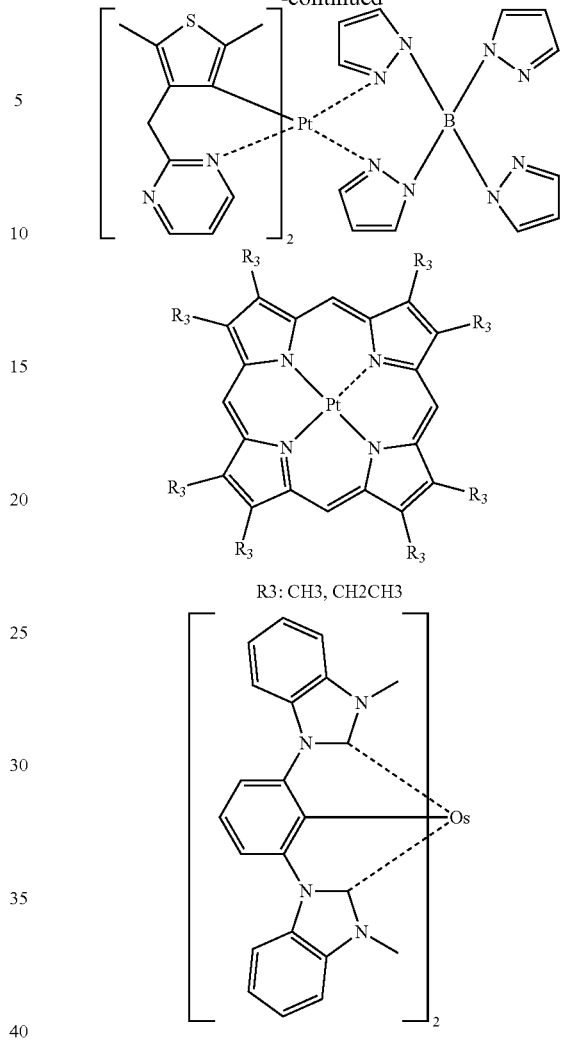

R3: CH3, CH2CH3

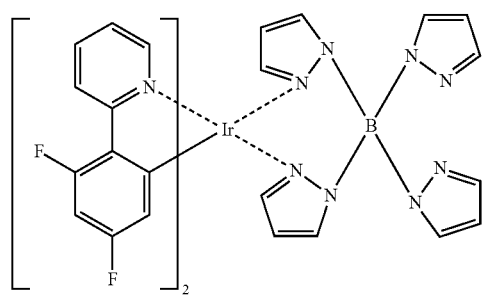

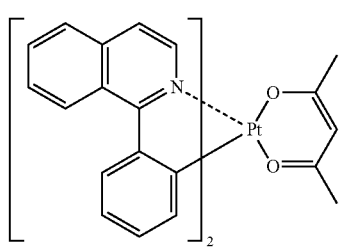

It is desirable that the content of the phosphorescent light-emitting dopant in the light-emitting layer fall within the range of from 2 wt % to 40 wt %, preferably from 5 wt % to 30 wt %.

The thickness of the light-emitting layer, which is not particularly limited, is typically from 1 nm to 300 nm, preferably from 5 nm to 100 nm, and a thin film serving as the layer is formed by the same method as that for the hole-transporting layer.

(7) Electron-Transporting Layer

The electron-transporting layer 6 is formed between the light-emitting layer 5 and the cathode 8 for the purpose of additionally improving the luminous efficiency of the element. A material for the electron-transporting layer is preferably an electron-transportable material that enables smooth injection of an electron from the cathode, and an arbitrary material that has been generally used can be used. Examples of the electron-transporting material that satisfies such condition include a metal complex (JP 59-194393 A) such as Alq3, a metal complex of 10-hydroxybenzo[h]quinoline, an oxadiazole derivative, a distyrylbiphenyl derivative, a silole derivative, a 3- or 5-hydroxyflavone metal complex, a benzoxazole metal complex, a benzothiazole metal complex, trisbenzimidazolylbenzene (U.S. Pat. No. 5,645,948 A), a quinoxaline compound (JP 6-207169 A), a phenanthroline derivative (JP 5-331459 A), 2-t-butyl- 9,10-N,N'-dicyanoanthraquinonediimine, n-type hydrogenated amorphous silicon carbide, n-type zinc sulfide, and n-type zinc selenide.

The thickness of the electron-transporting layer is typically from 1 nm to 300 nm, preferably from 5 nm to 100 nm. The electron-transporting layer is formed through lamination on the light-emitting layer by the application method or the vacuum deposition method as in the hole-transporting layer. The vacuum deposition method is typically employed.

(8) Cathode

The cathode 8 serves to inject an electron into the electron-transporting layer 6. Although the material to be used in the anode 2 can be used as a material to be used as the cathode, a metal having a low work function is preferred for efficient electron injection, and a proper metal such as tin, magnesium, indium, calcium, aluminum, or silver, or an alloy thereof is used. Specific examples of the cathode include low-work function alloy electrodes made of a magnesium-silver alloy, a magnesium-indium alloy, and an aluminum-lithium alloy.

The thickness of the cathode is typically the same as that of the anode. When a metal layer that has a high work function and is stable against the air is further laminated on the cathode formed of a low-work function metal for the purpose of protecting the cathode, the stability of the element improves. A metal such as aluminum, silver, copper, nickel, chromium, gold, or platinum is used for the purpose.

Further inserting an extremely thin insulating film (having a thickness of from 0.1 nm to 5 nm) made of LiF, $MgF_2$, $Li_2O$, or the like as the electron-injecting layer 7 between the cathode 8 and the electron-transporting layer 6 is also an effective method of improving the efficiency of the element.

It should be noted that a structure in inverse relation to that illustrated in FIG. 1 is permitted, i.e., the cathode 8, the electron-injecting layer 7, the electron-transporting layer 6, the light-emitting layer 5, the hole-transporting layer 4, the hole-injecting layer 3, and the anode 2 can be laminated in the stated order on the substrate 1. As described in the foregoing, the organic EL element of the present invention can be formed between two substrates at least one of which has high transparency. In this case as well, a layer can be added or omitted as required.

The organic EL element of the present invention can be any one of a single element, an element formed of structures placed in an array manner, and a structure in which the anode and the cathode are placed in an X-Y matrix manner. According to the organic EL element of the present invention, when the light-emitting layer is formed by using a mixed host formed of two host materials, and a specific compound is used as at least one of the host materials, an element that has high luminous efficiency and is significantly improved in driving stability while being capable of being driven at a low voltage is obtained, and the element can exhibit excellent performance in its application to a full-color or multi-color panel.

The present invention is described in more detail below by way of Examples. However, the present invention is not limited to Examples below, and can be carried out in various modes as long as the modes do not deviate from the gist thereof.

Example 1

Each thin film was stacked by a vacuum deposition method at a degree of vacuum of $4.0 \times 10^{-4}$ Pa on a glass substrate on which an anode formed of ITO having a thickness of 150 nm had been formed. First, copper phthalocyanine (CuPC) was formed into a hole-injecting layer having a thickness of 20 nm on the ITO. Next, 4,4-bis[N-(1-naphthyl)-N-phenylamino]biphenyl (NPB) was formed into a hole-transporting layer having a thickness of 20 nm. Next, Compound 1-2 as a first host, Compound 3-87 as a second host, and tris(2-phenylpyridine)iridium(III) ($Ir(PPy)_3$) as a light-emitting layer guest were co-deposited from vapor deposition sources different from one another to form a light-emitting layer having a thickness of 30 nm. At this time, a vapor deposition rate ratio among the first host, the second host, and $Ir(PPy)_3$ (volume rate ratio among vaporized products) was 47:47:6. Next, aluminum(III) bis(2-methyl-8-quinolinato)4-phenylphenolate (BAlq) was formed into a hole-blocking layer having a thickness of 10 nm. Next, tris(8-hydroxyquinolinato)aluminum(III) ($Alq_3$) was formed into an electron-transporting layer having a thickness of 40 nm. Further, lithium fluoride (LiF) was formed into an electron-injecting layer having a thickness of 0.5 nm on the electron-transporting layer. Finally, aluminum (Al) was formed into a cathode having a thickness of 100 nm on the electron-injecting layer. Thus, an organic EL element was produced.

An external power source was connected to the resultant organic EL element and a DC voltage was applied to the element. As a result, an emission spectrum having a local maximum wavelength of 517 nm was observed and hence it was found that light emission from $Ir(PPy)_3$ was obtained. The luminance, external quantum efficiency, and luminance half lifetime of the produced organic EL element are shown in Table 1.

Examples 2 to 4

Organic EL elements were each produced in the same manner as in Example 1 except that in Example 1, a compound shown in Table 1 was used as the light-emitting layer second host. An external power source was connected to each of the resultant organic EL elements and a DC voltage was applied to the element. As a result, an emission spectrum having a local maximum wavelength of 517 nm was observed for each of the organic EL elements and hence it was found that light emission from $Ir(PPy)_3$ was obtained. The luminance, external quantum efficiency, and luminance half lifetime of each of the produced organic EL elements are shown in Table 1.

Comparative Examples 1 to 5

Organic EL elements were each produced in the same manner as in Example 1 except that in Example 1, a compound shown in Table 1 was used alone as the light-emitting layer host. It should be noted that a host amount was set to the same amount as the total of the first host and second host in Example 1, and a guest amount was similarly set. A power source was connected to each of the resultant organic EL elements and a DC voltage was applied to the element. As a result, an emission spectrum having a local maximum wavelength of 517 nm was observed for each of the organic EL elements and hence it was found that light emission from $Ir(PPy)_3$ was obtained. The luminance, external quantum efficiency, and luminance half lifetime of each of the produced organic EL elements are shown in Table 1.

The luminance, external quantum efficiency, and luminance half lifetime of each of the produced organic EL elements are shown in Table 1. The luminance and the external quantum efficiency are values at a driving current of 2.5 $mA/cm^2$, and are initial characteristics. The luminance half time is a value at an initial luminance of 1,000 cd/m². Compound Nos. are numbers attached to the chemical formulae in the foregoing. H1 represents the first host and H2 represents the second host. The luminance and the external quantum efficiency are initial characteristics, and the luminance half lifetime is a lifetime characteristic.

TABLE 1

| | H1 compound (EA) | H2 compound (EA) | Luminance (cd/m²) | External quantum efficiency (%) | Luminance half time (h) |
|---|---|---|---|---|---|
| Example | | | | | |
| 1 | 1-2 (2.98 eV) | 3-87 (2.46 eV) | 1,055 | 10.9 | 22,333 |
| 2 | 1-2 (2.98 eV) | 3-88 (2.49 eV) | 1,135 | 11.7 | 16,865 |
| 3 | 1-2 (2.98 eV) | 3-45 (2.52 eV) | 1,089 | 11.3 | 16,697 |
| 4 | 1-2 (2.98 eV) | 3-140 (2.52 eV) | 1,098 | 11.4 | 16,236 |
| Comp. Example | | | | | |
| 1 | 1-2 (2.98 eV) | — | 610 | 6.4 | 11,518 |
| 2 | 3-87 (2.46 eV) | — | 270 | 2.9 | 3,310 |
| 3 | 3-88 (2.49 eV) | — | 566 | 6.3 | 2,916 |
| 4 | 3-45 (2.52 eV) | — | 217 | 2.4 | 2,854 |
| 5 | 3-140 (2.52 eV) | — | 243 | 2.5 | 2,698 |
| 6 | 1-2 (2.98 eV) | A (2.61 eV) | 768 | 8.0 | 9,547 |
| 7 | A (2.61 eV) | | 562 | 5.8 | 8,760 |

Comparison between Examples 1 to 4 of the present invention and Comparative Examples 1 to 5 in Table 1 shows that when two kinds of compounds each having a specific skeleton are used as light-emitting layer hosts, the luminance and the external quantum efficiency improve, and the luminance half time lengthens. Those results have revealed that according to the present invention, an organic EL phosphorescent element showing high efficiency and a good lifetime characteristic can be realized.

Comparative Example 6

Each thin film was stacked by a vacuum deposition method at a degree of vacuum of 4.0×10⁻⁴ Pa on a glass substrate on which an anode formed of ITO having a thickness of 150 nm had been formed. First, CuPC was formed into a hole-injecting layer having a thickness of 20 nm on the ITO. Next, NPB was formed into a hole-transporting layer having a thickness of 20 nm. Next, Compound 1-2 as a first host, Compound A shown below as a second host, and Ir(PPy)₃ as a light-emitting layer guest were co-deposited from vapor deposition sources different from one another to form a light-emitting layer having a thickness of 30 nm. At this time, a vapor deposition rate ratio among the first host, the second host, and Ir(PPy)₃ was 47:47:6. Next, BAlq was formed into a hole-blocking layer having a thickness of 10 nm. Next, Alq₃ was formed into an electron-transporting layer having a thickness of 40 nm. Further, lithium fluoride (LiF) was formed into an electron-injecting layer having a thickness of 0.5 nm on the electron-transporting layer. Finally, aluminum (Al) was formed into a cathode having a thickness of 100 nm on the electron-injecting layer. Thus, an organic EL element was produced.

Comparative Example 7

In addition, an organic EL element using Compound A shown below alone as the light-emitting layer host was similarly produced.

An external power source was connected to each of the resultant organic EL elements and a DC voltage was applied to the element. As a result, an emission spectrum having a local maximum wavelength of 517 nm was observed for both the organic EL elements and hence it was found that light emission from Ir(PPy)₃ was obtained. The luminance, external quantum efficiency, and luminance half lifetime of each of the produced organic EL elements are shown in Table 1.

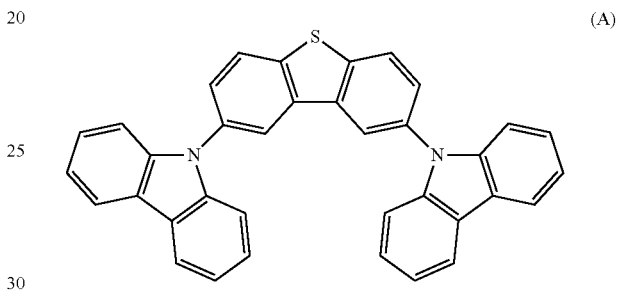

(A)

As apparent from Table 1, when the mixed host of Compound 1-2 and Compound A, and a single host of Compound A and a single host of Compound 1-2 (Comparative Example 1) are compared, the use of the mixed host of Compound 1-2 and Compound A as the light-emitting layer host improves the luminance and the external quantum efficiency, but shortens the luminance half time. The result has shown that when a mixed host of compounds each having a skeleton except a specific skeleton is used as a light-emitting layer host, a driving lifetime characteristic may deteriorate.

Example 5

Each thin film was stacked by a vacuum deposition method at a degree of vacuum of 4.0×10⁻⁴ Pa on a glass substrate on which an anode formed of ITO having a thickness of 150 nm had been formed. First, CuPC was formed into a hole-injecting layer having a thickness of 25 nm on the ITO. Next, NPB was formed into a first hole-transporting layer having a thickness of 10 nm, and 4,4',4"-tris(N-carbazolyl)-triphenylamine (TCTA) was formed into a second hole-transporting layer having a thickness of 10 nm. Next, Compound 1-114 as a first host, Compound 3-87 as a second host, and tris[1-14'-cyanophenyl)-3-methylbenzimidazol-2-ylidene-C²,C²']-iridium(III) (Ir(cn-pmic)₃) as a light-emitting layer guest were co-deposited from vapor deposition sources different from one another to form a light-emitting layer having a thickness of 30 nm. At this time, a vapor deposition rate ratio among the first host, the second host, and Ir(cn-pmic)₃ was 45:45:10. Next, 2,9-dimethyl-4,7-diphenyl-1,10-phenanthroline (BCP) was formed into a hole-blocking layer having a thickness of 10 nm. Next, Alq₃ was formed into an electron-transporting layer having a thickness of 25 nm. Further, lithium fluoride (LiF) was formed into an electron-injecting layer having a thickness of 0.5 nm on the electron-transporting layer. Finally, aluminum (Al) was formed into a cathode having a thickness of 100 nm on the electron-injecting layer. Thus, an organic EL element was produced.

An external power source was connected to the resultant organic EL element and a DC voltage was applied to the element. As a result, an emission spectrum having a local maximum wavelength of 460 nm was observed and hence it was found that light emission from Ir(cn-pmic)$_3$ was obtained. The luminance, external quantum efficiency, and luminance half lifetime of the produced organic EL element are shown in Table 2.

Example 6

Organic EL elements were each produced in the same manner as in Example 5 except that in Example 5, Compound 3-88 was used as the light-emitting layer second host. An external power source was connected to each of the resultant organic EL elements and a DC voltage was applied to the element. As a result, an emission spectrum having a local maximum wavelength of 460 nm was observed for each of the organic EL elements and hence it was found that light emission from Ir(cn-pmic)$_3$ was obtained. The luminance, external quantum efficiency, and luminance half lifetime of each of the produced organic EL elements are shown in Table 2.

Example 7

An organic EL element was produced in the same manner as in Example 5 except that in Example 5, Compound 2-9 was used as the light-emitting first host and Compound 3-87 was used as the light-emitting layer second host. An external power source was connected to each of the resultant organic EL elements and a DC voltage was applied to the element. As a result, an emission spectrum having a local maximum wavelength of 460 nm was observed for each of the organic EL elements and hence it was found that light emission from Ir(cn-pmic)$_3$ was obtained. The luminance, external quantum efficiency, and luminance half lifetime of each of the produced organic EL elements are shown in Table 2.

Example 8

An organic EL element was produced in the same manner as in Example 5 except that in Example 5, Compound 2-9 was used as the light-emitting first host and Compound 3-88 was used as the light-emitting layer second host. An external power source was connected to each of the resultant organic EL elements and a DC voltage was applied to the element. As a result, an emission spectrum having a local maximum wavelength of 460 nm was observed for each of the organic EL elements and hence it was found that light emission from Ir(cn-pmic)$_3$ was obtained. The luminance, external quantum efficiency, and luminance half lifetime of each of the produced organic EL elements are shown in Table 2.

Comparative Examples 7 to 10

Organic EL elements were each produced in the same manner as in Example 5 except that in Example 5, a compound shown in Table 2 was used alone as the light-emitting layer host. It should be noted that a host amount was set to the same amount as the total of the first host and second host in Example 5, and a guest amount was similarly set. A power source was connected to each of the resultant organic EL elements and a DC voltage was applied to the element. As a result, an emission spectrum having a local maximum wavelength of 460 nm was observed for each of the organic EL elements and hence it was found that light emission from Ir(cn-pmic)$_3$ was obtained. The luminance, external quantum efficiency, and luminance half lifetime of each of the produced organic EL elements are shown in Table 2.

The luminance, external quantum efficiency, and luminance half lifetime of each of the produced organic EL elements are shown in Table 2. The luminance and the external quantum efficiency are values at a driving current of 2.5 mA/cm$^2$, and are initial characteristics. The luminance half time is a value at an initial luminance of 1,000 cd/m$^2$.

TABLE 2

| | H1 compound (EA) | H2 compound (EA) | Luminance (cd/m$^2$) | External quantum efficiency (%) | Luminance half time (h) |
|---|---|---|---|---|---|
| Example | | | | | |
| 5 | 1-114 (2.23 eV) | 3-87 (2.46 eV) | 374 | 13.2 | 196 |
| 6 | 1-114 (2.23 eV) | 3-88 (2.49 eV) | 408 | 14.6 | 178 |
| 7 | 2-9 (2.05 eV) | 3-87 (2.46 eV) | 376 | 13.4 | 185 |
| 8 | 2-9 (2.05 eV) | 3-88 (2.49 eV) | 414 | 14.8 | 169 |
| Comp. Example | | | | | |
| 7 | 1-114 (2.23 eV) | — | 255 | 8.9 | 114 |
| 8 | 2-9 (2.05 eV) | — | 288 | 10.5 | 82 |
| 9 | 3-87 (2.46 eV) | — | 267 | 9.4 | 146 |
| 10 | 3-88 (2.49 eV) | — | 296 | 11.0 | 96 |

Comparison between Examples 5 to 8 of the present invention and Comparative Examples 7 to 10 in Table 2 shows that when two kinds of compounds each having a specific skeleton are used as light-emitting layer hosts, the luminance and the external quantum efficiency improve, and the luminance half time significantly lengthens. Those results have revealed that according to the present invention, an organic EL phosphorescent element showing high efficiency and a good lifetime characteristic can be realized.

INDUSTRIAL APPLICABILITY

The organic EL element of the present invention has a high technological value in its application to, for example, flat panel displays (such as a cellular phone display element, an on-vehicle display element, an OA computer display element, and a television), light sources each taking advantage of its feature as a surface emitter (such as illumination, a light source for a copying machine, and backlight sources for a liquid crystal display and meters), display boards, and marker lamps.

The invention claimed is:
1. An organic electroluminescent element, comprising one or more light-emitting layers between an anode and a cathode opposite to each other, wherein:
   at least one of the one or more light-emitting layers contains at least two host materials and at least one light-emitting dopant; and the at least two host materials comprise a material selected from compounds each represented by any one of the following general formulae (1) and (2), and a material selected from compounds each represented by the following general formula (3):

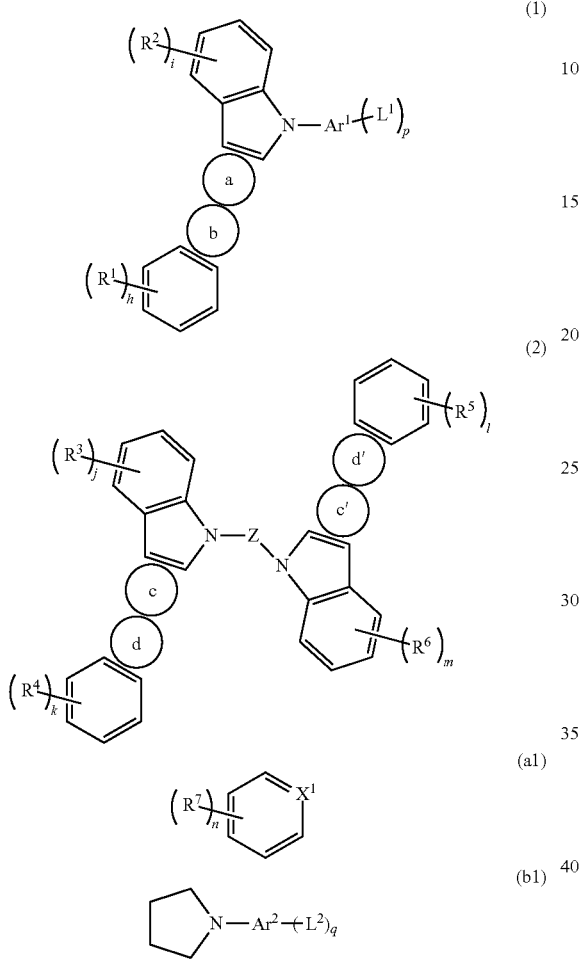

where:
- a ring a, a ring c, and a ring c' each independently represent an aromatic ring or heterocycle represented by the formula (a1) fused at arbitrary positions of two adjacent rings;
- a ring b, a ring d, and a ring d' each independently represent a heterocycle represented by the formula (b1) fused at arbitrary positions of two adjacent rings;
- $X^1$ represents $CR^7$ or N;
- $Ar^1$ and $Ar^2$ each independently represent an aromatic hydrocarbon group having 6 to 22 carbon atoms, or a monocyclic aromatic heterocyclic group having 3 to 6 carbon atoms;
- Z represents a divalent linking group selected from an aromatic hydrocarbon group having 6 to 22 carbon atoms, an aromatic heterocyclic group having 3 to 16 carbon atoms, and a linked aromatic group obtained by linking 2 to 10 aromatic rings of the aromatic hydrocarbon group and the aromatic heterocyclic group, and a group bonded to N comprises an aromatic hydrocarbon group having 6 to 22 carbon atoms, or a monocyclic aromatic heterocyclic group having 3 to 6 carbon atoms;
- $R^1$ to $R^7$ each independently represent hydrogen, a cyano group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 22 carbon atoms, or an aromatic heterocyclic group having 3 to 16 carbon atoms;
- $L^1$ and $L^2$ each independently represent an aromatic hydrocarbon group having 6 to 22 carbon atoms, an aromatic heterocyclic group having 3 to 16 carbon atoms, or a linked aromatic group obtained by linking 2 to 10 aromatic rings of the aromatic hydrocarbon group and the aromatic heterocyclic group; and
- p and q each represent an integer of from 0 to 7, h, i, j, k, l, and m each represent an integer of 4, n represents an integer of 2, when a plurality of $L^1$'s, $L^2$'s, $R^1$'s, $R^2$'s, $R^3$'s, $R^4$'s, $R^5$'s, $R^6$'s, or $R^7$'s exist, the plurality of groups may be identical to or different from each other, and the aromatic hydrocarbon group or aromatic heterocyclic group in any one of $Ar^1$, $Ar^2$, $L^1$, $L^2$, Z, and $R^1$ to $R^7$ may have a substituent, and when the group has a substituent, the substituent comprises a cyano group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, or an alkylsulfonyl group having 1 to 20 carbon atoms;

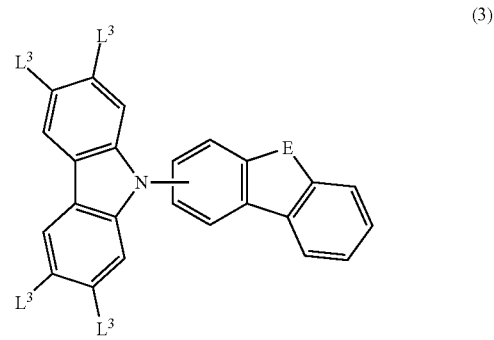

where $L^3$'s each independently represent hydrogen or a monovalent group, and E represents oxygen or sulfur, and wherein at least one of $L^3$'s in the general formula (3) represents a monovalent group represented by the formula (e1):

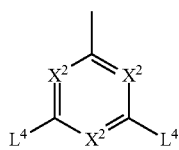

(e1)

where:

L⁴'s each independently represent hydrogen, a cyano group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a dialkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 22 carbon atoms, an aromatic heterocyclic group having 3 to 16 carbon atoms, or a linked aromatic group obtained by linking 2 to 10 aromatic rings of the aromatic hydrocarbon group and the aromatic heterocyclic group;

$X^2$'s each independently represent $CL^4$ or nitrogen; and the aromatic hydrocarbon group or aromatic heterocyclic group in $L^4$ may have a substituent, and when the group has a substituent, the substituent comprises a cyano group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a dialkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, or an alkylsulfonyl group having 1 to 20 carbon atoms.

2. An organic electroluminescent element according to claim 1, wherein a difference (ΔEA) in electron affinity between the material selected from the compounds each represented by any one of the general formulae (1) and (2), and the material selected from the compounds each represented by the general formula (3) is more than 0.1 eV.

3. An organic electroluminescent element according to claim 1, wherein in the general formulae (1) and (2), at least one of $Ar^1$ and $Ar^2$ represents a monocyclic aromatic heterocyclic group having 3 to 6 carbon atoms, and $X^1$ represents $CR^7$.

4. An organic electroluminescent element according to claim 1, wherein the compounds each represented by the general formula (3) comprise compounds each represented by the general formula (4):

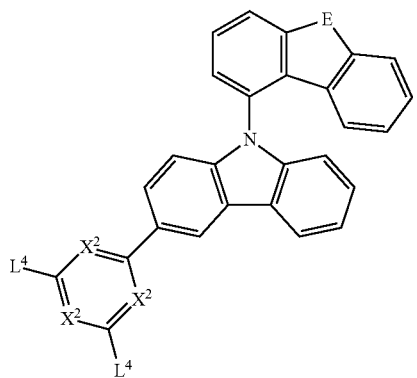

(4)

where $X^2$, $L^4$, and E are identical in meaning to $X^2$, $L^4$, and E in the general formula (3) and the formula (e1), respectively.

5. An organic electroluminescent element according to claim 4, wherein the compounds each represented by the general formula (4) comprise compounds each represented by the general formula (5):

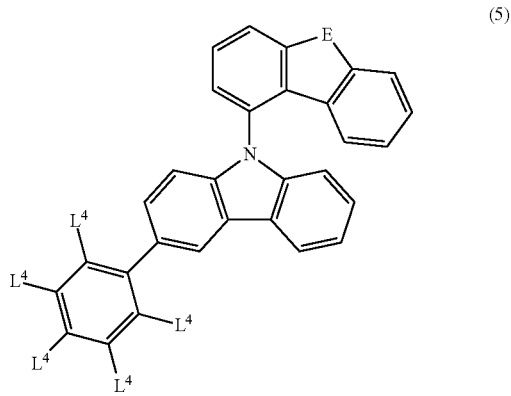

(5)

where $L^4$ and E are identical in meaning to $L^4$ and E in the general formula (4), respectively.

6. An organic electroluminescent element according to claim 1, wherein the light-emitting dopant comprises a phosphorescent light-emitting dopant formed of an organometallic complex containing at least one metal selected from ruthenium, rhodium, palladium, silver, rhenium, osmium, iridium, platinum, and gold.

7. An organic electroluminescent element according to claim 1, wherein in the general formulae (1) and (2), at least one of $Ar^1$ and $Ar^2$ represents a monocyclic aromatic heterocyclic group having 3 to 6 carbon atoms, and $X^1$ represents $CR^7$; and a difference (ΔEA) in electron affinity between the material selected from the compounds each represented by any one of the general formulae (1) and (2), and the material selected from the compounds each represented by the general formula (3) is more than 0.1 eV.

8. An organic electroluminescent element according to claim 2, wherein the difference (ΔEA) is 0.2-1.5 eV.

9. An organic electroluminescent element comprising one or more light-emitting layers between an anode and a cathode opposite to each other, wherein:

at least one of the one or more light-emitting layers contains at least two host materials and at least one light-emitting dopant; and the at least two host materials comprise a material selected from compounds each represented by any one of the following general formulae (1) and (2), and a material selected from compounds each represented by the following general formula (3):

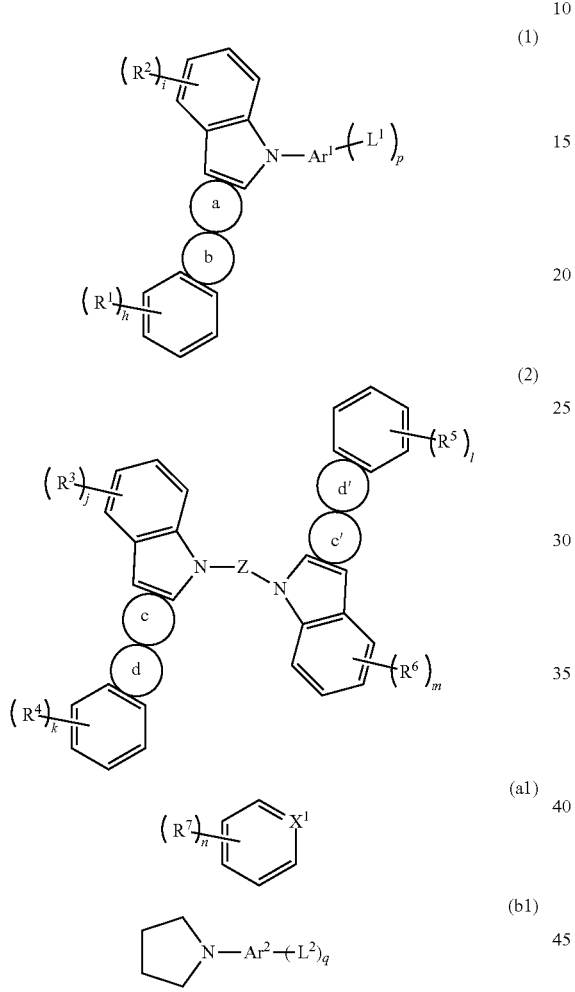

where:
a ring a, a ring c, and a ring c' each independently represent an aromatic ring or heterocycle represented by the formula (a1) fused at arbitrary positions of two adjacent rings;

a ring b, a ring d, and a ring d' each independently represent a heterocycle represented by the formula (b1) fused at arbitrary positions of two adjacent rings;

$X^1$ represents $CR^7$ or N;

$Ar^1$ and $Ar^2$ each independently represent an aromatic hydrocarbon group having 6 to 22 carbon atoms, or a monocyclic aromatic heterocyclic group having 3 to 6 carbon atoms;

Z represents a divalent linking group selected from an aromatic hydrocarbon group having 6 to 22 carbon atoms, an aromatic heterocyclic group having 3 to 16 carbon atoms, and a linked aromatic group obtained by linking 2 to 10 aromatic rings of the aromatic hydrocarbon group and the aromatic heterocyclic group, and a group bonded to N comprises an aromatic hydrocarbon group having 6 to 22 carbon atoms, or a monocyclic aromatic heterocyclic group having 3 to 6 carbon atoms;

$R^1$ to $R^7$ each independently represent hydrogen, a cyano group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, an aromatic hydrocarbon group having 6 to 22 carbon atoms, or an aromatic heterocyclic group having 3 to 16 carbon atoms;

$L^1$ and $L^2$ each independently represent an aromatic hydrocarbon group having 6 to 22 carbon atoms, an aromatic heterocyclic group having 3 to 16 carbon atoms, or a linked aromatic group obtained by linking 2 to 10 aromatic rings of the aromatic hydrocarbon group and the aromatic heterocyclic group; and p and q each represent an integer of from 0 to 7, h, i, j, k, l, and m each represent an integer of 4, n represents an integer of 2, when a plurality of $L^1$'s, $L^2$'s, $R^1$'s, $R^2$'s, $R^3$'s, $R^4$'s, $R^5$'s, $R^6$'s, or $R^7$'s exist, the plurality of groups may be identical to or different from each other, and the aromatic hydrocarbon group or aromatic heterocyclic group in any one of $Ar^1$, $Ar^2$, $L^1$, $L^2$, Z, and $R^1$ to $R^7$ may have a substituent, and when the group has a substituent, the substituent comprises a cyano group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, or an alkylsulfonyl group having 1 to 20 carbon atoms;

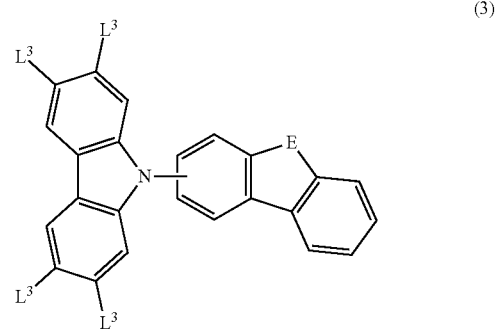

where $L^3$'s each independently represent hydrogen or a monovalent group, and E represents oxygen or sulfur, and wherein the material selected from compounds each represented by the general formula (3) is selected from compounds in the group consisting of:
3-1
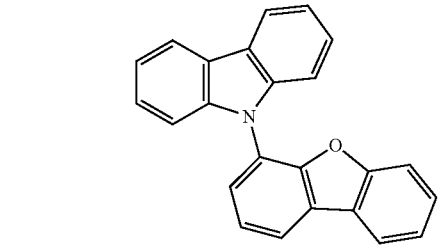
3-7
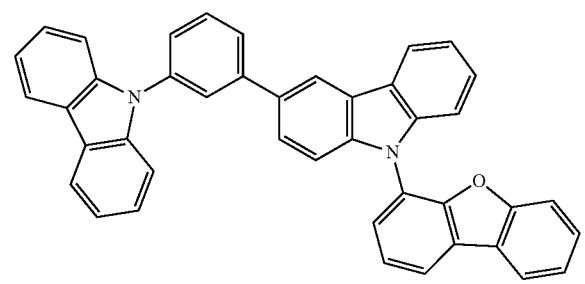
3-11
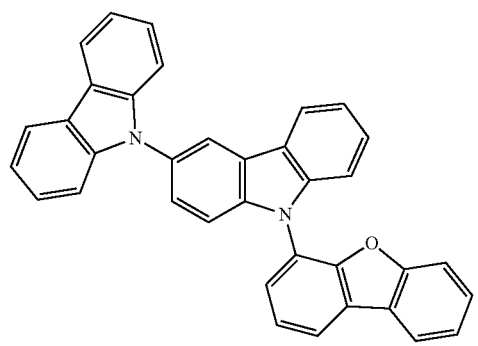
3-18
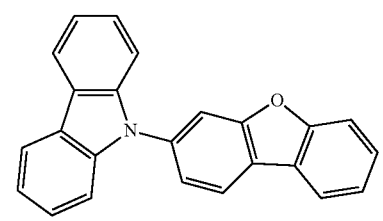
3-23
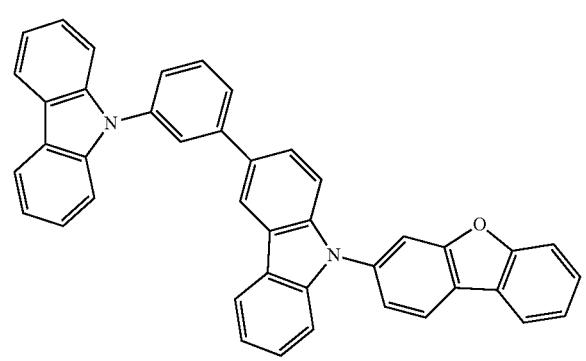
3-25
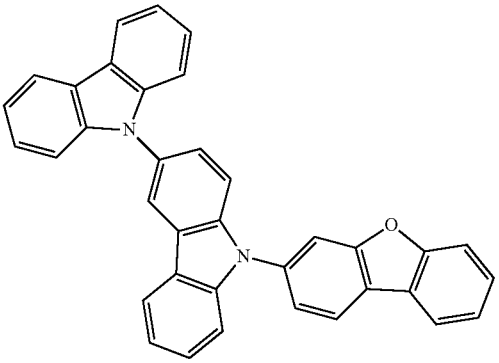
3-37
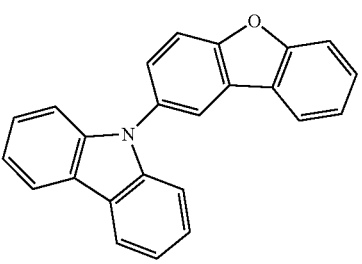
3-43
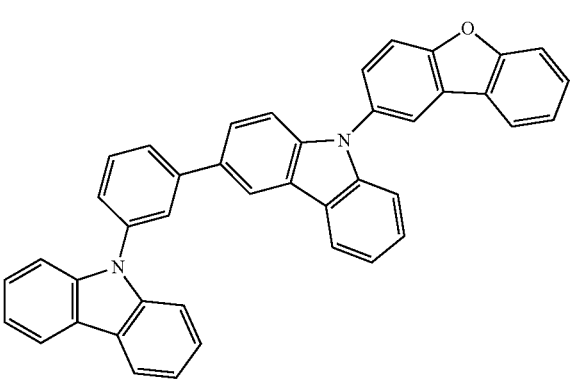
3-51
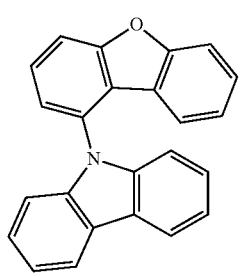

3-57
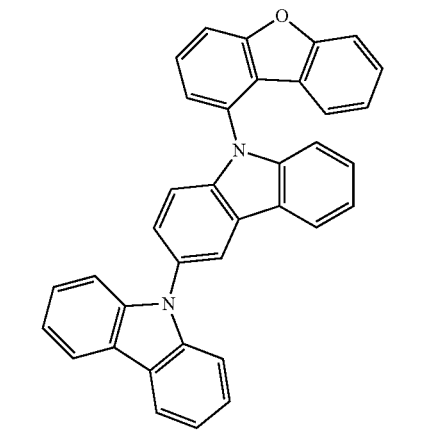
3-87
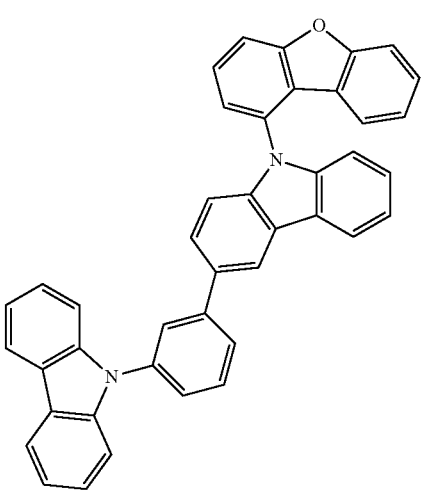
3-88
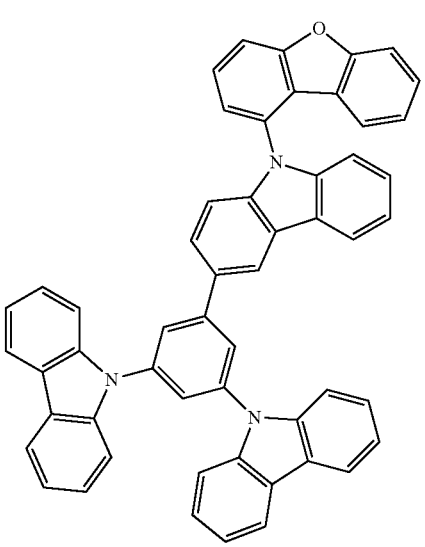
3-89
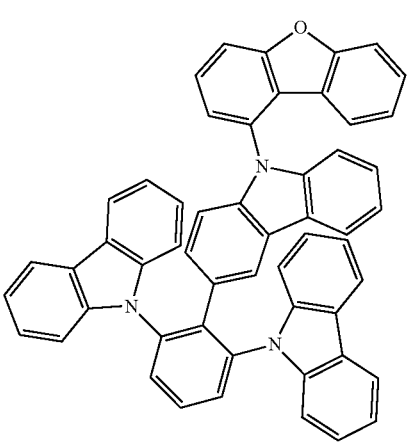
3-90
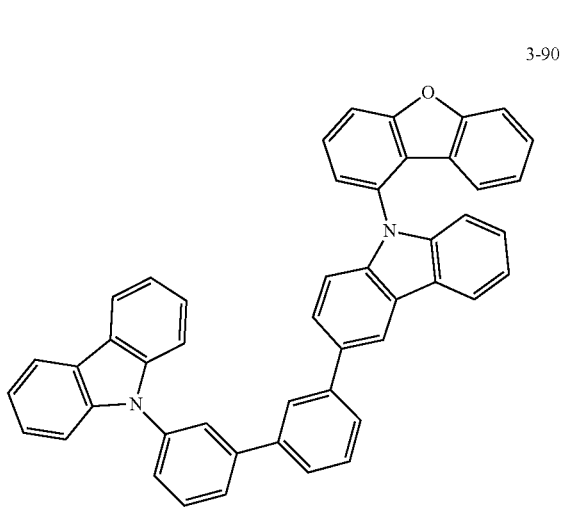
3-91
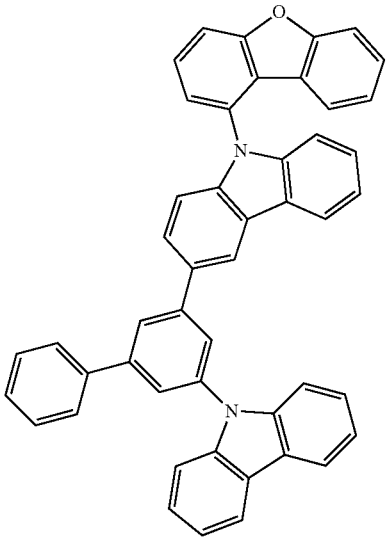

-continued
3-103
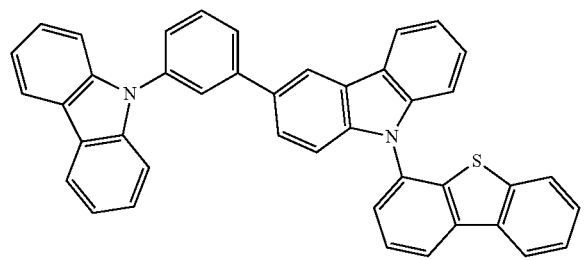
3-104
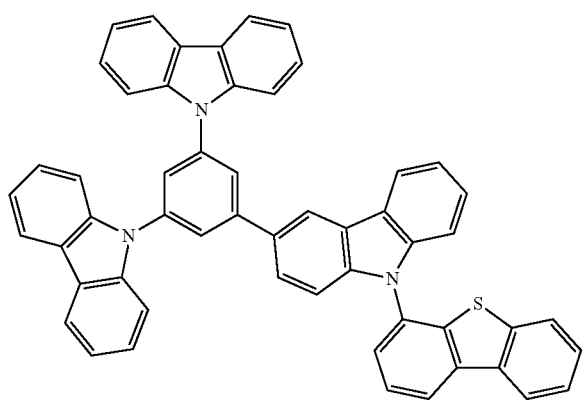
3-106
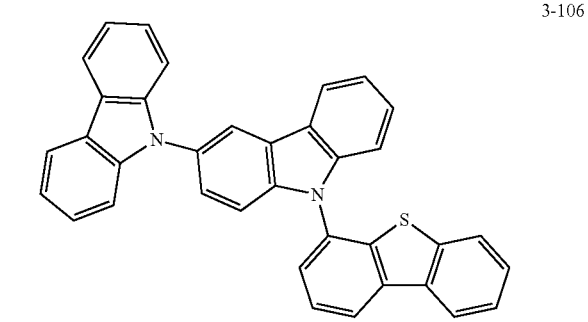
3-119
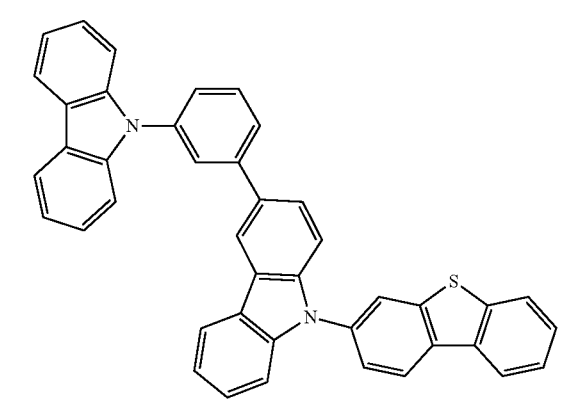
-continued
3-120
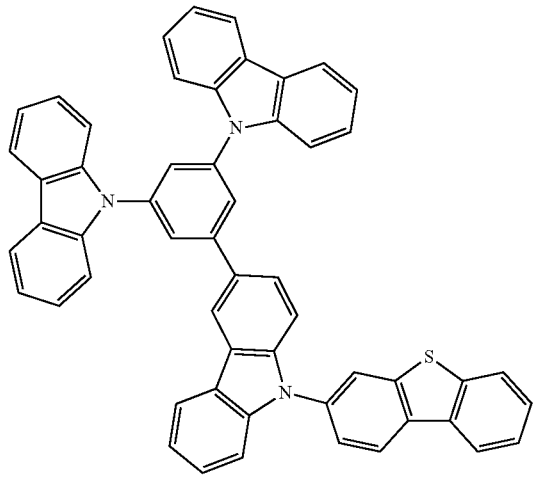
3-121
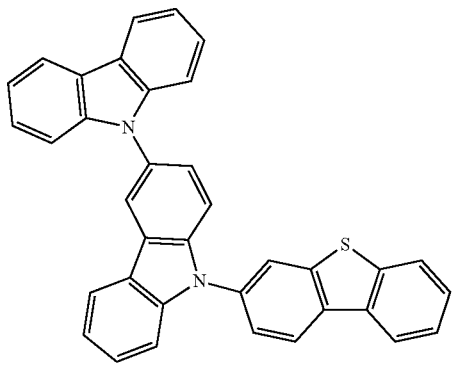
3-125
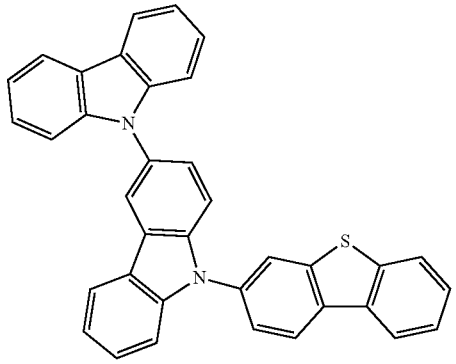
3-132
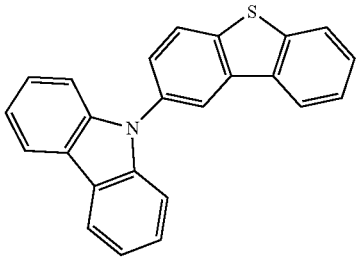

-continued
3-137
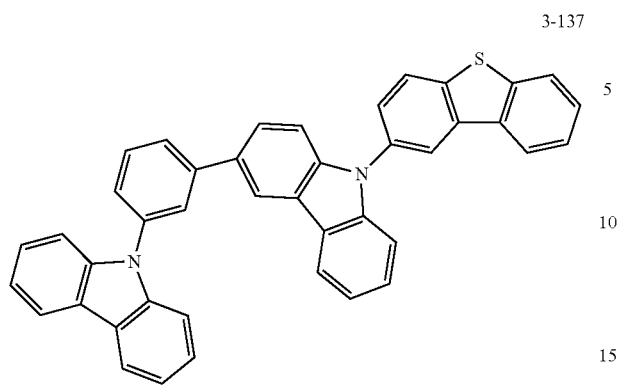
3-139
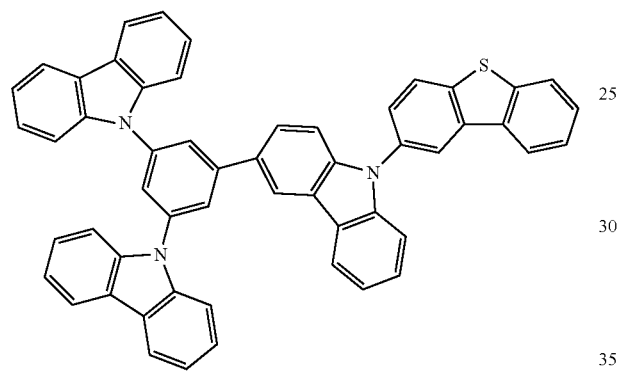
3-140
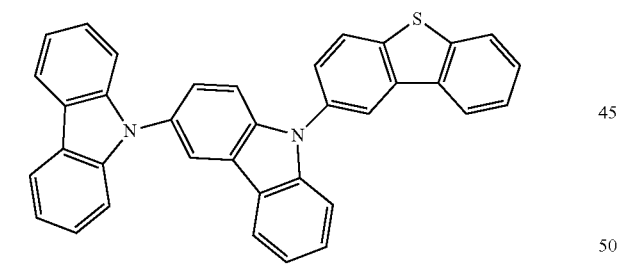
3-146
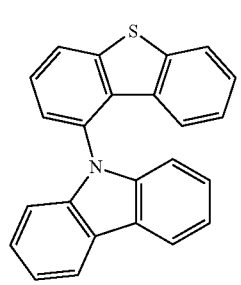
3-151
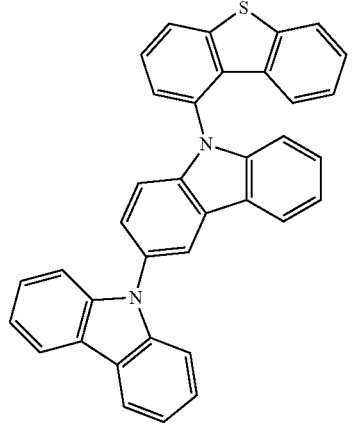
3-161
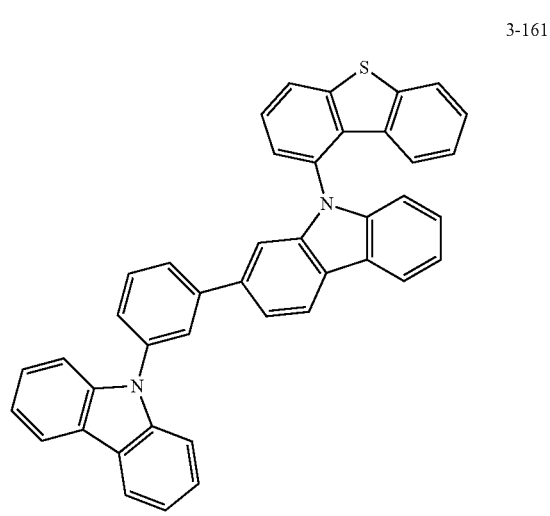
3-162
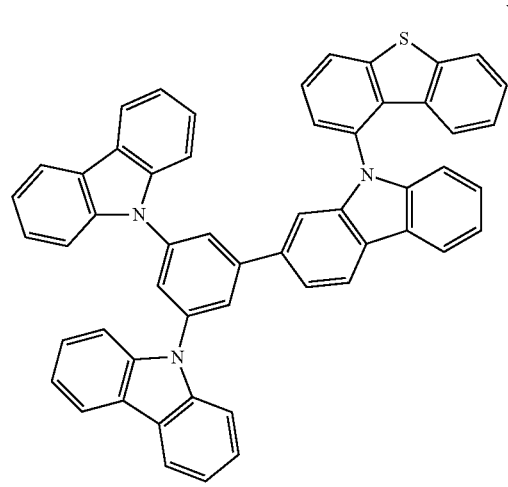

3-182
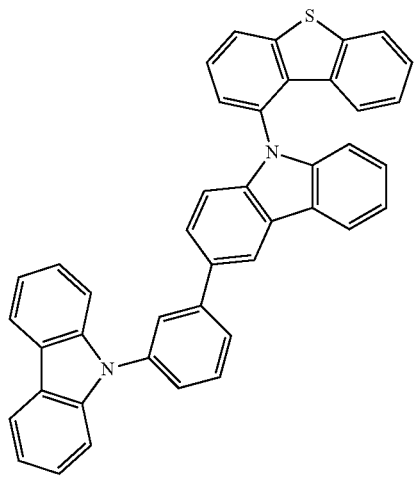
3-183
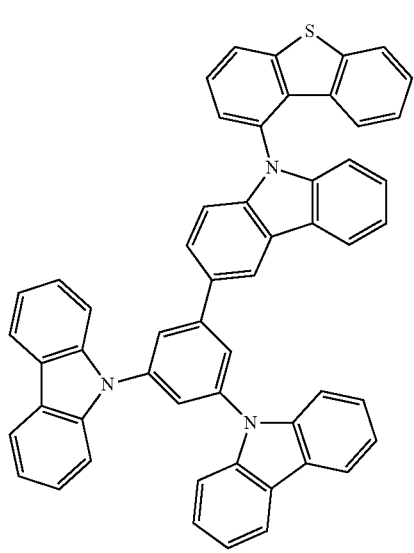
3-184
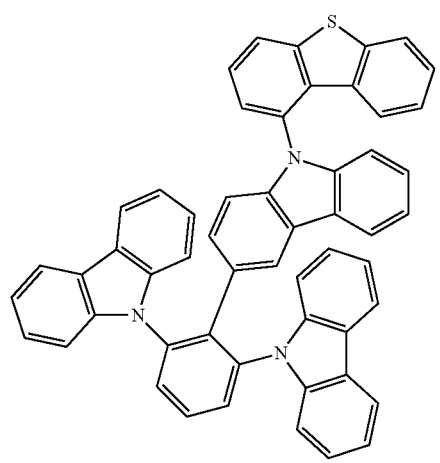
3-185
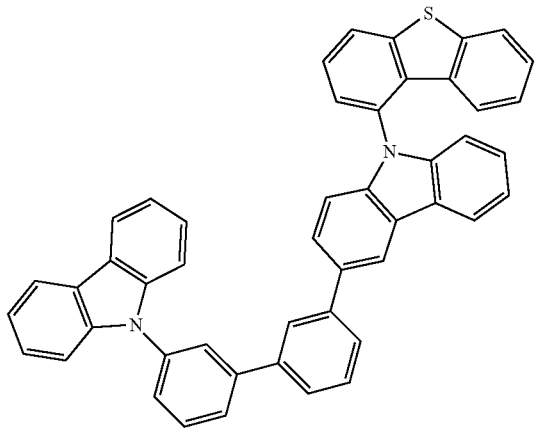
3-186
10. An organic electroluminescent element according to claim 9, wherein the material selected from compounds each represented by the general formula (3) is selected from compounds in the group consisting of:
3-87
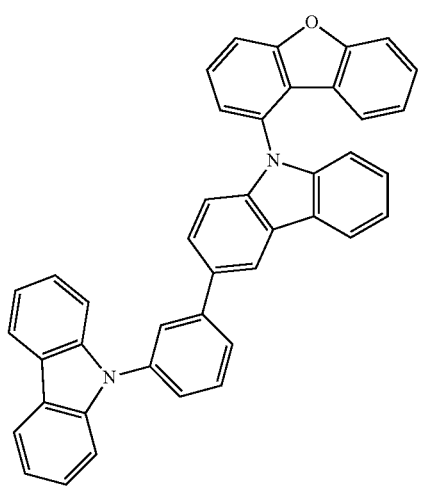

3-88
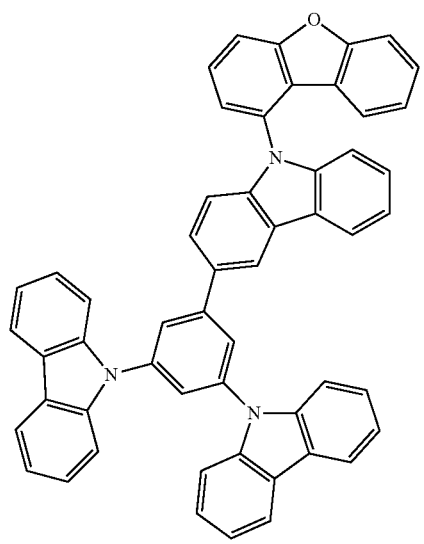
3-23
3-25
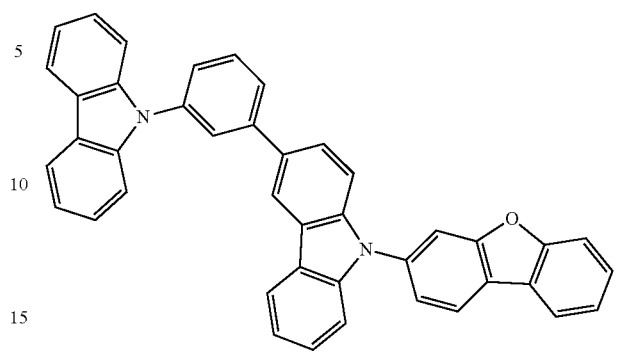
3-140
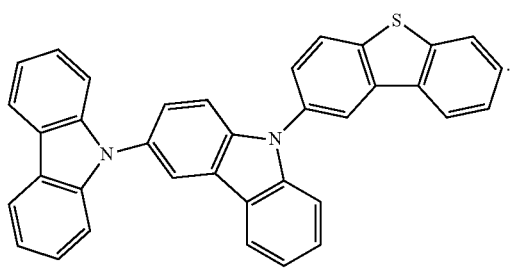
3-43
3-89
11. An organic electroluminescent element according to claim 9, wherein the material selected from compounds each represented by the general formula (3) is selected from compounds in the group consisting of:
3-7
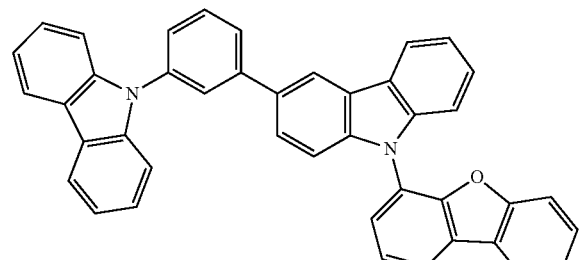
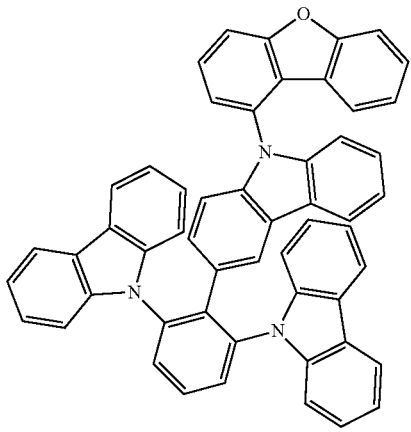

3-106
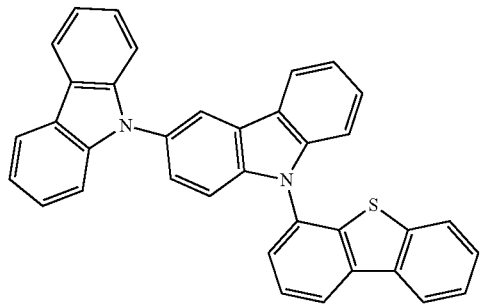
3-121
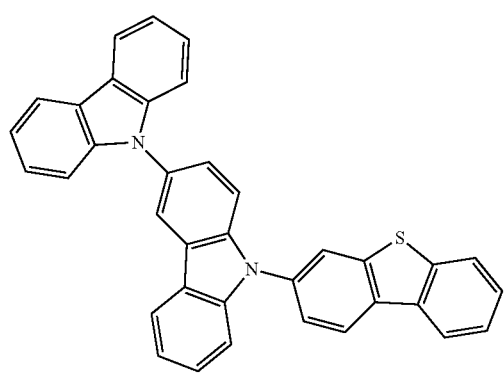
3-125
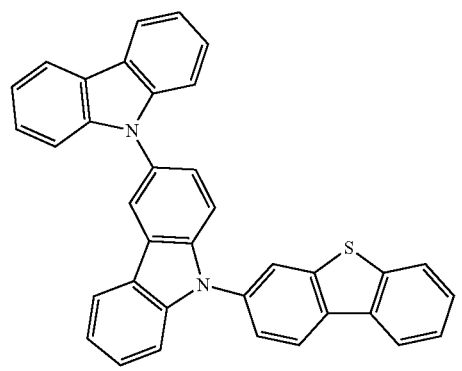
3-151
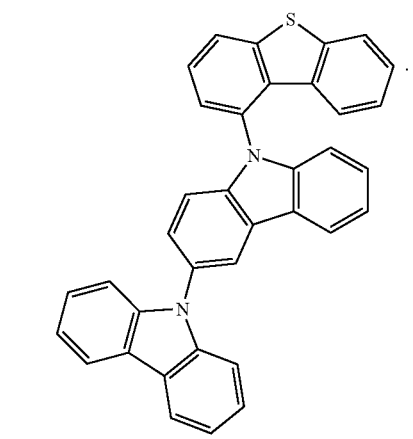
3-90
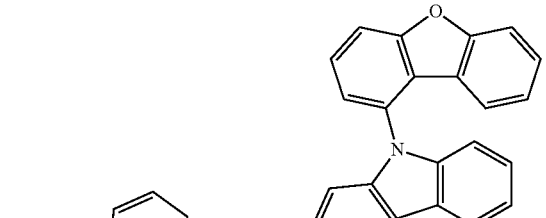
3-91
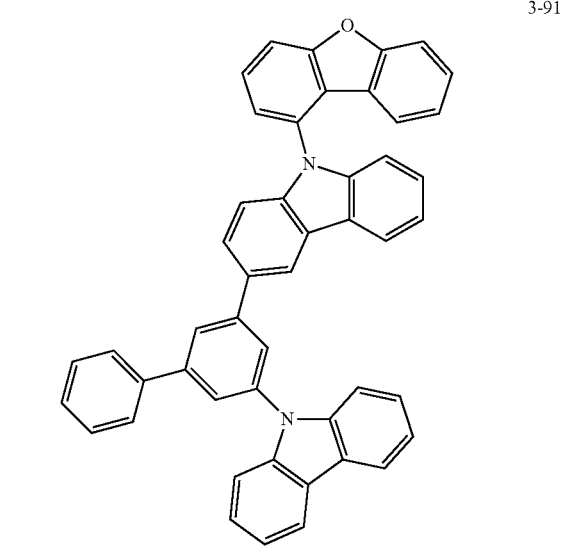
3-185
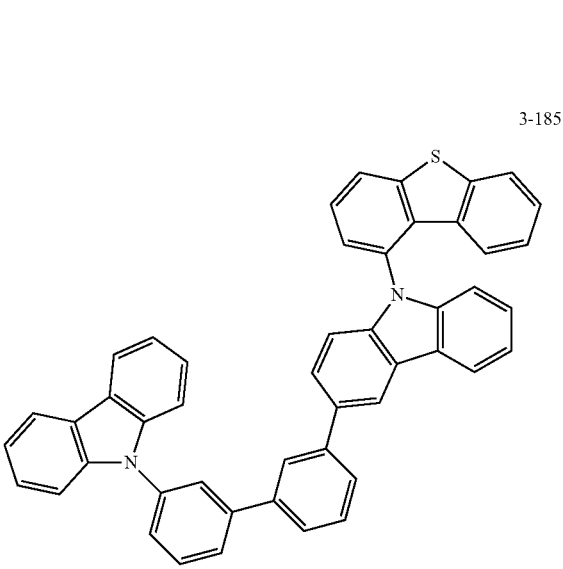
12. An organic electroluminescent element according to claim 9, wherein the material selected from compounds each represented by the general formula (3) is selected from compounds in the group consisting of:

3-186
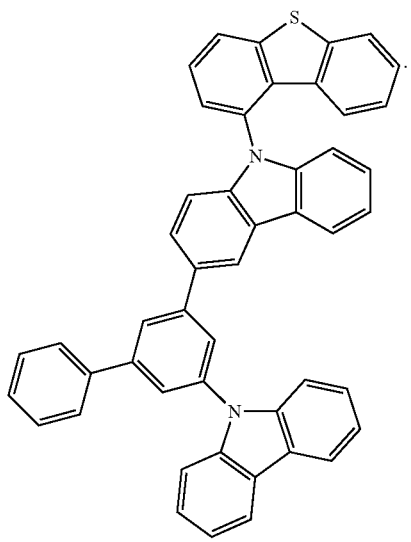
13. An organic electroluminescent element according to claim 9, wherein the material selected from compounds each represented by the general formula (3) is selected from compounds in the group consisting of:
3-103
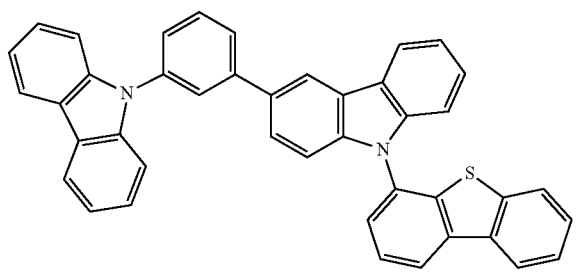
3-104
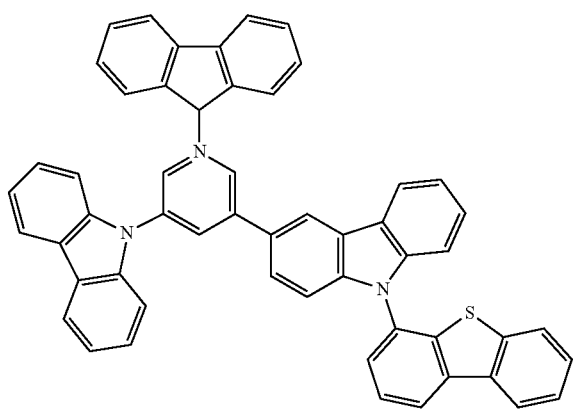
3-119
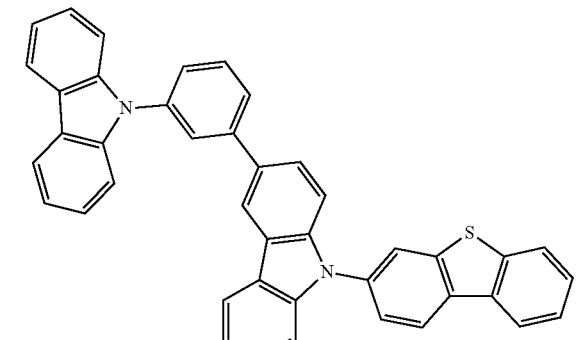
3-120
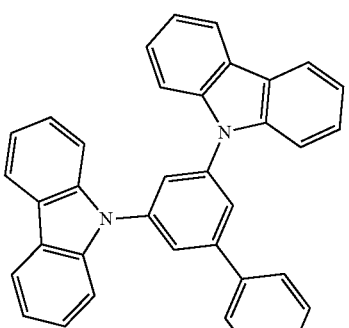
3-137
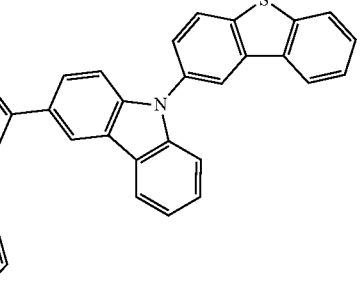
3-139
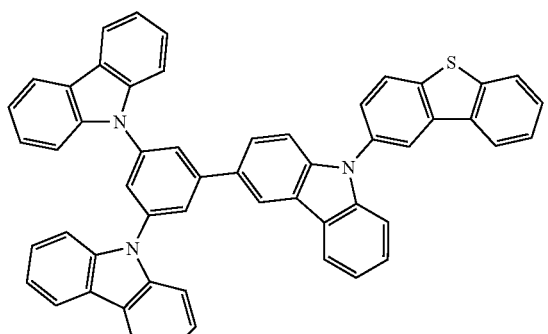

-continued
3-161
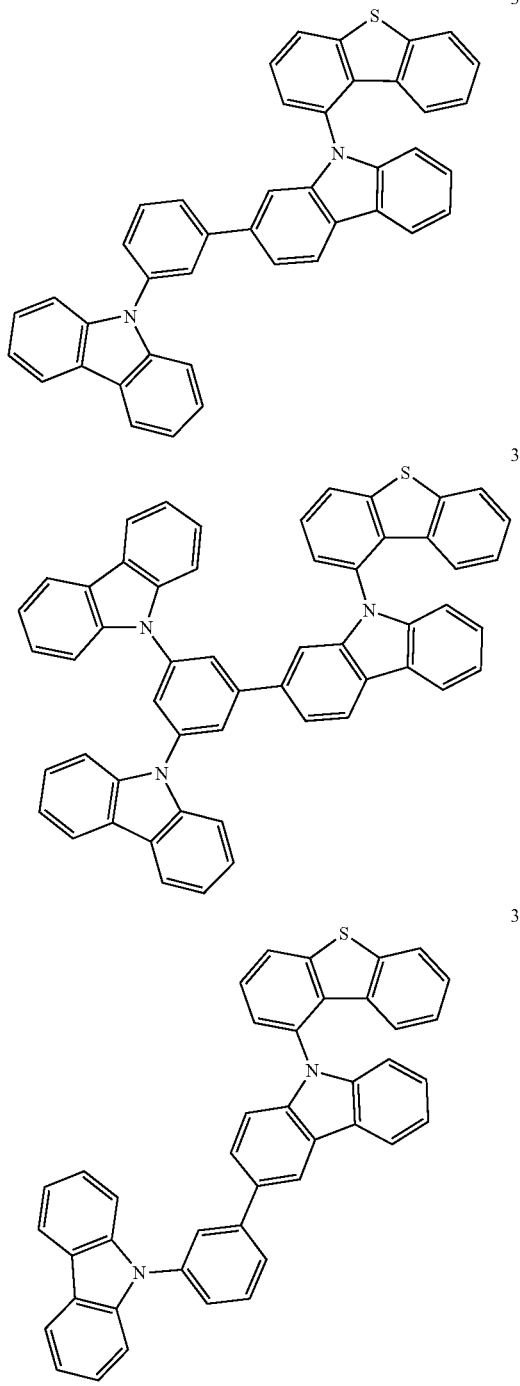
3-162
3-182
3-183
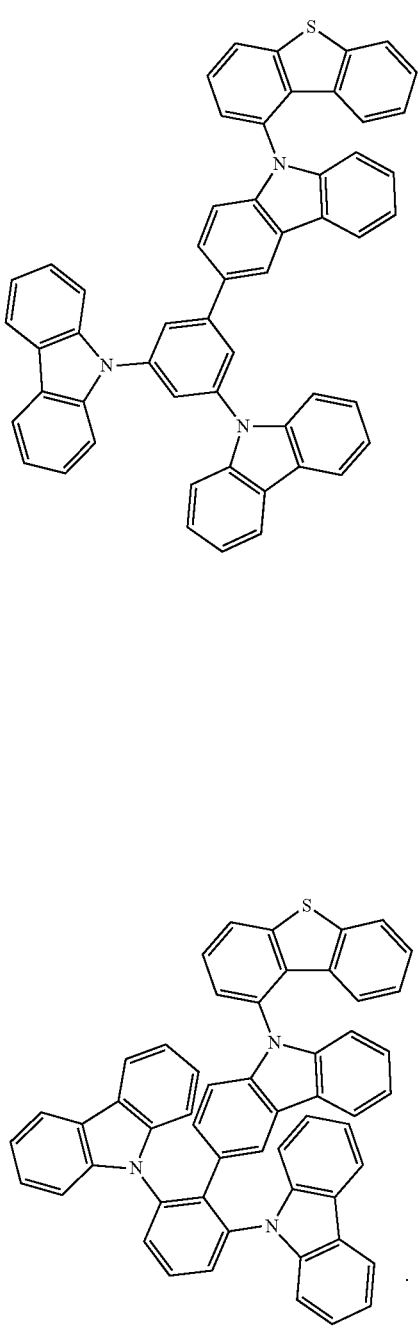
3-184
* * * * *